United States Patent
Bu et al.

(10) Patent No.: US 12,410,240 B2
(45) Date of Patent: *Sep. 9, 2025

(54) ANTIBODIES AND METHODS FOR THE DIAGNOSIS AND TREATMENT OF EPSTEIN BARR VIRUS INFECTION

(71) Applicants: The U.S.A., as represented by the Secretary, Department of Health and Human Services, Bethesda, MD (US); The Henry M. Jackson Foundation for the Advancement of Military Medicine, Inc., Bethesda, MD (US)

(72) Inventors: Wei Bu, Potomac, MD (US); Masaru Kanekiyo, North Bethesda, MD (US); Michael Gordon Joyce, Washington, DC (US); Jeffrey I. Cohen, Silver Spring, MD (US)

(73) Assignees: The United States of America, as represented by the Secretary, Department of Health and Human Services, Bethesda, MD (US); The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,344

(22) Filed: Feb. 13, 2024

(65) Prior Publication Data

US 2024/0174735 A1    May 30, 2024

Related U.S. Application Data

(60) Continuation of application No. 17/553,139, filed on Dec. 16, 2021, now Pat. No. 11,926,656, which is a division of application No. 16/608,386, filed as application No. PCT/US2018/029463 on Apr. 25, 2018, now Pat. No. 11,236,151.

(60) Provisional application No. 62/490,023, filed on Apr. 25, 2017.

(51) Int. Cl.
*C07K 16/08* (2006.01)
*A61K 38/00* (2006.01)
*C07K 14/05* (2006.01)

(52) U.S. Cl.
CPC ............ *C07K 16/085* (2013.01); *C07K 14/05* (2013.01); *A61K 38/00* (2013.01); *C07K 2317/10* (2013.01); *C07K 2317/21* (2013.01); *C07K 2317/565* (2013.01)

(58) Field of Classification Search
CPC .. C07K 16/085; C07K 14/05; C07K 2317/10; C07K 2317/21; C07K 2317/565; A61K 38/00
See application file for complete search history.

(56) References Cited

U.S. PATENT DOCUMENTS

| | | |
|---|---|---|
| 2012/0108492 A1 | 5/2012 | Holers et al. |
| 2020/0190168 A1 | 6/2020 | Bu et al. |
| 2022/0098284 A1 | 3/2022 | Bu et al. |

OTHER PUBLICATIONS

Bowie et al., "Deciphering the Message in Protein Sequences: Tolerance to Amino Acid Substitutions," *Science*, vol. 247:1306-1310, 2013.

Chen et al., "Human Monoclonal Antibodies Targeting the Haemagglutinin Glycoprotein can Neutralize H7N9 Influenza Virus," *Nat. Commun.*, vol. 6:6714, 2015.

Coghill et al., "High Levels of Antibody that Neutralize B-cell Infection of Epstein-Barr Virus that Bind EBV gp350 are Associated with a Lower Risk of Nasopharyngeal Carcinoma," *Clin. Cancer Res.*, vol. 22:3451-3457, 2016.

Collis et al., "Analysis of the Antigen Combining Site: Correlations Between Length and Sequence Composition of the Hypervariable Loops and the Nature of the Antigen," *J. Mol. Biol.*, vol. 325:337-354, 2003.

Dondelinger et al., "Understanding the Significance and Implications of Antibody Numbering and Antigen-Binding Surface/Residue Definition," *Front. Immunol.*, vol. 9:2278, (15 pages), 2018.

Herrman et al., "Epstein Barr Virus gp350 can Functionally Replace the Rhesus Lymphocryptovirus Major Membrane Glycoprotein and does not Restrict Infection of Rhesus Macaques," *J. Virol.*, vol. 90:1222-1230, 2016.

International Search Report and Written Opinion dated Jul. 25, 2018 for International Application No. PCT/US2018/029463.

International Preliminary Report on Patentability for International Application No. PCT/US2018/029463, dated Nov. 7, 2019, 13 pages.

Kanekiyo et al., "Rational Design of an Epstein-Barr Virus Vaccine Targeting the Receptor-Binding Site," *Cell*, vol. 162:1090-1100, 2015.

Kussie et al., "A Single Engineered Amino Acid Substitution Changes Antibody Fine Specificity," *J. Immunol.*, vol. 152:146-152, 1994.

(Continued)

*Primary Examiner* — Rachel B Gill
(74) *Attorney, Agent, or Firm* — Klarquist Sparkman, LLP

(57) ABSTRACT

Antibodies and compositions of matter useful for the detection, diagnosis and treatment of Epstein Barr Virus (EBV) infection in mammals, and methods of using those compositions of matter for the detection, diagnosis and treatment of EBV infection are described. Also described are proteins, referred to as anti-gp350 antibody probes, and anti-gp350 B-cell probes, that maintain the epitope structure of the CR2-binding region of gp350, but do not bind CR2.

16 Claims, 23 Drawing Sheets
Specification includes a Sequence Listing.

(56) References Cited

OTHER PUBLICATIONS

Ogembo et al., "A Chimeric EBV gp350/220-based VLP Replicates the Virion B-cell Attachment Mechanism and Elicits Long-Lasting Neutralizing Antibodies in Mice," *J. Transl. Med.*, vol. 13:50, (14 pages), 2015.
Sela-Culang et al., "The Structural Basis of Antibody-Antigen Recognition," *Front. Immunol.*, vol. 4:302, (13 pages), 2013.
Servat et al., "Identification of the Critical Attribute(s) of EBV gp350 Antigen Required for Elicitation of a Neutralizing Antibody Response in vivo," *Vaccine*, vol. 33:6771-6777, 2015.
Sirin et al., "AB-Bind: Antibody Binding Mutational Database for Computational Affinity Predictions," *Protein Sci.*, vol. 25:393-409, 2016.
Sitompuli et al., "Epitope Mapping of gp350/220 Conserved Domain of Epstein Barr Virus to Develop Nasopharyngeal Carcinoma (npc) Vaccine," *Bioinformation*, vol. 8:479-482, 2012.
Szakonyi et al., "Structure of the Epstein-Barr virus major envelope glycoprotein," *Nat Struct Mol Biol*, vol. 13:996-1001, 2006.
Tanner et al., "Construction and Characterization of a Humanized Anti-Epstein-Barr Virus gp350 Antibody with Neutralizing Activity in Cell Culture," *Cancers*, vol. 10:112, (18 pages), 2018.
Tanner et al., "Peptides Designed to Spatially Depict the Epstein-Barr Virus Major Virion Glycoprotein gp350 Neutralization of Epitope Elicit Antibodies that Block Virus-Neutralizing Antibody 72A1 Interaction with the Native gp350 Molecule," *J. Virol.*, vol. 89:4932-4941, 2015.
Tanner et al., "Soluble gp350/220 and deletion mutant glycoproteins block Epstein-Barr virus adsorption to lymphocyte," *J. Virol.*, vol. 62:4452-4464, 1988.
Tsuchiya et al., "The Diversity of H3 Loops Determines the Antigen-Binding Tendencies of Antibody CDR Loops," *Protein Sci.*, vol. 25:815-825, 2016.
Weiss et al., "High Epstein-Barr Virus Load and Genomic Diversity are Associated with Generation of gp350-Specific Neutralizing Antibodies following Acute Infectious Mononucleosis," *J. Virol.*, vol. 91:e01562-16, 2016.
Winkler et al., "Changing the Antigen Binding Specificity by Single Point Mutations of an Anti-p24 (HIV-1) Antibody," *J. Immunol.*, vol. 165:4505-4514, 2000.
Young et al., "Molecular basis of the interaction between complement receptor type 2 (CR2/CD21) and Epstein-Barr virus glycoprotein gp350," *J. Virol.*, vol. 82:11217-11227, 2008.
Zhao et al., "Immunization with Fc-Based Recombinant Epstein-Barr Virus gp350 Elicits Potent Neutralizing Humoral Immune Response in a BALB/c Mice Model," *Front. Immunol.*, vol. 9:932, 15 pages, 2018.

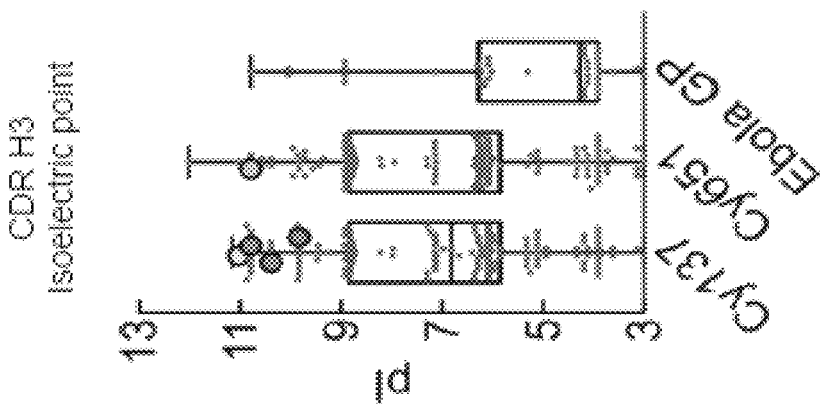
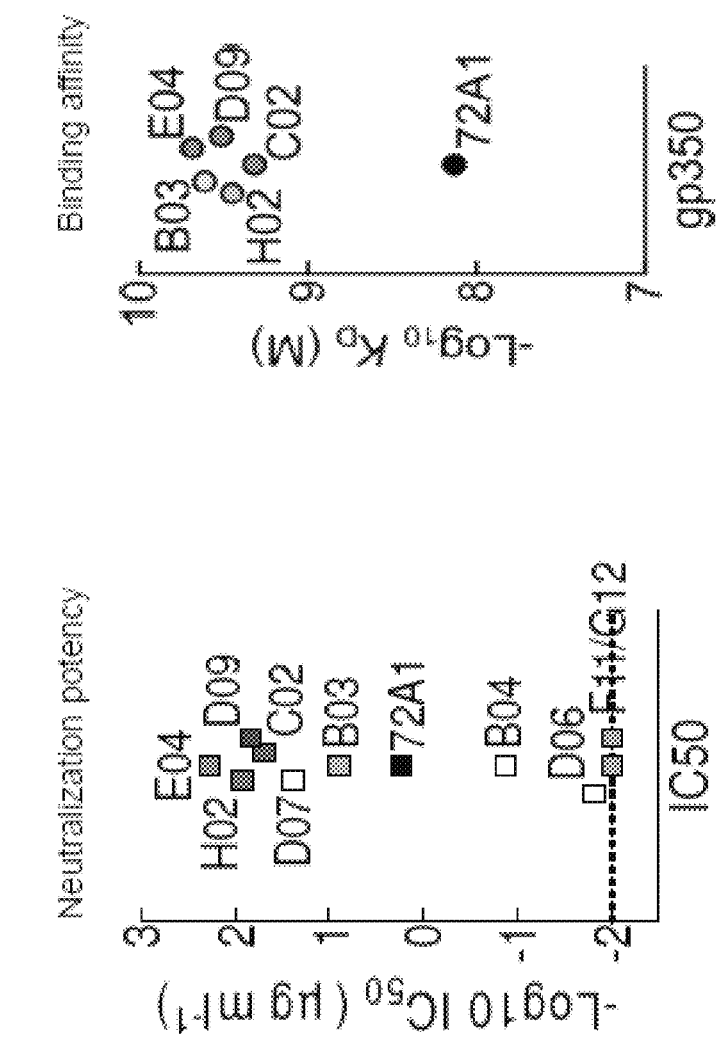
FIG. 10C
FIG. 10B
FIG. 10A

ANTIBODIES AND METHODS FOR THE DIAGNOSIS AND TREATMENT OF EPSTEIN BARR VIRUS INFECTION

CROSS-REFERENCE TO RELATED APPLICATIONS

This is a continuation application of U.S. application Ser. No. 17/553,139, filed Dec. 16, 2021, issued as U.S. Pat. No. 11,926,656 on Mar. 12, 2024, which is a divisional application of U.S. application Ser. No. 16/608,386, filed Oct. 25, 2019, issued as U.S. Pat. No. 11,236,151 on Feb. 1, 2022, which is a national stage application under 35 U.S.C. § 371 and claims the benefit of PCT Application No. PCT/US2018/029463 having an international filing date of Apr. 25, 2018, which designated the United States, which PCT application claims the benefit of priority under 35 U.S.C. § 119 (e) to U.S. Provisional Patent Application No. 62/490,023, filed Apr. 25, 2017. The entire disclosures of the above-listed applications are incorporated herein by reference.

FIELD OF THE INVENTION

The present invention is directed to compositions of matter useful for the diagnosis and treatment of Epstein Barr Virus infections in mammals and to methods of using those compositions of matter for the same.

INCORPORATION OF ELECTRONIC SEQUENCE LISTING

The electronic sequence listing, submitted herewith as an XML file named Sequence.xml (343,206 bytes), created on Apr. 17, 2024, is herein incorporated by reference in its entirety.

BACKGROUND

Epstein-Barr-Virus (EBV) is a human herpes virus that infects over 90% of the population world-wide with a life-long persistence in its host. In most cases, primary infection occurs during early childhood and is usually asymptomatic. In contrast, if infection is retarded and happens during adolescence or adulthood, it is regularly symptomatic, causing a benign, normally self-limiting, lymphoproliferative syndrome termed infectious mononucleosis (IM) in up to 50% of cases. Although the disease is normally self-limiting, prolonged forms of chronic active EBV infection (CAEBV) with fatal outcome have been reported. EBV infection also significantly increases the risk of developing Hodgkin disease and other types of lymphoma later in life. EBV infection is also an independent risk factor for multiple sclerosis later in life. In addition, EBV is causally associated with a heterogeneous group of malignant diseases like nasopharyngeal carcinoma, gastric carcinoma, and various types of lymphoma, and the WHO classifies EBV as a class I carcinogen.

Besides the above described medical conditions caused by EBV, patients with primary or secondary immune defects, like transplant recipients, are at elevated risk for EBV-associated diseases because of the detrimental effect of immunosuppressive agents on the immune-control of EBV-infected B-cells. EBV-associated post-transplant lymphoproliferative disorder (PTLD) is an important form of post-transplant complications, occurring in up to 20% of organ recipients. Importantly, immunocompromised transplant recipients who are immunologically naive for EBV at the onset of immunosuppression are at a particular high risk of developing life-threatening EBV positive PTLD due to a primary EBV infection, e.g. often caused after transplantation via transmission of the virus through a donor organ due to the high prevalence of EBV. Due to impaired T-cell immunity that results from exposure to immunosuppressive drugs, these patients are unable to effectively prime EBV-specific T-cells that play a critical role in controlling proliferation of EBV-infected B-cells. In contrast, patients who are EBV-seropositive at transplant have a much lower risk for developing PTLD, demonstrating the essential role of EBV-specific T-cells in eliminating virally infected cells. In general, patients who are EBV-seronegative before transplantation are at a much higher risk to develop EBV-associated diseases, since transmission of donor EBV in transplanted organs or natural infection with the virus causes lymphoproliferative disease in EBV-seronegative recipients after transplantation. As with many virus-associated diseases a promising approach for diagnosing and/or treating virus infection and its consequences in the host is the use of antibodies that specifically recognize the virus. This is also true in the case of reducing the high risk of PTLD in seronegative patients by identifying them and treating them prior to the transplantation.

These EBV-associated diseases highlight the need for a better understanding of herpes viruses and their role in mammalian diseases. As part of this understanding, there is a great need for additional diagnostic and therapeutic agents capable of detecting the presence of EBV in a mammal and effectively inhibiting EBV infection and replication. Accordingly, it is an objective of the present invention to specifically identify EBV-associated polypeptides and to use that identification specificity to produce compositions of matter useful in the therapeutic treatment and diagnostic detection of EBV in mammals.

SUMMARY

The invention is in part based on a variety of antibodies to Epstein Barr virus (EBV) glycoprotein 350 (gp350 protein; viral envelope glycoprotein that initiates EBV infection by binding to the B cell surface receptor, CR2) and their use in the detection and diagnosis during active EBV infection. The inventors isolated monoclonal antibodies (mAbs) from macaque monkeys immunized with a gp350 nanoparticle vaccine. Characterization using multiple methods with active virus and gp350 revealed the mAbs of this disclosure (including those monoclonal antibodies produced by the B03, E04, D09, C02, H02, B04, B05, D06, D07, A03, and G12 clones) were EBV-specific, and have as much as 100-fold greater EBV neutralizing activity than 72A1, a murine antibody that targets the putative CR2-binding site on gp350 and is the most potent EBV-neutralizing antibody reported to date. Thus, the mAbs of this disclosure can recognize both cell-associated and secreted forms of native gp350 from infected cell culture and are therefore high value mAbs with potential uses in immunoassay development and as immunodiagnostic reagents for clinical sample and tissue confirmation of EBV, and treatment or prevention of EBV-associated diseases and disorders.

This disclosure provides an antibody which binds, preferably specifically, to an EBV gp350 protein. Optionally, the antibody is a monoclonal antibody, antibody fragment, chimeric antibody, humanized antibody, single-chain antibody or antibody that competitively inhibits the binding of an anti-EBV gp350 protein antibody to its respective antigenic epitope. The antibodies of this disclosure may optionally be produced in CHO cells or bacterial cells and preferably inhibit the growth or proliferation of or induce the death of a cell to which they bind. For diagnostic purposes, the antibodies of this disclosure may be detectably labeled, attached to a solid support, or the like, such as a lateral flow assay device which provides for point-of-care detection and/or diagnosis of EBV infection.

This disclosure also provides vectors comprising DNA encoding any of the herein described antibodies. Host cells comprising any such vector are also provided. By way of example, the host cells may be CHO cells, E. coli cells, or yeast cells. A process for producing any of the herein described antibodies is further provided and comprises culturing host cells under conditions suitable for expression of the desired antibody and recovering the desired antibody from the cell culture.

The disclosure also provides a composition of matter comprising an anti-EBV gp350 antibody as described herein, in combination with a carrier. Optionally, the carrier is a pharmaceutically acceptable carrier.

This disclosure also provides an article of manufacture comprising a container and a composition of matter contained within the container, wherein the composition of matter may comprise an anti-EBV gp350 antibody as described herein. The article may optionally comprise a label affixed to the container, or a package insert included with the container, that refers to the use of the composition of matter for the therapeutic treatment or diagnostic detection of an EBV infection.

This disclosure also provides the use of an anti-EBV gp350 polypeptide antibody as described herein, for the preparation of a medicament useful in the treatment of a condition which is responsive to the anti-EBV gp350 protein antibody.

This disclosure also provides any isolated antibody comprising one or more of the complementary determining regions (CDRs), including a CDR-L1, CDR-L2, CDR-L3, CDR-H1, CDR-H2, or CDR-H3 sequence disclosed herein, or any antibody that binds to the same epitope as such antibody.

This disclosure also provides a method for inhibiting the growth of a cell that expresses an EBV gp350 protein, including contacting the cell with an antibody that binds to the EBV gp350 protein, wherein the binding of the antibody to the EBV gp350 protein causes inhibition of the growth of the cell expressing the EBV gp350 protein. In these methods, the cell may be one or more of a B-lymphocyte and an epithelial cell. Binding of the antibody to the EBV gp350 protein causes death of the cell expressing the EBV gp350 protein. Optionally, the antibody is a monoclonal antibody, antibody fragment, chimeric antibody, humanized antibody, or single-chain antibody. Antibodies employed in the methods of this disclosure may optionally be conjugated to a growth inhibitory agent or cytotoxic agent such as a toxin. The antibodies employed in the methods of this disclosure may optionally be produced in CHO cells or bacterial cells.

This disclosure also provides a method of therapeutically treating a mammal having an EBV infection by administering to the mammal a therapeutically effective amount of an antibody that binds to the EBV gp350 protein, thereby resulting in the effective therapeutic treatment of the infection in the mammal. In these therapeutic methods, the antibody may be a monoclonal antibody, antibody fragment, chimeric antibody, humanized antibody, or single-chain antibody. Antibodies employed in these methods may optionally be conjugated to a growth inhibitory agent or cytotoxic agent such as a toxin. The antibodies employed in these methods of this disclosure may optionally be produced in CHO cells or bacterial cells.

This disclosure also provides is a method of determining the presence of an EBV gp350 protein in a sample suspected of containing the EBV gp350 protein, by exposing the sample to an antibody that binds to the EBV gp350 protein and determining binding of the antibody to the EBV gp350 protein in the sample, wherein the presence of such binding is indicative of the presence of the EBV gp350 protein in the sample. Optionally, the sample may contain cells (which may be fibroblasts, keratinocytes, or dendritic cells) suspected of expressing the EBV gp350 protein. The antibody employed in these methods may optionally be detectably labeled, attached to a solid support, or the like.

This disclosure also provides methods of diagnosing the presence of an EBV infection in a mammal, by detecting the level of an EBV gp350 protein in a test sample of tissue cells obtained from the mammal, wherein detection of the EBV gp350 protein in the test sample is indicative of the presence of EBV infection in the mammal from which the test sample was obtained.

This disclosure also provides methods of diagnosing the presence of an EBV infection in a mammal, by contacting a test sample comprising tissue cells obtained from the mammal with an antibody that binds to an EBV gp350 protein and detecting the formation of a complex between the antibody and the EBV gp350 protein in the test sample, wherein the formation of a complex is indicative of the presence of an EBV infection in the mammal. Optionally, the antibody employed is detectably labeled, attached to a solid support, or the like. In these methods, the test sample of tissue cells may be obtained from an individual suspected of having a viral infection.

This disclosure also provides a method of treating or preventing an EBV infection-related disorder by administering to a subject in need of such treatment an effective amount of an antagonist of an EBV gp350 protein. The EBV infection-related disorder may be infectious mononucleosis (glandular fever), particular forms of cancer, such as Hodgkin's lymphoma, Burkitt's lymphoma, gastric cancer, nasopharyngeal carcinoma, and conditions associated with human immunodeficiency virus (HIV), such as hairy leukoplakia and central nervous system lymphomas, autoimmune diseases, including dermatomyositis, systemic lupus erythematosus, rheumatoid arthritis, Sjögren's syndrome, and multiple sclerosis, and post-transplant lymphoproliferative disorder (PTLD). In these methods, the antagonist of the EBV gp350 protein is an anti-EBV gp350 protein antibody of this disclosure. Effective treatment or prevention of the disorder may be a result of direct killing or growth inhibition of cells that express an EBV gp350 protein or by antagonizing the production of EBV gp350 protein.

This disclosure also provides methods of binding an antibody to a cell that expresses an EBV gp350 protein, by contacting a cell that expresses an EBV gp350 protein with the antibody of this disclosure under conditions which are suitable for binding of the antibody to the EBV gp350 protein and allowing binding therebetween. The antibody may be labeled with a molecule or compound that is useful for qualitatively and/or quantitatively determining the location and/or amount of binding of the antibody to the cell.

This disclosure also provides for the use of an EBV gp350 protein, a nucleic acid encoding an EBV gp350 protein, or a vector or host cell comprising that nucleic acid, or an anti-EBV gp350 protein antibody in the preparation of a medicament useful for (i) the therapeutic treatment or diagnostic detection of an EBV infection, or (ii) the therapeutic treatment or prevention of an EBV infection-related disorder.

This disclosure also provides a method for inhibiting the production of additional viral particles in an EBV-infected mammal or cell, wherein the growth of the EBV infected cell is at least in part dependent upon the expression of an EBV gp350 protein (wherein the EBV gp350 protein may be expressed either within the infected cell itself or a cell that produces polypeptide(s) that have a growth potentiating effect on the infected cells), by contacting the EBV gp350 protein with an antibody that binds to the EBV gp350 protein, thereby antagonizing the growth-potentiating activity of the EBV gp350 protein and, in turn, inhibiting the growth of the infected cell. Preferably the growth of the infected cell is completely inhibited. More preferably, binding of the antibody to the EBV gp350 protein induces the death of the infected cell. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

This disclosure also provides methods of treating a viral infection in a mammal, wherein the infection is at least in part dependent upon the expression of an EBV gp350 protein, by administering to the mammal a therapeutically effective amount of an antibody that binds to the EBV gp350 protein, thereby antagonizing the activity of the EBV gp350 protein and resulting in the effective therapeutic treatment of the infection in the mammal. Optionally, the antibody is a monoclonal antibody, antibody fragment, chimeric antibody, humanized antibody, or single-chain antibody. Antibodies employed in these methods may optionally be conjugated to a growth inhibitory agent or cytotoxic agent such as a toxin, or the like. The antibodies employed in the methods of this disclosure may optionally be produced in CHO cells or bacterial cells.

This disclosure also provides a protein useful for identifying an anti-gp350 antibody, or an anti-gp350 B-cell. Such a protein comprises: a) a polypeptide sequence at least 80%, at least 85%, at least 90%, at least 95%, at least 97% or at least 99% identical to the amino acid sequence of the CR2-binding region of EBV gp350; or b) a polypeptide sequence at comprising at least 100, at least 150, at least 200, at least 250, at last 300, at least 350, at least 400, or at least 425 contiguous amino acids from the amino acid sequence of the CR2-binding region of EBV gp350; wherein the protein can bind an anti-gp350 antibody, or a B-cell expressing an anti-the gp350 B-cell receptor (BCR), wherein binding of the B-cell is through the BCR, and wherein the protein is unable to bind CR2. In certain aspects, at least one amino acid residue corresponding to amino acid Q122, P158, I160, K161, W162, D163, N164, or D296, of SEQ ID NO:124 has been deleted, or has been substituted with one or more amino acid residues. In certain aspects, the amino acid sequence of the CR2-binding region comprises SEQ ID NO:125.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid Q122 of SEQ ID NO:124 has been deleted, or has been substituted with one or more amino acid residues. In certain aspects, the one or more amino acid residue is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid Q122 of SEQ ID NO:124 has been substituted with asparagine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid P158 of SEQ ID NO:124 has been deleted, or has been substituted with one or more amino acid residues. In certain aspects, the one or more amino acid residues is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid P158 of SEQ ID NO:124 has been substituted with arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid I160 of SEQ ID NO:124 has been deleted, or has been substituted with one or more amino acid residues. In certain aspects, the one or more amino acid residue is selected from the group consisting of serine, threonine, cysteine, proline, asparagine, glutamine, tyrosine, phenylalanine, tryptophan, glutamate, aspartate, arginine, glutamine, histidine and lysine. In certain aspects, the amino acid corresponding to amino acid I160 of SEQ ID NO:124 has been substituted with arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid W162 of SEQ ID NO:124 has been deleted, or has been substituted with one or more amino acid residues. In certain aspects, the one or more amino acid residue is selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine. In certain aspects, the amino acid corresponding to amino acid W162 of SEQ ID NO:124 has been substituted with alanine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues. In certain aspects, the one or more amino acid residue is selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine. In certain aspects, the amino acid corresponding to amino acid D163 of SEQ ID NO:124 has been substituted with asparagine. In certain aspects, at least one amino acid has been inserted between the amino acid corresponding to amino acid N164 of SEQ ID NO:124 and the amino acid corresponding to C165 of SEQ ID NO:124. In certain aspects, the at least one amino acid is selected from the group consisting of serine, threonine, cysteine, proline, asparagine, and glutamine. In certain aspects, a serine residue has been inserted between the amino acid corresponding to amino acid N164 of SEQ ID NO:124 and the amino acid corresponding to C165 of SEQ ID NO:124.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid N164 of SEQ ID NO:124 has been deleted, or has been substituted with one or more amino acid residues. In certain aspects, the one or more amino acid residue is selected from the group consisting of methionine, leucine, isoleucine, glycine, alanine, valine, phenylalanine, tyrosine, tryptophan, lysine, arginine, histidine, glutamate, serine, and aspartate. In certain aspects, the amino acid corresponding to amino acid N164 of SEQ ID NO:124 has been substituted with serine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has been deleted, or has been substituted with one or more amino acid residues. In certain aspects, the one or more amino acid residue is selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine. In certain aspects, the amino acid corresponding to amino acid D296 of SEQ ID NO:124 has been substituted with arginine. In certain aspects, the amino acid corresponding to amino acid I160 of SEQ ID NO:124 has been deleted, or has been substituted with at least one amino acid residue. In certain aspects, the at least one amino acid residue is selected from the group consisting of serine, threonine, cysteine, proline, asparagine, glutamine, tyrosine, phenylalanine, tryptophan, glutamate, aspartate, arginine, glutamine, histidine and lysine. In certain aspects, the amino acid corresponding to amino acid I160 of SEQ ID NO:124 has been substituted with arginine. In further aspects, the amino acid corresponding to amino acid P158 of SEQ ID NO:124 has been deleted, or has been substituted with at least one amino acid residue. In certain aspects, the at least one amino acid residue is selected from the group consisting of methionine, leucine, isoleucine, glycine, alanine, valine, phenylalanine, tyrosine, tryptophan, lysine, arginine, histidine, glutamate, and aspartate. In certain aspects, the amino acid corresponding to amino acid P158 of SEQ ID NO:124 has been substituted with arginine or asparagine. In certain aspects, the amino acid corresponding to amino acid I160 of SEQ ID NO:124, has been substituted with a threonine or an arginine.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein one or more amino acids has been inserted between the amino acid corresponding to amino acid N164 of SEQ ID NO:124 and the amino acid corresponding to C165 of SEQ ID NO:124. Inc certain aspects, the one or more amino acids are selected from the group consisting of serine, threonine, cysteine, proline, asparagine, and glutamine. In certain aspects, a serine residue has been inserted between the amino acid corresponding to amino acid N164 of SEQ ID NO:124 and the amino acid corresponding to C165 of SEQ ID NO:124.

This disclosure also provides a comprising an amino acid sequence at least 80% identical, at least 85% identical, at least 90% identical, at least 95% identical, at least 97% identical, or at least 99% identical to the amino acid sequence of an EBV gp350 CR2-binding region, wherein the amino acids corresponding to amino acids W162-N164 of SEQ ID NO:124 have been deleted, or have been substituted with one or more amino acid residues. In certain aspects, the one or more amino acid residue, is selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine. In certain aspects, the amino acids corresponding to amino acids W162-N164 of SEQ ID NO:124 have each been substituted with an alanine residue.

This disclosure also provides a protein having an amino acid sequence at least 85%, at least 90%, at least 95%, at least 97% or at least 999% identical to an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159. In certain aspects, the protein comprises an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159.

This disclosure also provides a nucleic acid molecule encoding a protein having an amino acid sequence at least 85%, at least 90%, at least 95%, at least 97% or at least 999% identical to an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO:157, and SEQ ID NO:159. In certain aspects, the nucleic acid molecule encodes a protein comprises an amino acid sequence selected from the group consisting of SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:145, SEQ ID NO:147, SEQ ID NO:149, SEQ ID NO:151, SEQ ID NO:153, SEQ ID NO:155, SEQ ID NO: 157, and SEQ ID NO: 159. In certain aspects, the nucleic acid molecule comprises a sequence selected from the group consisting of SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, SEQ ID NO: 146, SEQ ID NO: 148, SEQ ID NO: 150, SEQ ID NO: 152, SEQ ID NO: 154, SEQ ID NO: 156, SEQ ID NO:158, and SEQ ID NO:160.

This disclosure also provides a method of identifying an anti-gp350 antibody, comprising contacting a protein of the invention with a solution comprising antibodies, and isolating antibodies that specifically bind to the protein. In certain aspects, the protein comprises a His-tag, an epitope tag, or a detectable label.

This disclosure also provides a method of identifying an ant-gp350 B-cell, comprising contacting a protein of the invention with a solution comprising B-cells, and isolating B-cells that specifically bind to the protein. In certain aspects, the protein comprises a His-tag, an epitope tag, or a detectable label.

Further embodiments will be evident to the skilled artisan upon a reading of the present specification.

This disclosure contains the following Sequences:

| SEQ ID NO | Description | Sequence |
|---|---|---|
| 1 | B03 clone Heavy Chain aa sequence | QVQLQESGPGLVKPAETLSLTCTVSGGSFSSYWWG WIRQSPGKGLEWIGHISSGGNNYLNPSLKSRVTLSLD TSKNQFSLKLNSVTAADSAVYYCARAPRIVVRGRYF DQWGQGVLVTVSS |
| 2 | B03 clone Heavy Chain nucleotide sequence | caggtgcagctgcaggagtcgggcccaggactggtgaagcctgcggagaccct gtccctcacctgcactgtctctggtggctcttcagcagttactggtggggctggatc cgtcagtccccaggaagggactggagtggattgggcatatcagtagtggtggaa acaactaccttaatccgtccctcaagagtcgagtcaccctgtcactagacacgtcca agaaccagttctccctgaagctgaactctgtgaccgccgcggactcggccgtgtat tactgtgccagagccccccgtattgttgttagaggccgatactttgaccaatgggc cagggagtcctggtcaccgtctcctca |
| 3 | B03 clone Heavy Chain CDR1 | GGSFSSYW |
| 4 | B03 clone Heavy Chain CDR2 | ISSGGNN |
| 5 | B03 clone Heavy Chain CDR3 | APAPRIVVRGRYFDQW |
| 6 | B03 clone Kappa Chain aa sequence | DIQMTQSPSSLSASVGDTVTITCRASQGINIYLNWFQ QRPGKAPKLLIYAATTLQSGVPSRFSGSGSGTDFTLTI SSLQPEDFATYYCLQCESYPLTFGGGTKVEIK |
| 7 | B03 clone Kappa Chain nucleotide sequence | gacatccagatgacccagtctccatcctccctgtctgcatctgtaggagacactgtc accatcacttgccgggcaagtcagggtatcaatatctacctgaattggtttcagcag agaccagggaaagcccctaaactcctgatctatgctgcgaccactttacaaagtgg ggtcccatcaagattcagcggcagtggatctgggacagatttcactctcaccatcag cagcctgcagcctgaagatttcgcaacttattactgtctacagtgtgaaagttatccg ctcactttcggcggagggaccaaggtggagatcaaa |
| 8 | B03 clone Kappa Chain CDR1 | QGINIY |
| 9 | B03 clone Kappa Chain CDR2 | AAT |
| 10 | B03 clone Kappa Chain CDR3 | LQCESYPLT |
| 11 | E04 clone Heavy Chain aa sequence | QVQLQESGPGLVKPSETLSLTCTVSGGSISGAYYYW SWIRQPPGKGLDWIGYIYGSFGSAYYNPSLKSRATIS KDTPKNQFSLKLSSVTAADTAVYYCARGRRLGYSN WFDVWGPGVLVTVSS |
| 12 | E04 clone Heavy Chain nucleotide sequence | caggtgcaactgcaggagtcgggcccaggactggtgaagcctttcggagaccctg tccctcacctgcactgtctctggtggctccatcagcggtGCTTACtactactgg agctggattcgacagccccgggaagggactggactggattggatatatctatg gaagttttgggagtgcctactacaaccctccctcaagagtcgagccaccatttcaa aagacacgcccaagaaccagttctccctgaaactgagctctgtgaccgccgcgga cacggccgtgtattactgtgcgagaggaaggcgactaggctattcgaactggttcg atgtctggggcccgggagtcctggtcaccgtctcctca |
| 13 | E04 clone Heavy Chain CDR1 | GGSISGAYYY |
| 14 | E04 clone Heavy Chain CDR2 | IYGSFGSA |
| 15 | E04 clone Heavy Chain CDR3 | ARGRRLGYSNWFDVW |
| 16 | E04 clone Kappa Chain aa sequence | DIQMTQSPSSLSASVGDKVTITCRTSQDVSSYLAWY QQKPGKAPQLLIYAASSLQSGVPSRFTGSGSGAEFTL TISSLQPEDFASYYCQQYKNLPLTFGGGTKVEIK |
| 17 | E04 clone Kappa Chain nucleotide sequence | gacatccagatgacccagtctccatcttccctgtctgcatctgtaggagacaaagtc accatcacttgtcggacaagtcaggacgttagcagttatttagcctggtatcagcag aaaccagggaaagcccctcagctcctgatctatgctgcatccagtttgcaaagtgg ggtcccatcaaggttcaccggcagtggatctggggcagaattcactctcaccatca gcagccttcagcctgaagattttgcatcatattactgtcaacagtataaaaatctcccg ctcactttcggcggagggaccaaagtggagatcaaa |
| 18 | E04 clone Kappa Chain CDR1 | QDVSSY |
| 19 | E04 clone Kappa Chain CDR2 | AAS |
| 20 | E04 clone Kappa Chain CDR3 | QQYKNLPLT |
| 21 | D09 clone Heavy Chain aa sequence | QVQLQESGPGLVKPSETLSLTCDVSGGSFSGDFYWS WIRQPPGKGLDWIGNIHGSSAGTKYKPSLKSRVTISK DTSKNQFSLKLSSVTAADTAVYYCTRGPLSRIVAGF GRGINWFDVWGPGVLVTVSS |

| SEQ ID NO | Description | Sequence |
|---|---|---|
| 22 | D09 clone Heavy Chain nucleotide sequence | caggtgcagctgcaggagtcgggcccaggactggtgaagccttcggagaccctg tccctcacctgcgatgtctctggtggctccttcagcggtgatTTCtactggagctg gatccgccagccccagggaagggactggactggattgggaatatccatggcag cagtgcgggcaccaaatacaagccctccctcaagagtcgagtcaccatttcaaaa gacacgtccaagaaccagttctccctgaaactgagctctgtgaccgccgcggaca cggccgtctattactgtacgagaggcccccttagtaggatagtagctggttttggga gggggattaactggttcgatgtctggggcccggggagtcctggtcaccgtctcctca |
| 23 | D09 clone Heavy Chain CDR1 | GGSFSGDFY |
| 24 | D09 clone Heavy Chain CDR2 | IHGSSAGT |
| 25 | D09 clone Heavy Chain CDR3 | TRGPLSRIVAGFGRGINWFDVW |
| 26 | D09 clone Lambda Chain aa sequence | QPVLTQPTSLSASPGASVRLSCTLSSGINVGSYSIFWY QQKPGSPPRYLLFYFSDSSKHQSGVPSRFSGSKDTS ANAGLLLISGLQSEDEADYYCAIWHSSASVLFGGGT RLTVL |
| 27 | D09 clone Lambda Chain nucleotide sequence | cagcctgtgctgacccagccaacctccctctcagcatctccgggagcatcagtcag actcagctgcaccttgagcagtggcatcaatgttggtagttacagcatattctggtac cagcagaagccagggagtcctccccggtaccttctgttctatttctcagactcaagta agcaccagggctctggagtcccagccgtttctctggatccaaggatacttcagcc aatgcagggcttttactgatctctgggctccagtctgaagatgaggctgactattact gtgccatatggcacagcagcgcttctgtgttattcggaggagggaccggctgaca gtacta |
| 28 | D09 clone Lambda Chain CDR1 | TLSSGINVGSYSIF |
| 29 | D09 clone Lambda Chain CDR2 | YFSDSSK |
| 30 | D09 clone Lambda Chain CDR3 | AIWHSSASVL |
| 31 | C02 clone Heavy Chain aa sequence | QLQLQESGPGLVKPSETLSLTCAVSGGSISGYYWSWI RQPPGKGPEWIGFIDGNTVGTNYNPSLKSRVTLSKDT SKNQFSLKVSSVTAADTAVYYCARKPLRRYFWFDV WGPGVLVTVSS |
| 32 | C02 clone Heavy Chain nucleotide sequence | cagctgcagctgcaggagtcgggcccaggactggtgaagccttcggagaccctg tccctcacctgcgctgtctctggtggctccatcagcggttactactggagttggattc gccagcccccagggaagggaccggagtggattgggtttattgatggtaatactgtg ggcaccaactacaaccctccctcaagagtcgagtcaccattcaaaagacacgtc caagaatcagttctccctgaaggtgagttctgtgaccgccgcggacacggccgtgt attactgtgcgaggaagccgctacgccgttattctggttcgatgtctggggcccgg gagtcctggtcaccgtctcctca |
| 33 | C02 clone Heavy Chain CDR1 | GGSISGYY |
| 34 | C02 clone Heavy Chain CDR2 | IDGNTVGT |
| 35 | C02 clone Heavy Chain CDR3 | ARKPLRRYFWFDVW |
| 36 | C02 clone Lambda Chain aa sequence | QSVLTQPPSVSGDPGQRVTISCTGSSSNIGAGYYVYW YQQFPGTAPKLLIYQDNKRPSGVSDRFSGSKSGTSAS LTITGLQPGDEADYYCSAWDSSLSAVMFGRGTRLTV L |
| 37 | C02 clone Lambda Chain nucleotide sequence | cagtctgtgctgacgcagccgccctcagtgtctggggaccccgggcagagggtc accatctcgtgcactgggagcagctccaacatcgggGCGggttattatgtatact ggtaccagcagcttcccaggaacggccccccaaactcctcatctatcaagataataag cgaccctcaggggtttctgaccgattctctggctccaagtctggtacctcagcctcc ctgaccatcactgggctccagcctggggatgaggctgattattactgctcagcatgg gatagcagcctgagtgctgttatgttcggaagaggcaccaggctgacagtacta |
| 38 | C02 clone Lambda Chain CDR1 | SSNIGAGYY |
| 39 | C02 clone Lambda Chain CDR2 | QDN |
| 40 | C02 clone Lambda Chain CDR3 | SAWDSSLSAVM |

-continued

| SEQ ID NO | Description | Sequence |
|---|---|---|
| 41 | H02 clone Heavy Chain aa sequence | QLQLQESGPGVVKPSETLSLTCTISGGSFSTYYWTWI RQPPGKGLEWVGYIGNGGRSLNYNPSLKSRITLSVD ASKNQFSLKVTSVTAADTAVYYCGRARGLRGNWFD VWGPGVLVTVSS |
| 42 | H02 clone Heavy Chain nucleotide sequence | caactgcagttgcaggagtcgggcccaggagtggtgaagccttcggagaccctgt ccctcacctgcactatctctggtggctccttcagtacttactactggacctggattcgc cagccccagggaagggactggagtgggttgggtatatcggtaatggtggtcgta gcctcaactacaaccctccctcaagagtcgcatcaccctgtcagtagacgcgtcc aagaaccagttctccctgaaggtgacctctgtgaccgccgcggacacggccgtct attactgtgggagagccaggggactccgcggaaactggttcgatgtctggggccc gggagtcctggtcaccgtctcctca |
| 43 | H02 clone Heavy Chain CDR1 | GGSFSTYY |
| 44 | H02 clone Heavy Chain CDR2 | IGNGGRSL |
| 45 | H02 clone Heavy Chain CDR3 | GRARGLRGNWFDVW |
| 46 | H02 clone Lambda Chain aa sequence | QAALTQPPSVSGSPGQSVTISCTGTSSDIGGYNYVSW YQQHPGKAPKVMIYEVSKRPSGVSDRFSGSKSGNIA SLTISGLQAEDEADYYCSSYAGSNTFLFGGGTRLTVL |
| 47 | H02 clone Lambda Chain nucleotide sequence | caggctgccctgactcagcctcctctgtgtctgggtctcctggacagtcggtcacc atctcctgcactggaaccagcagtgacatcggtggttataactatgtctcctggtacc aacaacacccaggcaaagcccccaaagtcatgatttatgaggtcagtaagcggcc ctcaggggtctctgatcgcttctctggttccaaatctggcaacatagcctccctgacc atctctgggctccaggctgaggacgaggctgattattactgcagctcatatgcaggc agcaacactttcttattcggaggagggacccggctgacagtacta |
| 48 | H02 clone Lambda Chain CDR1 | SSDIGGYNY |
| 49 | H02 clone Lambda Chain CDR2 | EVS |
| 50 | H02 clone Lambda Chain CDR3 | SSYAGSNTFL |
| 51 | A03 clone Heavy Chain aa sequence | QVQLQESGPGLVKPSETLSLTCAVSGGSISSNYWSWI RQPPGKGLEWIGRIYGSGGSTDYNPSLKSRVTISTDT SKNQFSLKVSSVTAADTAVYYCARVRIQWVQLRGW FDVWGPGVLVTVSS |
| 52 | A03 clone Heavy Chain nucleotide sequence | caggtgcagctgcaggagtcgggcccaggactggtgaagccttcggagaccctg tccctcacctgcgctgtctctggtggctccatcagcagtaactactggagctggatc cgccagccccagggaagggactggagtggattggacgtatctatggtagtggtg ggagcaccgactacaaccctccctcaagagtcgagtcaccatttcaacagacac gtccaagaaccagttctccctgaaggtgagctctgtgaccgccgcggacacggcc gtgtattactgtgcgagagtgcggatacagtgggtacagttgcgaggctggttcgat gtctggggcccgggagtcctggtcaccgtctcctca |
| 53 | A03 clone Heavy Chain CDR1 | GGSISSNYWS |
| 54 | A03 clone Heavy Chain CDR2 | IYGSGGST |
| 55 | A03 clone Heavy Chain CDR3 | ARVRIQWVQLRGWFDVW |
| 56 | A03 clone Kappa Chain aa sequence | YIQMTQSPSSLSASVGDTVTFTGPASQSFSSSLAWYQ QKPGKAPNLLIYSASSLQCGVRSRFSGSKSGTDFTLTI SSLQPEDIASYYCQQYYSYPFTFGPGTKLDIK |
| 57 | A03 clone Kappa Chain nucleotide sequence | Tacatacagatgacgcagtctccatcctccctgtctgcatctgtaggagacacagtc accttcactggccccgcaagtcagagctttagtagtagtttagcctggtatcagcag aaaccagggaaagcccctaacctcctgatctatagtgcatccagtttgcaatgtggg gttcgttcgaggttcagtggcagtaagtctgggacagatttcactctcaccatcagca gcctgcagcctgaagatattgctagttattactgtcaacagtattacagttatccattca cttcggccccgggaccaaactggatatcaaa |
| 58 | A03 clone Kappa Chain CDR1 | QSFSSS |
| 59 | A03 clone Kappa Chain CDR2 | SAS |
| 60 | A03 clone Kappa Chain CDR3 | QQYYSYPFT |

| SEQ ID NO | Description | Sequence |
|---|---|---|
| 61 | B04 clone Heavy Chain aa sequence | QVQLQESGPGLVRPSETLSLTCAVSGGSISSNYWSWI RQPPGKGLEWIGYISGSTGSTYQNPSLKSRVTVSKDT SKNQFSLKLNSVTAADTAVYYCARSGRRGSSLDLW GRGVLVTVSS |
| 62 | B04 clone Heavy Chain nucleotide sequence | Caggtgcagctgcaggagtcgggcccaggactggtgaggccttcggagaccct atccctcacctgcgctgtctctggtggctccatcagcagtaactactggagctggatt cgccagccccagggaaggggctggagtggattgggtatatctctggtagtactg ggagcacctaccagaacccctccctcaagagtcgagtcaccgtttcaaaagacac gtctaagaaccagttctccctgaagctgaattctgtgaccgccgcggacacggccg tgtattactgtgcgagaagtgggagaagaggcagctcattggatttgtggggccgg ggagttctggtcaccgtctcctca |
| 63 | B04 clone Heavy Chain CDR1 | GGSISSNY |
| 64 | B04 clone Heavy Chain CDR2 | ISGSTGST |
| 65 | B04 clone Heavy Chain CDR3 | ARSGRRGSSLDLW |
| 66 | B04 clone Lambda Chain aa sequence | QSVLTQPPSVSGDPGQRVTISCTGSSSNIGAGYYVYW YQQFPGTAPKLLIYQDNKRPSGVSDRFSGSKSGTSAS LTITGLQPGDEADYYCSAWDSSLSAVFFGGGTRLTV L |
| 67 | B04 clone Lambda Chain nucleotide sequence | cagtctgtgctgacgcagccgcccctcagtgtctggggaccccgggcagagggtc accatctcgtgcactgggagcagctccaacatcgggGCGggttattatgtatact ggtaccagcagttcccaggaacggccccccaaactcctcatctatcaagataataag cgaccctcaggggtttctgaccgattctctggctccaagtctggtacctcagcctcc ctgaccatcactgggctccagcctggggatgaggctgattattactgctcagcatgg gatagcagcctgagtgctgtgttcttcggaggagggaccggctgacagtacta |
| 68 | B04 clone Lambda Chain CDR1 | SSNIGAGYY |
| 69 | B04 clone Lambda Chain CDR2 | QDN |
| 70 | B04 clone Lambda Chain CDR3 | SAWDSSLSAVF |
| 71 | B05 clone Heavy Chain aa sequence | QLQESGPGLVKPSETLSLTCTVSGGSISDTYRWSWIR QSPGKGLEWIAYIYGTTTSTNYNPSLKSRLTISKDTS KNQFSLNLRSVTAADTAVYYCARGDSGGRSAHVFH FWGQGLRVTVSS |
| 72 | B05 clone Heavy Chain nucleotide sequence | cagctgcaggagtcgggcccaggactggtgaagccttcggagaccctgtccctca cctgcactgtctctggtggctccatcagcgatacttacCGGtggagctggattcgc cagtccccagggaagggactggagtggattgcctacatctatggtactactacgag caccaactacaacccctccctcaagagtcgactcaccatttcaaaagacacgtcca agaaccagttctccttgaacctgaggtctgtgaccgccgcggacacggccgtgtat tactgtgcgagggggatagcggtggccggtcagcgcatgttttcatttctggggc caagggctcagggtcaccgtctcttca |
| 73 | B05 clone Heavy Chain CDR1 | GGSISDTYR |
| 74 | B05 clone Heavy Chain CDR2 | IYGTTTST |
| 75 | B05 clone Heavy Chain CDR3 | ARGDSGGRSAHVFHFW |
| 76 | B05 clone Lambda Chain aa sequence | QSVLTQPPSVFGDPGQRITISCTGSSSNIGAGYYVYW YQQFPGTAPKLLIYQDNKRPSGVSDRFSGSKSGSSAS LTITGLQPGDEADYYCSAWDSSLSVRVFGGGTRLTV L |
| 77 | B05 clone Lambda Chain nucleotide sequence | cagagtgttctgacgcagccgcccctcagtgtttggggaccccgggcagaggatca ccatctcgtgcactgggagcagctccaacatcgggGCGggttattatgtatactg gtaccagcagttcccaggaacggccccccaaactcctcatctatcaagataataagc gaccctcaggggtttctgaccgattttctggctccaagtctggttcctcagcctcct gaccatcactgggctccagcctggggatgaggctgattattactgctcagcatggg atagcagcctgagtgtacgggttttcggaggagggaccccggctgacagtacta |
| 78 | B05 clone Lambda Chain CDR1 | SSNIGAGYY |
| 79 | B05 clone Lambda Chain CDR2 | QDN |

| SEQ ID NO | Description | Sequence |
|---|---|---|
| 80 | B05 clone Lambda Chain CDR3 | SAWDSSLSVRV |
| 81 | D06 clone Heavy Chain aa sequence | EVQLVESGGGLVQPGGSLRLSCAASGFTFSSYGMN WVRQAPGKGLEWVSFITNTGKTTYYADSVRGRFTIS RDNAKKSVSLQMSSLRAEDTAVYYCTRGRGRHGWS SGVFDFWGQGLRVTVS |
| 82 | D06 clone Heavy Chain nucleotide sequence | Gaggtgcaactggtggagtctggaggaggcttggtccagcctggagggtccctg agactctcctgtgcagcctctggattcaccttcagtagttacggcatgaactgggtcc gccaggctccgggaaaggggctggagtgggtctcattcattactaacactggtaaa accacatactacgctgactctgtgaggggccgattcaccatctccagagacaacgc caagaagtcggtgtctctacaaatgagtagcctgagagccgaggacacggccgtc tattactgtactaggggaagaggtagacacggctggtccagtggtgttttgatttctg gggccaaggtctcagggtcaccgtctcttc |
| 83 | D06 clone Heavy Chain CDR1 | GFTFSSYG |
| 84 | D06 clone Heavy Chain CDR2 | ITNTGKTT |
| 85 | D06 clone Heavy Chain CDR3 | TGRGRHGWSSGVFDFW |
| 86 | D06 clone Lambda Chain aa sequence | QSVLTQPPSVFGDPGQRITISCTGSSSNIGAGYYVYW YQQFPGTAPKLLIYQDNKRPSGVSDRFSGSKFGSSAS LTITGVQRGDEGDYYCSAWDSSLSVRVLGGGTRLTV L |
| 87 | D06 clone Lambda Chain nucleotide sequence | cagtctgttctgacgcagccgcccctcagtgttcggggaccccgggcagaggatca ccatttcgtgcactgggagcagctccaacatcgggGCGggttattatgtatactg gtaccagcagttcccaggaacggcccccaaactcctcatctatcaagataataagc gacccctcaggggtttctgaccgattctctggctccaagtttggttcctcagcctccct gaccatcactggggtccagcgtggggatgagggtgattattactgctcagcatggg atagcagcctgagtgtacgggttttgggaggagggacccggctgacagtacta |
| 88 | D06 clone Lambda Chain CDR1 | SSNIGAGYY |
| 89 | D06 clone Lambda Chain CDR2 | QDN |
| 90 | D06 clone Lambda Chain CDR3 | SAWDSSLSVRV |
| 91 | D07 clone Heavy Chain aa sequence | EVQLVESGGGLVQPGGSLRLSCVASGFTFSDRYIDW VRQAPGKGLEWVSTISTGSGDTALYSDSVKGRFTISR DNAKNTLYLQMNSLRAEDTAVYYCARHSGTFYTHF DYWGQGVLVTVSS |
| 92 | D07 clone Heavy Chain nucleotide sequence | gaagtgcagttggtggagtctggggaggcttggtacagccggggggtccctg agactctcctgtgtagcctctggattcaccttcagtgaccgctacatagactgggtcc gccaggctccagggaagggcctggagtgggtctctactattagcactggtAGT ggtgataccgcattgtactcagactctgtcaagggccgattcaccatctccagagac aacgccaagaacacactgtatctgcaaatgaacagcctgagagccgaagacacg gctgtctattactgtgcgagacatagtggtactttttacacccactttgactactgggg ccaggagtcctggtcaccgtctcctca |
| 93 | D07 clone Heavy Chain CDR1 | GFTFSDRY |
| 94 | D07 clone Heavy Chain CDR2 | ISTGSGDTA |
| 95 | D07 clone Heavy Chain CDR3 | ARHSGTFYTHFDYW |
| 96 | D07 clone Kappa Chain aa sequence | DIQMTQSPSSLSASVGDTVTFTCRASRSISSWLAWYQ QKPGRAPKVLIYKASSLQSGVPSRFSGSGSGTDFTLTI SSLQSEDFATYYCQQYSSRPPTFGQGTKVEIR |
| 97 | D07 clone Kappa Chain nucleotide sequence | Gacatccagatgacccagtctccatcctccctgtctgcatctgtaggagacacagt caccttcacctgccgggcgagtcggagtattagcagctggttagcctggtatcagc agaaaccaggagagcccctaaagtcctgatctataaggcgtccagtttgcaaagt ggggtcccttcagcggcagtggatctgggacagacttcactctcaccatc agcagcctacagtctgaagattttgcaacatattattgtcaacagtatagtagtcgcc ctccgacgttcggccaagggaccaaggtggaaatcaga |
| 98 | D07 clone Kappa Chain CDR1 | RSISSW |

| SEQ ID NO | Description | Sequence |
|---|---|---|
| 99 | D07 clone Kappa Chain CDR2 | KAS |
| 100 | D07 clone Kappa Chain CDR3 | QQYSSRPPT |
| 101 | G12 clone Heavy Chain aa sequence | QVQLQESGPGLLKPSETLSLTCAVSGGSFSSFWWSW<br>LRQPPEKGLEWIGEINGDSGSTNYNPSLKSRVTISKD<br>ASKNQFSLKLTSVTAADTAVFYCARVRRILRSLDVW<br>GRGVLVTVSS |
| 102 | G12 clone Heavy Chain nucleotide sequence | Caggtgcagctgcaggagtcgggcccaggactgctgaagccttcggagaccct<br>gtccctcacctgcgctgtctctggtggctccttcagtagtttctggtggagctggctc<br>cgccagccccagaaagggactggagtggattggggagatcaatggtgatagt<br>gggagcaccaactacaacccctccctcaagagtcgagtcaccatttcaaaagacg<br>cgtccaagaaccagttctccctgaaactgacctctgtgaccgccgcggacacggc<br>cgttttttactgtgcgagagttcggcgaattctgaggtcattggatgtctggggccgg<br>ggagtctggtcaccgtctcctca |
| 103 | G12 clone Heavy Chain CDR1 | GGSFSSFW |
| 104 | G12 clone Heavy Chain CDR2 | INGDSGST |
| 105 | G12 clone Heavy Chain CDR3 | ARVRRILRSLDVW |
| 106 | G12 clone Kappa Chain aa sequence | DIQMTQSPFSLFAFVGDRVTITCQASQGISHLLAWYQ<br>QKPGKAPKLLIYSASTLQSGVPSRFSGSGFGTEFTLTI<br>SSLQPEDFATYYCQQHNSYPRTFGQGTKVEIK |
| 107 | G12 clone Kappa Chain nucleotide sequence | Gacatccagatgacccagtctcctttttccttgtttgcatttgtaggagacagagtcac<br>catcacttgccaagccagtcagggtattagccacttgttagcttggtatcagcagaa<br>accagggaaagcccctaagctccttatttattctgcatccactttgcaaagtggggtc<br>ccatcaaggttcagcggcagtggatttgggacggaattcactctcaccatcagcag<br>cctgcagcctgaagattttgcaacttattactgtcaacagcataatagttaccctcgga<br>cgttcggccaagggaccaaggtggaaatcaaa |
| 108 | G12 clone Kappa Chain CDR1 | QGISHL |
| 109 | G12 clone Kappa Chain CDR2 | SAS |
| 110 | G12 clone Kappa Chain CDR3 | QQHNSYPRT |
| 111 | Macaque HC backbone Nucleotide sequence | tcgcgcgttt cggtgatgac ggtgaaaacc tctgacacat gcagctcccg<br>gagacggtca cagcttgtct gtaagcggat gccgggagca gacaagcccg<br>tcaggcgcg tcagcgggtg ttggcgggtg tcgggctgg cttaactatg<br>cggcatcaga gcagattgta ctgagagtgc accatatgcg gtgtgaaata<br>ccgcacagat gcgtaaggag aaaataccgc atcagattgg<br>ctattggcca ttgcatacgt tgtatccata tcataatatg tacatttata<br>ttggctcatg tccaacatta ccgccatgtt gacattgatt attgactagt<br>tattaatagt aatcaattac ggggtcatta gttcatagcc catatatgga<br>gttccgcgtt acataactta cggtaaatgg cccgcctggc tgaccgccca<br>acgaccccg ccattgacg tcaataatga cgtatgttcc catagtaacg<br>ccaataggga ctttccattg acgtcaatgg gtggagtatt tacggtaaac<br>tgcccacttg gcagtacatc aagtgtatca tatgccaagt acgccccta<br>ttgacgtcaa tgacggtaaa tggcccgcct ggcattatgc ccagtacatg<br>accttatggg actttcctac ttggcagtac atctacgtat tagtcatcgc<br>tattaccatg gtgatgcggt tttggcagta catcaatggg cgtggatagc<br>ggtttgactc acggggattt ccaagtctcc accccattga cgtcaatggg<br>agtttgtttt ggcaccaaaa tcaacgggac tttccaaaat gtcgtaacaa<br>ctccgcccca ttgacgcaaa tgggcggtag gcgtgtacgg tgggaggtct<br>atataagcag agctcgttta gtgaaccgtc agatcgcctg gagacgccat<br>ccacgctgtt tgacctcca tagaagacac cgggaccgat ccagcctcca<br>tcggctcgca tctctccttc acgcgcccgc cgccctacct gaggccgcca<br>tccacgccgg ttgagtcgcg ttctgccgcc tccgcctgt ggtgcctcct<br>gaactgcgtc cgccgtctag gtaagtttaa agctcaggtc gagaccgggc<br>ctttgtccgg cgctcccttg gagcctacct agactcagcc ggctctccac<br>gctttgcctg acctgcttg ctcaactcta gttaacggtg gagggcagtg<br>tagtctgagc agtactcgtt gctgccgcgc gcgccaccag acataaatagc<br>tgacagacta acagactgtt cctttccatg ggtcttttct gcagtcaccg<br>tcgtcgacac gtgtgatcag atatcgcggc cgctctagac caccatggga<br>tggtcatgta tcatcctttt tctagtagca actgcaaccg gtgtacattc<br>ccaggtgcag ctggtgcagc tgcacgagtc gggcccagga ctggtgaagc<br>cttcggagac cctgtcctc acctgcgctg tctctggtgg ctctatcagc<br>agtagctact ggagctggat ccgccaggcc cagggaaggg gactggagtg<br>gattgggtat gtctatgta gtggtcgtga caccaacgac aacccctccc<br>tcaagagtcg agtcaccctg tcagtagaca cgtccaagaa ccagctctcc<br>ctgaagctga gatctgtgac cgccgcggac acggccgtgt attactgtgc<br>gagcagcggc tggcctcctg ggttggacta ctggggccag ggagtcacgg |

| SEQ ID NO | Description | Sequence |
|---|---|---|
| | | tcaccgtctc ctcagctagc accaagggcc ctagtgtgtt tcctctggcc cctagcagca gaagcacatc tgaatctaca gccgccctgg gctgcctggt gaaagattac ttccccgagc ccgtgaccgt gtcttggaat agcggctctc tgaccagcgg cgtgcacaca tttccagctg tgctgcagag cagcggcctg tattctctga gcagcgtggt gacagtgcca agcagctctc tgggcaccca gacctacgtg tgcaacgtga accacaagcc cagcaacacc aaggtggaca agcgggtgga aatcaagacc tgtggcggcg gaagcaagcc tcctacctgt cctccttgta ccagccctga actgctgggc ggacctagcg tgttcctgtt ccccccaaag cccaaggaca ccctgatgat cagcagaacc cccgaagtga cctgcgtggt ggtggatgtg tcccaggaag atcccgacgt gaagttcaat tggtacgtga acggcgccga ggtgcaccat gcccagacaa agcccagaga gacacagtac aacagcacct accgggtggt gtctgtgctg accgtgacac accaggactg gctgaacggc aaagagtaca catgcaaggt gtccaacaag gccctgcctg cccccatcca gaaaaccatc agcaaggaca agggccagcc cagagaacct caggtgtaca cactgccccc cagcagagag gaactgacca gaatcaggt gtccctgacc tgtctggtga aaggcttcta ccccagcgac atcgtggtgg aatgggagtc tagcggacag cccgagaaca cctacagac caccccctcca gtgctggata gcgacggcag ctacttcctg tacagcaagc tgaccgtgga caagagcaga tggcagcagg gcaacgtgtt cagctgctct gtgatgcacg aggccctgca caaccactac acccagaagt ctctgagcct gagccccgga aagtgatgat gaacacgtgg gatccagatc tgctgtgcct tctagttgcc agccatctgt tgtttgcccc tccccgtgc cttccttgac cctgaaggt gccactccca ctgtcctttc ctaataaaat gaggaaattg catcgcattg tctgagtagg tgtcattcta ttctgggggg tgggtgggg caggacagca aggggagga ttgggaagac aatagcaggc atgctgggga tgcggtggc tctatgggta cccaggtgct gaagaattga cccgttcct cctgggcag aaagaagcag gcacatcccc ttctctgtga cacaccctgt ccacgcccct ggttcttagt tccagcccca ctcataggac actcatagct caggagggct ccgccttcaa tcccacccgc taaagtactt ggagcggtct ctccctccct catcagccca ccaaaccaaa cctagcctcc aagagtggga agaaattaaa gcaagatagg ctattaagtg cagagggaga gaaatgcct ccaacatgtg aggaagtaat |
| | | gagagaaatc atagaatttt aaggccatga tttaaggcca tcatggcctt aatcttccgc ttcctcgctc actgactcgc tgcgctcggt cgttcggctg cggcgagcgg tatcagctca ctcaaaggcg gtaatacggt tatccacaga atcagggat aacgcaggaa agaacatgtg agcaaaaggc cagcaaaagg ccaggaaccg taaaaaggcc gcgttgctgg cgtttttcca taggctccgc cccctgacg agcatcacaa aaatcgacgc tcaagtcaga ggtggcgaaa cccgacagga ctataaagat accaggcgtt ccccctgga agctccctcg tgcgctctcc tgttccgacc ctgccgctta ccggatacct gtccgccttt ctcccttcgg aagcgtggc gctttctcat agctcacgct gtaggtatct cagttcggtg taggtcgttc gctccaagct gggctgtgtg cacgaacccc ccgttcagcc cgaccgctgc gccttatccg gtaactatcg tcttgagtcc aacccggtaa gacacgactt atcgccactg gcagcagcca ctggtaacag gattagcaga gcgaggtatg taggcggtgc tacagagttc ttgaagtggt ggcctaacta cggctacact agaagaacag tatttggtat ctgcgctctg ctgaagccag ttaccttcgg aaaaagagtt ggtagctctt gatccggcaa acaaaccacc gctggtagcg gtggtttttt tgtttgcaag cagcagatta cgcgcagaaa aaaaggatct caagaagatc ctttgatctt ttctacgggg tctgacgctc agtggaacga aaactcacgt taagggattt tggtcatgag attatcaaaa aggatcttca cctagatcct tttaaattaa aaatgaagtt ttaaatcaat ctaaagtata tatgagtaaa cttggtctga cagttaccaa tgcttaatca gtgaggcacc tatctcagcg atctgtctat ttcgttcatc catagttgcc tgactcgggg gggggggcg ctgaggtctg cctcgtgaag aaggtgttgc tgactcatac caggcctgaa tcgccccatc atccagccag aaagtgaggg agccacggtt gatgagacgt ttgttgtagg tggaccagtt ggtgattttg aacttttgct ttgccacgga acggtctgcg ttgtcgggaa gatgcgtgat ctgatccttc aactcagcaa aagttcgatt tattcaacaa agccgccgtc ccgtcaagtc agcgtaatgc tctgccagtg ttacaaccaa ttaaccaatt ctgattagaa aaactcatcg agcatcaaat gaaactgcaa tttattcata tcaggattat caataccata ttttgaaaa agccgtttct gtaatgaagg agaaaactca ccgaggcagt tccataggat ggcaagatcc tggtatcggt ctgcgattcc gactcgtcca acatcaatac aacctattaa tttcccctcg tcaaaaataa ggttatcaag tgagaaatca ccatgagtga cgactgaatc cggtgagaat ggcaaaagct tatgcatttc tttccagact tgttcaacag gccagccatt acgctcgtca tcaaaatcac tcgcatcaac caaaccgtta ttcattcgtg attgcgcctg agcgagacga atacgcgat cgctgttaaa aggacaatta caaacaggaa tcgaatgcaa ccggcgcagg aacactgcca gcgcatcaac aatattttca cctgaatcag gatattcttc taatacctgg aatgctgttt tccgggggat cgcagtggtg agtaaccatg catcatcagg agtacggata aaatgcttga tggtcggaag aggcataaat tccgtcagcc agtttagtct gaccatctca tctgtaacat cattggcaac gctacctttg ccatgtttca gaaacaactc tggcgcatcg ggcttcccat acaatcgata gattgtcgca cctgattgcc cgacattatc gcgagcccat ttatacccat ataaatcagc atccatgttg gaatttaatc gcggcctcga gcaagacgtt tcccgttgaa tatggctcat aacaccccct gtattactgt |

| SEQ ID NO | Description | Sequence |
|---|---|---|
| | | ttatgtaagc agacagtttt attgttcatg atgatatatt tttatcttgt
gcaatgtaac atcagagatt ttgagacaca acgtgccttt ccccccccc
ccattattga agcatttatc agggttattg tctcatgagc ggatacatat
ttgaatgtat ttagaaaaat aaacaaatag gggttccgcg cacatttccc
cgaaaagtgc cacctgacgt ctaagaaacc attattatca tgacattaac
ctataaaaat aggcgtatca cgaggccctt tcgtc |
| 112 | Macaque heavy chain backbone aa sequence | MGWSCIILFLVATATGVHSQVQLVQLHESGPGLVKP
SETLSLTCAVSGGSISSSYWSWIRQAPGKGLEWIGYV
YGSGRDTNDNPSLKSRVTLSVDTSKNQLSLKLRSVT
AADTAVYYCASSGWPPGLDYWGQGVTVTVSSASTK
GPSVFPLAPSSRSTSESTAALGCLVKDYFPEPVTVSW
NSGSLTSGVHTFPAVLQSSGLYSLSSVVTVPSSSLGT
QTYVCNVNHKPSNTKVDKRVEIKTCGGGSKPPTCPP
CTSPELLGGPSVFLFPPKPKDTLMISRTPEVTCVVVD
VSQEDPDVKFNWYVNGAEVHHAQTKPRETQYNSTY
RVVSVLTVTHQDWLNGKEYTCKVSNKALPAPIQKTI
SKDKGQPREPQVYTLPPSREELTKNQVSLTCLVKGF
YPSDIVVEWESSGQPENTYKTTPPVLDSDGSYFLYSK
LTVDKSRWQQGNVFSCSVMHEALHNHYTQKSLSLS
PGK |
| 113 | Macaque Kappa chain backbone nucleotide sequence | tcgcgcgttt cggtgatgac ggtgaaaacc tctgacacat gcagctccg
gagacggtca cagcttgtct gtaagcggat gccgggagca gacaagcccg
tcagggcgcg tcagcgggtg ttggcgggtg tcggggctgg cttaactatg
cggcatcaga gcagattgta ctgagagtgc accatatgcg gtgtgaaata
ccgcacagat gcgtaaggag aaaataccgc atcagattgc ctattggcca
ttgcatacgt tgtatccata tcataatatg tacatttata ttggctcatg
tccaacatta ccgccatgtt gacattgatt attgactagt tattaatagt
aatcaattac ggggtcatta gttcatagcc catatatgga gttccgcgtt
acataactta cggtaaatgg cccgcctggc tgaccgccca acgaccccg
cccattgacg tcaataatga cgtatgttcc catagtaacg ccaataggga
cttccattg acgtcaatgg gtggagtatt tacggtaaac tgcccacttg
gcagtacatc aagtgtatca tatgccaagt acgccccta ttgacgtcaa
tgacggtaaa tggcccgcct ggcattatgc ccagtacatg accttatggg
actttcctac ttggcagtac atctacgtat tagtcatcgc tattaccatg
gtgatgcggt tttggcagta catcaatggg cgtggatagc ggtttgactc
acggggattt ccaagtctcc accccattga cgtcaatggg agtttgtttt
ggcaccaaaa tcaacgggac tttccaaaat gtcgtaacaa ctccgcccca
ttgacgcaaa tgggcggtag cgtgtacgg tggaggtct atataagcag
agctcgttta gtgaaccgtc agatcgcctg gagacgccat ccacgctgtt
ttgacctcca tagaagacac cgggaccgat ccagcctcca tcggctcgca
tctctccttc acgcgccgc cgcctacct gaggccgcca tccacgccgg
ttgagtcgcg ttctgccgcc tccgccctgt ggtgcctcct gaactgcgtc
cgccgtctag gtaagtttaa agctcaggtc gagaccgggc ctttgtccgg
cgctcccttg agcctacct agactcagcc ggctctccac gctttgcctg
accctgcttg ctcaactcta gttaacggtg gagggcagtg tagtctgagc
agtacacgtt gctgccgcgc gcgccaccag acataatagc tgacagacta
acagactgtt cctttccatg ggtcttttct gcagtcaccg tcgtcgacac
gtgtgatcag atatcgcggc cgctctagac caccatggga tggtcatgta
tcatcctttt tctagtagca actgcaaccg gtgtacattc agaaattgtg
ttgacacagt ctccaggcac cctgtctttg tctccagggg aaacagccat
catctcttgt cggaccagtc agtatggttc cttagcctgg tatcaacaga
ggcccggcca ggccccagg ctcgtcatct attcgggctc tactcgggcc
gctggcatcc cagacaggtt cagcggcagt cggtggggc cagactacaa
tctcaccatc agcaacctgg agtcgggaga ttttggtgtt tattattgcc
agcagtatga atttttggc caggggacca aggtccaggt
cgacattaaa cgtacggtgg ctgcaccatc tgtcttcatc ttcccgccat
ctgaggatca ggtgaaatct ggaactgtct ctgttgtgtg cctgctgaat
aacttctatc ccagagaggc cagcgtaaag tggaaggtgg atggtgccct
caaaacgggt aactcccagg agagtgtcac agagcaggac agcaaggaca
acacctacag cctgagcagc accctgacgc tgagcagcac agagtaccag
agtcacaaag tctatgcctg cgaagtcacc catcagggc tgagctcgcc
cgtcaccaag agcttcaaca ggagagagtg ttagggatcc agatctgctg
tgccttctag ttgccagcca tctgttgttt gcccctcccc cgtgccttcc
ttgacccctg aaggtgccac tcccactgtc ctttcctaat aaaatgagga
aattgcatcg cattgtctga gtaggtgtca ttctattctg gggggtgggg
tggggcagga cagcaagggg gaggattggg aagacaatag
caggcatgct ggggatgcgg tgggctctat ggtacccag gtgctgaaga
attgacccgg ttcctcctgg gccagaaaga agcaggcaca tccccttctc
tgtgacacac cctgtccacg cccctggttc ttagttccag ccccactcat
aggacactca tagctcagga gggctccgcc ttcaatccca ccgctaaag
tacatggagc ggtctctccc tccctcatca gcccaccaaa ccaaacctag
cctccaagag tgggaagaaa ttaaagcaag ataggctatt aagtgcagag
ggagagaaaa tgcctccaac atgtgaggaa gtaatgagag aaatcataga
attttaaggc catgatttaa ggcatcatg ccttaatct tccgcttcct |

| SEQ ID NO | Description | Sequence |
|---|---|---|
| | | cgctcactga ctcgctgcgc tcggtcgttc ggctgcggcg agcggtatca<br>gctcactcaa aggcggtaat acggttatcc acagaatcag gggataacgc<br>aggaaagaac atgtgagcaa aaggccagca aaaggccagg<br>aaccgtaaaa aggccgcgtt gctggcgttt ttccataggc tccgccccc<br>tgacgagcat cacaaaaatc gacgctcaag tcagaggtgg cgaaacccga<br>caggactata aagataccag gcgtttcccc ctggaagctc cctcgtgcgc<br>tctcctgttc cgaccctgcc gcttaccgga tacctgtccg cctttctccc<br>ttcgggaagc gtggcgcttt ctcatagctc acgctgtagg<br>tatctcagtt cggtgtaggt cgttcgctcc aagctgggct gtgtgcacga<br>accccccgtt cagcccgacc gctgcgcctt atccggtaac tatcgtcttg<br>agtccaaccc ggtaagacac gacttatcgc cactggcagc agccactggt<br>aacaggatta gcagagcgag gtatgtaggc ggtgctacag agttcttgaa<br>gtggtggcct aactacggct acactagaag aacagtattt<br>ggtatctgcg ctctgctgaa gccagttacc ttcggaaaaa gagttggtag<br>ctcttgatcc ggcaaacaaa ccaccgctgg tagcggtggt ttttttgttt<br>gcaagcagca gattacgcgc agaaaaaaag gatctcaaga agatcctttg<br>atcttttcta cggggtctga cgctcagtgg aacgaaaact cacgttaagg<br>gattttggtc atgagattat caaaaggat cttcacctag atccttttaa<br>attaaaaatg aagttttaaa tcaatctaaa gtatatatga gtaaacttgg<br>tctgacagtt accaatgctt aatcagtgag gcacctatct cagcgatctg<br>tctatttcgt tcatccatag ttgcctgact cgggggggg gggcgctgag<br>gtctgcctcg tgaagaaggt gttgctgact cataccaggc ctgaatcgcc<br>ccatcatcca gccagaaagt gagggagcca cggttgatga gagctttgtt<br>gtaggtggac cagttggtga ttttgaactt tgctttgcc acggaacggt<br>ctgcgttgtc gggaagatgc gtgatctgat ccttcaactc agcaaaagtt<br>cgatttattc aacaaagccg ccgtccgtc aagtcagcgt aatgctctgc<br>cagtgttaca accaattaac caattctgat tagaaaaact catcgagcat<br>caaatgaaac tgcaatttat tcatatcagg attatcaata ccatattttt<br>gaaaaagccg tttctgtaat gaaggagaaa actcaccgag gcagttccat<br>aggatggcaa gatcctggta tcggtctgcg attccgactc<br>gtccaacatc aatacaacct attaattttcc cctcgtcaaa aataaggtta<br>tcaagtgaga atcaccatg agtgacgact gaatccggtg agaatggcaa<br>aagcttatgc atttctttcc agacttgttc aacaggccag ccattacgct<br>cgtcatcaaa atcactcgca tcaaccaaac cgttattcat tcgtgattgc<br>gcctgagcga gacgaaatac gcgatcgctg ttaaaaggac<br>aattacaaac aggaatcgaa tgcaaccggc gcaggaacac tgccagcgca<br>tcaacaatat tttcacctga atcaggatat tcttctaata cctggaatgc<br>tgttttcccg gggatcgcag tggtgagtaa ccatgcatca tcaggagtac<br>ggataaaatg cttgatggtc ggaagaggca taaattccgt cagccagttt<br>agtctgacca tctcatctgt aacatcattg gcaacgctac ctttgccatg<br>tttcagaaac aactctggcg catcgggctt cccatacaat cgatagattg<br>tcgcacctga ttgcccgaca ttatcgcgag cccatttata cccatataaa<br>tcagcatcca tgttggaatt taatcgcggc ctcgagcaag acgtttcccg<br>ttgaatatgg ctcataacac cccttgtatt actgtttatg taagcagaca<br>gttttattgt tcatgatgat atatttttat cttgtgcaat gtaacatcag agatttgag<br>acacaacgtg ctttccccc ccccccatt attgaagcat ttatcaggt<br>tattgtctca tgagcggata catattgaa tgtatttaga aaaataaaca<br>aatagggggtt ccgcgcacat ttccccgaaa agtgccacct gacgtctaag<br>aaaccattat tatcatgaca ttaacctata aaaataggcg tatcacgagg<br>ccctttcgtc |
| 114 | Macaque Kappa chain backbone aa sequence | MGWSCIILFLVATATGVHSEIVLTQSPGTLSLSPGETA<br>IISCRTSQYGSLAWYQQRPGQAPRLVIYSGSTRAAGI<br>PDRFSGSRWGPDYNLTISNLESGDFGVYYCQQYEFF<br>GQGTKVQVDIKRTVAAPSVFIFPPSEDQVKSGTVSVV<br>CLLNNFYPREASVKWKVDGALKTGNSQESVTEQDS<br>KDNTYSLSSTLTLSSTEYQSHKVYACEVTHQGLSSPV<br>TKSFNRGEC |
| 115 | Macaque Light chain backbone aa sequence | MGWSCIILFLVATATGVHSQSALTQPPSVSGSPGQSV<br>TISCTGTSSDVDGYNYVSWYQQHPGKAPKLMIYGVS<br>NRPSGVSDRFSGSKSGNTASLTISGLQAEDEADYYCC<br>SSTTSYTYIFGTGTKVTVLGQPKAAPSVTLFPPSSEEL<br>QANKATLVCLISDFYPGAVEVAWKADGSAVNAGVE<br>TTKPSKQSNNKYAASSYLSLTSDQWKSHKSYSCQVT<br>HEGSTVEKTVAPAECS |
| 116 | Macaque Heavy chain backbone nucleotide sequence-H02 | tcgcgcgttt cggtgatgac ggtgaaaacc tctgacacat gcagctcccg<br>gagacggtca cagcttgtct gtaagcggat gccgggagca acaagcccg<br>tcagggcgcg tcagcggggt tggcgggtg tcgggctgg cttaactatg<br>cggcatcaga gcagattgta ctgagagtgc accatatgcg gtgtgaaata<br>ccgcacagat gcgtaaggag aaaataccgc atcagattgg<br>ctattggcca ttgcatacgt tgtatccata tcataatatg tacatttata<br>ttggctcatg tccaacatta ccgccatgtt gacattgatt attgactagt<br>tattaatagt aatcaattac ggggtcatta gttcatagcc catatatgga<br>gttccgcgtt acataactta cggtaaatgg cccgcctggc tgaccgccca |

| SEQ ID NO | Description | Sequence |
|---|---|---|
| | | acgaccccccg cccattgacg tcaataatga cgtatgttcc |
| | | catagtaacg ccaataggga cttttccattg acgtcaatgg gtggagtatt |
| | | tacggtaaac tgcccacttg gcagtacatc aagtgtatca tatgccaagt |
| | | acgcccccta ttgacgtcaa tgacggtaaa tggcccgcct ggcattatgc |
| | | ccagtacatg acctatggg actttcctac ttggcagtac atctacgtat |
| | | tagtcatcgc tattaccatg gtgatgcggt tttggcagta catcaatggg |
| | | cgtggatagc ggtttgactc acggggattt ccaagtctcc accccattga |
| | | cgtcaatggg agtttgtttt ggcaccaaaa tcaacgggac ttttccaaaat |
| | | gtcgtaacaa ctccgcccca ttgacgcaaa tgggcggtag cgtgtacgg |
| | | tgggaggtct atataagcag agctcgttta gtgaaccgtc agatcgcctg |
| | | gagacgccat ccacgctgtt ttgacctcca tagaagacac cgggaccgat |
| | | ccagcctcca tcggctcgca tctctccttc acgcgcccgc |
| | | cgccctacct gaggccgcca tccacgccgg ttgagtcgcg ttctgccgcc |
| | | tcccgcctgt ggtgcctcct gaactgcgtc cgccgtctag gtaagtttaa |
| | | agctcaggtc gagaccgggc ctttgtccgg cgctcccttg gagcctacct |
| | | agactcagcc ggctctccac gctttgcctg accctgcttg ctcaactcta |
| | | gttaacggtg gagggcagtg tagtctgagc agtactcgtt gctgccgcgc |
| | | gcgccaccag acataatagc tgacagacta acagactgtt ccttttccatg |
| | | ggtcttttct gcagtcaccg tcgtcgacac gtgtgatcag atatcgcggc |
| | | cgctctagac caccatggga tggtcatgta tcatcctttt tctagtagca |
| | | actgcaaccg gtgtacattc caactgcag ttgcaggagt cgggcccagg |
| | | agtggtgaag ccttcggaga ccctgtccct cacctgcact atctctggtg |
| | | gctccttcag tacttactac tggacctgga ttcgccagcc cccagggaag |
| | | ggactggagt gggttgggta tatcggtaat ggtggtcgta gcctcaacta |
| | | caaccctcc ctcaagagtc gcatcaccct gtcagtagac gcgtccaaga |
| | | accagttctc cctgaaggtg acctctgtga ccgccgcgga cacggccgtc |
| | | tattactgtg ggagagccag gggactccgc ggaaactggt tcgatgtctg |
| | | gggccgggga gtcctggtca ccgtctcctc agctagcacc aagggcccta |
| | | gtgtgtttcc tctggcccct agcagcagaa gcacatctga atctacagcc |
| | | gccctgggct gcctggtgaa agattacttc cccgagcccg tgaccgtgtc |
| | | ttggaatagc ggctctctga ccagcggcgt gcacacattt ccagctgtgc |
| | | tgcagagcag cggcctgtat tctctgagca gcgtggtgac agtgccaagc |
| | | agctctctgg gcacccagac ctacgtgtgc aacgtgaacc acaagcccag |
| | | caacaccaag gtggacaagc gggtggaaat caagacctgt ggcggcggaa |
| | | gcaagcctcc tacctgtcct ccttgtacca gccctgaact gctgggcgga |
| | | cctagcgtgt tcctgttccc cccaaagccc aaggacaccc tgatgatcag |
| | | cagaaccccc gaagtgacct gcgtggtggt ggatgtgtcc caggaagatc |
| | | ccgacgtgaa gttcaattgg tacgtgaacg gcgccgaggt gcaccatgcc |
| | | cagacaaagc ccagagagac acagtacaac agcacctacc gggtggtgtc |
| | | tgtgctgacc gtgacacacc aggactggct gaacggcaaa gagtacacat |
| | | gcaaggtgtc caacaaggcc ctgcctgccc catccagaa aaccatcagc |
| | | aaggacaagg ccagcccag agaacctcag gtgtacacac tgcccccag |
| | | cagagaggaa ctgaccaaga tcaggtgtc cctgacctgt ctggtgaaag |
| | | gcttctaccc cagcgacatc gtggtggaat gggagtctag cggacagccc |
| | | gagaacacct acaagaccac ccctccagtg ctggatagcg acggcagcta |
| | | cttcctgtac agcaagctga ccgtggacaa gagcagatgg cagcagggca |
| | | acgtgttcag ctgctctgtg atgcacgagg ccctgcacaa ccactacacc |
| | | cagaagtctc tgagcctgag ccccggaaag tgatgatgaa cacgtgggat |
| | | ccagatctgc tgtgccttct agttgccagc catctgttgt ttgcccctcc |
| | | cccgtgcctt ccttgaccct ggaaggtgcc actcccactg tcctttccta |
| | | ataaaatgag gaaattgcat cgcattgtct gagtaggtgt cattctattc |
| | | tggggggtgg ggtggggcag gacagcaagg gggaggattg ggaagacaat |
| | | agcaggcatg ctggggatgc ggtgggctct atgggtaccc aggtgctgaa |
| | | gaattgaccc ggttcctcct gggccagaaa gaagcaggca catccccttc |
| | | tctgtgacac accctgtcca cgcccctggt tcttagttcc agccccactc |
| | | ataggacact catagctcag gagggctccg ccttcaatcc cacccgctaa |
| | | agtacttgga gcggtctctc cctccctcat cagcccacca aaccaaacct |
| | | agcctccaag agtgggaaga aattaaagca agataggcta ttaagtgcag |
| | | agggagagaa aatgcctcca acatgtgagg aagtaatgag agaaatcata |
| | | gaatttaag gccatgattt aaggccatca tggccttaat cttccgcttc |
| | | ctcgctcact gactcgctgc gctcggtcgt tcggctgcgg cgagcggtat |
| | | cagctcactc aaaggcggta atacggttat ccacagaatc aggggataac |
| | | gcaggaaaga acatgtgagc aaaaggccag caaaaggcca ggaaccgtaa |
| | | aaaggccgcg ttgctggcgt ttttccatag gctccgcccc cctgacgagc |
| | | atcacaaaaa tcgacgctca agtcagaggt ggcgaaaccc gacaggacta |
| | | taaagatacc aggcgtttcc ccctggaagc tccctcgtgc gctctcctgt |
| | | tccgaccctg ccgcttaccg gatacctgtc cgcctttctc ccttcgggaa |
| | | gcgtggcgct ttctcatagc tcacgctgta ggtatctcag ttcggtgtag |
| | | gtcgttcgct ccaagctggg ctgtgtgcac gaaccccccg ttcagcccga |
| | | ccgctgcgcc ttatccggta actatcgtct tgagtccaac ccggtaagac |
| | | acgacttatc gccactggca gcagccactg gtaacaggat tagcagagcg |
| | | aggtatgtag cggtgctac agagttcttg aagtggtggc ctaactacgg |
| | | ctacactaga agaacagtat ttggtatctg cgctctgctg aagccagtta |
| | | ccttcggaaa aagagttggt agctcttgat ccggcaaaca accaccgct |
| | | ggtagcggtg gtttttttgt ttgcaagcag cagattacgc gcagaaaaaa |
| | | aggatctcaa gaagatcctt tgatctttc tacggggtct gacgctcagt |

| SEQ ID NO | Description | Sequence |
|---|---|---|
| | | ggaacgaaaa ctcacgttaa gggatttttgg tcatgagatt atcaaaaagg |
| | | atcttcacct agatcctttt aaattaaaaa tgaagtttta aatcaatcta |
| | | aagtatatat gagtaaactt ggtctgacag ttaccaatgc ttaatcagtg |
| | | aggcacctat ctcagcgatc tgtctatttc gttcatccat agttgcctga |
| | | ctcggggggg ggggcgctg aggtctgcct cgtgaagaag gtgttgctga |
| | | ctcataccag gcctgaatcg ccccatcatc cagccagaaa gtgagggagc |
| | | cacgttgat gagagctttg ttgtaggtgg accagttggt gattttgaac |
| | | ttttgctttg ccacggaacg gtctgcgttg tcgggaagat gcgtgatctg |
| | | atccttcaac tcagcaaaag ttcgatttat tcaacaaagc cgccgtcccg |
| | | tcaagtcagc gtaatgctct gccagtgtta caaccaatta accaattctg |
| | | attagaaaaa ctcatcgagc atcaaatgaa actgcattt attcatatca |
| | | ggattatcaa taccatattt ttgaaaaagc cgtttctgta atgaaggaga |
| | | aaactcaccg aggcagttcc ataggatggc aagatcctgg |
| | | tatcggtctg cgattccgac tcgtccaaca tcaatacaac ctattaattt |
| | | cccctcgtca aaaataaggt tatcaagtga gaaatcacca tgagtgacga |
| | | ctgaatccgg tgagaatggc aaaagcttat gcatttcttt ccagacttgt |
| | | tcaacaggcc agccattacg ctcgtcatca aaatcactcg catcaaccaa |
| | | accgttattc attcgtgatt gcgcctgagc gagacgaaat acgcgatcgc |
| | | tgttaaaagg acaattacaa acaggaatcg aatgcaaccg gcgcaggaac |
| | | actgccagcg catcaacaat attttcacct gaatcaggat attcttctaa |
| | | tacctggaat gctgttttcc cggggatcgc agtggtgagt aaccatgcat |
| | | catcaggagt acggataaaa tgcttgatgg tcggaagagg cataaattcc |
| | | gtcagccagt ttagtctgac catctcatct gtaacatcat tggcaacgct |
| | | acctttgcca tgtttcagaa acaactctgg cgcatcgggc |
| | | ttcccataca atcgatagat tgtcgcacct gattgcccga cattatcgcg |
| | | agcccattta tacccatata aatcagcatc catgttgaa tttaatcgcg |
| | | gcctcgagca agacgtttcc cgttgaatat ggctcataac acccttgta |
| | | ttactgttta tgtaagcaga cagttttatt gttcatgatg atatattttt atcttgtgca |
| | | atgtaacatc agagattttg agacacaacg tggctttccc ccccccccca |
| | | ttattgaagc atttatcagg gttattgtct catgagcgga tacatatttg |
| | | aatgtattta gaaaaataaa caaatagggg ttccgcgcac atttccccga |
| | | aaagtgccac ctgacgtcta agaaaccatt attatcatga cattaaccta |
| | | taaaaatagg cgtatcacga ggcccttttcg tc |
| 117 | Macaque Heavy chain backbone aa sequence-H02 | MGWSCIILFLVATATGVHSQLQLQESGPGVVKPSET LSLTCTISGGSFSTYYWTWIRQPPGKGLEWVGYIGN GGRSLNYNPSLKSRITLSVDASKNQFSLKVTSVTAAD TAVYYCGRARGLRGNWFDVWGPGVLVTVSSASTK GPSVFPLAPSSRSTSESTAALGCLVKDYFPEPVTVSW NSGSLTSGVHTFPAVLQSSGLYSLSSVVTVPSSSLGT QTYVCNVNHKPSNTKVDKRVEIKTCGGGSKPPTCPP CTSPELLGGPSVFLFPPKPKDTLMISRTPEVTCVVVD VSQEDPDVKFNWYVNGAEVHHAQTKPRETQYNSTY RVVSVLTVTHQDWLNGKEYTCKVSNKALPAPIQKTI SKDKGQPREPQVYTLPPSREELTKNQVSLTCLVKGF YPSDIVVEWESSGQPENTYKTTPPVLDSDGSYFLYSK LTVDKSRWQQGNVFSCSVMHEALHNHYTQKSLSLS PGK |
| 118 | Macaque Light chain backbone nucleotide sequence-H02 | tcgcgcgttt cggtgatgac ggtgaaaacc tctgacacat gcagctcccg gagacggtca cagcttgtct gtaagcggat gccgggagca gacaagcccg tcagggcgcg tcagcgggtg ttggcgggtg tcggggctgg cttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgga gttccgcgtt acataactta cggtaaatgg cccgcctggc tgaccgccca acgacccccg cccattgacg tcaataatga cgtatgttcc catagtaacg ccaatagga ctttccattg acgtcaatgg gtggagtatt tacggtaaac tgcccacttg gcagtacatc aagtgtatca tatgccaagt acgccccta ttgacgtcaa tgacggtaaa tggcccgcct ggcattatgc ccagtacatg accttatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agctcgttta gtgaaccgtc agatcgcctg gagacgccat ccacgctgtt tgacctccca tagaagacac cgggaccgat ccagcctcca tcggctcgca tctctccttc acgcgcccgc cgccctacct gaggccgcca tccacgccgg ttgagtgcg ttctgccgc tcccgcctgt ggtgcctcct gaactgcgtc cgccgtctag gtaagtttaa agctcaggtc gagaccgggc ctttgtccgg cgctcccttg gagcctacct agactcagcc ggctctccac gctttgcctg acctgcttct ctcaactcta gttaacggtg gagggcagtg tagtctgagc agtcacgtt gctgccgcgc gcgccaccag acataatagc tgacagacta acagactgtt cctttccatg ggtcttttct gcagtcaccg |

| SEQ ID NO | Description | Sequence |
|---|---|---|
| | | tcgtcgacac gtgtgatcag atatcgcggc cgctctagac caccatggga |
| | | tggtcatgta tcatccttt tctagtagca actgcaaccg gtgtacattc |
| | | ccaggctgcc ctgactcagc ctccctctgt gtctgggtct cctggacagt |
| | | cggtcaccat ctcctgcact ggaaccagca gtgacatcgg tggttataac |
| | | tatgtctcct ggtaccaaca cacccaggc aaagcccca aagtcatgat |
| | | ttatgaggtc agtaagcggc cctcagggt ctctgatcgc ttctctggtt |
| | | ccaaatctgg caacatagcc tccctgacca tctctgggct ccaggctgag |
| | | gacgaggctg attattactg cagctcatat gcaggcagca cactttctt |
| | | attcggagga gggacccggc tgacagtact aggtcagccc aaggctgccc |
| | | cctcggtcac tctcttcccg ccctcctctg aggagcttca agccaacaag |
| | | gccacactag tgtgtctgat cagtgacttc tacccgggag ccgtggaagt |
| | | ggcctggaag gcagatggca gcgctgtcaa cgcgggagtg gagaccacca |
| | | aaccctccaa acagagcaac aacaagtacg cggccagcag ctacctgagc |
| | | ctgacgtccg accagtggaa gtcccacaag agctacgct gccaggtcac |
| | | gcacgaaggg agcaccgtgg agaagacagt ggccctgca gaatgttcat |
| | | agggatccaa atctgctgtg ccttctagtt gccagccatc tgttgttttgc |
| | | ccctcccccg tgccttcctt gaccctggaa ggtgccactc ccactgtcct |
| | | ttcctaataa aatgaggaaa ttgcatcgca ttgtctgagt aggtgtcatt |
| | | ctattctggg gggtggggtg gggcaggaca gcaaggggga |
| | | ggattgggaa gacaatagca ggcatgctgg ggatgcggtg ggctctatgg |
| | | gtacccaggt gctgaagaat tgacccggtt cctcctgggc cagaaagaag |
| | | caggcacatc cccttctctg tgacacaccc tgtccacgcc cctggttctt |
| | | agttccagcc ccactcatag gacactccata gctcaggagg gctccgcctt |
| | | caatcccacc cgctaaagta catggagcgg tctctccctc cctcatcagc |
| | | ccaccaaacc aaacctagcc tccaagagtg ggaagaaatt aaagcaagat |
| | | aggctattaa gtgcagaggg agagaaaatg cctccaacat gtgaggaagt |
| | | aatgagagaa atcatagaat tttaaggcca tgatttaagg ccatcatggc |
| | | cttaatcttc cgcttcctcg ctcactgact cgctgcgctc ggtcgttcgg |
| | | ctgcggcgag cggtatcagc tcactcaaag gcggtaatac ggttatccac |
| | | agaatcaggg gataacgcag gaaagaacat gtgagcaaaa ggccagcaaa |
| | | aggccaggaa ccgtaaaaag gccgcgttgc tggcgttttt ccataggctc |
| | | cgcccccctg acgagcatca caaaatcga cgctcaagtc agaggtggcg |
| | | aaacccgaca ggactataaa gataccaggc gtttccccct ggaagctccc |
| | | tcgtgcgctc tcctgttccg accctgccgc ttaccggata cctgtccgcc |
| | | tttctccctt cgggaagcgt ggcgctttct catagctcac gctgtaggta |
| | | tctcagttcg gtgtaggtcg ttcgctccaa gctgggctgt gtgcacgaac |
| | | cccccgttca gcccgaccgc tgcgccttat ccggtaacta tcgtcttgag |
| | | tccaacccgg taagacacga cttatcgcca ctggcagcag ccactggtaa |
| | | caggattagc agagcgaggt atgtaggcgg tgctacagag ttcttgaagt |
| | | ggtggcctaa ctacggctac actagaagaa cagtatttgg tatctgcgct |
| | | ctgctgaagc cagttacctt cggaaaaaga gttggtagct cttgatccgg |
| | | caaacaaacc accgctggta gcggtggttt ttttgtttgc aagcagcaga |
| | | ttacgcgcag aaaaaaagga tctcaagaag atcctttgat cttttctacg |
| | | gggtctgacg ctcagtggaa cgaaaactca cgttaaggga ttttggtcat |
| | | gagattatca aaaaggatct tcacctagat ccttttaaat taaaaatgaa |
| | | gttttaaatc aatctaaagt atatatgagt aaacttggtc tgacagttac |
| | | caatgcttaa tcagtgaggc acctatctca gcgatctgtc tatttcgttc |
| | | atccatagtt gcctgactcg ggggggggg gcgctgaggt |
| | | ctgcctcgtg aagaaggtgt tgctgactca taccaggcct gaatcgcccc |
| | | atcatccagc cagaaagtga gggagccacg gttgatgaga gctttgttgt |
| | | aggtggacca gttggtgatt ttgaactttt gctttgccac ggaacggtct |
| | | gcgttgtcgg gaagatgcgt gatctgatcc ttcaactcag caaagttcg |
| | | atttattcaa caaagccgcc gtcccgtcaa gtcagcgtaa tgctctgcca |
| | | gtgttacaac caattaacca attctgatta gaaaaactca tcgagcatca |
| | | aatgaaactg caatttattc atatcaggat tatcaatacc atatttttga |
| | | aaaagccgtt tctgtaatga aggagaaaac tcaccgaggc agttccatag |
| | | gatggcaaga tcctggtatc ggtctgcgat tccgactcgt ccaacatcaa |
| | | tacaacctat taatttcccc tcgtcaaaaa taaggttatc aagtgagaaa |
| | | tcaccatgag tgacgactga atccggtgag aatggcaaaa |
| | | gcttatgcat ttctttccag acttgttcaa caggccagcc attacgctcg |
| | | tcatcaaaat cactcgcatc aaccaaaccg ttattcattc gtgattgcgc |
| | | ctgagcgaga cgaaatacgc gatcgctgtt aaaaggacaa ttacaaacag |
| | | gaatcgaatg caaccggcgc aggaacactg ccagcgcatc aacaatattt |
| | | tcacctgaat caggatattc ttctaatacc tggaatgctg ttttcccggg |
| | | gatcgcagtg gtgagtaacc atgcatcatc aggagtacgg ataaaatgct |
| | | tgatggtcgg aagaggcata aattccgtca gccagtttag tctgaccatc |
| | | tcatctgtaa catcattggc aacgctacct ttgccatgtt tcagaaacaa |
| | | ctctggcgca tcgggcttcc catacaatcg atagattgtc gcacctgatt |
| | | gcccgacatt atcgcgagcc catttatacc catataaatc agcatccatg |
| | | ttggaattta atcgcggcct cgagcaagac gtttcccgtt gaatatgct |
| | | cataacaccc cttgtattac tgtttatgta agcagacagt tttattgttc |
| | | atgatgatat ttttatct tgtgcaatgt aacatcagag attttgagac |
| | | acaacgtggc tttcccccc ccccattat tgaagcattt atcagggtta |
| | | ttgtctcatg agcggataca tatttgaatg tatttagaaa aataaacaaa |
| | | tagggggttcc gcgcacattt ccccgaaaag tgccacctga cgtctaagaa |

| SEQ ID NO | Description | Sequence |
|---|---|---|
| | | accattatta tcatgacatt aacctataaa aataggcgta tcacgaggcc ctttcgtc |
| 119 | Macaque Light chain backbone aa sequence-H02 | MGWSCIILFLVATATGVHSQAALTQPPSVSGSPGQSV TISCTGTSSDIGGYNYVSWYQQHPGKAPKVMIYEVS KRPSGVSDRFSGSKSGNIASLTISGLQAEDEADYYCS SYAGSNTFLFGGGTRLTVLGQPKAAPSVTLFPPSSEE LQANKATLVCLISDFYPGAVEVAWKADGSAVNAGV ETTKPSKQSNNKYAASSYLSLTSDQWKSHKSYSCQV THEGSTVEKTVAPAECS |
| 120 | Humanized H02 heavy chain backbone nucleotide sequence | tcgcgcgttt cggtgatgac ggtgaaaacc tctgacacat gcagctcccg gagacggtca cagcttgtct gtaagcggat gccgggagca gacaagcccg tcaggcgcg tcagcgggtg ttggcgggtg tcgggctgg cttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgcg gttccgcgtt acataactta cggtaaatgg cccgcctggc tgaccgccca acgaccccg cccattgacg tcaatgatga cgtatgttcc catagtaacg ccaatagggac ctttccattg acgtcaatgg gtggagtatt tacggtaaac tgcccacttg gcagtacatc aagtgtatca tatgccaagt acgcccccta ttgacgtcaa tgacggtaaa tggcccgcct ggcattatgc ccagtacatg accttatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agctcgttta gtgaaccgtc agatcgcctg gagacgccat ccacgctgtt tgacctcca tagaagacac cgggaccgat ccagcctcca tcggctcgca tctctccttc acgcgcccgc cgcccaccct gaggccgcca tcccacgccg ttgagtcgcg ttctgccgcc tccgcctgt ggtgcctcct gaactgcgtc cgccgtctag gtaagtttaa agctcaggtc gagaccgggc ctttgtccgg cgctcccttg gagcctacct agactcagcc ggctctccac gctttgcctg accctgcttg ctcaactcta gttaacggtg gagggcagtg tagtctgagc agtactcgtt gctgccgcgc gcgccaccag acataatagc tgacagacta acagactgtt cctttccatg ggtcttttct gcagtcaccg tcgtcgacac gtgtgatcag atatcgcggc cgctctagac caccatggga tggtcatgta tcatcctttt tctagtagca actgcaaccg gtgtacattc ccaactgcaa ttgcaggagt cgggcccagg agtggtgaag ccttcggaga ccctgtccct cacctgcact atctctggtg gctccttcag tacttactac tggacctgga ttcgccagcc cccagggaag ggactggagt gggttgggta tatcggtaat ggtggtcgta gcctcaacta caaccccctcc ctcaagagtc gcatcaccct gtcagtagac gcgtccaaga accagttctc cctgaaggtg acctctgtga ccgccgcgga cacggccgtc tattactgtg ggagagccaa gggactccgc ggaaactggt tcgatgtctg ggcccgggga gtcctggtca ccgtctcctc agctagcacc aagggcccat cggtcttccc cctggcaccc tcctccaaga gcacctctgg gggcacagcg gccctgggct gcctggtcaa ggactacttc cccgaaccgg tgacggtgtc gtggaactca ggcgccctga ccagcggcgt gcacaccttc ccggctgtcc tacagtcctc aggactctac tccctcagca gcgtggtgac cgtgccctcc agcagcttgg gcacccagac ctacatctgc aacgtgaatc acaagcccag caacaccaag gtggacaaga agttgagcc caaatcttgt gacaaaactc acacatgccc accgtgccca gcacctgaac tcctgggggg accgtcagtc ttcctcttcc ccccaaaacc caaggacacc ctcatgatct cccggacccc tgaggtcaca tgcgtggtgg tggacgtgag ccacgaagac cctgaggtca agttcaactg gtacgtggac ggcgtggagg tgcataatgc caagacaaag ccgcgggagg agcagtacaa cagcacgtac cgtgtggtca gcgtcctcac cgtcctgcac caggactggc tgaatggcaa ggagtacaag tgcaaggtct ccaacaaagc cctcccagcc cccatcgaga aaaccatctc caaagccaaa gggcagcccc gagaaccaca ggtgtacacc ctgccccat cccgggatga gctgaccaag aaccaggtca gcctgacctg cctggtcaaa ggcttctatc ccagcgacat cgccgtggag tgggagagca atgggcagcc ggagaacaac tacaagacca cgcctcccgt gctggactcc gacggctcct tcttcctcta cagcaagctc accgtggaca agagcaggtg gcagcagggg aacgtcttct catgctccgt gatgcatgag gctctgcaca accactacac gcagaagagc ctctccctgt ctccgggtaa atgatgagga tccagatctg ctgtgccttc tagttgccag ccatctgttg tttgccctc ccccgtgcct ccttgaccc tggaaggtgc cactcccact gtccttttcct aataaaatga ggaaattgca tcgcattgtc tgagtaggtg tcattctatt ctggggggtg gggtgggggca ggacagcaag gggaggatt gggaagacaa tagcaggcat gctggggatg cggtgggctc tatgggtacc caggtgctga agaattgacc cggttcctcc tgggccagaa agaagcaggc acatcccctt ctctgtgaca caccctgtcc acgccctggt tcttagttc cagccccact cataggacac tcatagctca ggagggctcc gccttcaatc ccaccgcta agtactggg agcggtctct cctccctca tcagcccacc |

| SEQ ID NO | Description | Sequence |
|---|---|---|
| | | aaaccaaacc tagcctccaa gagtgggaag aaattaaagc aagataggct |
| | | attaagtgca gagggagaga aaatgcctcc aacatgtgag gaagtaatga |
| | | gagaaatcat agaattttaa ggccatgatt taaggccatc atggccttaa |
| | | tcttccgctt cctcgctcac tgactcgctg cgctcggtcg ttcggctgcg |
| | | gcgagcggta tcagctcact caaaggcggt aatacggtta tccacagaat |
| | | caggggataa cgcaggaaag aacatgtgag caaaaggcca gcaaaaggcc |
| | | aggaaccgta aaaaggccgc gttgctggcg ttttttccata ggctccgccc |
| | | ccctgacgag catcacaaaa atcgacgctc aagtcagagg tggcgaaacc |
| | | cgacaggact ataaagatac caggcgtttc ccctggaag ctccctcgtg |
| | | cgctctcctg ttccgaccct gccgcttacc ggatacctgt ccgcctttct |
| | | cccttcggga agcgtggcgc tttctcatag ctcacgctgt aggtatctca |
| | | gttcggtgta ggtcgttcgc tccaagctgg gctgtgtgca cgaaccccc |
| | | gttcagcccg accgctgcgc cttatccggt aactatcgtc ttgagtccaa |
| | | cccggtaaga cacgacttat cgccactggc agcagccact ggtaacagga |
| | | ttagcagagc gaggtatgta ggcggtgcta cagagttctt gaagtggtgg |
| | | cctaactacg gctacactag aagaacagta tttggtatct gcgctctgct |
| | | gaagccagtt accttcggaa aaagagttgg tagctcttga tccggcaaac |
| | | aaaccaccgc tggtagcggt ggtttttttg tttgcaagca gcagattacg |
| | | cgcagaaaaa aaggatctca agaagatcct ttgatctttt ctacggggtc |
| | | tgacgctcag tggaacgaaa actcacgtta agggattttg gtcatgagat |
| | | tatcaaaaag gatcttcacc tagatccttt taaattaaaa atgaagtttt |
| | | aaatcaatct aaagtatata tgagtaaact tggtctgaca gttaccaatg |
| | | cttaatcagt gaggcaccta tctcagcgat ctgtctattt cgttcatcca |
| | | tagttgcctg actcgggggg ggggggcgct gaggtctgcc tcgtgaagaa |
| | | ggtgttgctg actcatacca ggcctgaatc gccccatcat ccagccagaa |
| | | agtgagggag ccacggttga tgagagcttt gttgtaggtg gaccagttgg |
| | | tgattttgaa cttttgcttt gccacggaac ggtctgcgtt gtcgggaaga |
| | | tgcgtgatct gatccttcaa ctcagcaaaa gttcgattta ttcaacaaag |
| | | ccgccgtccc gtcaagtcag cgtaatgctc tgccagtgtt acaaccaatt |
| | | aaccaattct gattagaaaa actcatcgag catcaaatga aactgcaatt |
| | | tattcatatc aggattatca ataccatatt tttgaaaaag ccgtttctgt |
| | | aatgaaggag aaaactcacc gaggcagttc cataggatgg caagatcctg |
| | | gtatcggtct gcgattccga ctcgtccaac atcaatacaa cctattaatt |
| | | tcccctcgtc aaaaataagg ttatcaagtg agaaatcacc atgagtgacg |
| | | actgaatccg gtgagaatgg caaaagctta tgcatttctt ccagacttg |
| | | ttcaacaggc cagccattac gctcgtcatc aaaatcactc gcatcaacca |
| | | aaccgttatt cattcgtgat tgcgcctgag cgagacgaaa tacgcgatcg |
| | | ctgttaaaag gacaattaca acaggaatc gaatgcaacc ggcgcaggaa |
| | | cactgccagc gcatcaacaa tattttcacc tgaatcagga tattcttcta |
| | | atacctggaa tgctgttttc ccggggatcg cagtggtgag taaccatgca |
| | | tcatcaggag tacggataaa atgcttgatg gtcggaagag gcataaattc |
| | | cgtcagccag tttagtctga ccatctcatc tgtaacatca ttggcaacgc |
| | | tacctttgcc atgtttcaga acaactctg gcgcatcggg cttcccatac |
| | | aatcgataga ttgtcgcacc tgattgcccg acattatcgc gagcccattt |
| | | atacccatat aaatcagcat ccatgttgga atttaatcgc ggcctcgagc |
| | | aagacgtttc ccgttgaata tggctcataa caccccttgt attactgttt |
| | | atgtaagcag acagtttat tgttcatgat gatatatttt tatcttgtgc |
| | | aatgtaacat cagagatttt gagacacaac gtggctttcc ccccccccc |
| | | attattgaag catttatcag ggttattgtc tcatgagcgg atacatattt |
| | | gaatgtattt agaaaaataa acaataggg gttccgcgca catttcccg |
| | | aaaagtgcca cctgacgtct aagaaaccat tattatcatg acattaacct |
| | | ataaaaatag gcgtatcacg aggccctttc gtc |
| 121 | Humanized H02 heavy chain backbone aa sequence | MGWSCIILFLVATATGVHSQLQLQESGPGVVKPSET LSLTCTISGGSFSTYYWTWIRQPPGKGLEWVGYIGN GGRSLNYNPSLKSRITLSVDASKNQFSLKVTSVTAAD TAVYYCGRARGLRGNWFDVWGPGVLVTVSSASTK GPSVFPLAPSSKSTSGGTAALGCLVKDYFPEPVTVSW NSGALTSGVHTFPAVLQSSGLYSLSSVVTVPSSSLGT QTYICNVNHKPSNTKVDKKVEPKSCDKTHTCPPCPA PELLGGPSVFLFPPKPKDTLMISRTPEVTCVVVDVSH EDPEVKFNWYVDGVEVHNAKTKPREEQYNSTYRVV SVLTVLHQDWLNGKEYKCKVSNKALPAPIEKTISKA KGQPREPQVYTLPPSRDELTKNQVSLTCLVKGFYPS DIAVEWESNGQPENNYKTTPPVLDSDGSFFLYSKLT VDKSRWQQGNVFSCSVMHEALHNHYTQKSLSLSPG K |
| 122 | Humanized H02 light chain backbone aa sequence | tcgcgcgttt cggtgatgac ggtgaaaacc tctgacacat gcagctcccg gagacggtca cagcttgtct gtaagcggat gccgggagca gacaagcccg tcagggcgcg tcagcgggtg ttggcgggtg tcttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgga gttccgcgtt |

| SEQ ID NO | Description | Sequence |
|---|---|---|
| | | acataactta cggtaaatgg cccgcctggc tgaccgccca acgaccccg |
| | | cccattgacg tcaataatga cgtatgttcc catagtaacg ccaataggga |
| | | ctttccattg acgtcaatgg gtggagtatt tacggtaaac tgcccacttg |
| | | gcagtacatc aagtgtatca tatgccaagt acgcccccta ttgacgtcaa |
| | | tgacggtaaa tggcccgcct ggcattatgc ccagtacatg accttatggg |
| | | actttcctac ttggcagtac atctacgtat tagtcatcgc tattaccatg |
| | | gtgatgcggt tttggcagta catcaatggg cgtggatagc ggtttgactc |
| | | acggggattt ccaagtctcc accccattga cgtcaatggg agtttgtttt |
| | | ggcaccaaaa tcaacgggac tttccaaaat gtcgtaacaa ctccgcccca |
| | | ttgacgcaaa tgggcggtag gcgtgtacgg tgggaggtct atataagcag |
| | | agctcgttta gtgaaccgtc agatcgcctg gagacgccat ccacgctgtt |
| | | ttgacctcca tagaagacac cgggaccgat ccagcctcca tcggctcgca |
| | | tctctccttc acgcgcccgc cgcccacct gaggccgcca tccacgccgg |
| | | ttgagtcgcg ttctgccgcc tcccgcctgt ggtgcctcct gaactgcgtc |
| | | cgccgtctag gtaagtttaa agctcaggtc gagacgggc ctttgtccgg |
| | | cgctcccttg agcctacct agactcagcc ggctctccac gctttgcctg |
| | | accctgcttg ctcaactcta gttaacggtg gagggcagtg tagtctgagc |
| | | agtactcgtt gctgccgcgc gcgccaccag acataatagc tgacagacta |
| | | acagactgtt cctttccatg ggtcttttct gcagtcaccg tcgtcgacac |
| | | gtgtgatcag atatcgcggc cgctctagac caccatggga tggtcatgta |
| | | tcatcctttt tctagtagca actgcaaccg gtgtacattc ccaggctgcc |
| | | ctgactcagc ctccctctgt gtctgggtct cctggacagt cggtcaccat |
| | | ctcctgcact ggaaccagca gtgacatcgg tggttataac tatgtctcct |
| | | ggtaccaaca cacccaggc aaagccccca aagtcatgat ttatgaggtc |
| | | agtaagcggc cctcagggt ctctgatcgc ttctctggtt ccaaatctgg |
| | | caacatagcc tccctgacca tctctgggct ccaggctgag gacgaggctg |
| | | attattactg cagctcatat gcaggcagca cactttctt attcggagga |
| | | gggacccggc tgacagtCct aggtcagccc aaggctgccc cctcggtcac |
| | | tctgttcccg ccctcctctg aggagcttca agccaacaag gccacactgg |
| | | tgtgtctcat aagtgacttc tacccgggag ccgtgacagt ggcctggaag |
| | | gcagatagca gccccgtcaa ggcgggagtg gagaccacca cccctccaa |
| | | acaaagcaac aacaagtacg cggccagcag ctatctgagc ctgacgcctg |
| | | agcagtggaa gtccacagaa agctacagct gccaggtcac gcatgaaggg |
| | | agcaccgtgg agaagacagt ggcccctaca gaatgttcat gaggatccag |
| | | atctgctgtg ccttctagtt gccagccatc tgttgtttgc ccctcccccg |
| | | tgccttcctt gacccctggaa ggtgccactc ccactgtcct tcctaataa |
| | | aatgaggaaa ttgcatcgca ttgtctgagt aggtgtcatt ctattctggg |
| | | gggtggggtg gggcaggaca gcaaggggga ggattgggaa gacaatagca |
| | | ggcatgctgg ggatgcggtg ggctctatgg gtacccaggt gctgaagaat |
| | | tgacccggtt cctcctgggc cagaaagaag caggcacatc cccttctctg |
| | | tgacacaccc tgtccacgcc cctggttctt agttccagcc ccactcatag |
| | | gacactcata gctcaggagg gtccgccttc aatcccacc cgctaaagta |
| | | cttggagcgg tctctccctc cctcatcagc ccaccaaacc aaacctagcc |
| | | tccaagagtg ggaagaaatt aaagcaagat aggctattaa gtgcagaggg |
| | | agagaaaatg cctccaacat gtgaggaagt aatgagagaa atcatagaat |
| | | tttaaggcca tgatttaagg ccatcatggc cttaatcttc cgcttcctcg |
| | | ctcactgact cgctgcgctc ggtcgttcgg ctgcggcgag cggtatcagc |
| | | tcactcaaag gcggtaatac ggttatccac agaatcaggg gataacgcag |
| | | gaaagaacat gtgagcaaaa ggccagcaaa aggccaggaa ccgtaaaaag |
| | | gccgcgttgc tggcgttttt ccataggctc cgcccccctg acgagcatca |
| | | caaaaatcga cgctcaagtc agaggtggcg aaacccgaca ggactataaa |
| | | gataccaggc gtttccccct ggaagctccc tcgtgcgctc tcctgttccg |
| | | accctgccgc ttaccggata cctgtccgcc tttctccctt cgggaagcgt |
| | | ggcgctttct catagctcac gctgtaggta tctcagttcg gtgtaggtcg |
| | | ttcgctccaa gctgggctgt gtgcacgaac cccccgttca gcccgaccgc |
| | | tgcgccttat ccggtaacta tcgtcttgag tccaacccgg taagacacga |
| | | cttatcgcca ctggcagcag ccactggtaa caggattagc agagcgaggt |
| | | atgtaggcgg tgctacagag ttcttgaagt ggtggcctaa ctacggctac |
| | | actagaagaa cagtatttgg tatctgcgct ctgctgaagc cagttacctt |
| | | cggaaaaaga gttggtagct cttgatccgg caaacaaacc accgctggta |
| | | gcggtggttt ttttgtttgc aagcagcaga ttacgcgcag aaaaaaagga |
| | | tctcaagaag atcctttgat cttttctacg ggtctgacg ctcagtggaa |
| | | cgaaaactca cgttaaggga ttttggtcat gagattatca aaaaggatct |
| | | tcacctagat ccttttaaat taaaaatgaa gttttaaatc aatctaaagt |
| | | atatatgagt aaacttggtc tgacagttac caatgcttaa tcagtgaggc |
| | | acctatctca gcgatctgtc tatttcgttc atccatagtt gcctgactcg |
| | | ggggggggg gcgctgaggt ctgcctcgtg aagaaggtgt tgctgactca |
| | | taccaggcct gaatcgcccc atcatccagc cagaaagtga gggagccacg |
| | | gttgatgaga gctttgttgt aggtggacca gttggtgatt ttgaactttt |
| | | gctttgccac ggaacggtct gcgttgtcgg gaagatgcgt gatctgatcc |
| | | ttcaactcag caaaagttcg atttattcaa caaagccgcc gtcccgtcaa |
| | | gtcagcgtaa tgctctgcca gtgttacaac caattaacca attctgatta |
| | | gaaaaactca tcgagcatca aatgaaactg caatttattc atatcaggat |
| | | tatcaatacc atattttga aaaagccgtt tctgtaatga aggagaaaac |
| | | tcaccgaggc agttccatag gatggcaaga tcctggtatc ggtctgcgat |
| | | tccgactcgt ccaacatcaa tacaacctat taatttcccc tcgtcaaaaa |

| SEQ ID NO | Description | Sequence |
|---|---|---|
| | | taaggttatc aagtgagaaa tcaccatgag tgacgactga atccggtgag<br>aatggcaaaa gcttatgcat ttcttttccag acttgttcaa caggccagcc<br>attacgctcg tcatcaaaat cactcgcatc aaccaaaccg ttattcattc<br>gtgattgcgc ctgagcgaga cgaaatacgc gatcgctgtt aaaaggacaa<br>ttacaaacag gaatcgaatg caaccggcgc aggaacactg ccagcgcatc<br>aacaatattt tcacctgaat caggatattc ttctaatacc tggaatgctg<br>ttttcccggg gatcgcagtg gtgagtaacc atgcatcatc aggagtacgg<br>ataaaatgct tgatggtcgg aagaggcata aattccgtca gccagtttag<br>tctgaccatc tcatctgtaa catcattggc aacgctacct ttgccatgtt<br>tcagaaacaa ctctggcgca tcgggcttcc catacaatcg atagattgtc<br>gcacctgatt gcccgacatt atcgcgagcc catttatacc catataaatc<br>agcatccatg ttggaattta atcgcggcct cgagcaagac gtttcccgtt<br>gaatatggct cataacaccc cttgtattac tgtttatgta agcagacagt<br>tttattgttc atgatgatat atttttatct tgtgcaatgt aacatcagag<br>attttgagac acaacgtggc tttcccccc cccccattat tgaagcattt<br>atcagggtta ttgtctcatg agcggataca tatttgaatg tatttagaaa<br>aataaacaaa taggggttcc gcgcacattt ccccgaaaag tgccacctga<br>cgtctaagaa accattatta tcatgacatt aacctataaa aataggcgta<br>tcacgaggcc ctttcgtc |
| 123 | Humanized H02 light chain backbone aa sequence | MGWSCIILFLVATATGVHSQAALTQPPSVSGSPGQSV<br>TISCTGTSSDIGGYNYVSWYQQHPGKAPKVMIYEVS<br>KRPSGVSDRFSGSKSGNIASLTISGLQAEDEADYYCS<br>SYAGSNTFLFGGGTRLTVLGQPKAAPSVTLFPPSSEE<br>LQANKATLVCLISDFYPGAVTVAWKADSSPVKAGV<br>ETTTPSKQSNNKYAASSYLSLTPEQWKSHRSYSCQV<br>THEGSTVEKTVAPTECS |
| 124 | EBV gp350 GenBank: AIM62208.1 | MEAALLVCQYTIQSLIHLTGEDPGFFNVEIPEFPFYPTC<br>NVCTADVNVTINFDVGGKKHQLDLDFGQLTPHTKAVYQP<br>RGAFGGSENATNLFLLELLGAGELALTMRSKKLPINVTT<br>GEEQQVSLESVDVYFQDVFGTMWCHHAEMQNPVYLIPET<br>VPYIKWDNCNSTNITAVVRAQGLDVTLPLSLPTSAQDSN<br>FSVKTEMLGNEIDIECIMEDGEISQVLPGDNKFNITCSG<br>YESHVPSGGILTSTSPVATPIPGTGYAYSLRLTPRPVSR<br>FLGNNSILYVFYSGNGPKASGGDYCIQSNIVFSDEIPAS<br>QDMPTNTTDITYVGDNATYSVPMVTSEDANSPNVTVTAF<br>WAWPNNTETDFKCKWTLTSGTPSGCENISGAFASNRTFD<br>ITVSGLGTAPKTLIITRTATNATTTTHKVIFSKAPESTT<br>TSPTSNTTGFAAPNTTTGLPSSTHVPTNLTAPASTGPTV<br>STADVTSPTPAGTTSGASPVTPSPSPRDNGTESKAPDMT<br>SPTSAVTTPTPNATSPTSAVTTPTPNATSPTPAVTTPTP<br>NATSPTLGKTSPTSAVTTPTPNATSPTLGKTSPTSAVTT<br>PTPNATSPTLGKTSPTSAVTTPTPNATSPTVGETSPQAN<br>TTNHTLGGTSSTPVVTSPPKNATSAVTTGQHNITSSSTS<br>SMSLRPSSISETLSPSTSDNSTSHMPLLTSAHPTGGENI<br>TQVTPASTSTHHVSTSSPAPRPGTTSQASGPGNSSTSTK<br>PGEVNVTKGTPPKNATSPQAPSGQKTAVPTVTSTGGKAN<br>STTGGKHTTGHGARTSTEPTTDYGGDSTTPRTRYNATTY<br>LPPSTSSELRPRWTFTSPPVTTAQATVPVPPTSQPRFSN<br>LSMLVLQWASLAVLTLLLLLVMADCAFRRNLSTSHTYTT<br>PPYDDAETYV |
| 125 | gp350 B95-8 amino acids 2-425 Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 126 | NAM encoding SEQ ID NO: 125 | gaagctgccctgctcgtgtgccagtacaccatccagagcctgatccacctgaccg<br>gcgaggaccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgccctacatcaagtgggacaactgcaaca<br>gcaccaacatcaccgccgtcgtgcgggcccaggggactggatgtgacactgcctct<br>gagcctgcctaccagcgcccaggacagcaacttcagcgtgaaaaccgagatgct |

| SEQ ID NO | Description | Sequence |
|---|---|---|
| | | gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagaccgtgtccagattcctg<br>ggcaacaacagcatcctgtacgtgttctacagcggcaacggccccaaggcctctg<br>gcggcgattactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagcccaacgtgaccgt<br>gacagccttttgggcctggcctaacaacaccgagacagacttcaagtgcaagtgg<br>accctgacctccggcaccctagcggctgcgagaatatcagcggagccttcgcca<br>gcaaccggaccttcgatatcaccgtgtctggcctgggcaccgccccaagaccct<br>gatcatcaccagaaccgccacaaatgccaccaccacaacccacaaagtgatcttc<br>agcaaggcccccggctctggc |
| 127 | gp350 B95-8 (2-425)<br>Q122N*Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQNVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGS |
| 128 | NAM encoding SEQ ID NO: 127 | gaagctgccctgctcgtgtgccagtacaccatccagagcctgatccacctgaccg<br>gcgaggaccccggcttcttcaacgtggaaatccccgagttcccctctaccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggcctgaccatgagaagcaagaaactgc<br>ccatcaatgtgaccacaggcgaggaacagaacgtgtccctggaaagcgtggacg<br>tgtactttcaagacgtgttcggcaccatgtggtgccaccacgccgagatgcagaac<br>cccgtgtacctgatccccgagacagtgccctacatcaagtgggacaacagctgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagaccgtgtccagattcctg<br>ggcaacaacagcatcctgtacgtgttctacagcggcaacggccccaaggcctctg<br>gcggcgattactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagcccaacgtgaccgt<br>gacagccttttgggcctggcctaacaacaccgagacagacttcaagtgcaagtgg<br>accctgacctccggcaccctagcggctgcgagaatatcagcggagccttcgcca<br>gcaaccggaccttcgatatcaccgtgtctggcctgggcaccgccccaagaccct<br>gatcatcaccagaaccgccacaaatgccaccaccacaacccacaaagtgatcttc<br>agcaaggcccccggctct |
| 129 | gp350 B95-8 (2-425)<br>D163N*/164bSAvi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWNNSCNSTNITAVVRAQGLDVTLPLSLPTSAQDSN<br>FSVKTEMLGNEIDIECIMEDGEISQVLPGDNKFNITCSG<br>YESHVPSGGILTSTSPVATPIPGTGYAYSLRLTPRPVSR<br>FLGNNSILYVFYSGNGPKASGGDYCIQSNIVFSDEIPAS<br>QDMPTNTTDITYVGDNATYSVPMVTSEDANSPNVTVTAF<br>WAWPNNTETDFKCKWTLTSGTPSGCENISGAFASNRTFD<br>ITVSGLGTAPKTLIITRTATNATTTTHKVIFSKAPGS |
| 130 | NAM encoding SEQ ID NO: 129 | gaagctgccctgctcgtgtgccagtacaccatccagagcctgatccacctgaccg<br>gcgaggaccccggcttcttcaacgtggaaatccccgagttcccctctaccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggcctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgccctacatcaagtgggacaacagctgca<br>acagcaccaacatcaccgccgtcgtgcgggcccagggactggatgtgacactgc<br>ctctgagcctgcctaccagcgcccaggacagcaacttcagcgtgaaaaccgagat<br>gctgggcaacgagatcgacatcgagtgcatcatggaagatggcgagatcagcca<br>ggtgctgcccggcgacaacaagttcaacatcacatgcagcggctacgagagcca |

-continued

| SEQ ID NO | Description | Sequence |
|---|---|---|
| | | cgtgccatctggcggcatcctgaccagcacaagcccagtggccacacccatccct<br>ggcacaggctacgcctacagcctgagactgaccccagacccgtgtccagattcc<br>tgggcaacaacagcatcctgtacgtgttctacagcggcaacggccccaaggcctc<br>tggcggcgattactgtatccagagcaacatcgtgttcagcgacgagatccccgcca<br>gccaggacatgcccaccaataccaccgacatcacgtacgtgggcgacaatgcca<br>cctacagcgtgccaatggtcacctccgaggacgccaacagccccaacgtgaccg<br>tgacagccttttgggcctggcctaacaacaccgagacagacttcaagtgcaagtgg<br>accctgacctccggcaccccagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 131 | gp350 B95-8 (2-425) D296R Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGG<u>R</u>YCIQSNIVFSDEIPASQ<br>DMPTNTTDITYVGDNATYSVP<u>M</u>VTSEDANSPNVTVTAFW<br>AWPNNTETDFKCKWTLTSGTPSGCENISGAFASNRTFDI<br>TVSGLGTAPKTLIITRTATNATTTHKVIFSKAPGS |
| 132 | NAM encoding SEQ ID NO: 131 | gaagctgccctgctcgtgtgccagtacaccatccagagcctgatccacctgaccgg<br>cgaggaccccggcttcttcaacgtggaaatccccgagttccccttctacccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtggacg<br>tgtactttcaagacgtgttcggcaccatgtggtgccaccacgccgagatgcagaac<br>cccgtgtacctgatccccgagacagtgccctacatcaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgaccccagacccgtgtccagattcctg<br>gcaacaacagcatcctgtacgtgttctacagcggcaacggccccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagccccaacgtgaccgt<br>gacagccttttgggcctggcctaacaacaccgagacagacttcaagtgcaagtgg<br>accctgacctccggcaccccagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 133 | gp350 B95-8 (2-425) WDN162-4AAA Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKAAACNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTHKVIFSKAPGS |
| 134 | NAM encoding SEQ ID NO: 133 | gaagctgccctgctcgtgtgccagtacaccatccagagcctgatccacctgaccgg<br>cgaggaccccggcttcttcaacgtggaaatccccgagttccccttctacccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgccctacatcaaggccgccgcctgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgaccccagacccgtgtccagattcctg |

| SEQ ID NO | Description | Sequence |
|---|---|---|
| | | ggcaacaacagcatcctgtacgtgttctacagcggcaacggccccaaggcctctg
gcggcggattactgtatccagagcaacatcgtgttcagcgacgagatccccgccag
ccaggacatgcccaccaataccaccgacatcacgtacgtgggcgacaatgccac
ctacagcgtgccaatggtcacctccgaggacgccaacagcccaacgtgaccgt
gacagccttttgggcctggcctaacaacaccgagacagacttcaagtgcaagtgg
accctgacctccggcacccctagcggctgcgagaatatcagcggagccttcgcca
gcaacggaccttcgatatcaccgtgtctggcctgggcaccgcccccaagacccct
gatcatcaccagaaccgccacaaatgccaccaccacaacccacaaagtgatcttc
agcaaggccccggctct |
| 135 | gp350 B95-8 (2-425) D296R/I160R Avi | EAALLVCQYTIQSLIHLTGEDPGFFNVEIPEFPFYPTCN
VCTADVNVTINFDVGGKKHQLDLDFGQLTPHTKAVYQPR
GAFGGSENATNLFLLELLGAGELALTMRSKKLPINVTTG
EEQQVSLESVDVYFQDVFGTMWCHHAEMQNPVYLIPETV
PYRKWDNCSTNITAVVRAQGLDVTLPLSLPTSAQDSNF
SVKTEMLGNEIDIECIMEDGEISQVLPGDNKFNITCSGY
ESHVPSGGILTSTSPVATPIPGTGYAYSLRLTPRPVSRF
LGNNSILYVFYSGNGPKASGGRYCIQSNIVFSDEIPASQ
DMPTNTTDITYVGDNATYSVPMVTSEDANSPNVTVTAFW
AWPNNTETDFKCKWTLTSGTPSGCENISGAFASNRTFDI
TVSGLGTAPKTLIITRTATNATTTTHKVIFSKAPGS |
| 136 | NAM encoding SEQ ID NO: 135 | gaagctgccctgctcgtgtgccagtacaccatccagagcctgatccacctgaccg
gcgaggaccccggcttcttcaacgtggaaatccccgagttccccttctaccctacct
gcaacgtgtgcaccgccgacgtgaacgtgaccatcaacttcgacgtgggcggca
agaagcaccagctggacctggatttcggccagctgaccctcacaccaaggccgt
gtatcagcccagaggcgcctttggcggcagcgagaacgccaccaatctgtttctgc
tggaactcctaggcgccggcgagctggccctgaccatgagaagcaagaaactgc
ccatcaatgtgaccacaggcgaggaacagcaggtgtccctggaaagcgtggacg
tgtactttcaagacgtgttcggcaccatgtggtgccaccacgccgagatgcagaac
cccgtgtacctgatccccgagacagtgccctaccggaagtgggacaactgcaaca
gcaccaacatcaccgccgtcgtgcgggccagggactggatgtgacactgcctct
gagcctgcctaccagcgcccaggacagcaacttcagcgtgaaaaccgagatgct
gggcaacgagatcgacatcgagtgcatcatggaagatggcgagatcagccaggt
gctgcccggcgacaacaagttcaacatcacatgcagcggctacgagagccacgt
gccatctggcggcatcctgaccagcacaagcccagtggccacacccatccctgg
cacaggctacgcctacagcctgagactgaccccccagaccgtgtccagattcctg
ggcaacaacagcatcctgtacgtgttctacagcggcaacggccccaaggcctctg
gcggcggtactgtatccagagcaacatcgtgttcagcgacgagatccccgccag
ccaggacatgcccaccaataccaccgacatcacgtacgtgggcgacaatgccac
ctacagcgtgccaatggtcacctccgaggacgccaacagcccaacgtgaccgt
gacagccttttgggcctggcctaacaacaccgagacagacttcaagtgcaagtgg
accctgacctccggcacccctagcggctgcgagaatatcagcggagccttcgcca
gcaacggaccttcgatatcaccgtgtctggcctgggcaccgcccccaagacccct
gatcatcaccagaaccgccacaaatgccaccaccacaacccacaaagtgatcttc
agcaaggccccggctct |
| 137 | gp350 B95-8 (2-425) D296R/P158R Avi | EAALLVCQYTIQSLIHLTGEDPGFFNVEIPEFPFYPTCN
VCTADVNVTINFDVGGKKHQLDLDFGQLTPHTKAVYQPR
GAFGGSENATNLFLLELLGAGELALTMRSKKLPINVTTG
EEQQVSLESVDVYFQDVFGTMWCHHAEMQNPVYLIPETV
RYIKWDNCSTNITAVVRAQGLDVTLPLSLPTSAQDSNF
SVKTEMLGNEIDIECIMEDGEISQVLPGDNKFNITCSGY
ESHVPSGGILTSTSPVATPIPGTGYAYSLRLTPRPVSRF
LGNNSILYVFYSGNGPKASGGRYCIQSNIVFSDEIPASQ
DMPTNTTDITYVGDNATYSVPMVTSEDANSPNVTVTAFW
AWPNNTETDFKCKWTLTSGTPSGCENISGAFASNRTFDI
TVSGLGTAPKTLIITRTATNATTTTHKVIFSKAPGS |
| 138 | NAM encoding SEQ ID NO: 137 | gaagctgccctgctcgtgtgccagtacaccatccagagcctgatccacctgaccg
gcgaggaccccggcttcttcaacgtggaaatccccgagttccccttctaccctacct
gcaacgtgtgcaccgccgacgtgaacgtgaccatcaacttcgacgtgggcggca
agaagcaccagctggacctggatttcggccagctgaccctcacaccaaggccgt
gtatcagcccagaggcgcctttggcggcagcgagaacgccaccaatctgtttctgc
tggaactcctaggcgccggcgagctggccctgaccatgagaagcaagaaactgc
ccatcaatgtgaccacaggcgaggaacagcaggtgtccctggaaagcgtggacg acg
tgtactttcaagacgtgttcggcaccatgtggtgccaccacgccgagatgcagaac
cccgtgtacctgatccccgagacagtgcggtacatcaagtgggacaactgcaaca
gcaccaacatcaccgccgtcgtgcgggcccagggactggatgtgacactgcctct
gagcctgcctaccagcgcccaggacagcaacttcagcgtgaaaaccgagatgct
gggcaacgagatcgacatcgagtgcatcatggaagatggcgagatcagccaggt
gctgcccggcgacaacaagttcaacatcacatgcagcggctacgagagccacgt
gccatctggcggcatcctgaccagcacaagcccagtggccacacccatccctgg
cacaggctacgcctacagcctgagactgaccccccagaccgtgtccagattcctg
ggcaacaacagcatcctgtacgtgttctacagcggcaacggccccaaggcctctg
gcggcggtactgtatccagagcaacatcgtgttcagcgacgagatccccgccag |

| SEQ ID NO | Description | Sequence |
|---|---|---|
| | | ccaggacatgcccaccaataccaccgacatcacgtacgtgggcgacaatgccac<br>ctacagcgtgccaatggtcacctccgaggacgccaacagcccaacgtgaccgt<br>gacagccttttgggcctggcctaacaacaccgagacagacttcaagtgcaagtgg<br>accctgacctccggcaccccagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggccccccggctct |
| 139 | gp350 B95-8 (2-425) D296R/P158N*/I160T Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>NYTKWDNCNSTNITAVVRAQGLDVTLPLSLPTSAQDSNF<br><u>S</u>V<u>K</u>TEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGRYCIQSNIVFSDEIPASQ<br>DMPTNTTDITYVGDNATYSVP<u>M</u>VTSEDANSPNVTVTAFW<br>AWPNNTETDFKCKWTLTSGTPSGCENISGAFASNRTFDI<br>TVSGLGTAPKTLIITRTATNATTTHKVIFSKAPGS |
| 140 | NAM encoding SEQ ID NO: 139 | gaagctgccctgctcgtgtgccagtacaccatccagagcctgatccacctgaccg<br>gcgaggacccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtggacg<br>tgtactttcaagacgtgttcggcaccatgtggtgccaccacgccgagatgcagaac<br>cccgtgtacctgatccccgagacagtgaactacaccaagtgggacaactgcaaca<br>gcaccaacatcaccgccgtcgtgcgggcccagggactggatgtgacactgcctct<br>gagcctgcctaccagcgcccaggacagcaacttcagcgtgaaaaccgagatgct<br>gggcaacgagatcgacatcgagtgcatcatggaagatggcgagatcagccaggt<br>gctgcccggcgacaacaagttcaacatcacatgcagcggctacgagagccacgt<br>gccatctggcggcatcctgaccagcacaagcccagtggccacacccatccctgg<br>cacaggctacgcctacagcctgagactgacccccagaccgtgtccagattcctg<br>ggcaacaacagcatcctgtacgtgttctacagcggcaacggcccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagcccaacgtgaccgt<br>gacagccttttgggcctggcctaacaacaccgagacagacttcaagtgcaagtgg<br>accctgacctccggcaccccagcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggccccccggctct |
| 141 | gp350 B95-8 (2-425) D296R/P158R/I160R Avi | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>RYRKWDNCNSTNITAVVRAQGLDVTLPLSLPTSAQDSNF<br><u>S</u>V<u>K</u>TEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGRYCIQSNIVFSDEIPASQ<br>DMPTNTTDITYVGDNATYSVP<u>M</u>VTSEDANSPNVTVTAFW<br>AWPNNTETDFKCKWTLTSGTPSGCENISGAFASNRTFDI<br>TVSGLGTAPKTLIITRTATNATTTHKVIFSKAPGS |
| 142 | NAM encoding SEQ ID NO: 141 | gaagctgccctgctcgtgtgccagtacaccatccagagcctgatccacctgaccg<br>gcgaggacccccggcttcttcaacgtggaaatccccgagttccccttctaccctacct<br>gcaacgtgtgcaccgccgacgtgaacgtgaccatcaacttcgacgtgggcggca<br>agaagcaccagctggacctggatttcggccagctgaccccctcacaccaaggccgt<br>gtatcagcccagaggcgcctttggcggcagcgagaacgccaccaatctgtttctgc<br>tggaactcctaggcgccggcgagctggccctgaccatgagaagcaagaaactgc<br>ccatcaatgtgaccacaggcgaggaacagcaggtgtccctggaaagcgtgg acg<br>tgtactttcaagacgtgttcggcaccatgtggtgccaccacgccgagatgcagaac<br>cccgtgtacctgatccccgagacagtgcggtaccggaagtgggacaactgcaac<br>agcaccaacatcaccgccgtcgtgcgggcccagggactggatgtgacactgcct<br>ctgagcctgcctaccagcgcccaggacagcaacttcagcgtgaaaaccgagatg<br>ctgggcaacgagatcgacatcgagtgcatcatggaagatggcgagatcagccag<br>gtgctgcccggcgacaacaagttcaacatcacatgcagcggctacgagagccac<br>gtgccatctggcggcatcctgaccagcacaagcccagtggccacacccatccctg<br>gcacaggctacgcctacagcctgagactgacccccagaccgtgtccagattcctg<br>ggcaacaacagcatcctgtacgtgttctacagcggcaacggcccaaggcctctg<br>gcggccggtactgtatccagagcaacatcgtgttcagcgacgagatccccgccag<br>ccaggacatgcccaccaataccaccgacatcacgtacgtgggcgacaatgccac<br>ctacagcgtgccaatggtcacctccgaggacgccaacagcccaacgtgaccg |

| SEQ ID NO | Description | Sequence |
|---|---|---|
| | | tgacagccttttgggcctggcctaacaacaccgagacagacttcaagtgcaagtgg<br>accctgacctccggcaccccta gcggctgcgagaatatcagcggagccttcgcca<br>gcaaccggaccttcgatatcaccgtgtctggcctgggcaccgcccccaagaccct<br>gatcatcaccagaaccgccacaaatgccaccaccacaacccacaaagtgatcttc<br>agcaaggcccccggctct |
| 143 | gp350 B95-8 (2-425) Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 144 | NAM encoding SEQ ID NO: 143 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctacatcaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgacccccagacccgtgtccagattc<br>ctgggcaacaacagcatcctgtacgtgttctacagcggc<br>aacggccccaaggcctctggcggcgattactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcaccccta gcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacattttgaggcccagaagattgagtggcatgaacat<br>caccaccaccaccat |
| 145 | gp350 B95-8 (2-425) Q122N* Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQNVSLESVDVYFQDVFGTMWCHHAEMQNPVYLIPETV<br>PYIKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGDYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 146 | NAM encoding SEQ ID NO: 145 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgcctttggcggcagcgagaacgccaccaatctgttt<br>ctgctggaactcctaggcgccggcgagctggccctgacc |

| SEQ ID NO | Description | Sequence |
|---|---|---|
| | | atgagaagcaagaaactgcccatcaatgtgaccacaggc
gaggaacagaacgtgtccctggaaagcgtggacgtgtac
tttcaagacgtgttcggcaccatgtggtgccaccacgcc
gagatgcagaaccccgtgtacctgatccccgagacagtg
ccctacatcaagtgggacaactgcaacagcaccaacatc
accgccgtcgtgcgggcccagggactggatgtgacactg
cctctgagcctgcctaccagcgcccaggacagcaacttc
agcgtgaaaaccgagatgctgggcaacgagatcgacatc
gagtgcatcatggaagatggcgagatcagccaggtgctg
cccggcgacaacaagttcaacatcacatgcagcggctac
gagagccacgtgccatctggcggcatcctgaccagcaca
agcccagtggccacacccatccctggcacaggctacgcc
tacagcctgagactgaccccagacccgtgtccagattc
ctgggcaacaacagcatcctgtacgtgttctacagcggc
aacggccccaaggcctctggcggcgattactgtatccag
agcaacatcgtgttcagcgacgagatccccgccagccag
gacatgcccaccaataccaccgacatcacgtacgtgggc
gacaatgccacctacagcgtgccaatggtcacctccgag
gacgccaacagccccaacgtgaccgtgacagcctttttgg
gcctggcctaacaacaccgagacagacttcaagtgcaag
tggaccctgacctccggcaccctagcggctgcgagaat
atcagcggagccttcgccagcaaccggaccttcgatatc
accgtgtctggcctgggcaccgccccaagaccctgatc
atcaccagaaccgccacaaatgccaccaccacaacccac
aaagtgatcttcagcaaggcccccggctctggcctgaac
gacatttttgaggcccagaagattgagtggcatgaacat
caccaccaccat |
| 147 | gp350 B95-8 (2-425) D163N*/164bS Avi-His | EAALLVCQYTIQSLIHLTGEDPGFFNVEIPEFPFYPTCN
VCTADVNVTINFDVGGKKHQLDLDFGQLTPHTKAVYQPR
GAFGGSENATNLFLLELLGAGELALTMRSKKLPINVTTG
EEQQVSLESVDVYFQDVFGTMWCHHAEMQNPVYLIPETV
PYIKW<u>NNS</u>CNSTNITAVVRAQGLDVTLPLSLPTSAQDSN
FSVKT<u>EML</u>GNEIDIECIMEDGEISQVLPGDNKFNITCSG
YESHVPSGGILTSTSPVATPIPGTGYAYSLRLTPRPVSR
FLGNNSILYVFYSGNGPKASGGDYCIQSNIVFSDEIPAS
QDMPTNTTDITYVGDNATYSVPMVTSEDANSPNVTVTAF
WAWPNNTETDFKCKWTLTSGTPSGCENISGAFASNRTFD
ITVSGLGTAPKTLIITRTATNATTTTHKVIFSKAPGSGL
NDIFEAQKIEWHEHHHHHH |
| 148 | NAM encoding SEQ ID NO: 147 | gaagctgccctgctcgtgtgccagtacaccatccagagc
ctgatccacctgaccggcgaggaccccggcttcttcaac
gtggaaatccccgagttccccttctaccctacctgcaac
gtgtgcaccgccgacgtgaacgtgaccatcaacttcgac
gtgggcggcaagaagcaccagctggacctggatttcggc
cagctgaccccctcacaccaaggccgtgtatcagcccaga
ggcgcctttggcggcagcgagaacgccaccaatctgttt
ctgctggaactcctaggcgccggcgagctggccctgacc
atgagaagcaagaaactgcccatcaatgtgaccacaggc
gaggaacagcaggtgtccctggaaagcgtggacgtgtac
tttcaagacgtgttcggcaccatgtggtgccaccacgcc
gagatgcagaaccccgtgtacctgatccccgagacagtg
ccctacatcaagtggaacaacagctgcaacagcaccaac
atcaccgccgtcgtgcgggcccagggactggatgtgaca
ctgcctctgagcctgcctaccagcgcccaggacagcaac
ttcagcgtgaaaaccgagatgctgggcaacgagatcgac
atcgagtgcatcatggaagatggcgagatcagccaggtg
ctgcccggcgacaacaagttcaacatcacatgcagcggc
tacgagagccacgtgccatctggcggcatcctgaccagc
acaagcccagtggccacacccatccctggcacaggctac
gcctacagcctgagactgaccccagacccgtgtccaga
ttcctgggcaacaacagcatcctgtacgtgttctacagc
ggcaacggccccaaggcctctggcggcgattactgtatc
cagagcaacatcgtgttcagcgacgagatccccgccagc
caggacatgcccaccaataccaccgacatcacgtacgtg
ggcgacaatgccacctacagcgtgccaatggtcacctcc
gaggacgccaacagccccaacgtgaccgtgacagccttt
tgggcctggcctaacaacaccgagacagacttcaagtgc
aagtggaccctgacctccggcaccctagcggctgcgag
aatatcagcggagccttcgccagcaaccggaccttcgat
atcaccgtgtctggcctgggcaccgccccaagaccctg
atcatcaccagaaccgccacaaatgccaccaccacaacc
cacaaagtgatcttcagcaaggcccccggctctggcctg
aacgacatttttgaggcccagaagattgagtggcatgaa
catcaccaccaccaccat |

| SEQ ID NO | Description | Sequence |
|---|---|---|
| 149 | gp350 B95-8 (2-425) D296R Avi-His | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV PYIKWDNCNSTNITAVVRAQGLDVTLPLSLPTSAQDSNF SVKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGRYCIQSNIVFSDEIPASQ DMPTNTTDITYVGDNATYSVPMVTSEDANSPNVTVTAFW AWPNNTETDFKCKWTLTSGTPSGCENISGAFASNRTFDI TVSGLGTAPKTLIITRTATNATTTTHKVIFSKAPGSGLN DIFEAQKIEWHEHHHHHH |
| 150 | NAM encoding SEQ ID NO: 149 | gaagctgccctgctcgtgtgccagtacaccatccagagc ctgatccacctgaccggcgaggaccccggcttcttcaac gtggaaatccccgagttccccttctaccctacctgcaac gtgtgcaccgccgacgtgaacgtgaccatcaacttcgac gtgggcggcaagaagcaccagctggacctggatttcggc cagctgacccctcacaccaaggccgtgtatcagcccaga ggcgcctttggcggcagcgagaacgccaccaatctgttt ctgctggaactcctaggcgccggcgagctgggcctgacc atgagaagcaagaaactgcccatcaatgtgaccacaggc gaggaacagcaggtgtccctggaaagcgtggacgtgtac tttcaagacgtgttcggcaccatgtggtgccaccacgcc gagatgcagaaccccgtgtacctgatccccgagacagtg ccctacatcaagtgggacaactgcaacagcaccaacatc accgccgtcgtgcgggcccagggactggatgtgacactg cctctgagcctgcctaccagcgcccaggacagcaacttc agcgtgaaaaccgagatgctgggcaacgagatcgacatc gagtgcatcatggaagatggcgagatcagccaggtgctg cccggcgacaacaagttcaacatcacatgcagcggctac gagagccacgtgccatctggcggcatcctgaccagcaca agcccagtggccacacccatccctggcacaggctacgcc tacagcctgagactgaccccccagaccagcgtgtccagattc ctgggcaacaacagcatcctgtacgtgttctacagcggc aacggccccaaggcctctggcggccggtactgtatccag agcaacatcgtgttcagcgacgagatccccgccagccag gacatgcccaccaataccaccgacatcacgtacgtgggc gacaatgccacctacagcgtgccaatggtcacctccgag gacgccaacagccccaacgtgaccgtgacagccttttgg gcctggcctaacaacaccgagacagacttcaagtgcaag tggaccctgacctccggcacccctagcggctgcgagaat atcagcggagccttcgccagcaacaggaccttcgatatc accgtgtctggcctgggcaccgcccccaagaccctgatc atcaccagaaccgccacaaatgccaccaccacaacccac aaagtgatcttcagcaaggcccccggctctggcctgaac gacatttttgaggcccagaagattgagtggcatgaacat caccaccaccaccat |
| 151 | gp350 B95-8 (2-425) WDN162-4AAA Avi-His | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV PYIKAAACNSTNITAVVRAQGLDVTLPLSLPTSAQDSNF SVKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGDYCIQSNIVFSDEIPASQ DMPTNTTDITYVGDNATYSVPMVTSEDANSPNVTVTAFW AWPNNTETDFKCKWTLTSGTPSGCENISGAFASNRTFDI TVSGLGTAPKTLIITRTATNATTTTHKVIFSKAPGSGLN DIFEAQKIEWHEHHHHHH |
| 152 | NAM encoding SEQ ID NO: 151 | gaagctgccctgctcgtgtgccagtacaccatccagagc ctgatccacctgaccggcgaggaccccggcttcttcaac gtggaaatccccgagttccccttctaccctacctgcaac gtgtgcaccgccgacgtgaacgtgaccatcaacttcgac gtgggcggcaagaagcaccagctggacctggatttcggc cagctgacccctcacaccaaggccgtgtatcagcccaga ggcgcctttggcggcagcgagaacgccaccaatctgttt ctgctggaactcctaggcgccggcgagctgggcctgacc atgagaagcaagaaactgcccatcaatgtgaccacaggc gaggaacagcaggtgtccctggaaagcgtggacgtgtac tttcaagacgtgttcggcaccatgtggtgccaccacgcc gagatgcagaaccccgtgtacctgatccccgagacagtg ccctacatcaaggccgccgcctgcaacagcaccaacatc |

| SEQ ID NO | Description | Sequence |
|---|---|---|
| | | accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgaccccagacccgtgtccagattc<br>ctgggcaacaacagcatcctgtacgtgttctacagcggc<br>aacggccccaaggcctctggcggcgattactgtatccag<br>agcaacatcgtgttcagcgacgagatccccgcagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 153 | gp350 B95-8 (2-425) D296R/I160R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>PYRRKWDNCNSTNITAVVRAQGLDVTLPLSLPTSAQDSNF<br>SVKTEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGRYCIQSNIVFSDEIPASQ<br>DMPTNTTDITYVGDNATYSVPMVTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 154 | NAM encoding SEQ ID NO: 153 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgacccctcacaccaaggccgtgtatcagcccaga<br>ggcgccttttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>ccctaccggaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgaccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgcagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcacccctagcggctgcgagaat<br>atcagcggagccttcgccagcaaccggaccttcgatatc<br>accgtgtctggcctgggcaccgcccccaagaccctgatc<br>atcaccagaaccgccacaaatgccaccaccacaacccac<br>aaagtgatcttcagcaaggcccccggctctggcctgaac<br>gacatttttgaggcccagaagattgagtggcatgaacat<br>caccaccaccaccat |
| 155 | gp350 B95-8 (2-425) D296R/P158R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV |

| SEQ ID NO | Description | Sequence |
|---|---|---|
| | | RYIKWDNCNSTNITAVVRAQGLDVTLPLSLPTSAQDSNF <u>S</u>VKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGRYCIQSNIVFSDEIPASQ DMPTNTTDITYVGDNATYSVP<u>M</u>VTSEDANSPNVTVTAFW AWPNNTETDFKCKWTLTSGTPSGCENISGAFASNRTFDI TVSGLGTAPKTLIITRTATNATTTHKVIFSKAPGSGLN DIFEAQKIEWHEHHHHHH |
| 156 | NAM encoding SEQ ID NO: 155 | gaagctgccctgctcgtgtgccagtacaccatccagagc ctgatccacctgaccggcgaggaccccggcttcttcaac gtggaaatccccgagttccccttctaccctacctgcaac gtgtgcaccgccgacgtgaacgtgaccatcaacttcgac gtgggcggcaagaagcaccagctggacctggatttcggc cagctgaccccctcacaccaaggccgtgtatcagcccaga ggcgcctttggcggcagcgagaacgccaccaatctgttt ctgctggaactcctaggcgccggcgagctggccctgacc atgagaagcaagaaactgcccatcaatgtgaccacaggc gaggaacagcaggtgtccctggaaagcgtggacgtgtac tttcaagacgtgttcggcaccatgtggtgccaccacgcc gagatgcagaaccccgtgtacctgatccccgagacagtg cggtacatcaagtgggacaactgcaacagcaccaacatc accgccgtcgtgcgggcccagggactggatgtgacactg cctctgagcctgcctaccagcgcccaggacagcaacttc agcgtgaaaaccgagatgctgggcaacgagatcgacatc gagtgcatcatggaagatggcgagatcagccaggtgctg cccggcgacaacaagttcaacatcacatgcagcggctac gagagccacgtgccatctggcggcatcctgaccagcaca agcccagtggccacacccatccctggcacaggctacgcc tacagcctgagactgaccccagacccgtgtccagattc ctgggcaacaacagcatcctgtacgtgttctacagcggc aacgggcccaaggcctctggcggccgggtactgtatccag agcaacatcgtgttcagcgacgagatccccgccagccag gacatgcccaccaataccaccgacatcacgtacgtgggc gacaatgccacctacagcgtgccaatggtcacctccgag gacgccaacagcccaacgtgaccgtgacagcctttgg gcctggcctaacaacaccgagacagacttcaagtgcaag tggaccctgacctccggcacccctagcggctgcgagaat atcagcggagccttcgccagcaaccggaccttcgatatc accgtgtctggcctgggcaccgcccccaagaccctgatc atcaccagaaccgccacaaatgccaccaccacaacccac aaagtgatcttcagcaaggccccggctctggcctgaac gacatttttgaggcccagaagattgagtggcatgaacat caccaccaccaccat |
| 157 | gp350 B95-8 (2-425) D296R/P158N*/I160T Avi-His | EAALLVCQYTIQSLIHLTGEDPGFFNVEIPEFPFYPTCN VCTADVNVTINFDVGGKKHQLDLDFGQLTPHTKAVYQPR GAFGGSENATNLFLLELLGAGELALTMRSKKLPINVTTG EEQQVSLESVDVYFQDVFGTMWCHHAEMQNPVYLIPETV NYTKWDNCNSTNITAVVRAQGLDVTLPLSLPTSAQDSNF <u>S</u>VKTEMLGNEIDIECIMEDGEISQVLPGDNKFNITCSGY ESHVPSGGILTSTSPVATPIPGTGYAYSLRLTPRPVSRF LGNNSILYVFYSGNGPKASGGRYCIQSNIVFSDEIPASQ DMPTNTTDITYVGDNATYSVP<u>M</u>VTSEDANSPNVTVTAFW AWPNNTETDFKCKWTLTSGTPSGCENISGAFASNRTFDI TVSGLGTAPKTLIITRTATNATTTHKVIFSKAPGSGLN DIFEAQKIEWHEHHHHHH |
| 158 | NAM encoding SEQ ID NO: 157 | gaagctgccctgctcgtgtgccagtacaccatccagagc ctgatccacctgaccggcgaggaccccggcttcttcaac gtggaaatccccgagttccccttctaccctacctgcaac gtgtgcaccgccgacgtgaacgtgaccatcaacttcgac gtgggcggcaagaagcaccagctggacctggatttcggc cagctgaccccctcacaccaaggccgtgtatcagcccaga ggcgcctttggcggcagcgagaacgccaccaatctgttt ctgctggaactcctaggcgccggcgagctggccctgacc atgagaagcaagaaactgcccatcaatgtgaccacaggc gaggaacagcaggtgtccctggaaagcgtggacgtgtac tttcaagacgtgttcggcaccatgtggtgccaccacgcc gagatgcagaaccccgtgtacctgatccccgagacagtg aactacaccaagtgggacaactgcaacagcaccaacatc accgccgtcgtgcgggcccagggactggatgtgacactg cctctgagcctgcctaccagcgcccaggacagcaacttc agcgtgaaaaccgagatgctgggcaacgagatcgacatc gagtgcatcatggaagatggcgagatcagccaggtgctg cccggcgacaacaagttcaacatcacatgcagcggctac |

| SEQ ID NO | Description | Sequence |
|---|---|---|
| | | gagagccacgtgccatctggcggcatcctgaccagcaca<br>agcccagtggccacacccatccctggcacaggctacgcc<br>tacagcctgagactgaccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcaccccctagcggctgcgagaat<br>atcagcggagccttcgccagcaaccggaccttcgatatc<br>accgtgtctggcctgggcaccgccccaagaccctgatc<br>atcaccagaaccgccacaaatgccaccaccacaacccac<br>aaagtgatcttcagcaaggccccggctctggcctgaac<br>gacatttttgaggcccagaagattgagtggcatgaacat<br>caccaccaccaccat |
| 159 | gp350 B95-8 (2-425) D296R/P158R/I160R Avi-His | EAALLVCQYTIQSLIHLTGEDPGFFNVEIPEFPFYPTCN<br>VCTADVNVTINFDVGGKKHQLDLDFGQLTPHTKAVYQPR<br>GAFGGSENATNLFLLELLGAGELALTMRSKKLPINVTTG<br>EEQQVSLESVDVYFQDVFGTMWCHHAEMQNPVYLIPETV<br>R̲Y̲R̲KWDNCNSTNITAVVRAQGLDVTLPLSLPTSAQDSNF<br>S̲V̲K̲TEMLGNEIDIECIMEDGEISQVLPGDNKFNITCSGY<br>ESHVPSGGILTSTSPVATPIPGTGYAYSLRLTPRPVSRF<br>LGNNSILYVFYSGNGPKASGGR̲Y̲CIQSNIVFSDEIPASQ<br>DMPTNTTDITYVGDNATYSVPM̲VTSEDANSPNVTVTAFW<br>AWPNNTETDFKCKWTLTSGTPSGCENISGAFASNRTFDI<br>TVSGLGTAPKTLIITRTATNATTTTHKVIFSKAPGSGLN<br>DIFEAQKIEWHEHHHHHH |
| 160 | NAM encoding SEQ ID NO: 159 | gaagctgccctgctcgtgtgccagtacaccatccagagc<br>ctgatccacctgaccggcgaggaccccggcttcttcaac<br>gtggaaatccccgagttccccttctaccctacctgcaac<br>gtgtgcaccgccgacgtgaacgtgaccatcaacttcgac<br>gtgggcggcaagaagcaccagctggacctggatttcggc<br>cagctgaccccctcacaccaaggccgtgtatcagcccaga<br>ggcgcctttggcggcagcgagaacgccaccaatctgttt<br>ctgctggaactcctaggcgccggcgagctggccctgacc<br>atgagaagcaagaaactgcccatcaatgtgaccacaggc<br>gaggaacagcaggtgtccctggaaagcgtggacgtgtac<br>tttcaagacgtgttcggcaccatgtggtgccaccacgcc<br>gagatgcagaaccccgtgtacctgatccccgagacagtg<br>cggtaccggaagtgggacaactgcaacagcaccaacatc<br>accgccgtcgtgcgggcccagggactggatgtgacactg<br>cctctgagcctgcctaccagcgcccaggacagcaacttc<br>agcgtgaaaaccgagatgctgggcaacgagatcgacatc<br>gagtgcatcatggaagatggcgagatcagccaggtgctg<br>cccggcgacaacaagttcaacatcacatgcagcggctac<br>gagagccacgtgccatctggcggcatcctgaccagcaca<br>agcccagtggccacacccatccctggcacaggctacgcc<br>tacagcctgagactgaccccagacccgtgtccagattc<br>ctgggcaacaacagcatcctgtacgtgttctacagcggc<br>aacggccccaaggcctctggcggccggtactgtatccag<br>agcaacatcgtgttcagcgacgagatccccgccagccag<br>gacatgcccaccaataccaccgacatcacgtacgtgggc<br>gacaatgccacctacagcgtgccaatggtcacctccgag<br>gacgccaacagccccaacgtgaccgtgacagccttttgg<br>gcctggcctaacaacaccgagacagacttcaagtgcaag<br>tggaccctgacctccggcaccccctagcggctgcgagaat<br>atcagcggagccttcgccagcaaccggaccttcgatatc<br>accgtgtctggcctgggcaccgccccaagaccctgatc<br>atcaccagaaccgccacaaatgccaccaccacaacccac<br>aaagtgatcttcagcaaggccccggctctggcctgaac<br>gacatttttgaggcccagaagattgagtggcatgaacat<br>caccaccaccaccat |
| 161 | E7 clone Heavy Chain aa sequence | QVQLVQSGADVRKPGASVKVSCKASTYIFTGYYIH<br>WVRQAPGRGLEWLGWIHPNSGGTTYSQMFQGRVT<br>MTRDRSITTSYMELSRLQSDDTAIYYCATLRFVEYSF<br>DSWGQGTLVTVSS |
| 162 | E7 clone Heavy Chain nucleotide sequence | CAGGTGCAGCTGGTGCAGTCTGGCGCAGACGTGA<br>GGAAGCCAGGAGCCTCCGTGAAGGTGTCTTGTAA<br>GGCCAGCACCTACATCTTCACAGGCTACTATATCC<br>ACTGGGTGAGGCAGGCACCAGGAAGGGGCCTGGA |

| SEQ ID NO | Description | Sequence |
|---|---|---|
| | | GTGGCTGGGCTGGATTCACCCTAACTCTGGCGGCA CCACATACAGCCAGATGTTTCAGGGCAGAGTGAC CATGACACGGGACAGATCCATCACCACATCTTATA TGGAGCTGAGCCGGCTGCAGTCCGACGATACCGC CATCTACTATTGCGCCACACTGAGATTCGTGGAGT ATTCTTTTGATAGCTGGGGCCAGGGCACCCTGGTG ACAGTGAGCTCC |
| 163 | E7 clone Heavy Chain CDR1 | TYIFTGY |
| 164 | E7 clone Heavy Chain CDR2 | HPNSGG |
| 165 | E7 clone Heavy Chain CDR3 | LRFVEYSFDS |
| 166 | E7 clone Kappa Chain aa sequence | EIVLTQSPGTLSLSPGERATLSCRASQSISSTYLAWYQ QIPGQAPRLLIYGASSRAAGIPDRFSGGGSGTDFTLTI SRLEPEDFAVYYCQQYGSSPRSFGQGTKLEIK |
| 167 | E7 clone Kappa Chain nucleotide sequence | GAGATCGTGCTGACCCAGAGCCCAGGCACACTGA GCCTGTCCCCAGGAGAGAGGGCCACCCTGTCCTGT AGAGCCTCTCAGAGCATCAGCTCCACATACCTGGC CTGGTATCAGCAGATCCCAGGACAGGCACCTAGG CTGCTGATCTACGGAGCCTCTAGCAGGGCAGCAG GCATCCCCGACCGCTTCTCCGGCGGAGGCTCTGGC ACCGACTTCACCCTGACAATCTCTCGGCTGGAGCC TGAGGACTTCGCCGTGTACTATTGCCAGCAGTATG GCTCCTCTCCAAGGTCCTTTGGCCAGGGCACAAAG CTGGAGATCAAG |
| 168 | E7 clone Kappa Chain CDR1 | RASQSISSTYLA |
| 169 | E7 clone Kappa Chain CDR2 | GASSRAA |
| 170 | E7 clone Kappa Chain CDR3 | QQYGSSPRS |
| 171 | B8 clone Heavy Chain aa sequence | EVQLLESGGALVQPGGSLRLSCAASGFTFKTYAMSW VRQVPGKGLEWVSAISGSGTASYYADSVKGRFTLSR DNSKNTLYLQLSSLRDEDTGVYYCARRFLDWFGMD VWGLGTTVTVSS |
| 172 | B8 clone Heavy Chain nucleotide sequence | GAGGTGCAGCTGCTGGAGAGCGGCGGCGCCCTGG TGCAGCCAGGAGGCAGCCTGCGGCTGTCCTGTGCC GCCTCTGGCTTCACCTTTAAGACATACGCCATGTC CTGGGTGAGGCAGGTGCCTGGCAAGGGCCTGGAG TGGGTGTCTGCCATCTCCGGCTCTGGCACCGCCTC TTACTATGCCGACAGCGTGAAGGGCAGGTTCACCC TGAGCCGCGATAACTCCAAGAATACACTGTATCTG CAGCTGAGCTCCCTGCGGGACGAGGATACCGGCG TGTACTATTGCGCCCGGAGATTCCTGGACTGGTTT GGCATGGACGTGTGGGGCCTGGGCACCACAGTGA CAGTGTCTAGC |
| 173 | B8 clone Heavy Chain CDR1 | GFTFKTY |
| 174 | B8 clone Heavy Chain CDR2 | SGSGTA |
| 175 | B8 clone Heavy Chain CDR3 | RFLDWFGMDV |
| 176 | B8 clone Kappa Chain aa sequence | DIVMTQSPLSLPVTPGEPASISCLSSQSLLQSNGYNYV DWYLQKPGQSPQLLIYLGSNRASGVPDRFSGSGSGT DFTLKISRVEAEDVGVYYCMVTLHPPTFGQGAKVEI K |
| 177 | B8 clone Kappa Chain nucleotide sequence | GACATCGTGATGACCCAGTCCCCTCTGTCTCTGCC AGTGACACCCGGCGAGCCTGCCTCTATCAGCTGTC TGAGCTCCCAGAGCCTGCTGCAGTCCAACGGCTAC AATTATGTGGATTGGTACCTGCAGAAGCCAGGCC AGTCCCCCCAGCTGCTGATCTATCTGGGCTCTAAC AGGGCCAGCGGCGTGCCCGACAGATTCTCCGGCT CTGGCAGCGGCACCGACTTCACCCTGAAGATCTCT CGGGTGGAGGCAGAGGACGTGGGCGTGTACTATT GCATGGTGACCCTGCACCCACCTACATTCGGCCAG GGAGCCAAGGTGGAGATCAAG |
| 178 | B8 clone Kappa Chain CDR1 | LSSQSLLQSNGYNYVD |

| SEQ ID NO | Description | Sequence |
|---|---|---|
| 179 | B8 clone Kappa Chain CDR2 | LGSNRAS |
| 180 | B8 clone Kappa Chain CDR3 | MVTLHPPT |
| 181 | B3 clone Heavy Chain aa sequence | EGQLVQSGGGLVQPGGSLTLSCEVSGFTFKNYEMN WVRQAPGKGLEWVSYISSGGIAIPHADSVKGRFTVS RDNAKNLLYLQMNSLRVEDTAVYYCARDENNVRR PFDHWGQGTLVTVSS |
| 182 | B3 clone Heavy Chain nucleotide sequence | GAGGGACAGCTGGTGCAGTCCGGCGGAGGCCTGG TGCAGCCAGGAGGCTCCCTGACCCTGTCTTGTGAG GTGAGCGGCTTCACCTTCAAGAACTACGAGATGA ATTGGGTGCGGCAGGCACCTGGCAAGGGCCTGGA GTGGGTGTCTTATATCAGCTCCGGCGGAATCGCAA TCTTCCACGCAGATTCCGTGAAGGGCAGGTTTACC GTGTCTCGCGACAACGCCAAGAATCTGCTGTACCT GCAGATGAACAGCCTGCGGGTGGAGGACACAGCC GTGTACTATTGCGCCAGGGATGAGAACAACGTGC GGCGGCCCTTCGACCACTGGGGACAGGGCACCCT GGTGACAGTGTCTAGC |
| 183 | B3 clone Heavy Chain CDR1 | GFTFKNY |
| 184 | B3 clone Heavy Chain CDR2 | SSGGIA |
| 185 | B3 clone Heavy Chain CDR3 | DENNVRRPFDH |
| 186 | B3 clone Lambda Chain aa sequence | QSVLTQPPSASGSPGQSVTISCTGSSSDVGAYDFVSW FQQYPGQAPKLIIYEVNKRPSGVPARFSGSKSGNTAS LTVSGLQAEDEADYFCFSYGGTTNLRVFGGGTKLT |
| 187 | B3 clone Lambda Chain nucleotide sequence | CAGTCTGTGCTGACCCAGCCACCTAGCGCCTCCGG CTCTCCCGGCCAGAGCGTGACCATCTCCTGTACAG GCAGCTCCTCTGACGTGGGCGCCTACGATTTCGTG AGCTGGTTTCAGCAGTATCCAGGCCAGGCCCCCAA GCTGATCATCTACGAGGTGAACAAGCGGCCTTCCG GCGTGCCAGCCAGATTCAGCGGCTCCAAGTCTGGC AATACCGCCTCTCTGACAGTGAGCGGCCTGCAGGC AGAGGACGAGGCAGATTACTTCTGCTTTTCTTATG GCGGCACCACAAACCTGCGGGTGTTTGGCGGCGG CACCAAGCTGACA |
| 188 | B3 clone Kappa Chain CDR1 | TGSSSDVGAYDFVS |
| 189 | B3 clone Kappa Chain CDR2 | EVNKRPS |
| 190 | B3 clone Kappa Chain CDR3 | FSYGGTTNLRV |
| 191 | C7 clone Heavy Chain aa sequence | EVQLVESGGNLVQPGASLRLSCTASRFNFNKYAMH WVRQTPGKGLEWVSAISWDSTYIDYGNSVKGRFTIS RDNTRNSLYLQMNSLTAEDTALYYCAKCEDYLRLC SAYDIWGHGTMVTVSS |
| 192 | C7 clone Heavy Chain nucleotide sequence | GAGGTGCAGCTGGTGGAGAGCGGCGGAAACCTGG TGCAGCCAGGAGCCTCTCTGAGGCTGAGCTGTACC GCCTCCCGCTTCAACTTTAATAAGTACGCAATGCA CTGGGTGCGGCAGACCCCTGGCAAGGGCCTGGAG TGGGTGTCTGCCATCAGCTGGGACTCCACATACAT CGATTATGGCAACTCCGTGAAGGGCAGGTTCACC ATCTCTCGGGACAACACAAGGAAATAGCCTGTATCT GCAGATGAATTCCCTGACCGCCGAGGATACAGCC CTGTACTATTGCGCCAAGTGTGAGGACTACCTGCG GCTGTGCTCTGCCTATGATATCTGGGGCCACGGCA CCATGGTGACAGTGAGCTCC |
| 193 | C7 clone Heavy Chain CDR1 | RFNFNKY |
| 194 | C7 clone Heavy Chain CDR2 | SWDSTY |
| 195 | C7 clone Heavy Chain CDR3 | CEDYLRLCSAYDI |
| 196 | C7 clone Kappa Chain aa sequence | DIVMTQSPLSLPVTPGESASISCRSSQSLLHSNGKNYL SWYLQKPGQSPQLLIDLGSNRASGVSDRFSGSGSGT DFTLKISRVEADDVGVYYCMQAVQTPITFGQGTRLA IK |

-continued

| SEQ ID NO | Description | Sequence |
|---|---|---|
| 197 | C7 clone Kappa Chain nucleotide sequence | GACATCGTGATGACCCAGTCTCCTCTGAGCCTGCC CGTGACACCTGGCGAGTCTGCCAGCATCTCCTGTC GGAGCTCCCAGAGCCTGCTGCACTCCAACGGCAA GAATTACCTGTCTTGGTATCTGCAGAAGCCAGGCC AGAGCCCCCAGCTGCTGATCGATCTGGGCTCCAAC AGGGCCTCCGGCGTGTCTGACAGATTCTCTGGCAG CGGCTCCGGCACCGACTTCACCCTGAAGATCAGCA GGGTGGAGGCCGACGATGTGGGCGTGTACTATTG CATGCAGGCCGTGCAGACCCCAATCACATTCGGCC AGGGAACCCGCCTGGCCATCAAG |
| 198 | C7 clone Kappa Chain CDR1 | RSSQSLLHSNGKNYLS |
| 199 | C7 clone Kappa Chain CDR2 | LGSNRAS |
| 200 | C7 clone Kappa Chain CDR3 | MQAVQTPIT |
| 201 | A9 clone Heavy Chain aa sequence | QVQLVQSGAELKTPGASVKVSCKASGYTFTGYYIH WVRQAPGEGLEWTGWINPNSGATRYGQKFQGRVTL TSDTSSSTVYMEVSNLTSDDSAVYYCARELSYSIRGT GPLGYWGLGTLVTVSS |
| 202 | A9 clone Heavy Chain nucleotide sequence | CAGGTGCAGCTGGTGCAGTCCGGCGCAGAGCTGA AGACCCCAGGAGCCAGCGTGAAGGTGTCCTGTAA GGCCTCTGGCTACACCTTCACAGGCTACTATATCC ACTGGGTGCGGCAGGCACCAGGAGAGGGCCTGGA GTGGACCGGCTGGATCAACCCTAATAGCGGCGCC ACAAGATACGGCCAGAAGTTTCAGGGCCGCGTGA CCCTGACAAGCGACACCAGCTCCTCTACAGTGTAT ATGGAGGTGTCCAACCTGACCTCCGACGATTCTGC CGTGTACTATTGCGCCCGGGAGCTGTCTTACAGCA TCAGAGGAACAGGACCACTGGGATATTGGGGCCT GGGCACCCTGGTGACAGTGAGCTCC |
| 203 | A9 clone Heavy Chain CDR1 | GYTFTGY |
| 204 | A9 clone Heavy Chain CDR2 | NPNSGA |
| 205 | A9 clone Heavy Chain CDR3 | ELSYSIRGTGPLGY |
| 206 | A9 clone Kappa Chain aa sequence | EIVLTQSPGTLSLSPGERATLSCRASQSVASKYLAWY QQKPGQAPRLLIYGASSRATGIPDRFSGSGSGTDFTL TISRLEPEDFAVYYCQYYGSSPLTFGQGTKVEIK |
| 207 | A9 clone Kappa Chain nucleotide sequence | GAGATCGTGCTGACCCAGTCTCCAGGCACACTGTC CCTGTCTCCAGGAGAGAGGGCCACCCTGTCTTGTA GAGCCAGCCAGTCCGTGGCCAGCAAGTACCTGGC CTGGTATCAGCAGAAGCCAGGACAGGCACCTAGG CTGCTGATCTACGGAGCCAGCTCCAGGGCAACCG GCATCCCCGACCGCTTCTCTGGCAGCGGCTCCGGC ACAGACTTCACCCTGACAATCTCCAGGCTGGAGCC TGAGGACTTCGCCGTGTACTATTGCCAGTACTATG GCTCTAGCCCACTGACCTTTGGCCAGGGCACAAAG GTGGAGATCAAG |
| 208 | A9 clone Kappa Chain CDR1 | RASQSVASKYLA |
| 209 | A9 clone Kappa Chain CDR2 | GASSRAT |
| 210 | A9 clone Kappa Chain CDR3 | QYYGSSPLT |
| 211 | A2 clone Heavy Chain aa sequence | EVQLAESGGGVVHPGGSLRLSCTASGFTFSRHSMHW VRQAPGKGLEWVAVISHDGSHKFYVDSVKGRFSISR DNAKNTLYLQMSSLSGADTAVYYCVKDISSRSYGY LAGDSWGQGSLVTVSS |
| 212 | A2 clone Heavy Chain nucleotide sequence | GAGGTGCAGCTGGCCGAGTCTGGCGGAGGAGTGG TGCACCCAGGAGGCTCCCTGAGGCTGTCTTGTACC GCCAGCGGCTTCACATTTTCTAGGCACAGCATGCA CTGGGTGCGCCAGGCACCTGGCAAGGGCCTGGAG TGGGTGGCCGTGATCTCCCACGACGGCTCTCACAA GTTCTACGTGGATTCCGTGAAGGGCCGGTTTAGCA TCTCCAGAGACAACGCCAAGAATACCCTGTATCTG CAGATGAGCTCCCTGTCTGGCGCCGACACAGCCGT GTACTATTGCGTGAAGGATATCTCTAGCAGGAGCT |

| SEQ ID NO | Description | Sequence |
|---|---|---|
| | | ACGGCTATCTGGCAGGCGATAGCTGGGGACAGGG CTCCCTGGTGACCGTGTCCTCT |
| 213 | A2 clone Heavy Chain CDR1 | GFTFSRH |
| 214 | A2 clone Heavy Chain CDR2 | SHDGSH |
| 215 | A2 clone Heavy Chain CDR3 | DISSRSYGYLAGDS |
| 216 | A2 clone Kappa Chain aa sequence | DIQMTQSPSSLSASVGDIITITCRASQSVVTYLNWYQ QKPGGAPRLLIYTTSKLQSGVPSRFSGSGSGTLFTLTI NGLRPEDFATYYCQQSYGTPPFTFGPGTRVEIN |
| 217 | A2 clone Kappa Chain nucleotide sequence | GATATTCAGATGACTCAGTCCCCAAGCAGCCTGAG CGCCTCCGTGGGCGACATCATCACCATCACATGCA GGGCCTCTCAGAGCGTGGTGACCTACCTGAACTGG TATCAGCAGAAGCCAGGAGGAGCACCTAGGCTGC TGATCTACACCACATCCAAGCTGCAGTCTGGCGTG CCATCCAGATTCTCCGGCTCTGGCAGCGGCACCCT GTTTACCCTGACAATCAATGGCCTGCGGCCCGAGG ATTTCGCCACATACTATTGTCAGCAGAGCTATGGA ACCCCCCCCTTTACTTTTGGACCAGGCACAAGAGT GGAGATTAAC |
| 218 | A2 clone Kappa Chain CDR1 | RASQSVVTYLN |
| 219 | A2 clone Kappa Chain CDR2 | TTSKLQS |
| 220 | A2 clone Kappa Chain CDR3 | QQSYGTPPFT |
| 221 | E1 clone Heavy Chain aa sequence | QVHLQQWGAGLVKPSETLSLTCAVQGGPFSGYYWS WIRQPPGKGLEWIGEINHSGNTHYNPSLKSRVTISVD TSGNYFSLKLTSVTAADAAVYFCARGQQLLRNYYY YSGMDVWGQGTTVTVSS |
| 222 | E1 clone Heavy Chain nucleotide sequence | CAGGTGCACCTGCAGCAGTGGGGAGCAGGCCTGG TGAAGCCATCCGAGACACTGTCTCTGACATGTGCA GTGCAGGGAGGACCCTTCTCTGGCTACTATTGGAG CTGGATCAGGCAGCCACCTGGCAAGGGCCTGGAG TGGATCGGCGAGATCAACCACAGCGGCAATACCC ACTACAACCCCTCTCTGAAGAGCCGGGTGACCATC AGCGTGGACACATCCGGCAATTACTTCTCCCTGAA GCTGACCTCTGTGACAGCCGCCGATGCCGCCGTGT ATTTTTGCGCCCGGGGCCAGCAGCTGCTGAGAAAC TACTATTACTATTCCGGCATGGACGTGTGGGGACA GGGAACCACAGTGACAGTGAGCTCC |
| 223 | E1 clone Heavy Chain CDR1 | GGPFSGY |
| 224 | E1 clone Heavy Chain CDR2 | NHSGN |
| 225 | E1 clone Heavy Chain CDR3 | GQQLLRNYYYYSGMDV |
| 226 | E1 clone Kappa Chain aa sequence | EIVLTQSPGTLSLSPGERATLSCRASQSVTSTYLAWY QQKLGQPPRLLIFGASNRATGIPDRFSGSGSGTDFTLT ITRLEPEDFAVYYCQRYGGSITFGQGTRLEIK |
| 227 | E1 clone Kappa Chain nucleotide sequence | GAGATCGTGCTGACACAGTCCCCAGGCACCCTGA GCCTGTCCCCAGGAGAGCGGGCCACACTGTCCTGT AGAGCCTCTCAGAGCGTGACCTCTACATACCTGGC CTGGTATCAGCAGAAGCTGGGCCAGCCCCCTAGG CTGCTGATCTTCGGCGCCTCTAACAGGGCCACAGG CATCCCTGACCGCTTCTCCGGCTCTGGCAGCGGCA CCGACTTCACCCTGACAATCACCAGACTGGAGCCC GAGGACTTCGCCGTGTACTATTGCCAGCGGTACGG CGGCAGCATCACATTTGGCCAGGGCACCAGACTG GAGATCAAG |
| 228 | E1 clone Kappa Chain CDR1 | RASQSVTSTYLA |
| 229 | E1 clone Kappa Chain CDR2 | GASNRAT |
| 230 | E1 clone Kappa Chain CDR3 | QRYGGSIT |
| 231 | C10 clone Heavy Chain aa sequence | EVQLVQSGGGVVQPRRSLRLSCAASGFTFSNYGMH WVRQVPGKGLQWVAIIWYDGSNKHYAASVQGRFRI |

| SEQ ID NO | Description | Sequence |
|---|---|---|
| | | SRDNSKNTVYLQMDGLRAEDTGMYYCVRDATTAT TEGTSQYYFDLWGQGALVTVSS |
| 232 | C10 clone Heavy Chain nucleotide sequence | GAGGTGCAGCTGGTGCAGTCCGGCGGAGGAGTGG TGCAGCCACGGAGATCTCTGAGGCTGAGCTGTGCC GCCTCCGGCTTCACCTTTTCTAACTACGGAATGCA CTGGGTGCGCCAGGTGCCTGGCAAGGGCCTGCAG TGGGTGGCCATCATCTGGTACGACGGCTCCAATAA GCACTATGCCGCCTCTGTGCAGGGCAGGTTCCGCA TCTCTCGGGATAACAGCAAGAATACCGTGTATCTG CAGATGGACGGCCTGCGGGCCGAGGATACAGGCA TGTACTATTGCGTGAGAGACGCCACCACAGCCACC ACAGAGGGCACCAGCCAGTACTATTTTGATCTGTG GGGACAGGGCGCCCTGGTGACAGTGAGCTCC |
| 233 | C10 clone Heavy Chain CDR1 | GFTFSNY |
| 234 | C10 clone Heavy Chain CDR2 | WYDGSN |
| 235 | C10 clone Heavy Chain CDR3 | DATTATTEGTSQYYFDL |
| 236 | C10 clone Kappa Chain aa sequence | DIVMTQSPDSLAVSLGERATINCKSSQTLLYTSNSKN YLAWYQQKVGQPPRLLIYWASTRESGVPDRFSGSGS GTDFTLTISSLLAEDVAVYYCQQYYTTPLTFGGGTK VEVK |
| 237 | C10 clone Kappa Chain nucleotide sequence | GACATCGTGATGACCCAGAGCCCCGATTCCCTGGC CGTGTCTCTGGGAGAGAGGGCAACAATCAACTGT AAGAGCTCCCAGACCCTGCTGTACACATCCAACTC TAAGAATTACCTGGCCTGGTATCAGCAGAAAGTG GGACAGCCACCTAGGCTGCTGATCTATTGGGCCTC TACCAGGGAGAGCGGCGTGCCAGACAGATTCAGC GGCTCCGGCTCTGGCACAGACTTCACCCTGACAAT CTCTAGCCTGCTGGCCGAGGACGTGGCCGTGTACT ATTGCCAGCAGTACTATACCACACCCCTGACCTTC GGCGGCGGCACAAAGGTGGAGGTGAAG |
| 238 | C10 clone Kappa Chain CDR1 | KSSQTLLYTSNSKNYLA |
| 239 | C10 clone Kappa Chain CDR2 | WASTRES |
| 240 | C10 clone Kappa Chain CDR3 | QQYYTTPLT |
| 241 | B12 clone Heavy Chain aa sequence | EVQLVESGGGVVHPGKSLTLSCEASGFTFNDHGIHW VRRAPGKGLEWLALISKDGSKEYSTDSVKGRFTVSR DNSRNTVFLQMKSLTTEDTAIYYCAKDMGQCSSPSC STMDSYFAMDVWGQGTTVIVSS |
| 242 | B12 clone Heavy Chain nucleotide sequence | GAGGTGCAGCTGGTGGAGTCCGGCGGAGGAGTGG TGCACCCTGGCAAGTCTCTGACCCTGAGCTGTGAG GCCAGCGGCTTCACCTTCAACGACCACGGCATCCA CTGGGTGCGGAGAGCACCTGGCAAGGGCCTGGAG TGGCTGGCCCTGATCTCTAAGGACGGCAGCAAGG AGTACAGCACCGATTCCGTGAAGGGCCGGTTCAC AGTGTCCAGGGATAACTCTCGCAATACCGTGTTTC TGCAGATGAAGTCTCTGACCACAGAGGACACAGC CATCTACTATTGCGCCAAGGATATGGGCCAGTGCA GCTCCCCCTCCTGTTCTACCATGGACAGCTATTTC GCAATGGACGTGTGGGGACAGGGAACCACAGTGA TCGTGTCTAGC |
| 243 | B12 clone Heavy Chain CDR1 | GFTFNDH |
| 244 | B12 clone Heavy Chain CDR2 | SKDGSK |
| 245 | B12 clone Heavy Chain CDR3 | DMGQCSSPSCSTMDSYFAMDV |
| 246 | B12 clone Kappa Chain aa sequence | DIVMTQSPLSLPVTPGEPASISCRSSQNLRHNNGYNY LNWYLQKPGQSPQLLIYLGSIRASGVPDRFSGSGSGT DFTLKISRVEAEDVGVYYCMQALQTPPWTFGQGTK VDFK |
| 247 | B12 clone Kappa Chain nucleotide sequence | GACATCGTGATGACCCAGTCCCCTCTGTCTCTGCC AGTGACACCCGGCGAGCCTGCCTCTATCAGCTGTC GGAGCTCCCAGAACCTGAGACACAACAATGGCTA CAACTATCTGAATTGGTACCTGCAGAAGCCAGGCC |

| SEQ ID NO | Description | Sequence |
|---|---|---|
| | | AGTCTCCCCAGCTGCTGATCTATCTGGGCAGCATC AGGGCCTCCGGCGTGCCCGACCGCTTCTCCGGCTC TGGCAGCGGCACCGACTTCACCCTGAAGATCAGC CGGGTGGAGGCAGAGGACGTGGGCGTGTACTATT GCATGCAGGCCCTGCAGACCCCCCCTTGGACATTC GGCCAGGGCACCAAGGTGGACTTCAAG |
| 248 | B12 clone Kappa Chain CDR1 | RSSQNLRHNNGYNYLN |
| 249 | B12 clone Kappa Chain CDR2 | LGSIRAS |
| 250 | B12 clone Kappa Chain CDR3 | MQALQTPPWT |
| 251 | G7 clone Heavy Chain aa sequence | QVQLVQSGAEVKKPGASVKVSCKASGYTFTSHYMH WVRQAPGQGLEWMGIISPTGDFTNYAQKFQGRVTL TRDTSTSTDYMEVTSLRSEDTAVYYCARDCSAWAP DYWGQGTLVTVSS |
| 252 | G7 clone Heavy Chain nucleotide sequence | CAGGTGCAGCTGGTGCAGTCCGGCGCAGAGGTGA AGAAGCCAGGAGCCAGCGTGAAGGTGTCCTGTAA GGCCTCTGGCTACACCTTCACATCTCACTATATGC ACTGGGTGCGGCAGGCACCAGGACAGGGCCTGGA GTGGATGGGCATCATCAGCCCTACAGGCGACTTCA CCAACTACGCCCAGAAGTTTCAGGGCCGGGTGAC CCTGACAAGAGACACCTCTACAAGCACCGATTAT ATGGAGGTGACATCCCTGAGGTCTGAGGATACCG CCGTGTACTATTGCGCAAGGGACTGTTCCGCCTGG GCCCCCGATTACTGGGGACAGGGCACACTGGTGA CCGTGAGCTCC |
| 253 | G7 clone Heavy Chain CDR1 | GYTFTSH |
| 254 | G7 clone Heavy Chain CDR2 | SPTGDF |
| 255 | G7 clone Heavy Chain CDR3 | DCSAWAPDY |
| 256 | G7 clone Kappa Chain aa sequence | QSALTRPPSVSRCPGQSITISCSGTSSDVGHDNHVSW YQQHPGRAPKLMVYEVRNRPSGVSDRFSGSKSGNT ASLTISGLQAEDEATYYCCSYTTTHRYIFGGGTKLT |
| 257 | G7 clone Kappa Chain nucleotide sequence | CAGTCTGCCCTGACAAGGCCCCCTTCTGTGAGCCG CTGCCCTGGACAGAGCATCACAATCTCCTGTTCTG GCACCAGCTCCGACGTGGGCCACGATAACCACGT GTCCTGGTACCAGCAGCACCCAGGAAGGGCACCC AAGCTGATGGTGTATGAGGTGCGGAACAGACCAA GCGGCGTGTCCGACAGGTTCAGCGGCTCCAAGTCT GGCAATACAGCCTCTCTGACCATCAGCGGCCTGCA GGCAGAGGATGAGGCAACCTACTATTGCTGTTCTT ACACCACAACCCACCGGTATATCTTTGGCGGCGGC ACAAAGCTGACC |
| 258 | G7 clone Kappa Chain CDR1 | SGTSSDVGHDNHVS |
| 259 | G7 clone Kappa Chain CDR2 | EVRNRPS |
| 260 | G7 clone Kappa Chain CDR3 | CSYTTTHRYI |
| 261 | E11 clone Heavy Chain aa sequence | QVQLLGSGPGLVKPSETLSLTCTVSGASISSPGYYWG FIRQSPGKGLEWIGSMVSGGTTYYNPSLKSRVTISMD MSNNQFSLRLNSVTAADTALYYCARGSRQLVRRATI DYWGQGALFTVSP |
| 262 | E11 clone Heavy Chain nucleotide sequence | CAGGTGCAGCTGCTGGGCAGCGGCCCAGGCCTGG TGAAGCCTTCTGAGACACTGAGCCTGACCTGTACA GTGTCTGGCGCCAGCATCAGCTCCCCAGGCTACTA TTGGGGCTTCATCAGGCAGAGCCCAGGCAAGGGC CTGGAGTGGATCGGCTCCATGGTGTCTGGCGGCAC CACATACTATAACCCTAGCCTGAAGTCCCGGGTGA CAATCTCCATGGACATGTCTAACAATCAGTTCAGC CTGAGGCTGAATTCCGTGACCGCCGCCGATACAGC CCTGTACTATTGCGCAAGGGGCTCCCGCCAGCTGG TGCGGAGAGCAACCATCGACTACTGGGGACAGGG CGCCCTGTTTACAGTGTCTCCC |
| 263 | E11 clone Heavy Chain CDR1 | GASISSPGY |

| SEQ ID NO | Description | Sequence |
|---|---|---|
| 264 | E11 clone Heavy Chain CDR2 | VSGGT |
| 265 | E11 clone Heavy Chain CDR3 | GSRQLVRRATIDY |
| 266 | E11 clone Lambda Chain aa sequence | QSVLTGPPSVSAGPGQQVFISCSGNSSNIGNNYVSWY QQLPGTAPKLLIYDSNKRPSGIPDRFSGSKSGTSATLG ITGLQTGDEADYYCGTWDSSLSAGVFGGGTKLT |
| 267 | E11 clone Lambda Chain nucleotide sequence | CAGTCTGTGCTGACCGGACCACCTTCCGTGTCTGC CGGACCAGGACAGCAGGTGTTCATCAGCTGTTCCG GCAACAGCTCCAATATCGGCAACAATTACGTGTCT TGGTATCAGCAGCTGCCAGGCACAGCCCCCAAGC TGCTGATCTACGACTCTAACAAGCGGCCTAGCGGC ATCCCAGATAGATTCTCTGGCAGCAAGTCCGGCAC CAGCGCCACACTGGGCATCACCGGCCTGCAGACA GGCGACGAGGCAGATTACTATTGCGGAACCTGGG ACTCTAGCCTGTCCGCCGGCGTGTTTGGAGGAGGA ACCAAGCTGACA |
| 268 | E11 clone Lambda Chain CDR1 | SGNSSNIGNNYVS |
| 269 | E11 clone Lambda Chain CDR2 | DSNKRPS |
| 270 | E11 clone Lambda Chain CDR3 | GTWDSSLSAGV |
| 271 | G5 clone Heavy Chain aa sequence | EVQLVESGGGLVKPGESLRLSCAASGFTFSSYSMSW VRQAPGKGLEWVSCITSSGHTYYADSVKGRFAISRD NGKNSLYLQMNNLRAEDTAVYFCAKELGAHSGLFY NGVFDYWGQGNPVTVSS |
| 272 | G5 clone Heavy Chain nucleotide sequence | GAGGTGCAGCTGGTGGAGTCCGGCGGAGGCCTGG TGAAGCCAGGCGAGTCTCTGAGGCTGAGCTGTGC CGCCTCCGGCTTCACCTTTAGCTCCTACAGCATGT CCTGGGTGCGCCAGGCACCTGGCAAGGGCCTGGA GTGGGTGTCCTGCATCACCTCTAGCGGCCACACAT ACTATGCCGACTCTGTGAAGGGCCGGTTCGCCATC AGCCGGGATAACGGCAAGAATAGCCTGTACCTGC AGATGAACAATCTGCGGGCCGAGGACACCGCCGT GTATTTTTGTGCAAAGGAGCTGGGAGCACACTCTG GCCTGTTCTACAACGGCGTGTTTGATTATTGGGGC CAGGGCAATCCCGTGACAGTGTCCTCT |
| 273 | G5 clone Heavy Chain CDR1 | GFTFSSY |
| 274 | G5 clone Heavy Chain CDR2 | TSSGH |
| 275 | G5 clone Heavy Chain CDR3 | ELGAHSGLFYNGVFDY |
| 276 | G5 clone Lambda Chain aa sequence | QSALTQPASVSGSPGQSITISCTGTSSDVGGYNYVSW YQQHPGKAPKLMIYEVSNRPSGVSNRFSGSKGNTAS LTISGLRGEDEADYYCSSYTSSSTLVVFGGGTKLT |
| 277 | G5 clone Lambda Chain nucleotide sequence | CAGTCCGCCCTGACCCAGCCAGCCTCCGTGTCTGG CAGCCCCGGCCAGTCTATCACAATCAGCTGTACCG GCACAAGCTCCGACGTGGGCGGCTACAACTACGT GAGCTGGTACCAGCAGCACCCAGGCAAGGCACCT AAGCTGATGATCTATGAGGTGTCCAACAGGCCAA GCGGCGTGTCCAATAGATTCTCCGGCTCTAAGGGC AATACCGCCTCCCTGACAATCTCTGGCCTGAGGGG AGAGGACGAGGCAGATTACTATTGCTCTAGCTAC ACCTCCTCTAGCACACTGGTGGTGTTTGGCGGCGG CACCAAGCTGACA |
| 278 | G5 clone Lambda Chain CDR1 | TGTSSDVGGYNYVS |
| 279 | G5 clone Lambda Chain CDR2 | EVSNRPS |
| 280 | G5 clone Lambda Chain CDR3 | SSYTSSSTLVV |
| 281 | H8 clone Heavy Chain aa | QVHLQQWGAGLVKPSETLSLTCAVQGGPFSGYYWS |

| SEQ ID NO | Description | Sequence |
|---|---|---|
| | sequence | WIRQPPGKGLEWIGEINHSGNTHYNPSLKSRVTISVD TSGNYFSLKLTSVTAADAAVYFCARGQQLLRNYYY YSGMDVWGQGTTVTVSS |
| 282 | H8 clone Heavy Chain nucleotide sequence | CAGGTGCACCTGCAGCAGTGGGGAGCAGGCCTGG TGAAGCCATCCGAGACACTGTCTCTGACATGTGCA GTGCAGGGAGGACCCTTCTCTGGCTACTATTGGAG CTGGATCAGGCAGCCACCTGGCAAGGGCCTGGAG TGGATCGGCGAGATCAACCACAGCGGCAATACCC ACTACAACCCCTCTCTGAAGAGCCGGGTGACCATC AGCGTGGACACATCCGGCAATTACTTCTCCCTGAA GCTGACCTCTGTGACAGCCGCCGATGCCGCCGTGT ATTTTTGCGCCCGGGGCCAGCAGCTGCTGAGAAAC TACTATTACTATTCCGGCATGGACGTGTGGGGACA GGGAACCACAGTGACAGTGAGCTCC |
| 283 | H8 clone Heavy Chain CDR1 | GGPFSGY |
| 284 | H8 clone Heavy Chain CDR2 | NHSGN |
| 285 | H8 clone Heavy Chain CDR3 | GQQLLRNYYYYSGMDV |
| 286 | H8 clone Lambda Chain aa sequence | QSALTQPASVSGSPGQSITISCTETSRDVGDYNYVSW YQQHPGPAPKLIMYEVHKRPSGISNRFSGSKSGTTAS LTISGLQADDEGDYYCSSYTDKNTYVFGSGTQVT |
| 287 | H8 clone Lambda Chain nucleotide sequence | CAGTCTGCCCTGACCCAGCCAGCCTCTGTGAGCGG CTCCCCTGGCCAGTCCATCACAATCTCTTGTACCG AGACATCTCGGGACGTGGGCGATTACAACTATGT GAGCTGGTACCAGCAGCACCCAGGACCTGCACCA AAGCTGATCATGTATGAGGTGCACAAGCGGCCCT CTGGCATCAGCAATAGATTCTCTGGCAGCAAGTCC GGCACCACAGCCAGCCTGACCATCTCCGGCCTGCA GGCAGACGATGAGGGCGACTACTATTGCAGCTCC TACACCGATAAGAACACATACGTGTTCGGCAGCG GCACCCAGGTGACA |
| 288 | H8 clone Lambda Chain CDR1 | TETSRDVGDYNYVS |
| 289 | H8 clone Lambda Chain CDR2 | EVHKRPS |
| 290 | H8 clone Lambda Chain CDR3 | SSYTDKNTYV |
| 291 | gp350 B95-8 (2-425) D296R/I160R Avi-His | EAALLVCQYTIQSLIHLTGEDPGFFNVEIPEFPFYPTC NVCTADVNVTINFDVGGKKHQLDLDFGQLTPHTKA VYQPRGAFGGSENATNLFLLELLGAGELALTMRSKK LPINVTTGEEQQVSLESVDYFQDVFGTMWCHHAE MQNPVYLIPETVPYI<u>D</u>WDNCNSTNITAVVRAQGLDV TLPLSLPTSAQDSNF<u>S</u>VKTEMLGNEIDIECIMEDGEIS QVLPGDNKFNITCSGYESHVPSGGILTSTSPVATPIPG TGYAYSL<u>R</u>LTPRPVSRFLGNNSILYVFYSGNGPKASG GRYCIQS<u>N</u>IVFSDEIPASQDMPTNTTDITYVGDNATY SVPMVTSEDANSPNVTVTAFWAWPNNTETDFKCKW TLTSGTPSGCENISGAFASNRTFDITVSGLGTAPKTLII TRTATNATTTHKVIFSKAPGSGLNDIFEAQKIEWHE HHHHHH |
| 292 | NAM encoding SEQ ID NO: 281 | GAAGCTGCCCTGCTCGTGTGCCAGTACACCATCCA GAGCCTGATCCACCTGACCGGCGAGGACCCCGGC TTCTTCAACGTGGAAATCCCCGAGTTCCCCTTCTA CCCTACCTGCAACGTGTGCACCGCCGACGTGAACG TGACCATCAACTTCGACGTGGGCGGCAAGAAGCA CCAGCTGGACCTGGATTTCGGCCAGCTGACCCCTC ACACCAAGGCCGTGTATCAGCCCAGAGGCGCCTTT GGCGGCAGCGAGAACGCCACCAATCTGTTTCTGCT GGAACTCCTAGGCGCCGGCGAGCTGGCCCTGACC ATGAGAAGCAAGAAACTGCCCATCAATGTGACCA CAGGCGAGGAACAGCAGGTGTCCCTGGAAAGCGT GGACGTGTACTTTCAAGACGTGTTCGGCACCATGT GGTGCCACCACGCCGAGATGCAGAACCCCGTGTA CCTGATCCCCGAGACAGTGCCCTACATCGATTGGG ACAACTGCAACAGCACCAACATCACCGCCGTCGT GCGGGCCCAGGGACTGGATGTGACACTGCCTCTG |

| SEQ ID NO | Description | Sequence |
|---|---|---|
| | | AGCCTGCCTACCAGCGCCCAGGACAGCAACTTCA |
| | | GCGTGAAAACCGAGATGCTGGGCAACGAGATCGA |
| | | CATCGAGTGCATCATGGAAGATGGCGAGATCAGC |
| | | CAGGTGCTGCCCGGCGACAACAAGTTCAACATCA |
| | | CATGCAGCGGCTACGAGAGCCACGTGCCATCTGG |
| | | CGGCATCCTGACCAGCACAAGCCCAGTGGCCACA |
| | | CCCATCCCTGGCACAGGCTACGCCTACAGCCTGAG |
| | | ACTGACCCCCAGACCCGTGTCCAGATTCCTGGGCA |
| | | ACAACAGCATCCTGTACGTGTTCTACAGCGGCAAC |
| | | GGCCCCAAGGCCTCTGGCGGCCGGTACTGTATCCA |
| | | GAGCAACATCGTGTTCAGCGACGAGATCCCCGCC |
| | | AGCCAGGACATGCCCACCAATACCACCGACATCA |
| | | CGTACGTGGGCGACAATGCCACCTACAGCGTGCC |
| | | AATGGTCACCTCCGAGGACGCCAACAGCCCCAAC |
| | | GTGACCGTGACAGCCTTTTGGGCCTGGCCTAACAA |
| | | CACCGAGACAGACTTCAAGTGCAAGTGGACCCTG |
| | | ACCTCCGGCACCCCTAGCGGCTGCGAGAATATCA |
| | | GCGGAGCCTTCGCCAGCAACCGGACCTTCGATATC |
| | | ACCGTGTCTGGCCTGGGCACCGCCCCAAGACCCT |
| | | GATCATCACCAGAACCGCCACAAATGCCACCACC |
| | | ACAACCCACAAAGTGATCTTCAGCAAGGCCCCCG |
| | | GCTCTGGCCTGAACGACATTTTTGAGGCCCAGAAG |
| | | ATTGAGTGGCATGAACATCACCACCACCACCAT |
| 293 | Macaque Light chain backbone nucleotide sequence | tcgcgcgttt cggtgatgac ggtgaaaacc tctgacacat gcagctcccg gagacggtca cagcttgtct gtaagcggat gccgggagca gacaagcccg tcagggcgcg tcagcgggtg ttggcgggtg tcggggctgg cttaactatg cggcatcaga gcagattgta ctgagagtgc accatatgcg gtgtgaaata ccgcacagat gcgtaaggag aaaataccgc atcagattgg ctattggcca ttgcatacgt tgtatccata tcataatatg tacatttata ttggctcatg tccaacatta ccgccatgtt gacattgatt attgactagt tattaatagt aatcaattac ggggtcatta gttcatagcc catatatgga gttccgcgtt acataactta cggtaaatgg cccgcctggc tgaccgccca acgaccccg cccattgacg tcaataatga cgtatgttcc catagtaacg ccaatagggac ttttccattg acgtcaatgg gtggagtatt tacggtaaac tgcccacttg gcagtacatc aagtgtatca tatgccaagt acgccccta ttgacgtcaa tgacggtaaa tggcccgcct ggcattatgc ccagtacatg accttatggg actttcctac ttggcagtac atctacgtat tagtcatcgc tattaccatg gtgatgcggt tttggcagta catcaatggg cgtggatagc ggtttgactc acggggattt ccaagtctcc accccattga cgtcaatggg agtttgtttt ggcaccaaaa tcaacgggac tttccaaaat gtcgtaacaa ctccgcccca ttgacgcaaa tgggcggtag gcgtgtacgg tgggaggtct atataagcag agctcgttta gtgaaccgtc agatcgcctg gagacgccat ccacgctgtt ttgacctcca tagaagacac cgggaccgat ccagcctcca tcggctcgca tctctccttc acgcgccgc cgccctacct gaggccgcca tccacgccgg ttgagtcgcg ttctgccgcc tcccgcctgt ggtgcctcct gaactgcgtc cgccgtctag gtaagtttaa agctcaggtc gagaccgggc ctttgtccgg cgctcccttg gagcctacct agactcagcc ggctctccac gctttgcctg accctgcttg ctcaactcta gttaacggtg gagggcagtg tagtctgagc agtacacgtt gctgccgcgc gcgccaccag acataatagc tgacagacta acagactgtt cctttccatg ggtcttttct gcagtcaccg tcgtcgacac gtgtgatcag atatcgcggc cgctctagac caccatggga tggtcatgta tcatcctttt tctagtagca actgcaaccg tgtacattc ccagtctgcc ctgactcagc ctccctctgt gtctgggtct cctggacagt cggtcaccat ctcctgcact ggaaccagca gtgacgttga tggttataac tatgtctcct ggtaccaaca acatccaggc aaagccccca aactcatgat ttatggtgtc agcaatcggc cctcagggt ctctgatcgc ttctctggct ccaagtctgg caacacggcc tccctgacca tctctgggct ccaggctgag gacgaggctg attattactg ttgttcatct acaaccagtt acacttacat cttcggaact gggaccaagg tcacagtact aggtcagccc aaggctgccc cctcggtcac tctcttcccg ccctcctctg aggagcttca agccaacaag gccacactag tgtgtctgat cagtgacttc tacccgggag ccgtggaagt ggcctggaag gcagatggca gcgctgtcaa cgcgggagtg gagaccacca accctccaa acagagcaac aacaagtacg cggccagcag ctacctgagc ctgacgtccg accagtggaa gtcccacaag agctacagct gccaggtcac gcacgaaggg agcaccgtgg agaagacagt ggcccctgca gaatgttcat agggatccag atctgctgtg ccttctagtt gccagccatc tgttgtttgc cctcccccg tgccttcctt gaccctggaa ggtgccactc ccactgtcct ttcctaataa aatgaggaaa ttgcatcgca ttgtctgagt aggtgtcatt ctattctggg gggtggggtg ggcaggaca gcaagggga ggattgggaa gacaatagca ggcatgctgg ggatgcggtg ggctctatgg gtacccaggt gctgaagaat tgacccggtt cctcctgggc cagaaagaag caggcacatc ccttctctg tgacacaccc tgtccacgcc cctggttctt agttccagcc ccactcatag gacactcata gctcaggagg gctccgcctt caatcccacc cgctaaagta catggagcgg tctctccctc |

| SEQ ID NO | Description | Sequence |
|---|---|---|
| | | cctcatcagc ccaccaaacc aaacctagcc tccaagagtg ggaagaaatt
aaagcaagat aggctattaa gtgcagaggg agagaaaatg cctccaacat
gtgaggaagt aatgagagaa atcatagaat tttaaggcca tgatttaagg
ccatcatggc cttaatcttc cgcttcctcg ctcactgact cgctgcgctc
ggtcgttcgg ctgcggcgag cggtatcagc tcactcaaag
gcggtaatac ggttatccac agaatcaggg gataacgcag gaaagaacat
gtgagcaaaa ggccagcaaa aggccaggaa ccgtaaaaag gccgcgttgc
tggcgttttt ccataggctc cgccccctg acgagcatca caaaaatcga
cgctcaagtc agaggtggcg aaacccgaca ggactataaa gataccaggc
gtttccccct ggaagctccc tcgtgcgctc tcctgttccg
accctgccgc ttaccggata cctgtccgcc tttctccctt cgggaagcgt
ggcgctttct catagctcac gctgtaggta tctcagttcg gtgtaggtcg
ttcgctccaa gctgggctgt gtgcacgaac cccccgttca gcccgaccgc
tgcgccttat ccggtaacta tcgtcttgag tccaacccgg taagacacga
cttatcgcca ctggcagcag ccactggtaa caggattagc
agagcgaggt atgtaggcgg tgctacagag ttcttgaagt ggtggcctaa
ctacggctac actagaagaa cagtatttgg tatctgcgct ctgctgaagc
cagttacctt cggaaaaaga gttggtagct cttgatccgg caaacaaacc
accgctggta gcggtggttt ttttgtttgc aagcagcaga ttacgcgcag
aaaaaaagga tctcaagaag atcctttgat cttttctacg gggtctgacg
ctcagtggaa cgaaaactca cgttaaggga ttttggtcat gagattatca
aaaaggatct tcacctagat cctttaaat taaaaatgaa gttttaaatc
aatctaaagt atatatgagt aaacttggtc tgacagttac caatgcttaa
tcagtgaggc acctatctca gcgatctgtc tatttcgttc atccatagtt
gcctgactcg ggggggggg gcgctgaggt ctgcctcgtg aagaaggtgt
tgctgactca taccaggcct gaatcgcccc atcatccagc cagaaagtga
gggagccacg gttgatgaga gctttgttgt aggtggacca gttggtgatt
ttgaacttt gctttgccac ggaacggtct gcgttgtcgg gaagatgcgt
gatctgatcc ttcaactcag caaaagttcg atttattcaa caaagccgcc
gtcccgtcaa gtcagcgtaa tgctctgcca gtgttacaac caattaacca
attctgatta gaaaaactca tcgagcatca aatgaaactg caatttattc
atatcaggat tatcaatacc atattttga aaaagccgtt tctgtaatga
aggagaaaac tcaccgaggc agttccatag gatggcaaga tcctggtatc
ggtctgcgat tccgactcgt ccaacatcaa tacaacctat taatttcccc
tcgtcaaaaa taaggttatc aagtgagaaa tcaccatgag tgacgactga
atccggtgag aatggcaaaa gcttatgcat ttctttccag acttgttcaa
caggccagcc attacgctcg tcatcaaaat cactcgcatc aaccaaaccg
ttattcattc gtgattgcgc ctgagcgaga cgaaatacgc gatcgctgtt
aaaaggacaa ttacaaacag gaatcgaatg caaccggcgc aggaacactg
ccagcgcatc aacaatattt tcacctgaat caggatattc ttctaatacc
tggaatgctg ttttcccggg gatcgcagtg gtgagtaacc atgcatcatc
aggagtacgg ataaaatgct tgatggtcgg aagaggcata aattccgtca
gccagtttag tctgaccatc tcatctgtaa catcattggc aacgctacct
ttgccatgtt tcagaaacaa ctctggcgca tcgggcttcc catacaatcg
atagattgtc gcacctgatt gcccgacatt atcgcgagcc catttatacc
catataaatc agcatccatg ttggaattta atcgcggcct cgagcaagac
gtttcccgtt gaatatggct cataacaccc cttgtattac tgtttatgta
agcagacagt tttattgttc atgatgatat attttatct tgtgcaatgt
aacatcagag attttgagac acaacgtggc tttccccccc cccccattat
tgaagcattt atcagggtta ttgtctcatg agcggataca tatttgaatg
tatttagaaa aataaacaaa taggggttcc gcgcacattt ccccgaaaag
tgccacctga cgtctaagaa accattatta tcatgacatt aacctataaa
aataggcgta tcacgaggcc ctttcgtc | bolded/underlined letters indicate amino acids that differ from wild-type.

BRIEF DESCRIPTION OF THE FIGURES

FIG. 3A: Lymphocytes were gated by SSC and FSC. FIG. 3: B cells were gated by CD19 and excluding non-B cell surface markers. FIG. 3C: Surface IgG+ B cells were further gated by IgG and excluding IgM. SSC and FSC denote side- and forward-scatter, respectively. FIGS. 3D-3F: staining profile of IgG+ B cells with various EBV gp350 probes. There were three gp350 variants used to co-stain with anti-CD21 (complement receptor 2, CR2); WT, wild-type gp350 (FIG. 3D); D296R (FIG. 3E); and D296R/I160R (FIG. 3F). All the mutant probes were designed to reduce the CR2-binding property of gp350. WT and D296R gp350 probes bind to virtually all the IgG+ B cells while the D296R/I160R gp350 probe completely knocked down non-specific gp350 staining of B cells.

FIG. 5A shows rhesus macaque immunization schedule with EBV gp350 nanoparticles followed by B cell sorting. FIG. 5B shows animals Cy137 and Cy651 displayed the highest neutralization titers and were selected for B cell sorting. FIGS. 5C-5F show the results of B cell sorting strategy for non-human primate B cells.

FIG. 6A shows gp350-specific B cell sorting. FIG. 6B shows the neutralization analysis of select antibodies (72A1 antibody from ATCC is shown for reference).

FIG. 8A shows that humanized H02, as well as murinized H02, neutralize EBV equivalent to the parental macaque H02. FIG. 8B shows that the neutralizing potency of H02 (human, mouse and macaque) is about 50-fold higher than 72A1 antibody (shown for reference).

FIG. 9A is a schematic of the competition-based FACS assay. FIG. 9B shows flow cytometry plots of gp350-binding to B cells in the presence and absence of control antibodies. FIG. 9C shows flow cytometry plots of rhesus macaque antibodies described in this disclosure (two non-neutralizing antibodies F11 and G12 are shown for reference).

FIGS. 10A-10C: Analysis of Vaccine-elicited Anti-gp350 mAbs: characterization of antibodies.

FIG. 10A shows the neutralization potency of select antibodies. FIG. 10B shows the affinity of antibodies to gp350. FIG. 10C shows the CDR H3 isoelectric point of select antibodies, indicating that gp350-specific neutralizing antibodies tend to have a higher isoelectric point than typical antibodies (Ebola GP-elected antibodies are shown for reference).

DETAILED DESCRIPTION

I. Definitions

Figure 1:
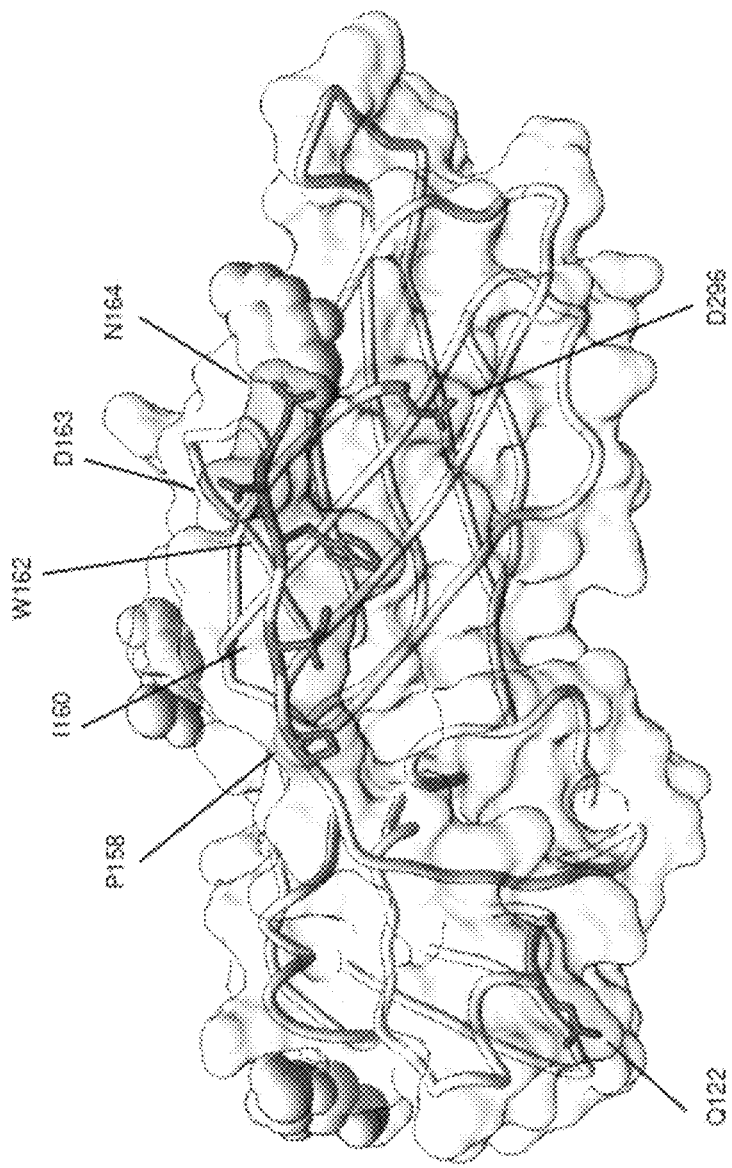
FIG. 1: Design of gp350 probes that knock out CR2-binding property. Selected residues substantially involved in CR2-binding, but less in antibody (H02) recognition, are defined by structures of gp350-CR2 and gp350-H02 Fab complexes. CR2-knock out (KO) mutations are designed by substitution of one or more residues among the selected residues. Experimentally tested mutations include Q122N (glycan addition at 122); D163N/164bS (glycan addition at 163 and one residue insertion between 164 and 165); D296R; W162A/D163A/N164A; D296R/I160R; D296R/P158R; D296R/P158N/I160T (glycan addition at 158); D296R/P158R/I160R.
Figure 2:
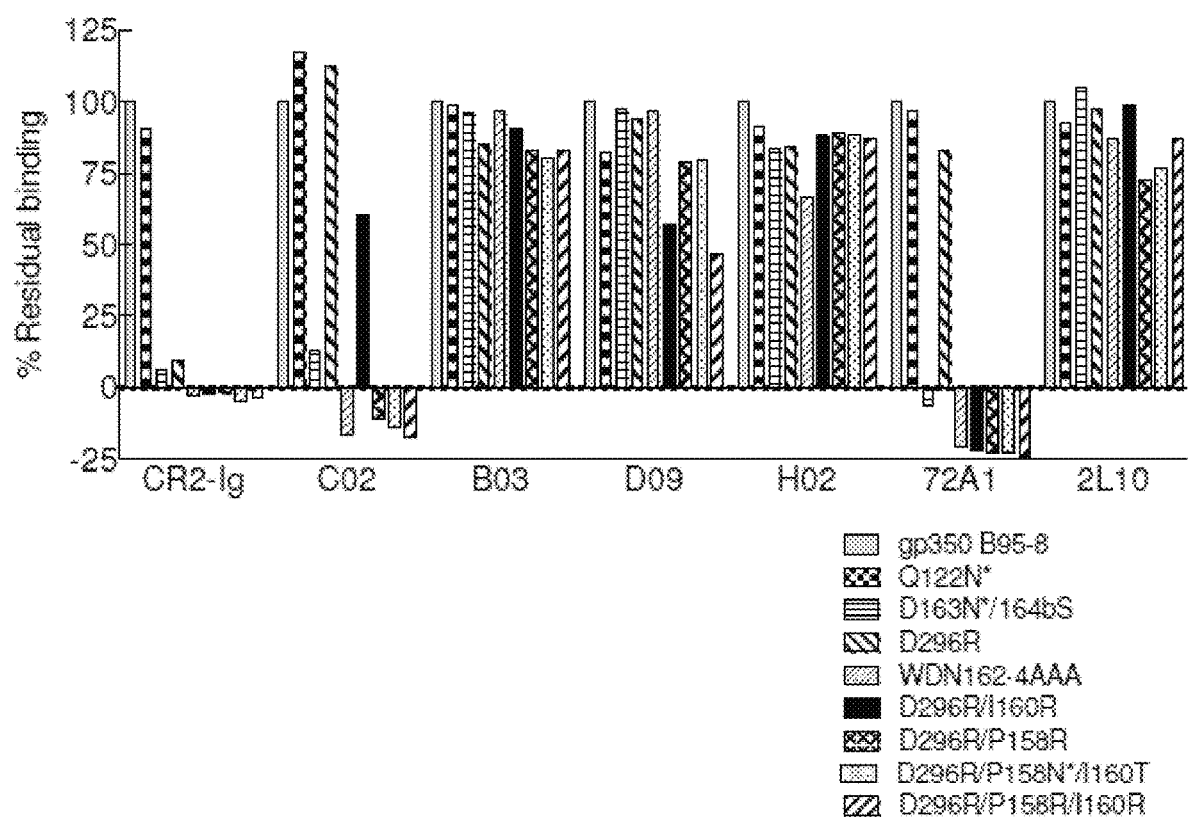
FIG. 2: CR2- and antibody-binding profile of gp350 mutants. Binding of CR2-Ig (chimeric molecule of CR2 SCR1-2 domain and IgG Fc region) and a set of gp350-specific monoclonal antibodies were measured by biolayer interferometry using Octet instrument. CR2-Ig or antibodies were immobilized on biosensors through protein A or anti-mouse Fc antibody (for 2L10) and assessed binding properties of various recombinant gp350 mutants. Graph shows percent binding of each mutant relative to its parental (wild-type) gp350. D296R mutation greatly (but not completely) eliminated CR2-binding while retaining binding of all the monoclonal antibodies. An additional mutation on D296R mutant completely abrogated the CR2-binding property of gp350. Among these variants, D296R/I160R retained binding of most monoclonal antibodies and was therefore chosen for further characterization. 2L10 is a murine non-CR2-binding site targeting antibody, used as a control.
Figure 3A:
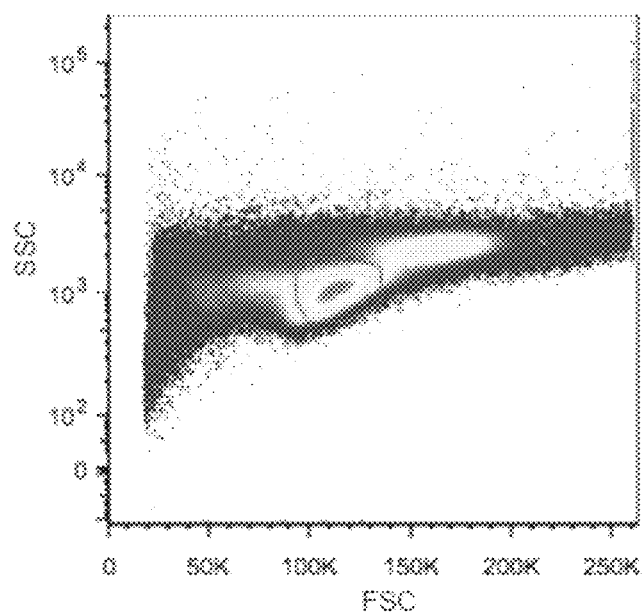
FIGS. 3A-3F: Gating strategy of IgG+ B cell subset in human PBMCs.
Figure 3B:
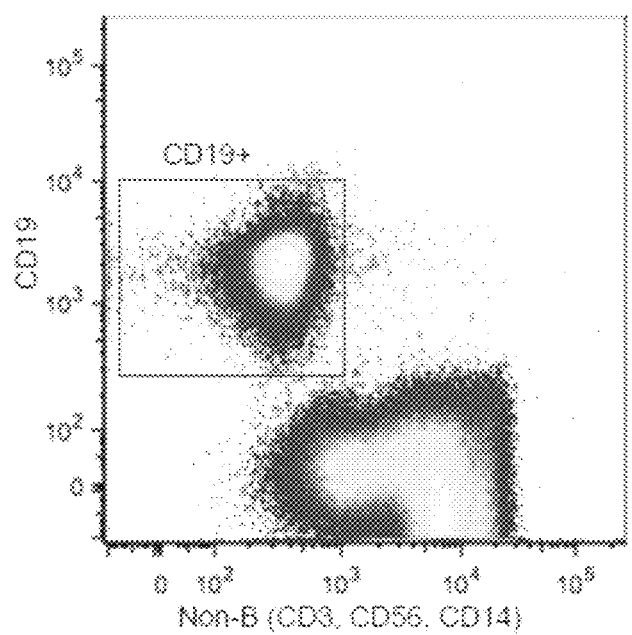
Figure 3C:
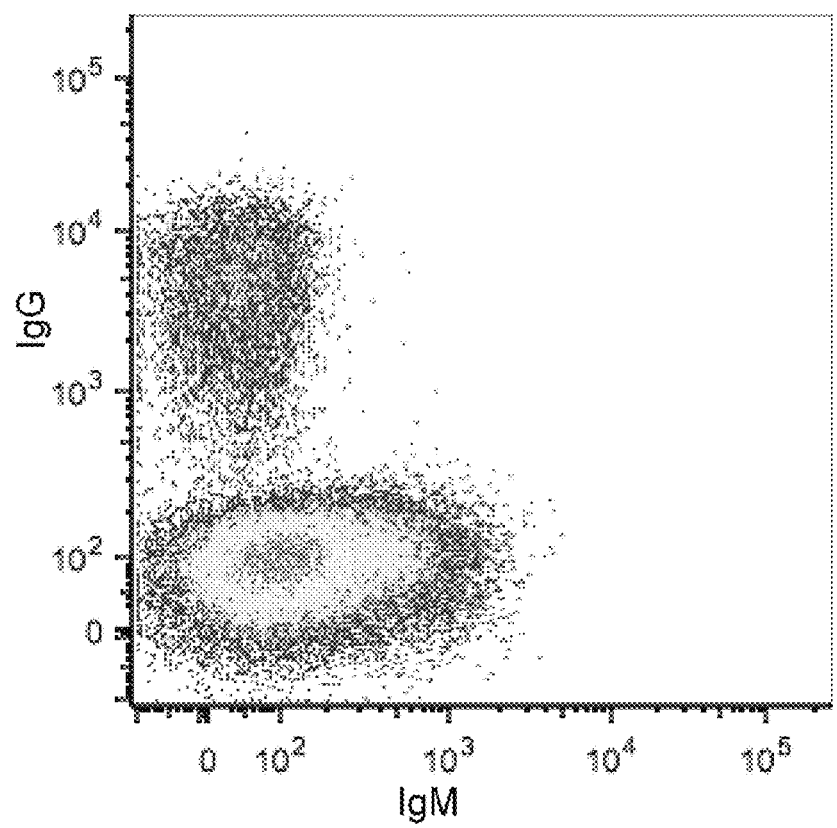
Figure 3D:
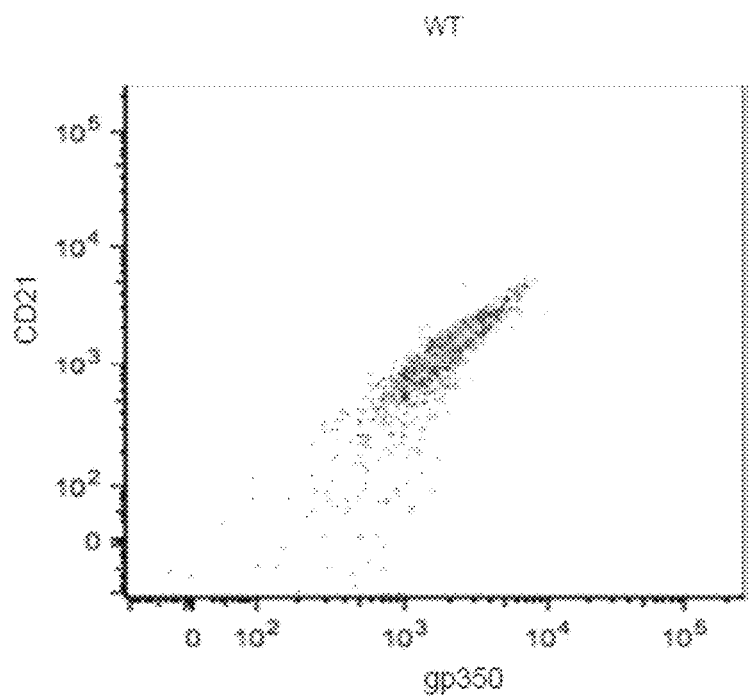
Figure 3E:
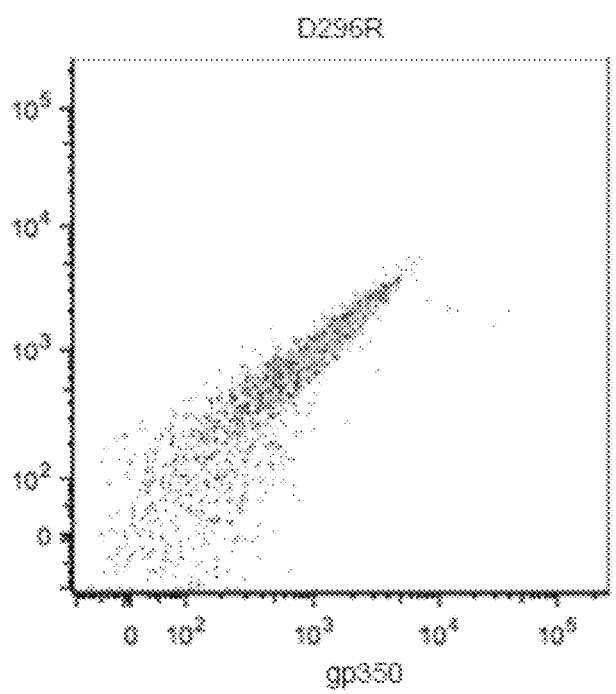
Figure 3F:
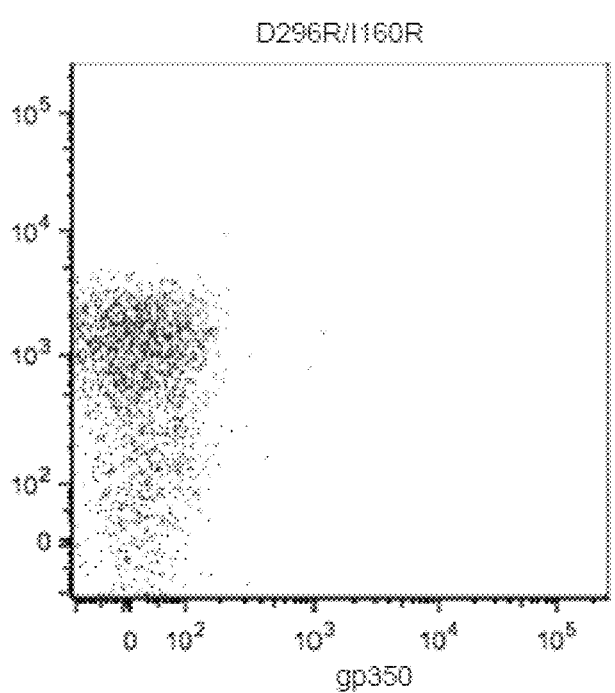
Figure 4A:
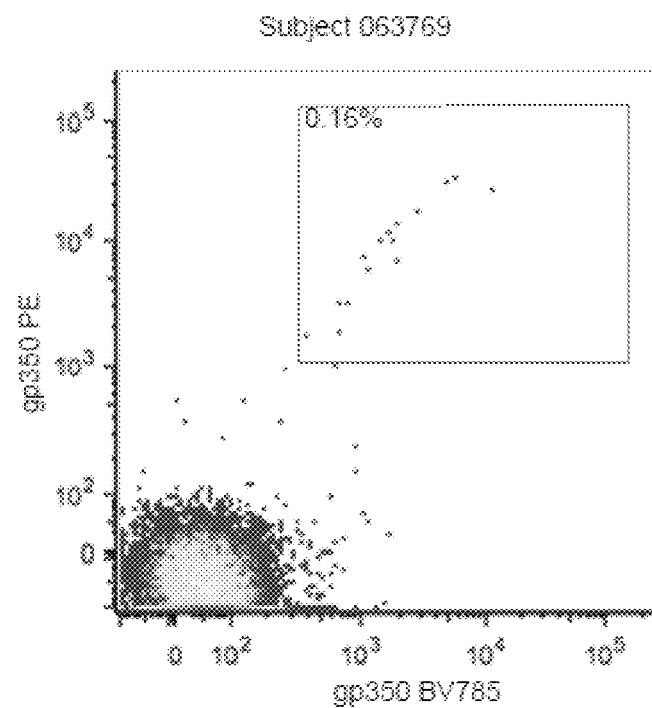
FIGS. 4A and 4B: Identification of EBV gp350-specific IgG+ B cells in individuals who have high serum neutralization titers. Cryopreserved PMBCs were stained with cell lineage differentiation markers as well as gp350 D296R/I160R probe. The gp350 probe were conjugated with two different fluorochromes (PE and BV785) to eliminate false positive events and increase confidence for specificity of stained B cells. Plots shown were IgG+ B cells gated as in previous figures. Rectangles indicate IgG+B cells stained with gp350 D296R/I160R in two different colors.
Figure 4B:
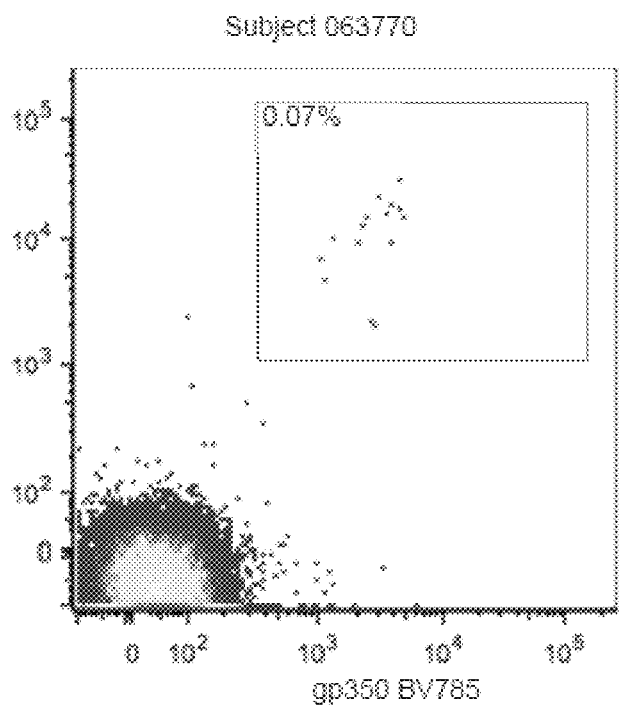
Figure 5A:
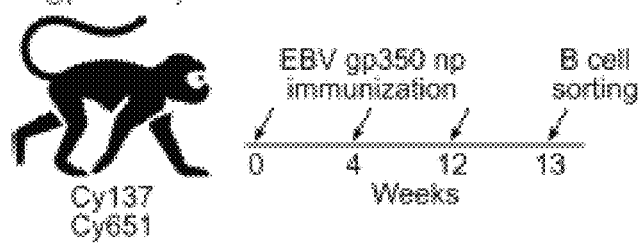
FIGS. 5A-5F: Isolation of gp350-specific B cells from Immunized Macaques.
Figure 5B:
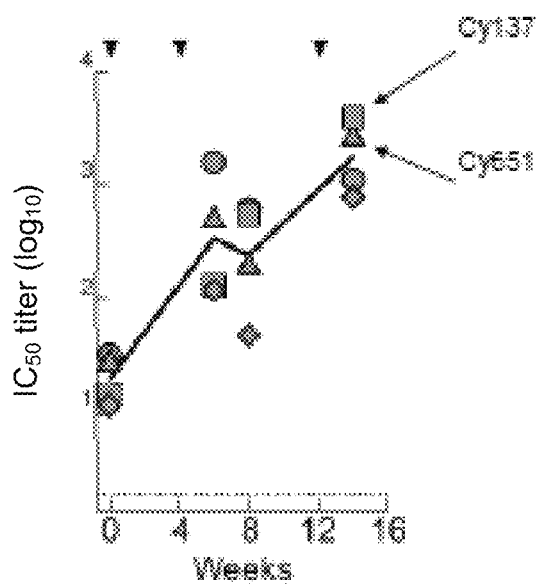
Figure 5C:
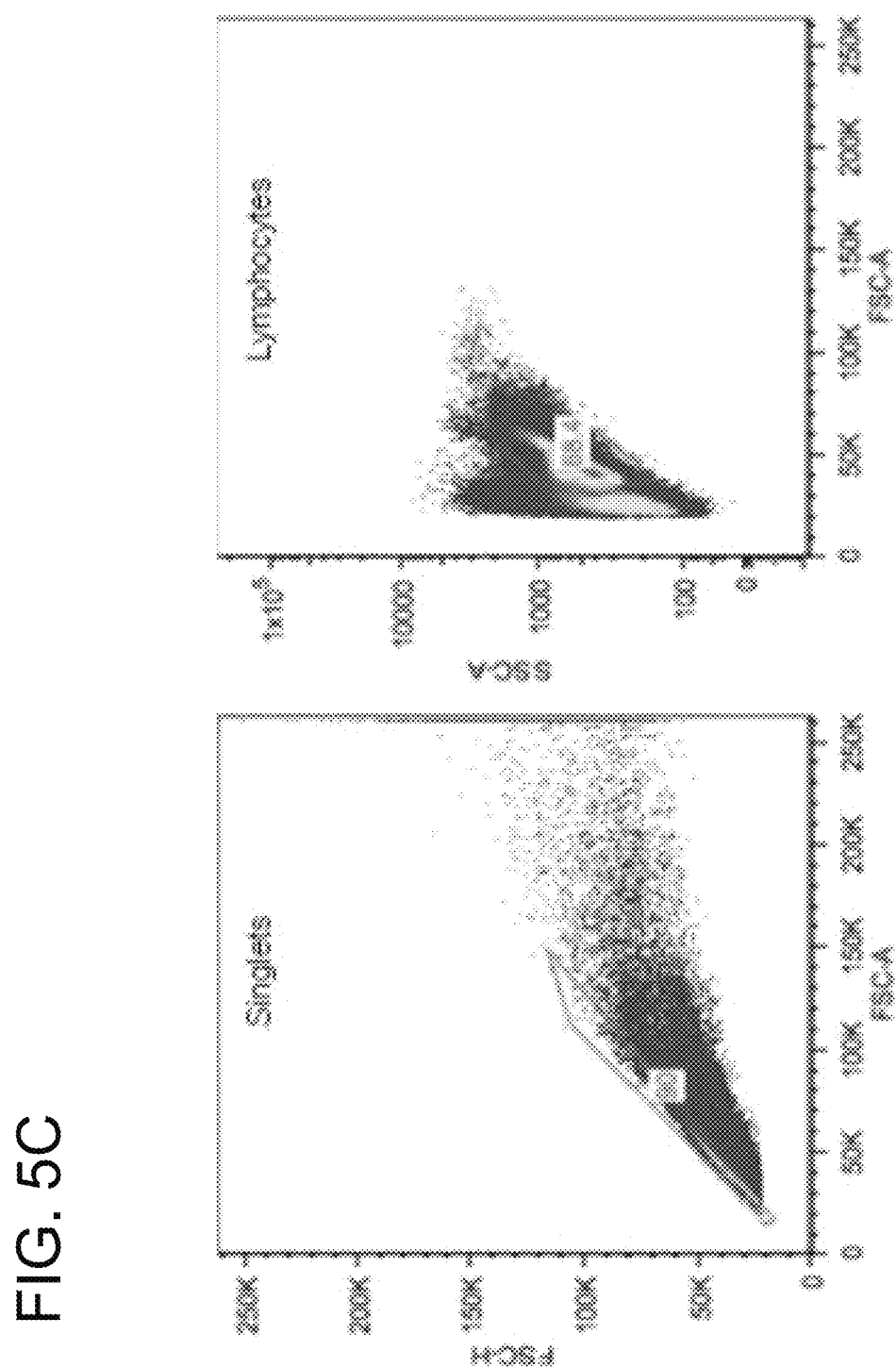
Figure 5D:
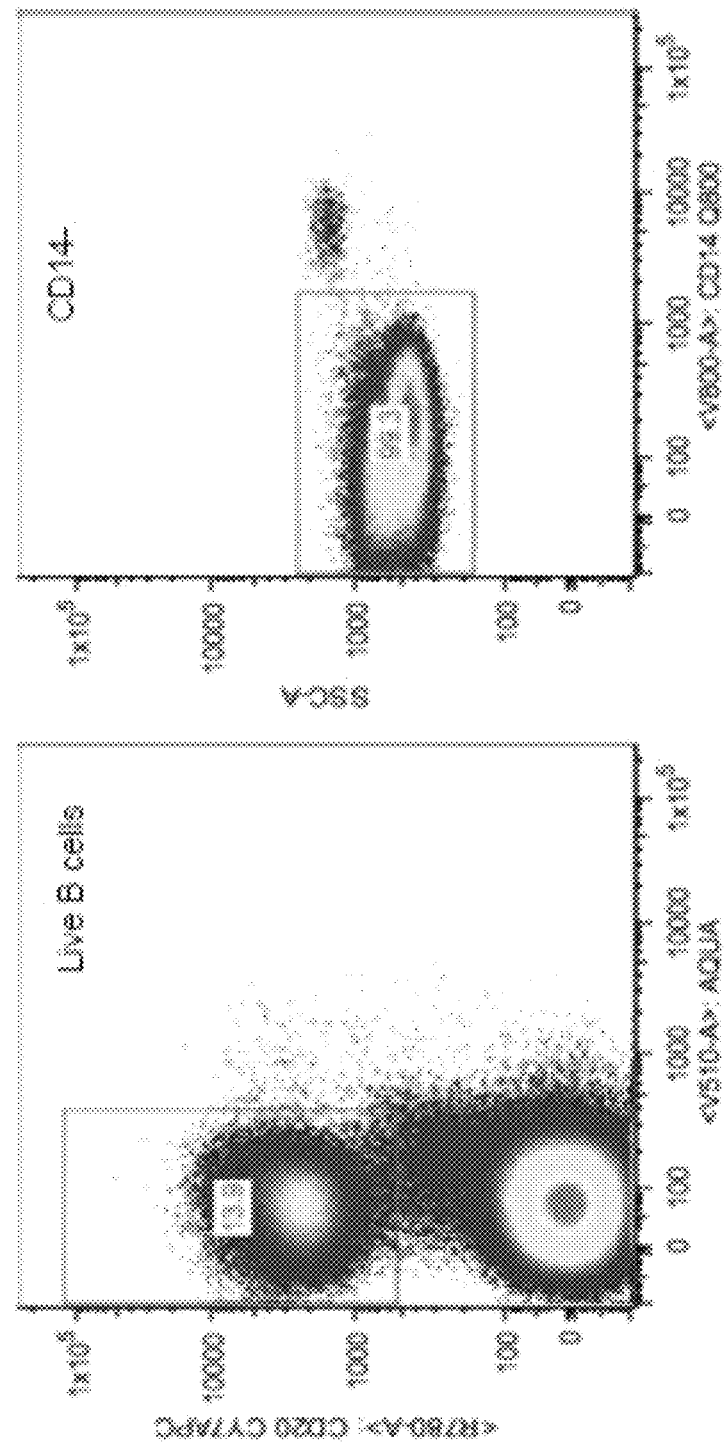
Figure 5E:
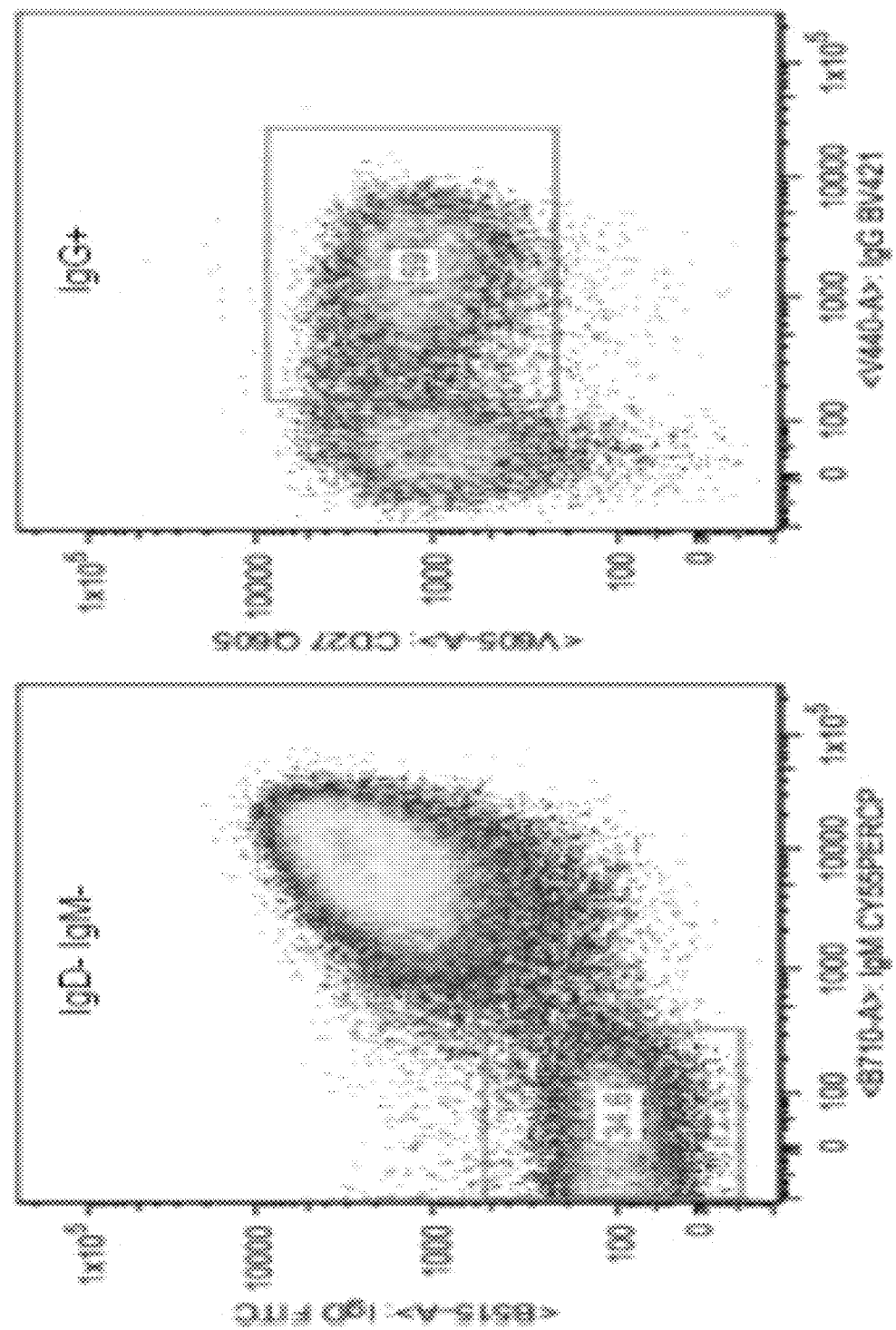
Figure 5F:
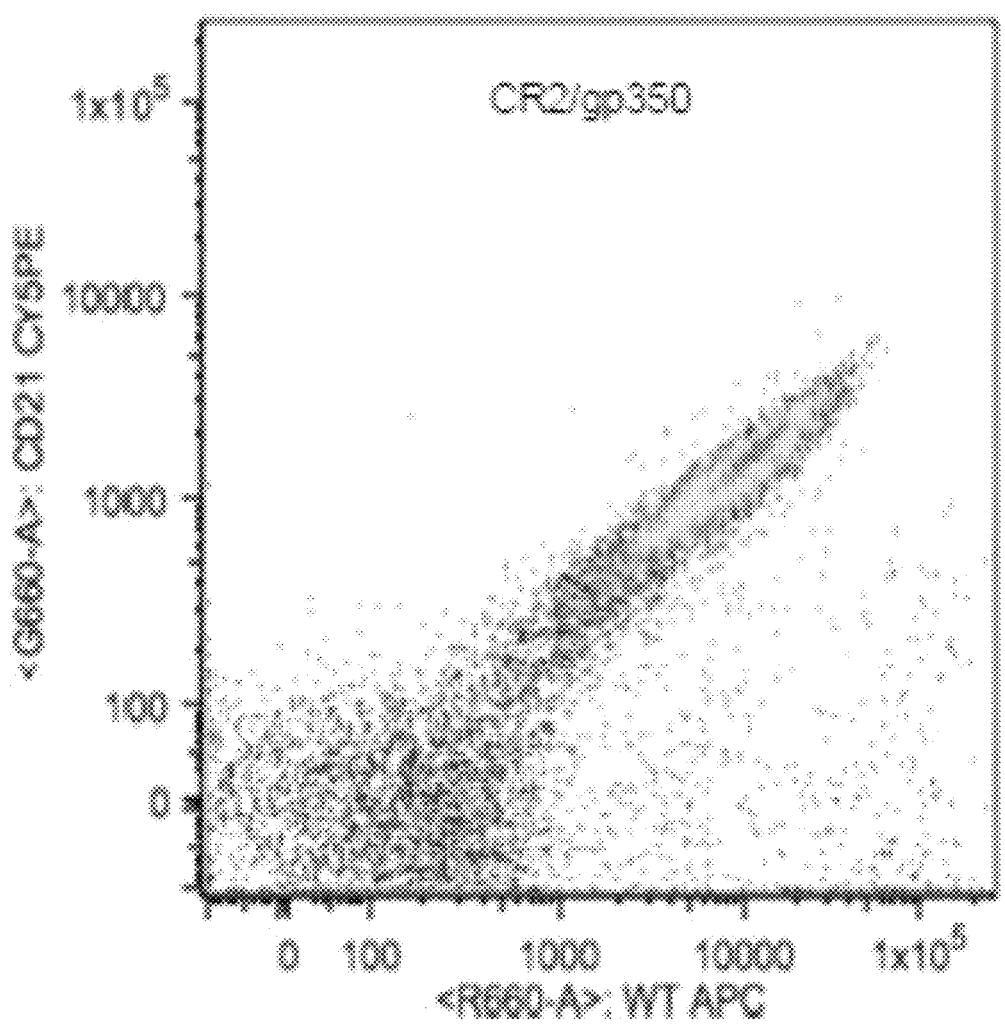
Figure 6A:
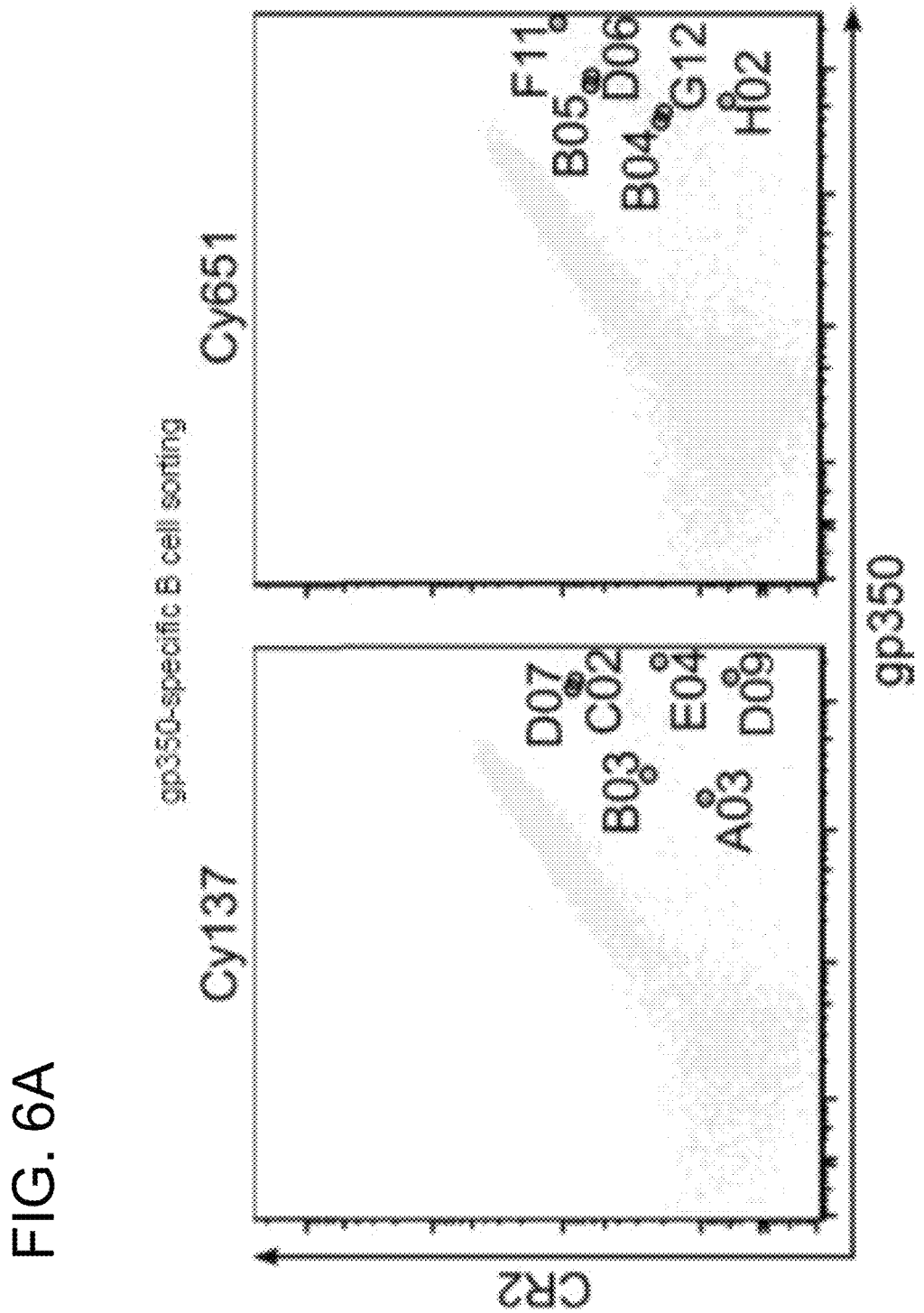
FIGS. 6A and 6B: Identification and analysis of Vaccine-elicited anti-gp350 mAbs.
Figure 6B:
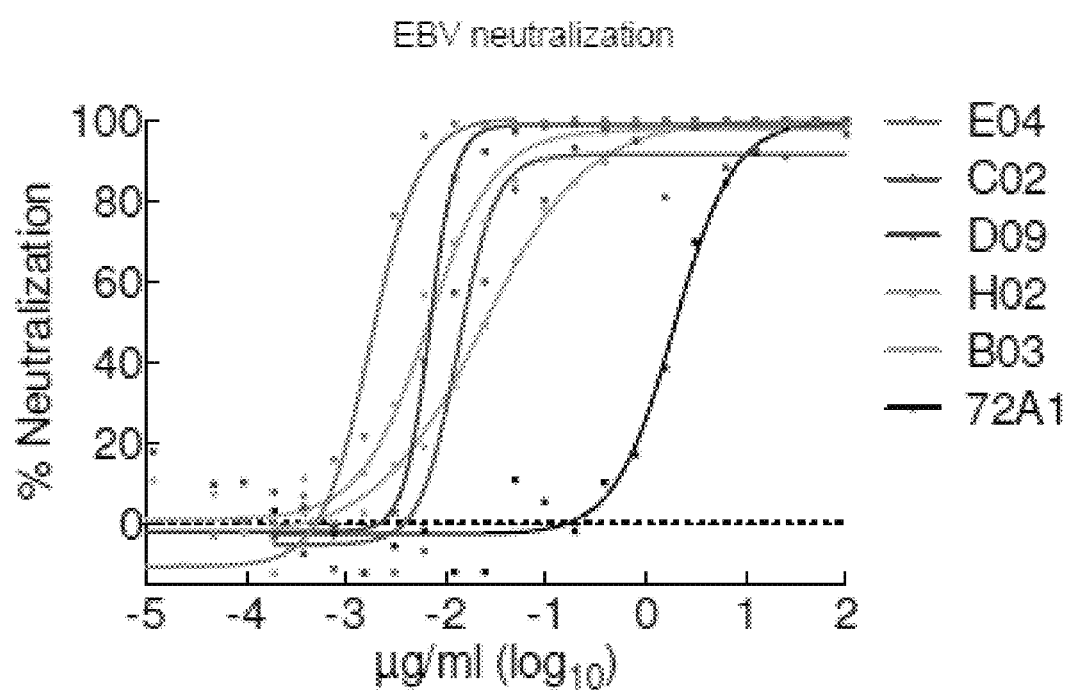
Figure 7:
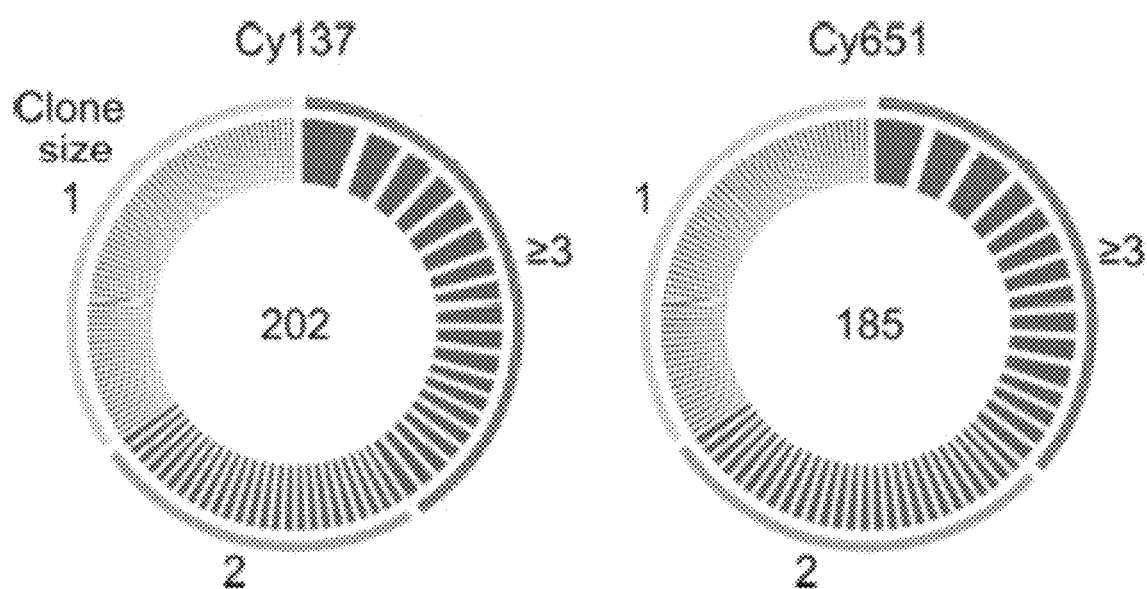
FIG. 7: Clonotype analysis of immunoglobulin heavy chain sequences. Approximately 200 B cells were isolated from each of the two rhesus macaques analyzed. The B cell receptor sequences indicated low clonal expansion in the B cells isolated as judged by the sequence similarity of each B cell receptor.
Figure 8A:
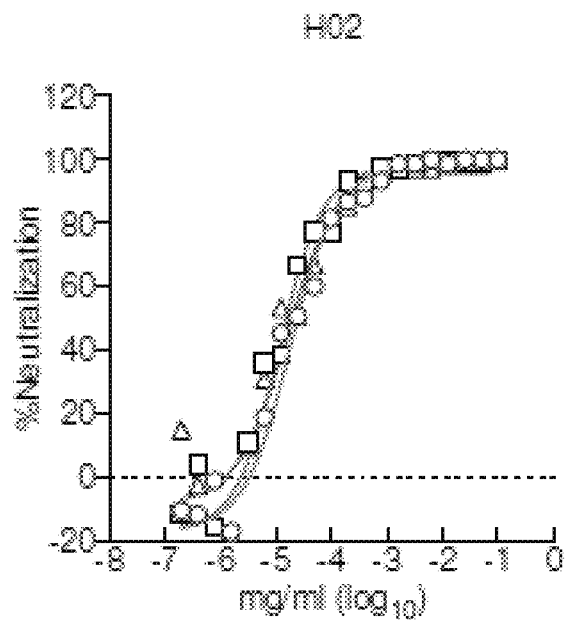
FIGS. 8A and 8B: Neutralization potency of humanized mAb H02.
Figure 8B:
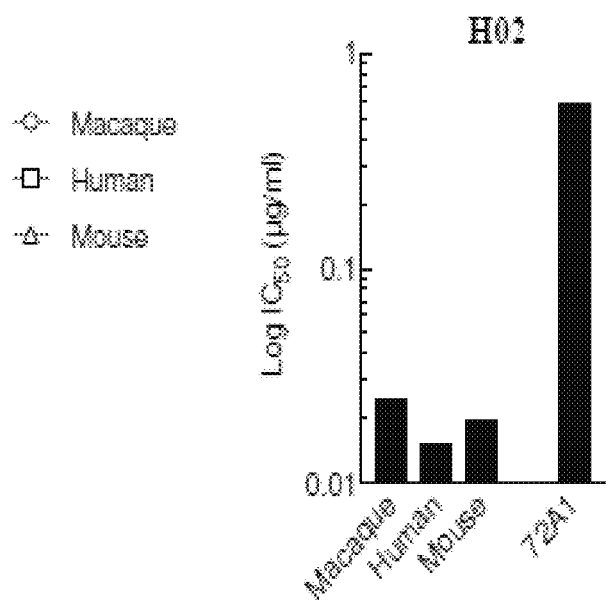
Figure 9A:
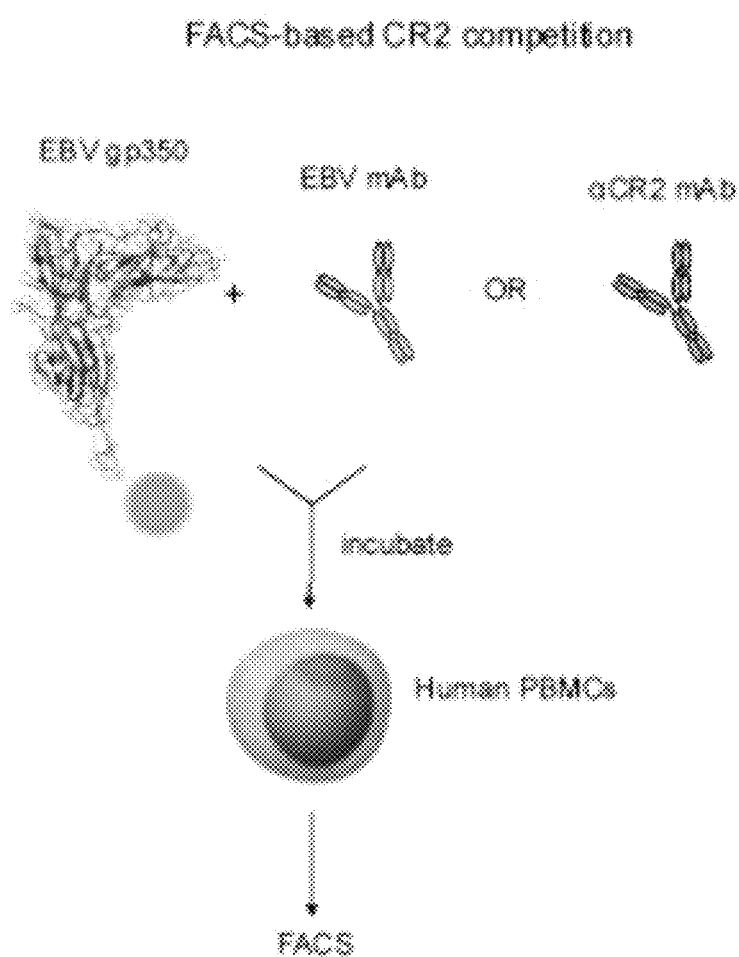
FIGS. 9A-9C: Targeting the receptor (CR2)-binding site of gp350: Flow cytometry based CR2 epitope mapping.
Figure 9B:
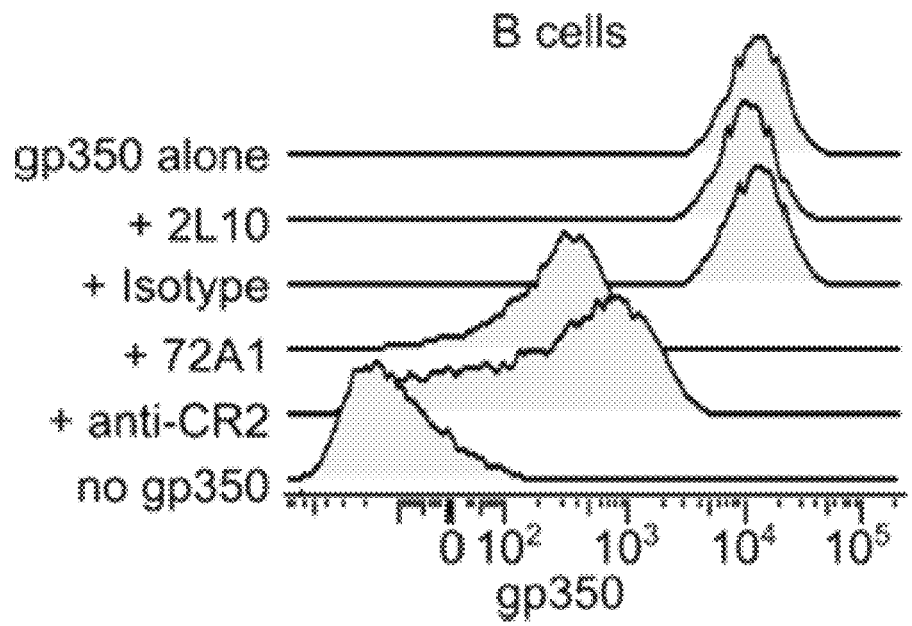
Figure 9C:
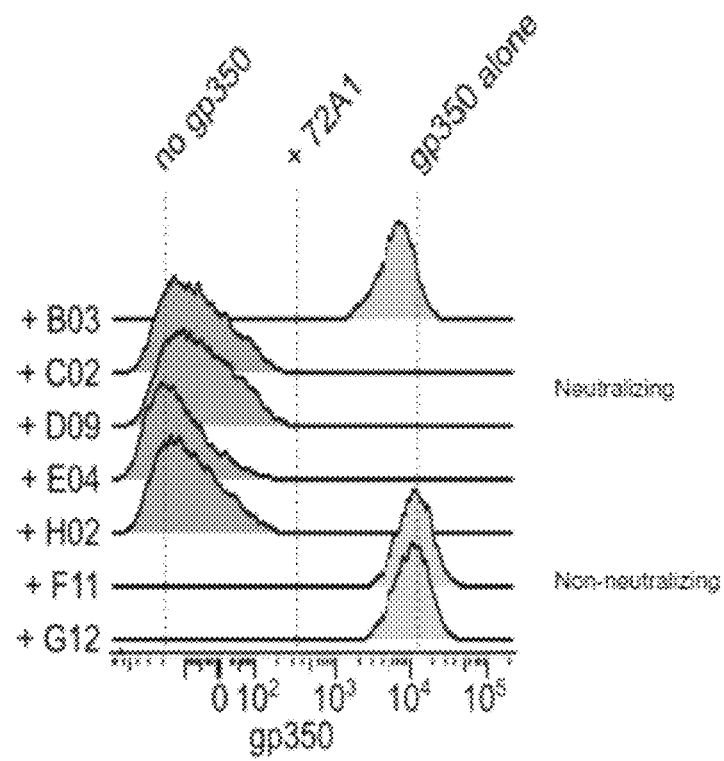
Figures 11, 12:
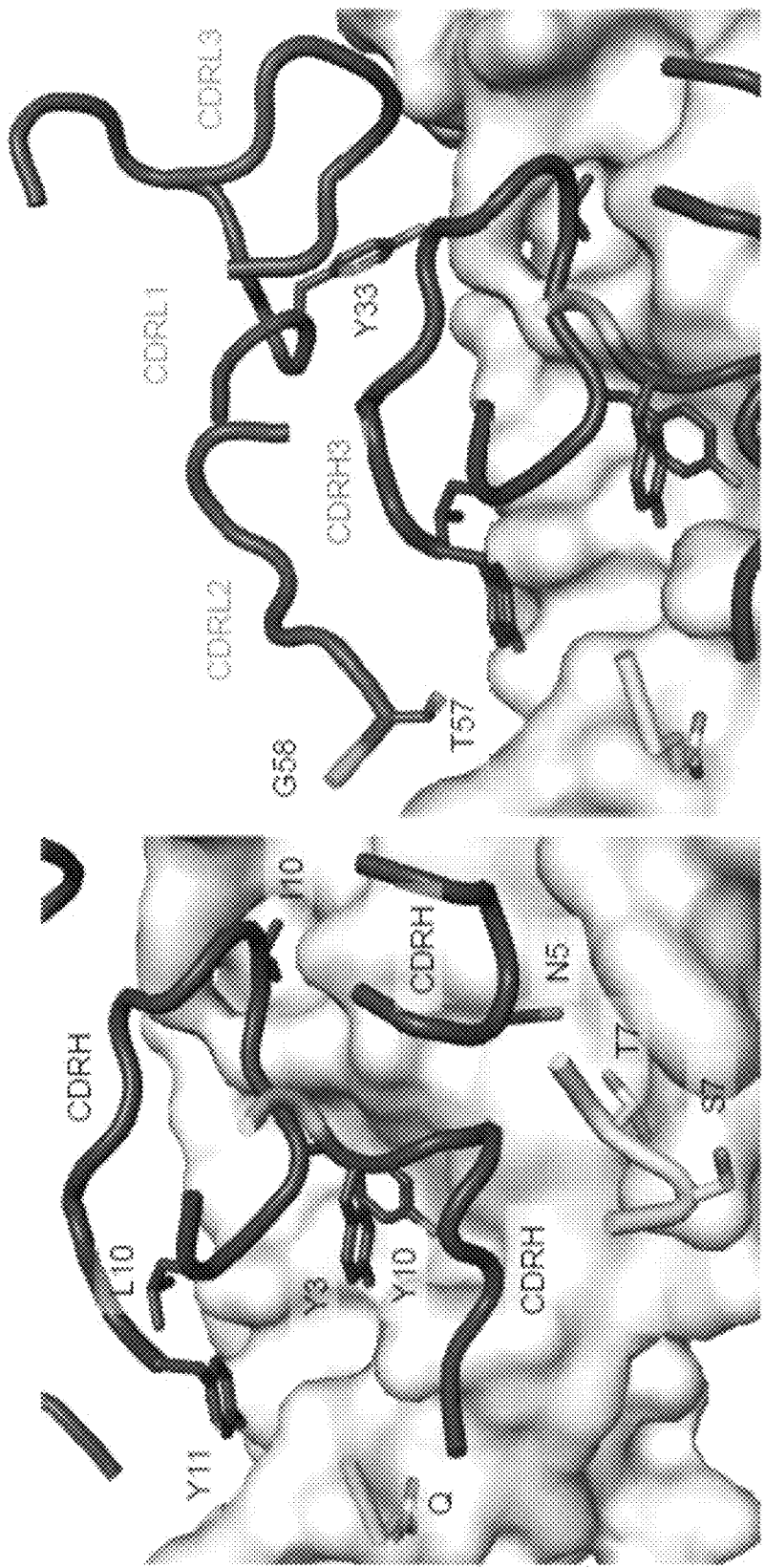
FIG. 11 shows the location of mutations entered into the heavy chain residues of clain A9.
FIG. 12 shows the location of mutations entered into the light chain residues of clain A9.
Figure 13:
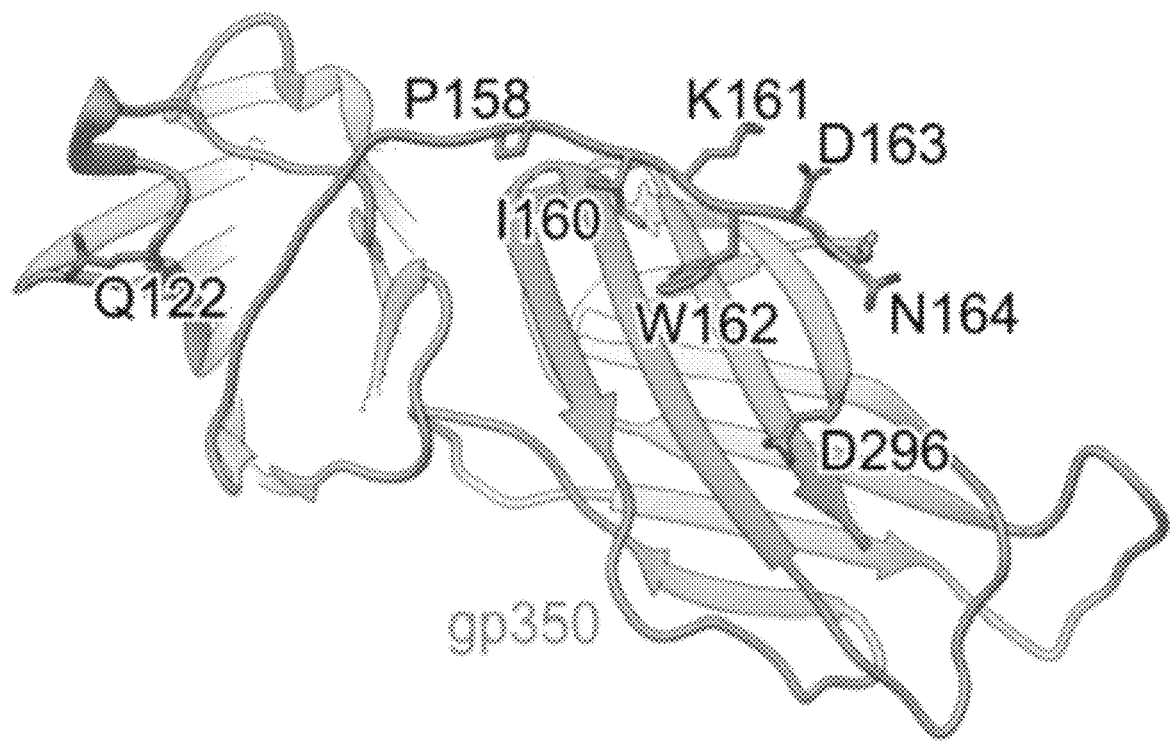
FIG. 13 shows the design of the CR2-binding knockout gp350 probe, including specific residues that were substituted to knock down CR2-binding.
Figure 14:
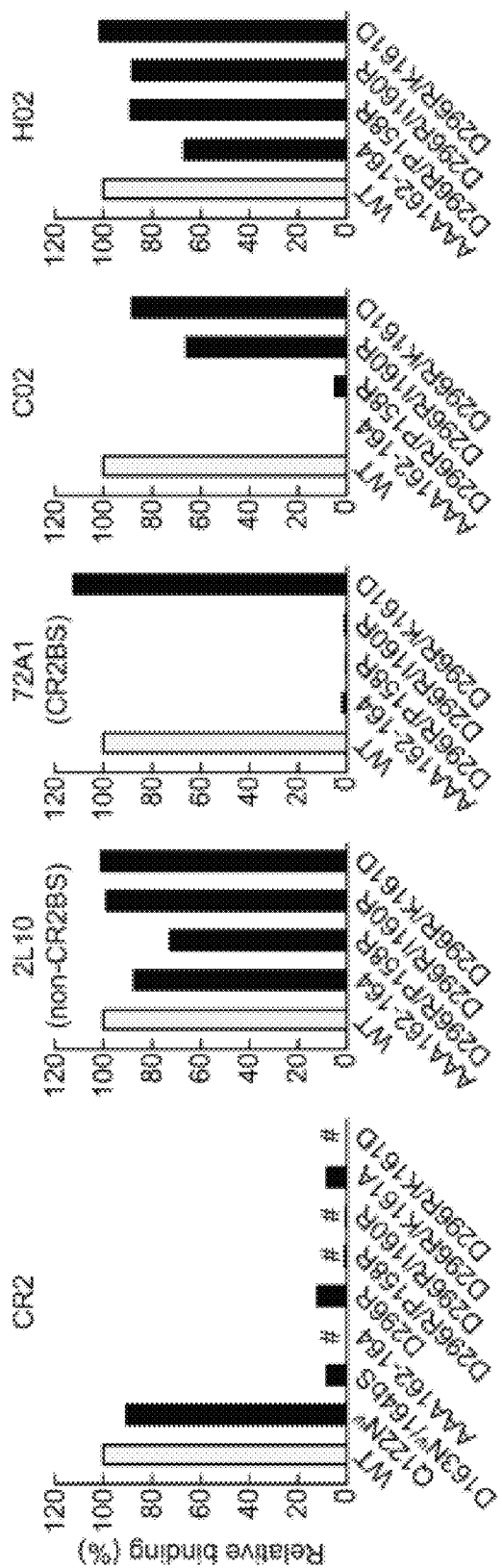
FIG. 14 shows the binding properties of the gp350 mutants. In this figure, # indicates no binding.
Figure 15:
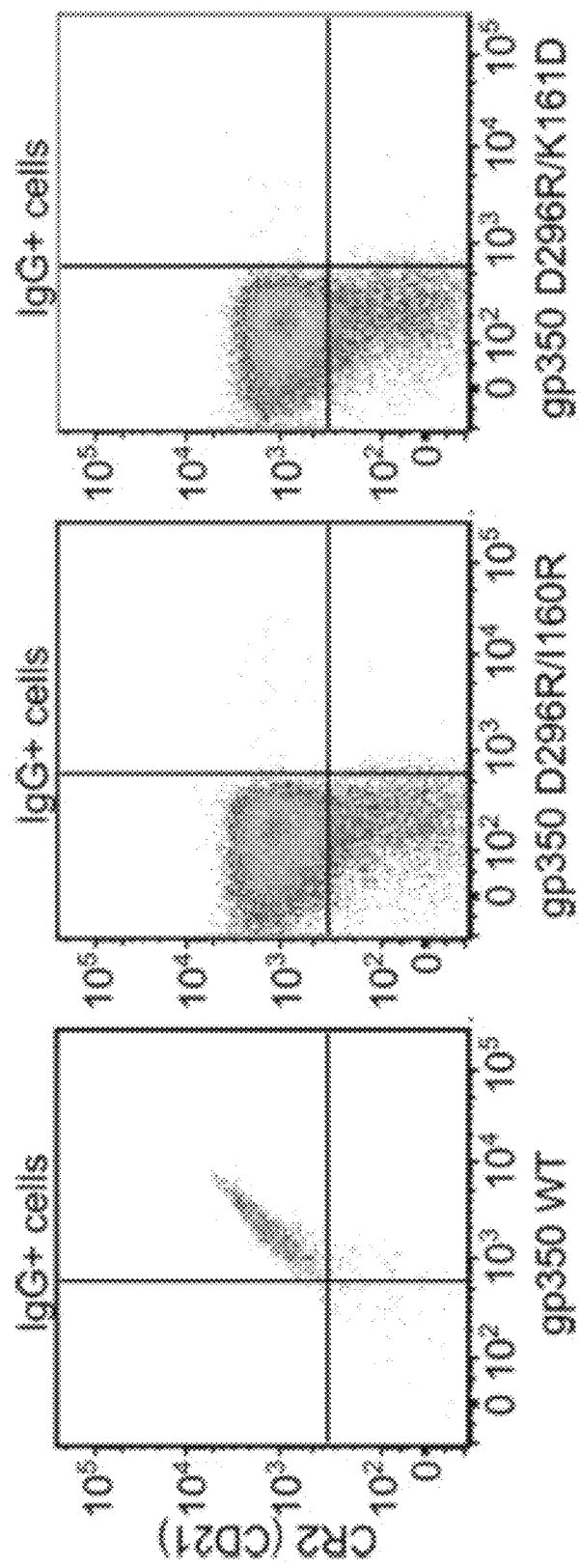
FIG. 15 shows the B cell staining profile of the new CR2-binding knock-out gp350 probe (D296R/K161D).
Figure 16:
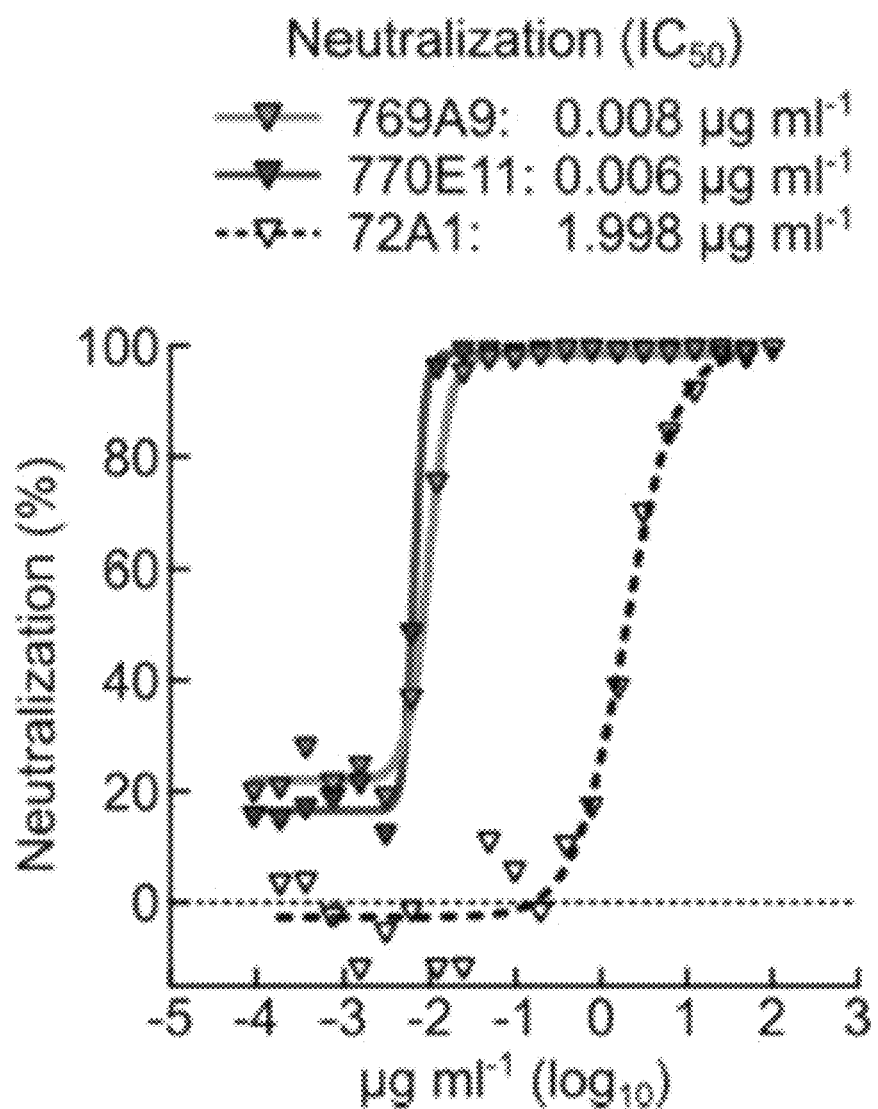
FIG. 16 shows the EBV neutralization potency of the two best human monoclonal antibodies (from clones A9 and E11). In these two clones, mutations were introduced in a structure-guided potency improving mutation analysis. For the mAb of clone A9, the introduced mutations were (referring to Kabat numbering) in the heavy chain were: Q1R, Y32R+Y98I, N53F, T70I, T70F, L96R, Y98R, Y98W, I100F, I100W, and Y102E; in the light chain were Y32E, G57D, T56Q, and T56E. For the mAb of clone E11, the introduced mutations were (referring to Kabat numbering) in the heavy chain were: V100F, V100I, V100W, V100R, V100Y, Q98R, Q98Y, and Y58R (residues 30-33 and 53-56 were also targeted for mutagenesis); in the light chain, residues 1, 27, 27a, 30, 32, 49, 50, 52, 53, 56, and 93-95 were targeted for mutagenesis.

The terms "EBV gp350 protein" and "gp350" as used herein, refer to various Epstein Barr Virus polypeptides. The EBV gp350 proteins described herein may be isolated from a variety of sources, such as from human tissue types or from another source, or prepared by recombinant or synthetic methods. The term "EBV gp350 protein" refers to each individual gp350 polypeptide disclosed herein. All disclosures in this specification which refer to the "EBV gp350 protein" refer to each of the polypeptides individually as well as jointly. For example, descriptions of the preparation of, purification of, derivation of, formation of antibodies to or against, formation of gp350 binding oligopeptides to or against, administration of, compositions containing, treatment of a disease with, etc., pertain to each polypeptide of the disclosure individually. The term "EBV gp350 protein" also includes variants of the gp350 polypeptides disclosed herein.

A "native sequence EBV gp350 protein" comprises a polypeptide having the same amino acid sequence as the corresponding EBV gp350 protein derived from nature. Such native sequence EBV gp350 proteins can be isolated from nature or can be produced by recombinant or synthetic means. The term "native sequence EBV gp350 protein" specifically encompasses naturally-occurring truncated or secreted forms of the specific EBV gp350 protein (e.g., an extracellular domain sequence), naturally-occurring variant forms (e.g., alternatively spliced forms) and naturally-occurring allelic variants of the polypeptide. The native sequence EBV gp350 proteins disclosed herein may be mature or full-length native sequence polypeptides comprising the full-length amino acids sequences.

"EBV gp350 protein variant" means an EBV gp350 protein, preferably an active EBV gp350 protein, as defined herein having at least about 80% amino acid sequence identity with a full-length native sequence EBV gp350 protein sequence as disclosed herein, an extracellular domain of an EBV gp350 protein, as disclosed herein or any other fragment of a full-length EBV gp350 protein sequence as disclosed herein (such as those encoded by a nucleic acid that represents only a portion of the complete coding sequence for a full-length EBV gp350 protein). Such EBV gp350 protein variants include, for instance, EBV gp350 proteins wherein one or more amino acid residues are added or deleted, at the N- or C-terminus of the full-length native amino acid sequence. Ordinarily, an EBV gp350 protein variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence EBV gp350 protein sequence as disclosed herein, or any other specifically defined fragment of a full-length EBV gp350 protein sequence as disclosed herein. Optionally, gp350 variant polypeptides will have no more than one conservative amino acid substitution as compared to the native EBV gp350 protein sequence, alternatively no more than 2, 3, 4, 5, 6, 7, 8, 9, or 10 conservative amino acid substitution as compared to the native EBV gp350 protein sequence.

"Percent (%) amino acid sequence identity" with respect to the EBV gp350 protein sequences identified herein is defined as the percentage of amino acid residues in a candidate sequence that are identical to the amino acid residues in the specific EBV gp350 protein sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, % amino acid sequence identity values may be generated using the sequence comparison computer program ALIGN-2, wherein the complete source code for the ALIGN-2 program is provided in U.S. Pat. No. 7,160,985, which is incorporated herein by reference. The ALIGN-2 sequence comparison computer program was authored by Genentech, Inc. and the source code thereof has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, California or may be compiled from the source code. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as 100 times the fraction X/Y, where X is the number of amino acid residues scored as identical matches by the sequence alignment program ALIGN-2 in that program's alignment of A and B, and where Y is the total number of amino acid residues in B. Where the length of amino acid sequence A is not equal to the length of amino acid sequence B, the % amino acid sequence identity of A to B will not equal the % amino acid sequence identity of B to A.

"gp350 variant polynucleotide" or "gp350 variant nucleic acid sequence" means a nucleic acid molecule which encodes an EBV gp350 protein, preferably an active EBV gp350 protein, as defined herein and which has at least about 80% nucleic acid sequence identity with a nucleic acid sequence encoding a full-length native sequence EBV gp350 protein sequence as disclosed herein, an extracellular domain of an EBV gp350 protein, as disclosed herein or any other fragment of a full-length EBV gp350 protein sequence as disclosed herein (such as those encoded by a nucleic acid that represents only a portion of the complete coding sequence for a full-length EBV gp350 protein). Ordinarily, a gp350 variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence EBV gp350 protein sequence, an extracellular domain of an EBV gp350 protein or any other fragment of a full-length EBV gp350 protein sequence. Variants do not encompass the native nucleotide sequence.

Ordinarily, gp350 variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Isolated," when used to describe the various EBV gp350 proteins disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or silver stain. Isolated polypeptide includes polypeptide in situ within recombinant cells, since at least one component of the EBV gp350 protein natural environment will not be present. Ordinarily, however, isolated polypeptide will be prepared by at least one purification step.

An "isolated" EBV gp350 protein-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers (1995).

"Stringent conditions" or "high stringency conditions" as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" used herein refers to a chimeric polypeptide comprising an EBV gp350 protein or anti-gp350 antibody fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of an EBV gp350 protein which retain a biological and/or an immunological activity of native or naturally-occurring gp350, wherein "biological" activity refers to a biological function (either inhibitory or stimulatory) caused by a native or naturally-occurring gp350 other than the ability to induce the production of an antibody against an antigenic epitope possessed by a native or naturally-occurring gp350 and an "immunological" activity refers to the ability to induce the production of an antibody against an antigenic epitope possessed by a native or naturally-occurring gp350.

The term "antagonist" is used in the broadest sense, and includes any molecule that partially or fully blocks, inhibits, or neutralizes a biological activity of a native EBV gp350 protein disclosed herein. In a similar manner, the term "agonist" is used in the broadest sense and includes any molecule that mimics a biological activity of a native EBV gp350 protein disclosed herein. Suitable agonist or antagonist molecules specifically include agonist or antagonist antibodies or antibody fragments, fragments or amino acid sequence variants of native EBV gp350 proteins, peptides, antisense oligonucleotides, small organic molecules, etc. Methods for identifying agonists or antagonists of an EBV gp350 protein may comprise contacting an EBV gp350 protein with a candidate agonist or antagonist molecule and measuring a detectable change in one or more biological activities normally associated with the EBV gp350 protein.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an EBV gp350 protein-expressing viral infection if, after receiving a therapeutic amount of an anti-gp350 antibody or gp350 binding oligopeptide according to the methods of this disclosure, the patient shows observable and/or measurable reduction in or absence of one or more of the following: reduction in the number of infected cells or absence of the infected cells; reduction in the number of infected cells; inhibition (i.e., slow to some extent and preferably stop) of EBV infection including the spread of infection into neurological tissues; inhibition (i.e., slow to some extent and preferably stop) of infection spread; inhibition, to some extent, and/or relief to some extent, of one or more of the symptoms associated with the viral infection; reduced morbidity and mortality, and improvement in quality of life issues. To the extent the anti-gp350 antibody or gp350 binding oligopeptide may prevent growth or infection and/or kill existing infected cells, it may be cytostatic and/or cytotoxic. Reduction of these signs or symptoms may also be felt by the patient. The above parameters for assessing successful treatment and improvement in the EBV-associated diseases and disorders are readily measurable by routine procedures familiar to a medical provider.

"Chronic" administration refers to administration of the agent(s) in a continuous mode as opposed to an acute mode, to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a viral infection refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody or gp350 binding oligopeptide of this disclosure can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate or a lateral flow assay device; in others, it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an EBV gp350 protein, an antibody thereto or a gp350 binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody or gp350 binding oligopeptide, or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, or gp350 binding oligopeptide, or other drug effective to "treat" a disease or disorder in a subject or mammal. In the case of an EBV infection, the therapeutically effective amount of the drug may reduce the number of infected cells; inhibit (i.e., slow to some extent and preferably stop) spread of the infection into other cells, such as lymphatic or neurological cells organs; and/or relieve to some extent one or more of the symptoms associated with the infection. See the definition herein of "treating." To the extent the drug may prevent growth and/or kill existing infected cells, it may be cytostatic, cytotoxic, anti-inflammatory, immunomodulatory, and/or immunosuppressing.

A "growth inhibitory amount" of an anti-gp350 antibody or gp350 binding oligopeptide is an amount capable of inhibiting the growth of a cell, especially virus infected cell, either in vitro or in vivo. A "growth inhibitory amount" of an anti-gp350 antibody or gp350 binding oligopeptide for purposes of inhibiting infected cell growth may be determined empirically and in a routine manner.

A "cytotoxic amount" of an anti-gp350 antibody or gp350 binding is an amount capable of causing the destruction of a cell, especially virus infected cell, either in vitro or in vivo. A "cytotoxic amount" of an anti-gp350 antibody or gp350 binding oligopeptide for purposes of inhibiting cell growth may be determined empirically and in a routine manner.

The term "antibody" is used in the broadest sense and specifically covers, for example, single anti-gp350 monoclonal antibodies (including agonist, antagonist, and neutralizing antibodies), anti-gp350 antibody compositions with polyepitopic specificity, polyclonal antibodies, single chain anti-gp350 antibodies, and fragments of anti-gp350 antibodies (see below) as long as they exhibit the desired biological or immunological activity or specificity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells because at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, C T, 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses based on relatively minor differences in CH sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of an antibody for its antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 3-30, or more typically, 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD. (1991)). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, useful monoclonal antibodies of this disclosure may be prepared by the hybridoma methodology first described by Kohler et al., Nature, 256: 495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with, or homologous to, corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape, etc.), and human constant region sequences.

An "intact" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')2 fragment which roughly corresponds to two disulfide-linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) can recognize and bind antigen, although at a lower affinity than the entire binding site.

"Single-chain Fv" (also abbreviated as "sFv" or "scFv") are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all at least one, and typically two, variable domains, in which all or substantially all the hypervariable loops correspond to those of a non-human immunoglobulin and all or substantially all the FRs are those of a human immunoglobulin sequence. The humanized antibody optionally also will comprise at least a portion of an immunoglobulin constant region (Fe), typically that of a human immunoglobulin. For further details, see Jones et al., Nature 321:522-25 (1986); Riechmann et al., Nature 332:323-329 (1988); and Presta, Curr. Op. Struct. Biol. 2:593-96 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "binds specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50-fold, or at least about 500-fold, or at least about 1000-fold, weaker than its binding affinity for the human antigen. The species-dependent antibody can be of any of the various types of antibodies as defined above, but preferably is a humanized or human antibody.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the disclosure and the other associated with a reference/comparator antibody) such that one of skill in the art would consider the difference between the two values to be of little or no biological and/or statistical significance within the context of the biological characteristic measured by the values (e.g., Kd values). The difference between the two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of this disclosure. Illustrative embodiments are described in the following.

The "Kd" or "Kd value" according to this disclosure is measured by a radiolabeled antigen binding assay (RIA) performed with the Fab version of an antibody of interest and its antigen as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) are coated overnight with 5 mcg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate, 100 pM or 26 pM [125I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 microliter/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. The Kd or Kd value may also be measured by using surface plasmon resonance assays using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) is calculated as the ratio koff/kon. See, e.g., Chen, Y., et al., (1999) J. Mol Biol 293:865-881. If the on-rate exceeds $10^6$ M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrometer (Aviv Instruments) or a 8000-series SLM-Aminco spectrophotometer (ThermoSpectronic) with a stir red cuvette.

An "on-rate" or "rate of association" or "association rate" or "kon" according to this disclosure can also be determined with the same surface plasmon resonance technique described above using a BIAcore™-2000 or a BIAcore™-3000 (BIAcore, Inc., Piscataway, NJ) at 25° C. with immobilized antigen CM5 chips at approx. 10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 mcg/ml (approx. 0.2 uM) before injection at a flow rate of 5 microliter/minute to achieve approximately 10 response units (RU) of coupled protein. Following the injection of 1M ethanolamine to block unreacted groups. For kinetics measurements, two-fold serial dilutions of Fab (0.78 nM to 500 nM) are injected in PBS with 0.05% Tween 20 (PBST) at 25° C. at a flow rate of approximately 25 microliter/min. Association rates (kon) and dissociation rates (koff) are calculated using a simple one-to-one Langmuir binding model (BIAcore Evaluation Software version 3.2) by simultaneous fitting the association and dissociation sensorgram. The equilibrium dissociation constant (Kd) was calculated as the ratio koff/kon. See, e.g., Chen, Y., et al., (1999) J. Mol Biol 293:865-81. However, if the on-rate exceeds $10^6$ M-1 S-1 by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The phrase "substantially reduced," or "substantially different", as used herein, denotes a sufficiently high degree of difference between two numeric values (generally one associated with an antibody of the disclosure and the other associated with a reference/comparator antibody) such that one of skill in the art would consider the difference between the two values to be of statistical significance within the context of the biological characteristic measured by the values (e.g., Kd values, HAMA response). The difference between the two values is preferably greater than about 10%, preferably greater than about 20%, preferably greater than about 30%, preferably greater than about 40%, preferably greater than about 50% as a function of the value for the reference/comparator antibody.

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is an EBV gp350 polypeptide. An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H and 78H; for instance, the amino acid residues at those positions may be 71A, 73T and/or 78A. The VL acceptor human framework may be identical in sequence to the VL human immunoglobulin framework sequence or human consensus framework sequence.

Antibodies of this disclosure may be able to compete for binding to the same epitope as is bound by a second antibody. Monoclonal antibodies are considered to share the "same epitope" if each blocks binding of the other by 40% or greater at the same antibody concentration in a standard in vitro antibody competition binding analysis.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., supra. For the VL, the subgroup may be subgroup kappa I as in Kabat et al. For the VH, the subgroup is subgroup III as in Kabat et al.

A "VH subgroup III consensus framework" comprises the consensus sequence obtained from the amino acid sequences in variable heavy subgroup III of Kabat et al.

A "VL subgroup I consensus framework" comprises the consensus sequence obtained from the amino acid sequences in variable light kappa subgroup I of Kabat et al.

An "unmodified human framework" is a human framework which has the same amino acid sequence as the acceptor human framework, e.g. lacking human to non-human amino acid substitution(s) in the acceptor human framework.

An "altered hypervariable region" for the purposes herein is a hypervariable region comprising one or more (e.g. one to about 16) amino acid substitution(s) therein.

An "un-modified hypervariable region" for the purposes herein is a hypervariable region having the same amino acid sequence as a non-human antibody from which it was derived, i.e. one which lacks one or more amino acid substitutions therein.

The term "hypervariable region", "HVR", "HV" or "CDR", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). Several hypervariable region delineations are in use and are encompassed herein. The Kabat Complementarity Determining Regions (CDRs) are based on sequence variability and are the most commonly used. The "contact" hypervariable regions are based on an analysis of the available complex crystal structures. The residues from each of these hypervariable regions are noted below. Unless otherwise denoted, Kabat numbering is employed. Hypervariable region locations are generally: amino acids 24-34 (HVR-L1), amino acids 49-56 (HVR-L2), amino acids 89-97 (HVR-L3), amino acids 26-35A (HVR-H1), amino acids 49-65 (HVR-H2), and amino acids 93-102 (HVR-H3). Hypervariable regions may also comprise "extended hypervariable regions" as follows: amino acids 24-36 (L1), and amino acids 46-56 (L2) in the VL, numbered according to Kabat et al., supra for each of these definitions.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity or binding specificity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-55 (1995); Yelton et al. J. Immunol. 155:1994-2004 (1995); Jackson et al., J. Immunol. 154(7):3310-19 (1995); and Hawkins et al, J. Mol. Biol. 226:889-96 (1992).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "gp350 binding oligopeptide" is an oligopeptide that binds, preferably specifically, to an EBV gp350 protein. gp350 binding oligopeptides may be chemically synthesized using known oligopeptide synthesis methodology or may be prepared and purified using recombinant technology. gp350 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides are capable of binding, preferably specifically, to an EBV gp350 protein. gp350 binding oligopeptides of this disclosure preferably comprise or consist of at least one complementarity determining region (CDR) of the antibodies of this disclosure. gp350 binding oligopeptides may be identified without undue experimentation using well known techniques. In this regard, techniques for screening oligopeptide libraries for oligopeptides that are capable of specifically binding to a polypeptide target are known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

An antibody, oligopeptide or other organic molecule "which binds" an antigen of interest, e.g. an EBV polypeptide antigen target, is one that binds the antigen with sufficient affinity such that the antibody or oligopeptide is useful as a diagnostic and/or therapeutic agent in targeting a viral particle, or a cell or a tissue expressing the antigen, and does not significantly cross-react with other proteins, such as other herpes virus proteins. The extent of binding of the antibody or oligopeptide to a "non-target" protein will often be less than about 10% of the binding of the antibody or oligopeptide to its target protein as determined by fluorescence activated cell sorting (FACS) analysis or radioimmunoprecipitation (RIA). Regarding the binding of an antibody or oligopeptide to a target molecule, the terms "specific binding" or "specifically binds to" or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or "is specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" may refer to binding where a molecule binds to a particular polypeptide or epitope on a particular polypeptide without substantially binding to any other polypeptide or polypeptide epitope.

An antibody or oligopeptide that "inhibits the growth of infected cells expressing an EBV gp350 protein" or a "growth inhibitory" antibody or oligopeptide is one which results in measurable growth inhibition of infected cells expressing or overexpressing the appropriate EBV gp350 protein. The EBV gp350 protein may be a transmembrane polypeptide expressed on the surface of an infected cell or may be a polypeptide that is produced and secreted by an infected cell. Preferred growth inhibitory anti-gp350 antibodies or oligopeptides inhibit growth of gp350-expressing cells by greater than 20%, preferably from about 20% to about 50%, and even more preferably, by greater than 50% (e.g., from about 50% to about 100%) as compared to the appropriate control, the control typically being cells not treated with the antibody or oligopeptide being tested. Growth inhibition can be measured at an antibody concentration of about 0.1 to 30 mcg/ml or about 0.5 nM to 200 nM in cell culture, where the growth inhibition is determined 1-10 days after exposure of the cells to the antibody. Growth inhibition of cells in vivo can be determined in various ways such as is described in the Examples section below. The antibody is growth inhibitory in vivo if administration of the anti-gp350 antibody at about 1 μg/kg to about 100 mg/kg body weight results in reduction in infected cells or inhibited EBV proliferation within about 1 day to 3 months from the first administration of the antibody, preferably within about 1 to 5 days.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. (USA) 95:652-56 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

An antibody or oligopeptide which "induces cell death" is one which causes a viable cell to become nonviable. The cell is one which expresses an EBV gp350 protein or is infected with EBV. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody or oligopeptide can induce cell death, loss of membrane integrity as evaluated by uptake of propidium iodide (PI), trypan blue (see Moore et al. Cytotechnology 17:1-11 (1995)) or 7AAD can be assessed relative to untreated cells.

A "gp350-expressing cell" is a cell which expresses an endogenous or transfected EBV gp350 protein which may include expression either on the cell surface or in a secreted form.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD, or IgM.

The word "label" when used herein refers to a detectable compound or composition which is conjugated directly or indirectly to an antibody or oligopeptide to generate a "labeled" antibody or oligopeptide. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., At211, I131, I125, Y90, Re186, Re188, Sm153, Bi212, P32 and radioactive isotopes of Lu), chemotherapeutic agents, enzymes and fragments thereof such as nucleolytic enzymes, antibiotics, immune suppressants, and toxins such as small molecule toxins or enzymatically active toxins of bacterial, fungal, plant or animal origin, including fragments and/or variants thereof. An antiviral agent causes destruction of virus-infected cells.

A "growth inhibitory agent" when used herein refers to a compound or composition which inhibits growth of a cell, especially an EBV-infected cell, either in vitro or in vivo. Thus, the growth inhibitory agent may be one which significantly reduces the percentage of EBV-infected cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-ß; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

II. Compositions and Methods

A. Anti-gp350 Antibodies

This disclosure provides anti-gp350 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous or intraperitoneal injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, SOCl2, or R1N=C=NR, where R and R1 are different alkyl groups.

Animals are immunized against the antigen, immunogenic conjugates, or derivatives by combining, e.g., 100 mcg or 5 mcg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites.

Seven to fourteen days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, California USA, and SP-2 and derivatives e.g., X63-Ag8-653 cells available from the American Type Culture Collection, Manassas, Virginia, USA. Human myeloma and mouse-human heteromyeloma cell lines also have been described for producing human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs. 130:151-188 (1992).

Monoclonal antibodies or antibody fragments may be isolated from antibody phage libraries generated using the techniques described in McCafferty et al., Nature, 348:552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-66 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-gp350 antibodies of this disclosure may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fe), typically that of a human immunoglobulin (Jones et al., Nature, 321:522-25 (1986); Riechmann et al., Nature, 332:323-29 (1988); and Presta, Curr. Op. Struct. Biol., 2:593-96 (1992)).

Methods for humanizing non-human antibodies are known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is important to reduce antigenicity and HAMA response (human anti-mouse antibody) when the antibody is intended for human therapeutic use. According to the "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a framework region derived from the consensus sequence of all human antibodies of a subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, humanized antibodies may be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity or specificity for the target antigen(s), is achieved. In general, the hypervariable region residues are directly and most substantially involved in influencing antigen binding.

Various forms of humanized anti-gp350 antibodies are contemplated. For example, the humanized antibody may be an antibody fragment, such as a Fab, which is optionally conjugated with one or more cytotoxic agent(s) to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-58 (1993); Bruggemann et al., Year in Immuno. 7:33 (1993); U.S. Pat. Nos. 5,545,806, 5,569,825, 5,591,669 (all of GenPharm); 5,545,807; and WO 97/17852.

Alternatively, phage display technology (McCafferty et al., Nature 348:552-53 (1990)) can be used to produce human antibodies and antibody fragments in vitro, from immunoglobulin variable (V) domain gene repertoires from unimmunized donors. Using this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Current Opinion in Structural Biology 3:564-71 (1993). Several sources of V-gene segments can be used for phage display. Clackson et al., Nature, 352:624-28 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-97 (1991), or Griffith et al., EMBO J. 12:725-34 (1993). See, also, U.S. Pat. Nos. 5,565,332 and 5,573,905.

As discussed above, human antibodies may also be generated in vitro in activated B cells (see, for example, U.S. Pat. Nos. 5,567,610 and 5,229,275).

4. Antibody Fragments

In certain circumstances, there are advantages to using antibody fragments, rather than whole antibodies. The smaller size of the fragments allows for rapid clearance, and may lead to improved access to EBV-infected cells or organs in a mammal.

Various techniques have been developed to produce antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-67 (1992)). Using another approach, F(ab')2 fragments can be isolated directly from recombinant host cell culture. Fab and F(ab')2 fragment with increased in vivo half-life comprising a salvage receptor binding epitope residues are described in U.S. Pat. No. 5,869,046. Other techniques to produce antibody fragments will be apparent to the skilled practitioner. The antibody of choice may also be a single chain Fv fragment (scFv). See WO 93/16185; U.S. Pat. Nos. 5,571, 894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870. Such linear antibody fragments may be monospecific or bispecific.

5. Bispecific Antibodies

Bispecific antibodies have binding specificities for at least two different epitopes. Exemplary bispecific antibodies may bind to two different epitopes of a gp350 protein. Other such antibodies may combine a gp350 binding site with a binding site for another protein. Alternatively, an anti-gp350 arm may be combined with an arm which binds to a triggering molecule on a leukocyte such as a T-cell receptor molecule (e.g. CD3) (see, e.g., Baeuerle, et al., Curr. Opin. Mol. Ther. 11(1):22-30 (2009)), or Fc receptors for IgG (FcγR), such as FcγRI (CD64), FcγRII (CD32) and FcγRIII (CD16), to focus and localize cellular defense mechanisms to the gp350-expressing cell. Bispecific antibodies may also be used to localize cytotoxic agents to EBV-infected cells which express gp350. These antibodies possess a gp350-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')2 bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. Nos. 5,821,337 and 6,407,213 teach bispecific anti-ErbB2/anti-CD3 antibodies. Additional bispecific antibodies that bind an epitope on the CD3 antigen and a second epitope have been described in U.S. Pat. No. 5,078,998 (anti-CD3/tumor cell antigen); U.S. Pat. No. 5,601,819 (anti-CD3/IL-2R; anti-CD3/CD28; anti-CD3/CD45); U.S. Pat. No. 6,129, 914 (anti-CD3/malignant B cell antigen); 7,112,324 (anti-CD3/CD19); U.S. Pat. No. 6,723,538 (anti-CD3/CCR5); U.S. Pat. No. 7,235,641 (anti-CD3/EpCAM); U.S. Pat. No. 7,262,276 (anti-CD3/ovarian tumor antigen); and U.S. Pat. No. 5,731,168 (anti-CD3/CD4IgG).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-39 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-59 (1991).

Using a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, CH2, and CH3 regions. It is preferred to have the first heavy-chain constant region (CH1) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three-polypeptide fragment when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Preferably, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

Using another approach described in U.S. Pat. No. 5,731, 168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with several cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-25 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed could bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., J. Immunol. 148(5):1547-53 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized to produce antibody homodimers. The "diabody" technology described by Hollinger et al., Proc. Natl. Acad. Sci. USA 90:6444-48 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments using single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Heteroconjugate Antibodies

Heteroconjugate antibodies are also within the scope of this disclosure. Heteroconjugate antibodies are composed of two covalently joined antibodies. Such antibodies have been proposed to target immune system cells to unwanted cells (see U.S. Pat. No. 4,676,980), and for treatment of HIV infection (see WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of this disclosure may be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody preferably further comprises at least two (and preferably four) light chain variable domain polypeptides. The multivalent antibody may comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the disclosure with respect to effector function, e.g., to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-95 (1992) and Shopes, B. J. Immunol. 148:2918-22 (1992). Homodimeric antibodies with enhanced anti-viral activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-30 (1989).

To increase the serum half-life of the antibody, a salvage receptor binding epitope may be incorporated into the antibody (especially an antibody fragment) as described in U.S. Pat. No. 5,739,277. The term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

9. Immunoconjugates

The disclosure also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate). Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

This disclosure further contemplates an immunoconjugate formed between an antibody and a compound with nucleolytic activity (e.g., a ribonuclease or a DNA endonuclease such as a deoxyribonuclease; DNase).

For selective destruction of an EBV-infected cell, the antibody may comprise a radioactive atom. A variety of radioactive isotopes are available to produce radioconjugated anti-gp350 antibodies. Examples include At211, I131, I125, Y90, Re186, Re188, Sm153, Bi212, P32, Pb212 and radioactive isotopes of Lu. When the conjugate is used for diagnosis, it may comprise a radioactive atom for scintigraphic studies, for example tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as tc99m or I123, Re186, Re188 and In111 can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the disclosure expressly contemplate, but are not limited to, an ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone) benzoate) which are commercially available from Pierce Biotechnology, Inc., Rockford, IL).

Alternatively, a fusion protein comprising the anti-EBV gp350 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The antibody may also be conjugated to a "receptor" (such streptavidin) for utilization in pre-targeting of viral infected cells, wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-gp350 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of this disclosure can be conjugated to the liposomes as described in Martin et al., J. Biol. Chem. 257:286-288 (1982) via a disulfide interchange reaction. A chemotherapeutic agent is optionally contained within the liposome. See Gabizon et al., J. National Cancer Inst. 81(19):1484 (1989).

B. gp350 Binding Oligopeptides gp350 binding oligopeptides of this disclosure are oligopeptides that bind, preferably specifically, to an EBV gp350 protein. gp350 binding oligopeptides may be chemically synthesized using known oligopeptide synthesis methodology or may be prepared and purified using recombinant technology. gp350 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an EBV gp350 protein. gp350 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

Bacteriophage (phage) display is one known technique used to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249:386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215:439 (1998); Zhu et al., Cancer Research, 58(15): 3209-14 (1998); Jiang et al., Infection & Immunity, 65(11): 4770-77 (1997); Ren et al., Gene, 195(2):303-11 (1997); Ren, Protein Sci., 5: 1833 (1996); Efimov et al., Virus Genes, 10:173 (1995)) and T7 phage display systems (Smith and Scott, Methods in Enzymology, 217: 228-57 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of Staphlylococcus aureus protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432, 018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. Screening for Anti-Gp350 Antibodies and Gp350 Binding Oligopeptides with the Desired Properties Techniques for generating antibodies or oligopeptides that bind to EBV gp350 proteins have been described above. One may further select antibodies or oligopeptides with certain biological characteristics, as desired.

The growth inhibitory effects of an anti-gp350 antibody of this disclosure may be assessed by methods known in the art, e.g., using cells which express an EBV gp350 protein either endogenously or following transfection with the gp350 gene. For example, appropriate EBV infected cells may be treated with an anti-gp350 monoclonal antibody or oligopeptide of this disclosure at various concentrations for a few days (e.g., 2-7) and stained with crystal violet or MTT or analyzed by some other colorimetric assay. Another method of measuring proliferation would be by comparing 3H-thymidine uptake by the cells treated in the presence or absence an anti-gp350 antibody, or gp350 binding oligopeptide of the disclosure. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of infected cells in vivo can be determined in various ways known in the art. Preferably, the anti-gp350 antibody, or gp350 binding oligopeptide will inhibit cell proliferation of an EBV infected cell in vitro or in vivo by about 25-100% compared to the untreated infected cell, more preferably, by about 30-100%, and even more preferably by about 50-100% or 70-100%. Growth inhibition can be measured at an antibody concentration of about 0.5 to 30 µg/ml or about 0.5 nM to 200 nM in cell culture, where the growth inhibition is determined 1-10 days after exposure of the cells to the antibody. The antibody is growth inhibitory in vivo if administration of the anti-gp350 antibody at about 1 µg/kg to about 100 mg/kg body weight results in reduction in cell growth or proliferation within about 5 days to 3 months from the first administration of the antibody, preferably within about 5 to 30 days.

To select for an anti-gp350 antibody, gp350 binding oligopeptide which induces cell death, loss of membrane integrity as indicated by, e.g., propidium iodide (PI), trypan blue or 7AAD uptake may be assessed relative to control. A PI uptake assay can be performed in the absence of complement and immune effector cells. EBV gp350 protein-expressing cells are incubated with medium alone or medium containing the appropriate anti-gp350 antibody (e.g., at about 10 g/ml), gp350 binding oligopeptide. The cells are incubated for a 3-day time period. Following each treatment, cells are washed and aliquoted into 35 mm strainer-capped 12×75 tubes (1 ml per tube, 3 tubes per treatment group) for removal of cell clumps. Tubes then receive PI (10 g/ml). Samples may be analyzed using a FACSCAN® flow cytometer and FACSCONVERT® CellQuest software (Becton Dickinson). Those anti-gp350 antibodies, or gp350 binding oligopeptides that induce statistically significant levels of cell death as determined by PI uptake may be selected as cell death-inducing anti-gp350 antibodies or gp350 binding oligopeptides.

To screen for antibodies or oligopeptides which bind to an epitope on an EBV gp350 protein bound by an antibody of interest, a routine cross-blocking assay such as that described in Antibodies, A Laboratory Manual, Cold Spring Harbor Laboratory, Ed Harlow and David Lane (1988), can be performed. This assay can be used to determine if a test antibody or oligopeptide binds the same site or epitope as a known anti-gp350 antibody. Alternatively or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an EBV gp350 protein can be used in competition assays with the test antibodies or with a test antibody and an antibody with a characterized or known epitope.

D. Anti-Gp350 Antibody and EBV Gp350 Binding Oligopeptide Variants

In addition to the anti-gp350 antibodies described herein, it is contemplated that anti-gp350 antibody variants can be prepared. Anti-gp350 antibody variants can be prepared by introducing appropriate nucleotide changes into the encoding DNA, and/or by synthesis of the desired antibody or polypeptide. Those skilled in the art will appreciate that amino acid changes may alter post-translational processes of the anti-gp350 antibody, such as changing the number or position of glycosylation sites or altering the membrane anchoring characteristics.

Variations in the anti-gp350 antibodies described herein can be made, for example, using any of the techniques and guidelines for conservative and non-conservative mutations set forth, for instance, in U.S. Pat. No. 5,364,934. Variations may be a substitution, deletion, or insertion of one or more codons encoding the antibody or polypeptide that results in a change in the amino acid sequence as compared with the native sequence antibody or polypeptide. Optionally, the variation is by substitution of at least one amino acid with any other amino acid in one or more of the domains of the anti-gp350 antibody. Guidance in determining which amino acid residue may be inserted, substituted or deleted without adversely affecting the desired activity may be found by comparing the sequence of the anti-gp350 antibody with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions, or substitutions of amino acids in the sequence and testing the resulting variants for activity exhibited by the full-length or mature native sequence.

Anti-gp350 antibody fragments are provided herein. Such fragments may be truncated at the N-terminus or C-terminus, or may lack internal residues, for example, when compared with a full length native antibody. Certain fragments lack amino acid residues that are not essential for a desired biological activity of the anti-gp350 antibody.

Anti-gp350 antibody fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-gp350 antibody fragments share at least one biological and/or immunological activity with the native anti-gp350 antibodies disclosed herein.

Conservative substitutions of interest are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the anti-gp350 antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the anti-gp350 antibody variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-85 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of the anti-gp350 antibody also may be substituted, generally with serine, to improve the oxidative stability of the molecule and prevent aberrant crosslinking. Conversely, cysteine bond(s) may be added to the anti-gp350 antibody to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. To identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and EBV gp350 protein. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-gp350 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-gp350 antibody.

E. Modifications of Anti-gp350 Antibodies

Covalent modifications of anti-gp350 antibodies and EBV gp350 proteins are included within the scope of this disclosure. One type of covalent modification includes reacting targeted amino acid residues of an anti-gp350 antibody with an organic derivatizing agent that can react with selected side chains or the N- or C-terminal residues of the anti-gp350 antibody. Derivatization with bifunctional agents is useful, for instance, for crosslinking anti-gp350 antibody to a water-insoluble support matrix or surface for use in purifying anti-gp350 antibodies, or detection of gp350 protein in biological samples, or EBV diagnostic assays. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification of the anti-gp350 antibody included within the scope of this disclosure comprises altering the native glycosylation pattern of the antibody or polypeptide. "Altering the native glycosylation pattern" is intended for purposes herein to mean deleting one or more carbohydrate moieties found in native sequence anti-gp350 antibody (either by removing the underlying glycosylation site or by deleting the glycosylation by chemical and/or enzymatic means), and/or adding one or more glycosylation sites that are not present in the native sequence anti-gp350 antibody. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl galactosamine, galactose, or xylose to a hydroxyamino acid, most commonly serine or threonine, although 5-hydroxyproline or 5-hydroxylysine may also be used.

Addition of glycosylation sites to the anti-gp350 antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original anti-gp350 antibody (for O-linked glycosylation sites). The anti-gp350 antibody amino acid sequence may optionally be altered through changes at the DNA level, particularly by mutating the DNA encoding the anti-gp350 antibody at preselected bases such that codons are generated that will translate into the desired amino acids.

Another means of increasing the number of carbohydrate moieties on the anti-gp350 antibody is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the anti-gp350 antibody may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved using a variety of endo- and exo-glycosidases as described by Thotakura et al., Meth. Enzymol., 138:350 (1987).

Another type of covalent modification of anti-gp350 antibody comprises linking the antibody or polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-gp350 antibody of this disclosure may also be modified in a way to form chimeric molecules comprising an anti-gp350 antibody fused to another, heterologous polypeptide or amino acid sequence.

Such a chimeric molecule may comprise a fusion of the anti-gp350 antibody with a tag polypeptide which provides an epitope to which an anti-tag antibody can selectively bind. The epitope tag is generally placed at the amino- or carboxyl-terminus of the anti-gp350 antibody. The presence of such epitope-tagged forms of the anti-gp350 antibody can be detected using an antibody against the tag polypeptide. Also, provision of the epitope tag enables the anti-gp350 antibody to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto (Evan et al., Molecular and Cellular Biology, 5:3610-16 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-10 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

Alternatively, the chimeric molecule may comprise a fusion of the anti-gp350 antibody with an immunoglobulin or a region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-gp350 antibody in place of at least one variable region within an Ig molecule. Preferably, the immunoglobulin fusion includes the hinge, CH2 and CH3, or the hinge, CH1, CH2 and CH3 regions of an IgG1 molecule. For the production of immunoglobulin fusions, see also U.S. Pat. No. 5,428,130.

F. Preparation of Anti-Gp350 Antibodies and EBV Gp350 Binding Oligopeptides

The description below relates primarily to production of anti-gp350 antibodies and EBV gp350 binding oligopeptides by culturing cells transformed or transfected with a vector containing anti-gp350 antibody-, or EBV gp350 binding oligopeptide-encoding nucleic acid. It is, of course, contemplated that alternative methods, which are well known in the art, may be employed to prepare anti-gp350 antibodies and EBV gp350 binding oligopeptides. For instance, the appropriate amino acid sequence, or portions thereof, may be produced by direct peptide synthesis using solid-phase techniques (e.g., Stewart et al., Solid-Phase Peptide Synthesis, W.H. Freeman Co., San Francisco, C A (1969); Merrifield, J. Am. Chem. Soc., 85:2149-54 (1963)). In vitro protein synthesis may be performed using manual techniques or by automation. Automated synthesis may be accomplished, for instance, using an Applied Biosystems Peptide Synthesizer (Foster City, CA) using manufacturer's instructions. Various portions of the anti-gp350 antibody may be chemically synthesized separately and combined using chemical or enzymatic methods to produce the desired anti-gp350 antibody.

1. Isolation of DNA Encoding Anti-Gp350 Antibody

DNA encoding anti-gp350 antibody may be obtained from a cDNA library prepared from tissue believed to possess the anti-gp350 antibody mRNA and to express it at a detectable level. Accordingly, human anti-gp350 antibody DNA can be conveniently obtained from a cDNA library prepared from human tissue. The anti-gp350 antibody-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding anti-gp350 antibody is to use PCR methodology [Sambrook et al., supra; Dieffenbach et al., PCR Primer: A Laboratory Manual (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like 32P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acids having protein coding sequences may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-gp350 antibody production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, CaPO4, liposome-mediated, and electroporation. Depending on the host cell used, transformation is performed using standard techniques appropriate to such cells. The calcium treatment employing calcium chloride, as described in Sambrook et al., supra, or electroporation is generally used for prokaryotes. Infection with Agrobacterium tumefaciens is used for transformation of certain plant cells, as described by Shaw et al., Gene, 23:315 (1983) and WO 89/05859 published 29 Jun. 1989. For mammalian cells without such cell walls, the calcium phosphate precipitation method of Graham and van der Eb, Virology, 52:456-457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527-537 (1990) and Mansour et al., Nature, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). Other suitable prokaryotic host cells include Enterobacteriaceae such as Escherichia, e.g., E. coli, Enterobacter, Erwinia, Klebsiella, Proteus, Salmonella, e.g., Salmonella typhimurium, Serratia, e.g., Serratia marcescans, and Shigella, as well as Bacilli such as B. subtilis and B. licheniformis (e.g., B. licheniformis 41P disclosed in DD 266,710 published 12 Apr. 1989), Pseudomonas such as P. aeruginosa, and Streptomyces. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including E. coli W3110 strain 1A2, which has the complete genotype tonA; E. coli W3110 strain 9E4, which has the complete genotype tonA ptr3; E. coli W3110 strain 27C7 (ATCC 55,244), which has the complete genotype tonA ptr3 phoA E15 (argF-lac)169 degP ompT kanr; E. coli W3110 strain 37D6, which has the complete genotype tonA ptr3 phoA E15 (argF-lac)169 degP ompT rbs7 ilvG kanr; E. coli W3110 strain 40B4, which is strain 37D6 with a non-kanamycin resistant degP deletion mutation; and an E. coli strain having mutant periplasmic protease disclosed in U.S. Pat. No. 4,946,783. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in EBV or EBV-infected cell destruction. Full length antibodies have greater half-life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the E. coli cell paste in a soluble fraction and can be purified through, e.g., a protein A or G column depending on the isotype. Final purification can be carried out similar to the process for purifying antibody expressed, e.g., in CHO cells.

In addition to prokaryotes, eukaryotic microbes such as filamentous fungi or yeast are suitable cloning or expression hosts for anti-gp350 antibody-encoding vectors. Saccharomyces cerevisiae is a commonly used lower eukaryotic host microorganism. Others include Schizosaccharomyces pombe (Beach and Nurse, Nature, 290: 140 [1981]; EP 139,383 published 2 May 1985); Kluyveromyces hosts (U.S.

Pat. No. 4,943,529; Fleer et al., Bio/Technology, 9:968-975 (1991)) such as, e.g., *K. lactis* (MW98-8C, CBS683, CBS4574; Louvencourt et al., J. Bacteriol., 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus; yarrowia* (EP 402,226); *Pichia pastoris* (EP 183,070; Sreekrishna et al., J. Basic Microbiol., 28:265-278 [1988]); *Candida; Trichoderma reesia* (EP 244,234); *Neurospora crassa* (Case et al., Proc. Natl. Acad. Sci. USA, 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., Biochem. Biophys. Res. Commun., 112:284-289 [1983]; Tilburn et al., Gene, 26:205-221 [1983]; Yelton et al., Proc. Natl. Acad. Sci. USA, 81: 1470-1474 [1984]) and *A. niger* (Kelly and Hynes, EMBO J., 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, The Biochemistry of Methylotrophs, 269 (1982).

Suitable host cells for the expression of glycosylated anti-gp350 antibody are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to this disclosure, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-gp350 antibody production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-gp350 antibody may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The anti-gp350 monoclonal antibodies may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-gp350 antibody-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion, the signal sequence may be, e.g., the yeast invertase leader, alpha factor leader (including *Saccharomyces* and *Kluyveromyces* a-factor leaders, the latter described in U.S. Pat. No. 5,010, 182), or acid phosphatase leader, the *C. albicans* glucoamylase leader (EP 362,179), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-gp350 antibody-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast lacking the ability to grow in tryptophan, for example, ATCC No. 44076 or PEP4-1 (Jones, Genetics, 85:12 (1977)).

Expression and cloning vectors usually contain a promoter operably linked to the anti-gp350 antibody-encoding nucleic acid sequence to direct mRNA synthesis. Promoters recognized by a variety of potential host cells are well known. Promoters suitable for use with prokaryotic hosts include the β-lactamase and lactose promoter systems (Chang et al., Nature, 275:615 (1978); Goeddel et al., Nature, 281:544 (1979)), alkaline phosphatase, a tryptophan (trp) promoter system (Goeddel, Nucleic Acids Res., 8:4057 (1980)), and hybrid promoters such as the tac promoter (deBoer et al., Proc. Natl. Acad. Sci. USA, 80:21-25 (1983)). Promoters for use in bacterial systems also will contain a Shine-Dalgarno sequence operably linked to the DNA encoding anti-gp350 antibody.

Examples of suitable promoting sequences for use with yeast hosts include the promoters for 3-phosphoglycerate kinase (Hitzeman et al., J. Biol. Chem., 255:2073 (1980)) or other glycolytic enzymes (Hess et al., J. Adv. Enzyme Reg., 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-gp350 antibody transcription from vectors in mammalian host cells is controlled, for example, by promoters obtained from the genomes of viruses such as polyoma virus, fowlpox virus (UK 2,211,504), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-gp350 antibody by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, a-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-gp350 antibody coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-gp350 antibody.

Still other methods, vectors, and host cells suitable for adaptation to the synthesis of anti-gp350 antibody in recombinant vertebrate cell culture are described in Gething et al., Nature, 293:620-25 (1981); Mantei et al., Nature, 281:40-46 (1979); EP 117,060; and EP 117,058.

4. Culturing the Host Cells

The host cells used to produce the anti-gp350 antibody of this disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence EBV gp350 protein or against a synthetic peptide based on the DNA sequences provided herein or against exogenous sequence fused to gp350 DNA and encoding a specific antibody epitope.

6. Purification of Anti-Gp350 Antibodies and Gp350 Binding Oligopeptides

Forms of anti-gp350 antibody may be recovered from culture medium or from host cell lysates. If membrane-bound, it can be released from the membrane using a suitable detergent solution (e.g. Triton-X 100) or by enzymatic cleavage. Cells employed in expression of anti-gp350 antibody can be disrupted by various physical or chemical means, such as freeze-thaw cycling, sonication, mechanical disruption, or cell lysing agents.

It may be desired to purify anti-gp350 antibody from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-gp350 antibody and EBV gp350 protein. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the anti-gp350 antibody produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, NJ) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

G. Pharmaceutical Formulations

Therapeutic formulations of the anti-gp350 antibodies or gp350 binding oligopeptides of this disclosure are prepared for storage by mixing the antibody, polypeptide, or oligopeptide having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the indication being treated, preferably those with complementary activities that do not adversely affect each other. For example, in addition to an anti-gp350 antibody or gp350 binding oligopeptide, it may be desirable to include in the one formulation, an additional antibody, e.g., a second anti-gp350 antibody which binds a different epitope on the EBV gp350 protein. Alternatively, or additionally, the composition may further comprise a cytokine, an anti-inflammatory agent, or an interferon. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences, 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

H. Diagnosis and Treatment with Anti-Gp350 Antibodies or Gp350 Binding Olilopeptides gp350 expression may be evaluated using an in vivo diagnostic assay, e.g., by administering a molecule (such as an anti-gp350 antibody or gp350 binding oligopeptide) which binds the molecule to be detected and is tagged with a detectable label (e.g., a radioactive isotope or a fluorescent label) and externally scanning the patient for localization of the label.

As described above, the anti-gp350 antibodies or oligopeptides of this disclosure have various non-therapeutic applications. The anti-gp350 antibodies or oligopeptides of this disclosure are useful for diagnosis and staging of EBV infections. The antibodies or oligopeptides are also useful for purification or immunoprecipitation of EBV gp350 protein from cells, for detection and quantitation of EBV gp350 protein in vitro, e.g., in an ELISA or a Western blot, to kill and eliminate gp350-expressing cells from a population of mixed cells as a step in the purification of other cells.

Currently, EBV infection prevention and treatment involves preventing transmission of the virus, vaccination, or administration of interferons. Anti-gp350 antibody or oligopeptide therapy (such as by passive immunotherapy) may be especially desirable in elderly patients or immunocompromised patients or pregnant patients who may not tolerate the side effects of vaccination or vaccine components or interferons, or who cannot mount an immunological response.

A conjugate comprising an anti-gp350 antibody or oligopeptide conjugated with a cytotoxic agent may be administered to the patient. Preferably, the immunoconjugate bound to the anti-gp350 antibody is internalized by the cell, resulting in increased therapeutic efficacy of the immunoconjugate in killing the infected cell to which it binds. Preferably, the cytotoxic agent targets or interferes with the nucleic acid in the infected cell. The anti-gp350 antibodies or oligopeptides or conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody or oligopeptide is preferred.

Other therapeutic regimens may be combined with the administration of the anti-gp350 antibody or oligopeptide. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-gp350 antibody or antibodies or oligopeptides with administration of an antibody directed against another EBV antigen.

The therapeutic treatment methods of this disclosure may include the combined administration of an anti-gp350 antibody (or antibodies) or oligopeptides and an interferon.

For the prevention or treatment of EBV infection or EBV-associated disease, the dosage and mode of administration of these antibodies and therapeutic proteins will be chosen by the medical provider according to known criteria. The appropriate dosage of antibody or oligopeptide will depend on the type of disease to be treated, as defined above, the severity and course of the disease, whether the antibody or oligopeptide is administered for preventive or therapeutic purposes, previous therapy, the patient's clinical history and response to the antibody or oligopeptide and the discretion of the medical provider. The antibody or oligopeptide is suitably administered to the patient at one time or over a series of treatments. Preferably, the antibody or oligopeptide is administered by intravenous infusion or by subcutaneous injections. Depending on the type and severity of the disease, about 1 mcg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-gp350 antibody. However, other dosage regimens may be useful. A typical daily dosage might range from about 1 mcg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to medical providers of skill in the art.

Aside from administration of the anti-gp350 antibody to a patient, this disclosure contemplates administration of the antibody by gene therapy. Such administration of nucleic acid encoding the antibody is encompassed by the expression "administering a therapeutically effective amount of an antibody." See, for example, WO96/07321 concerning the use of gene therapy to generate intracellular antibodies.

There are two major approaches to getting the nucleic acid (optionally contained in a vector) into the patient's cells; in vivo and ex vivo. For in vivo delivery, the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

The anti-gp350 antibodies of the disclosure can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail above, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, to minimize side effects or therapeutic complications, certain other Fc regions may be used.

These antibodies may include an antibody that competes for binding or binds substantially to, the same epitope as the antibodies of the disclosure. Antibodies having the biological characteristics of the present anti-gp350 antibodies of this disclosure are also contemplated, specifically including the in vivo targeting, and infection inhibiting or preventing, or cytotoxic characteristics.

The present anti-gp350 antibodies or oligopeptides are useful for treating an EBV infection or alleviating one or more symptoms of the infection in a mammal. The antibody or oligopeptide can bind to at least a portion of an infected cell that express EBV gp350 protein in the mammal. Preferably, the antibody or oligopeptide is effective to destroy or kill gp350-expressing cells or inhibit the growth of such cells, in vitro or in vivo, upon binding to EBV gp350 protein on the cell. Such an antibody includes a naked anti-gp350 antibody (not conjugated to any agent). Naked antibodies that have cytotoxic or cell growth inhibition properties can be further harnessed with a cytotoxic agent to render them even more potent in EBV or EBV-infected cell destruction. Cytotoxic properties can be conferred to an anti-gp350 antibody by, e.g., conjugating the antibody with a cytotoxic agent, to form an immunoconjugate as described herein. The cytotoxic agent or a growth inhibitory agent is preferably a small molecule.

This disclosure also provides a composition comprising an anti-gp350 antibody or oligopeptide of the disclosure, and a carrier. For the purposes of treating EBV infection, compositions can be administered to the patient in need of such treatment, wherein the composition can comprise one or more anti-gp350 antibodies present as an immunoconjugate or as the naked antibody. The compositions may comprise these antibodies or oligopeptides in combination with other therapeutic agents. The formulation may be a therapeutic formulation comprising a pharmaceutically acceptable carrier.

This disclosure also provides isolated nucleic acids encoding the anti-gp350 antibodies. Nucleic acids encoding both the H and L chains and especially the hypervariable region residues, chains which encode the native sequence antibody as well as variants, modifications and humanized versions of the antibody, are encompassed.

The disclosure also provides methods useful for treating an EBV infection or alleviating one or more symptoms of the infection in a mammal, comprising administering a therapeutically effective amount of an anti-gp350 antibody or oligopeptide of this disclosure to the mammal. The antibody or oligopeptide therapeutic compositions can be administered short term (acutely) or chronically, or intermittently as directed by a medical professional. Also provided are methods of inhibiting the growth of, and killing an EBV gp350 protein-expressing cell.

This disclosure also provides methods useful for treating or preventing post-transplant lymphoproliferative disorder (PTLD) in a mammal. In these methods, the antibodies or fragments thereof, are particularly effective for PTLD in EBV-seronegative persons (i.e., not previously infected with EBV) and given within a few days of solid organ or bone marrow transplant. In these methods, multiple doses of the antibodies, or functional fragments thereof, may be given over time (for example, in persons undergoing solid organ transplants, these proteins may be given within 72 hours of transplant and additional doses may be given at 1, 4, 6, 8, 12, and 16 weeks after transplant). Virtually all transplant recipients are screened for EBV and CMV serology prior to transplant. The antibodies, or functional fragments thereof, may also be administered to EBV-seropositive persons, but the rate of PTLD is lower is EBV seropositive persons than seronegative persons. In these methods, the antibodies, or functional fragments thereof, and an EBV vaccine may be co-administered. In these co-administration methods, the antibodies, or functional fragments thereof, and the vaccine (s) may be administered on the same day at different sites, as is done for combined treatment with vaccine and immunoglobulin for rabies, hepatitis B, or tetanus exposure. In these methods, a single dose of the antibodies, or functional fragments thereof, would likely be given because the recipient would be expected to produce antibody in response to the vaccine.

J. Articles of Manufacture and Kits

This disclosure also provides assay devices, kits, and articles of manufacture comprising at least one anti-gp350 antibody or oligopeptide of this disclosure, optionally linked to a label, such as a fluorescent or radiolabel. The articles of manufacture may contain materials useful for the detection, diagnosis, or treatment of EBV infection. A preferred device is a lateral flow assay device which provides for point-of-care detection and/or diagnosis of an EBV infection. The article of manufacture comprises a container and a label or package insert on or associated with the container. Suitable containers include, for example, bottles, vials, syringes, etc. The containers may be formed from a variety of materials such as glass or plastic. The container holds a composition which is effective for detecting or treating the EBV infection and may have a sterile access port (for example the container may be an intravenous solution bag or a vial having a stopper pierceable by a hypodermic injection needle). At least one active agent in the composition is an anti-gp350 antibody or oligopeptide of this disclosure. The label or package insert indicates that the composition is used for detecting or treating EBV infection. The label or package insert may further comprise instructions for using the antibody or oligopeptide composition, e.g., in the testing or treating of the infected patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for EBV-infected cell killing assays, for purification, or immunoprecipitation of EBV gp350 protein from cells. For isolation and purification of EBV gp350 protein, the kit can contain an anti-gp350 antibodies or oligopeptides coupled to beads (e.g., sepharose beads). Kits can be provided which contain the antibodies or oligopeptides for detection and quantitation of EBV gp350 protein in vitro, e.g., in an ELISA or a Western blot. As with the article of manufacture, the kit comprises a container and a label or package insert on or associated with the container. The container holds a composition comprising at least one anti-gp350 antibody or oligopeptide of the disclosure. Additional containers may be included that contain, e.g., diluents and buffers, control antibodies. The label or package insert may provide a description of the composition as well as instructions for the intended in vitro or diagnostic use.

The anti-gp350 antibody or oligopeptide of this disclosure may also be provided as part of an assay device. Such assay devices include lateral flow assay devices. A common type of disposable lateral flow assay device includes a zone or area for receiving the liquid sample, a conjugate zone, and a reaction zone. These assay devices are commonly known as lateral flow test strips. They employ a porous material, e.g., nitrocellulose, defining a path for fluid flow capable of supporting capillary flow. Examples include those described in U.S. Pat. Nos. 5,559,041, 5,714,389, 5,120,643, and 6,228,660 all of which are incorporated herein by reference in their entireties. The anti-gp350 antibody or oligopeptide of this disclosure may also be used in a lateral flow assay device in conjunction with other antibodies to detect multiple EBV proteins or other herpesvirus proteins using a single biological sample from a subject or patient being tested on one portable, point-of-care device.

Another type of assay device is a non-porous assay device having projections to induce capillary flow. Examples of such assay devices include the open lateral flow device as disclosed in PCT International Publication Nos. WO 2003/103835, WO 2005/089082, WO 2005/118139, and WO 2006/137785, all of which are incorporated herein by reference in their entireties.

K. Anti-Gp350 Antibody Probes and B-Cell Probes

Anti-gp350 antibody and anti-gp350 B-cell probes of this disclosure are polypeptides that bind, preferably specifically, to an anti-gp350 antibody, or a B-cell expressing an anti-gp350 B cell receptor (BCR) (anti-gp350 B cell). Accordingly, the three-dimensional structure of such a probe resembles the three-dimensional structure of at least a portion of the EBV gp350 protein. The three-dimensional structure of an anti-gp350 antibody probe, or an anti-gp350 B-cell probe, of this disclosure may resemble the three-dimensional structure of the CR2-binding region of an EBV gp350 protein. An anti-gp350 antibody probe, or an anti-gp350 B-cell probe, of this disclosure may comprise an amino acid sequence from the CR2-binding region of an EBV gp350 protein. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, or at least 350 contiguous amino acids from the amino acid sequence forming the CR2-binding region of an EBV gp350 protein, wherein the probe has the ability to bind an anti-gp350 antibody, or a B-cell expressing an anti-gp350 BCR, and wherein the binding of the B-cell is through the BCR. An anti-gp350 antibody probe, or anti-gp350 B-cell probe, of this disclosure may comprise an amino acid sequence at least 90%, at least 95%, at least 97% or at least 99% identical to the amino acid sequence of the CR2-binding region of EBV gp350, wherein the probe can bind an anti-gp350 antibody, or a B-cell expressing an anti-gp350 BCR, and wherein the binding of the B-cell is through the BCR.

Anti-gp350 antibody probes, and anti-gp350 B-cell probes, of this disclosure can be any size sufficient to bind to an anti-gp350 antibody or an anti-gp350 B-cell. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, at last 300, at least 350, at least 400, or at least 450 amino acids in length. An anti-gp350 antibody probe, or an anti-gp350 B-cell probe, of this disclosure may comprise at least 10, at least 20, at least 30, at least 40, at east 50, at least 75, at least 100, at least 150, at least 200, at least 250, at last 300, at east 350, at least 400, or at least 450 contiguous amino acids from the amino acid sequence forming the CR2-binding region of and EBV gp350 protein, wherein the probe has the ability to bind an anti-gp350 antibody, or a B-cell expressing an anti-gp350 BCR, and wherein the binding of the B-cell is through the BCR.

Using an anti-gp350 antibody probe, or anti-gp350 B-cell probe, of this disclosure having a sequence identical to that of EBV gp35, to isolate gp350-specific B-cells might be problematic, because most B-cells, including memory B-cells, constitutively express CR2 on their surface. Consequently, probes having a three-dimensional structure, and/or a sequence, identical to the three-dimensional structure, and/or sequence, of the CR2-binding region of EBV gp350 will bind to almost all B-cells. Thus, anti-gp350 antibody probes, and anti-gp350 B-cell probes, of this disclosure may lack the ability to bind CR2. Such anti-gp350 antibody probes, and anti-gp350 B-cell probes, can be constructed, for example, by using the sequence of the CR2-binding region of an EBV gp350 protein to construct the probe, and then altering the sequence so that it no longer binds CR2. Thus, anti-gp350 antibody probes, or an anti-gp350 B-cell probes, of this disclosure may comprise a variant sequence of an EBV gp350 CR2 binding region. An anti-gp350 antibody probe, or anti-gp350 B-cell probe, of this disclosure comprises the sequence of an EBV gp350 CR2 binding region, wherein the sequence has been altered to reduce, or eliminate, binding of the probe to CR2. Such alterations include, but are not limited to, substitutions, insertions, and deletions of amino acid residues. Such probes preferentially bind to an anti-gp350 antibody, or an anti-gp350 BCR, but do not bind CR2. An anti-gp350 antibody probe, or anti-gp350 B-cell probe, of this disclosure may comprise an amino acid sequence at least 80% identical, at last 85% identical, at least 90% identical, at least 95% identical, at least 97% identical, or at least 99% identical to an EBV gp350 CR2 binding region, wherein the probe binds to an anti-gp350 antibody, or an anti-gp350 BCR, and wherein the probe does not bind CR2. An anti-gp350 antibody probe, or anti-gp350 B-cell probe, of this disclosure may comprise an amino acid sequence at least 80% identical, at last 85% identical, at least 90% identical, at least 95% identical, at least 97% identical, or at least 99% identical to SEQ ID NO:124, wherein the probe binds to an anti-gp350 antibody, or an anti-gp350 BCR, and wherein the probe, does not bind CR2.

An anti-gp350 antibody probe, or an anti-gp350 B-cell probe, of the disclosure, that binds to an anti-gp350 antibody or an anti-gp350 B cell expressing an anti-gp350 BCR, but that does not bind CR2, can be designed using methods known to those skilled in the art. For example, nucleic acid molecules encoding the CR2-binding region of an EBV gp350 protein can be randomly mutated, the mutated molecules inserted into expression vectors, the vectors introduced into cells capable of expressing them, and the cells cultured such that the encoded, mutated probes are expressed on the cells surface. The cells could then be screened to identify antibodies, B-cells, that bind to the expressed probes. Following identification of such antibodies, and/or B-cells, the identified antibodies, and/or B-cells, can then be tested for their ability to bind CR2. In an alternative method, the three-dimensional model of a complex between EBV gp350 and an anti-gp350 antibody is determined, and the amino acid residues involved in binding of the two molecules determined. A second molecule of a complex between gp350 and CR2 could also be produced, and the amino acid residues involved in formation of this complex determined. Using these models, a person skilled in the art could then chose specific locations within the gp350 protein that could be altered. For example, amino acid residues involved in pairing of gp350 and CR2, but which are not involved in pairing of gp350 and an anti-gp350 antibody, could be chosen for alteration. Once a variant sequence has been designed, nucleic acid molecules encoding the variant proteins can be synthesized, or produced from wild-type sequences using mutagenesis techniques E.g., PCR), and the encoded proteins expressed and tested for activity.

Using methodology such as that described above, the present inventors have identified amino acid residues involved in binding of EBV gp350 to CR2 and to an anti-gp350 antibody. In particular, the inventors have determined that at least residues Q122, P158, 1160, K161, W162, D163, N164, and D296 of the EBV gp350 protein (amino acid number 1 is the first residue of the protein represented by SEQ ID NO:124) are involved in binding of the protein with CR2. Thus, an anti-gp350 antibody probe, or an anti-gp350 B-cell probe, of this disclosure may comprise an amino acid sequence from the CR2-binding region an EBV gp350 protein, wherein at least one amino acid corresponding to amino acid Q122, P158, 1160, K161, W162, D163, N164, or D296, of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein at least one amino acid corresponding to amino acid Q122, P158, 1160, K161, W162, D163, N164, or D296, of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. When an amino acid residue is substituted, it is preferred that that the substituting amino acid residue have binding properties (e.g., ionic charge, hydrophobicity, etc.) different from the amino acid residue being replaced.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 Cr2-binding region, wherein the amino acid corresponding to amino acid Q122 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with asparagine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid P158 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid P158 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid P158 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid Q122 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid I160 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid W162 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with an amino acid residue selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with alanine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with asparagine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid N164 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, serine, and aspartate, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid N164 of SEQ ID NO:124 has been substituted with a serine residue, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein one or more amino acids has been inserted between the amino acid corresponding to amino acid N164 of SEQ ID NO:124 and the amino acid corresponding to C165 of SEQ ID NO:124, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein one or more amino acids selected from the group consisting of serine, threonine, cysteine, proline, asparagine, and glutamine, has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D163 of SEQ ID NO:124 has been deleted, or has been substituted with one or more amino acid residues, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been deleted, or has been substituted with one or more amino acid residues, wherein one or more amino acids has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D163 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein one or more amino acids selected from the group consisting of serine, threonine, cysteine, proline, asparagine, and glutamine, has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid W162 of SEQ ID NO:124 has been substituted with asparagine, wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 Cr2-binding region, wherein the amino acids corresponding to amino acids W162-N164 of SEQ ID NO:124 have been deleted, or have been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have been deleted, or have been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have been deleted, or have been substituted with an amino acid residue selected from the group consisting of serine, threonine, cysteine, proline, asparagine, glutamine, aspartate, glutamate, asparagine, arginine, glutamate, histidine, glycine, alanine, valine, leucine, methionine, isoleucine, and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acids corresponding to amino acids W162-N164 of SEQ ID NO:124 have each been substituted with an alanine residue, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has substituted with one or more amino acid residues, wherein the amino acid corresponding to amino acid I160 of SEQ ID NO:124 has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the amino acid corresponding to amino acid I160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid D296 of SEQ ID NO:124 has substituted with one or more amino acid residues, wherein the amino acid corresponding to amino acid P158 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has substituted with one or more amino acid residues, wherein the amino acid corresponding to amino acid P158 of SEQ ID NO:124 has been substituted with one or more amino acid residues, wherein the amino acid corresponding to amino acid I160 of SEQ ID NO:124 has substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with an amino acid residue selected from the group consisting of tyrosine, phenylalanine, tryptophan, serine, threonine, cysteine, proline, asparagine, glutamine, lysine, arginine, histidine, glycine, alanine, valine, leucine, methionine, and isoleucine, wherein the amino acid corresponding to amino acid P158 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, and aspartate, wherein the amino acid corresponding to amino acid 1160 of SEQ ID NO:124 has been substituted with an amino acid residue selected from the group consisting of serine, threonine, cysteine, proline, asparagine, glutamine, tyrosine, phenylalanine, tryptophan, glutamate, aspartate, arginine, glutamine, histidine and lysine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid P158 of SEQ ID NO:124 has been substituted with asparagine, wherein the amino acid corresponding to amino acid I160 of SEQ ID NO:124 has been substituted with threonine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid D296 of SEQ ID NO:124 has been substituted with arginine, wherein the amino acid corresponding to amino acid P158 of SEQ ID NO:124 has been substituted with arginine, wherein the amino acid corresponding to amino acid I160 of SEQ ID NO:124 has been substituted with arginine, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to the amino acid sequence of an EBV gp350 CR2-binding region, wherein the amino acid corresponding to amino acid K161 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid K161 of SEQ ID NO:124 has been deleted, or has been substituted with one or more amino acid residues, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:125, wherein the amino acid corresponding to amino acid K161 of SEQ ID NO:124 has been substituted with an amino acid residue selected from the group consisting of methionine, leucine, isoleucine, glycine, alanine, valine, phenylalanine, tyrosine, tryptophan, lysine, arginine, histidine, glutamate, serine, and aspartate, wherein the probe lacks the ability to bind CR2, and wherein the probe specifically binds to an anti-gp350 antibody or an anti-gp350 B-cell.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:127 or SEQ ID NO:145, wherein the amino acid corresponding to amino acid Q122 of SEQ ID NO:124 is asparagine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:127 or SEQ ID NO:145.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:129 or SEQ ID NO:147, wherein the amino acid corresponding to amino acid D163 of SEQ ID NO:124 is asparagine, and wherein a serine residue has been inserted between the amino acid corresponding to amino acid N164 of SEQ ID NO:124 and the amino acid corresponding to C165 of SEQ ID NO:124, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:129 or SEQ ID NO:147.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:131 or SEQ ID NO:149, wherein the amino acid corresponding to amino acid D296 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:131 or SEQ ID NO:149.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:133 or SEQ ID NO:151, wherein the amino acid corresponding to amino acids W162-N164 of SEQ ID NO:124 have each been substituted with an alanine residue, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:133 or SEQ ID NO:151.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:135 or SEQ ID NO:153, wherein the amino acid corresponding to amino acid D296 of SEQ ID NO:124 is arginine, wherein the amino acid corresponding to amino acid I160 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:135 or SEQ ID NO:153.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:137 or SEQ ID NO:155, wherein the amino acid corresponding to amino acid D296 of SEQ ID NO:124 is arginine, wherein the amino acid corresponding to amino acid P158 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:137 or SEQ ID NO:155.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:139 or SEQ ID NO:157, wherein the amino acid corresponding to amino acid D296 of SEQ ID NO:124 is arginine, wherein the amino acid corresponding to amino acid P158 of SEQ ID NO:124 is asparagine, wherein the amino acid corresponding to amino acid I160 of SEQ ID NO:124 is threonine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:139 or SEQ ID NO:157.

An anti-gp350 antibody probe, or an anti-gp350 B-cell probe, of this disclosure may comprise an amino acid sequence at least 80% identical, at least 85% identical, at least 90% identical, at least 95% identical, at least 97% identical, or at least 99% identical to SEQ ID NO:141 or SEQ ID NO:159, wherein the amino acid corresponding to amino acid D296 of SEQ ID NO:124 is arginine, wherein the amino acid corresponding to amino acid P158 of SEQ ID NO:124 is arginine, wherein the amino acid corresponding to amino acid I160 of SEQ ID NO:124 is arginine, wherein the probe lacks the ability to bind CR2, and wherein the probe specifically binds to an anti-gp350 antibody or an anti-gp350 B-cell. An anti-gp350 antibody probe, or an anti-gp350 B-cell probe, of this disclosure may comprise SEQ ID NO:141 or SEQ ID NO:159.

Thus, this disclosure includes a nucleic acid molecule encoding an anti-gp350 antibody probe, or an anti-gp350 B-cell probe, disclosed herein. Such nucleic acid molecule includes DNA, RNA, mixtures thereof, and modified forms thereof. This disclosure also includes nucleic acid vectors, such as, for example, plasmids, expression vectors, viral vectors, etc., as well as cells comprising such nucleic acid vectors. Methods of producing nucleic acid molecules and nucleic acid vectors of the invention have been described herein.

Anti-gp350 antibody and anti-gp350 B-cell probes of this disclosure can be produced chemically (e.g., oligopeptide synthesis methodology), or they can be produced using recombinant technology. For example, an anti-gp350 antibody probe, or anti-gp350 B-cell probe can be deigned, by producing a nucleic acid molecule encoding the probe, and the nucleic acid molecule introduced into a cell where it can be expressed.

This disclosure includes methods of identifying anti-gp350 antibodies, comprising contacting a test solution containing antibodies with an anti-gp350 antibody probe, or an anti-gp350 B-cell probe, of the disclosure, and isolating an antibody that specifically binds to the anti-gp350 antibody probe, or the anti-gp350 B-cell probe, thereby identifying an anti-gp350 antibody. The anti-gp350 antibody probe may be joined to an affinity tag such as, for example, a His tag, an epitope tag or a labeled tag (e.g., fluorescent label). The anti-gp350 antibody probe, or the anti-gp350 B-cell, may be immobilized on a surface.

This disclosure also includes methods of identifying an anti-gp350 B-cell (i.e., a B-cell expressing an anti-gp350 B-cell receptor), comprising contacting a test solution containing B-cells with an anti-gp350 antibody probe, or an anti-gp350 B-cell probe, of the disclosure, and isolating a B-cell that specifically binds to the anti-gp350 antibody probe, or the anti-gp350 B-cell probe, thereby identifying a B-cell expressing an anti-gp350 B-cell receptor. The anti-gp350 antibody probe, or the anti-gp350 B-cell probe, may be joined to an affinity tag such as, for example, a His tag, an epitope tag or a labeled tag (e.g., fluorescent label). The anti-gp350 antibody probe, or the anti-gp350 B-cell probe, may be immobilized on a surface.

All patent and literature references cited in the present specification are hereby incorporated by reference in their entirety.

The foregoing disclosure is sufficient to enable one skilled in the art to practice the invention. The present invention is not to be limited in scope by the constructs described, because the described embodiments are intended as illustrations of certain aspects of the invention and any constructs that are functionally equivalent are within the scope of this invention.

Example

The inventors isolated and characterized a set of human monoclonal antibodies from two blood bank donors who have extraordinally high serum neutralizing antibody titers to EBV. Using the receptor-binding null gp350 probes described in this invention they successfully identified gp350-specific B cells in peripheral blood mononuclear cells without having issues with non-targeting memory B cells that ubiquitously express CR2 (i.e. gp350 receptor) on their surface. Of those monoclonal antibodies, antibodies named A9 and E11 derived from 2 independent donors possessed the highest neutralization activity against EBV, and hence, they were structurally characterized. Structures of antigen-binding fragment (Fab) of A9 and E11 were solved to resolution of 2.4 and 1.8 Å, respectively. Additionally, the structure of Fab A9 in complex with gp350 receptor-binding domain was solved to 3.5 Å. Based on the structural information they designed a set of mutations on both antibodies A9 and E11 that potentially improve affinity and therefore, enhance neutralization potency.

These highly potent neutralizing monoclonal antibodies are useful in prophylaxis to prevent EBV infection in EBV-naïve transplantation recipients who revive organs/bone marrow from EBV-positive donors. These EBV-naïve transplantation recipients are at high risk for developing lymphoproliferative disease caused by EBV. Also, patients with certain genetic disorders (e.g. XLP1) are at high risk of developing fatal mononucleosis after primary infection with the virus. Currently, there are no such countermeasures that specifically target EBV.

These antibodies are also useful as therapeutics to treat infectious mononucleosis or to prevent reactivation of virus in persistently EBV infected individuals.

The invention claimed is:

1. An isolated antibody that binds Epstein Barr Virus (EBV) gp350 protein, comprising a variable heavy (VH) domain and a variable light (VL) domain, wherein:
   (a) the VH domain comprises the complementarity determining region 1 (CDR1), CDR2 and CDR3 sequences of SEQ ID NO: 1, and the VL domain comprises the CDR1, CDR2 and CDR3 sequences of SEQ ID NO: 6;
   (b) the VH domain comprises the CDR1, CDR2 and CDR3 sequences of SEQ ID NO: 11, and the VL domain comprises the CDR1, CDR2 and CDR3 sequences of SEQ ID NO:
   (c) the VH domain comprises the CDR1, CDR2 and CDR3 sequences of SEQ ID NO: 21, and the VL domain comprises the CDR1, CDR2 and CDR3 sequences of SEQ ID NO: 26;
   (d) the VH domain comprises the CDR1, CDR2 and CDR3 sequences of SEQ ID NO: 31, and the VL domain comprises the CDR1, CDR2 and CDR3 sequences of SEQ ID NO: 36;
   (e) the VH domain comprises the CDR1, CDR2 and CDR3 sequences of SEQ ID NO: 41, and the VL domain comprises the CDR1, CDR2 and CDR3 sequences of SEQ ID NO: 46;
   (f) the VH domain comprises the CDR1, CDR2 and CDR3 sequences of SEQ ID NO: 161, and the VL domain comprises the CDR1, CDR2 and CDR3 sequences of SEQ ID NO: 166, wherein the antibody is an engineered antibody;
   (g) the VH domain comprises the CDR1, CDR2 and CDR3 sequences of SEQ ID NO: 171, and the VL domain comprises the CDR1, CDR2 and CDR3 sequences of SEQ ID NO: 176, wherein the antibody is an engineered antibody;
   (h) the VH domain comprises the CDR1, CDR2 and CDR3 sequences of SEQ ID NO: 181, the VL domain comprises the CDR1, CDR2 and CDR3 sequences of SEQ ID NO: 186, wherein the antibody is an engineered antibody;
   (i) the VH domain comprises the CDR1, CDR2 and CDR3 sequences of SEQ ID NO: 191, and the VL domain comprises the CDR1, CDR2 and CDR3 sequences of SEQ ID NO: 196, wherein the antibody is an engineered antibody;
   (j) the VH domain comprises the CDR1, CDR2 and CDR3 sequences of SEQ ID NO: 201, and the VL domain comprises the CDR1, CDR2 and CDR3 sequences of SEQ ID NO: 206, wherein the antibody is an engineered antibody;
   (k) the VH domain comprises the CDR1, CDR2 and CDR3 sequences of SEQ ID NO: 211, and the VL domain comprises the CDR1, CDR2 and CDR3 sequences of SEQ ID NO: 216, wherein the antibody is an engineered antibody;
   (l) the VH domain comprises the CDR1, CDR2 and CDR3 sequences of SEQ ID NO: 221, and the VL domain comprises the CDR1, CDR2 and CDR3 sequences of SEQ ID NO: 226, wherein the antibody is an engineered antibody;
   (m) the VH domain comprises the CDR1, CDR2 and CDR3 sequences of SEQ ID NO: 231, and the VL domain comprises the CDR1, CDR2 and CDR3 sequences of SEQ ID NO: 236, wherein the antibody is an engineered antibody;
   (n) the VH domain comprises the CDR1, CDR2 and CDR3 sequences of SEQ ID NO: 241, and the VL domain comprises the CDR1, CDR2 and CDR3 sequences of SEQ ID NO: 246, wherein the antibody is an engineered antibody;
   (o) the VH domain comprises the CDR1, CDR2 and CDR3 sequences of SEQ ID NO: 251, and the VH domain comprises the CDR1, CDR2 and CDR3 sequences of SEQ ID NO: 256, wherein the antibody is an engineered antibody;
   (p) the VH domain comprises the CDR1, CDR2 and CDR3 sequences of SEQ ID NO: 261, and the VL domain comprises the CDR1, CDR2 and CDR3 sequences of SEQ ID NO: 266, wherein the antibody is an engineered antibody;
   (q) the VH domain comprises the CDR1, CDR2 and CDR3 sequences of SEQ ID NO: 271, and the VL domain comprises the CDR1, CDR2 and CDR3 sequences of SEQ ID NO: 276, wherein the antibody is an engineered antibody; or (r) the VH domain comprises the CDR1, CDR2 and CDR3 sequences of SEQ ID NO: 281, and the VL domain comprises the CDR1, CDR2 and CDR3 sequences of SEQ ID NO: 286, wherein the antibody is an engineered antibody.

2. The antibody of claim 1, which is conjugated to a solid support selected from a support formed partially or entirely of glass, a polysaccharide, a polyacrylamide, a polystyrene, a polyvinyl alcohol, a silicone, an assay plate, and a purification column.

3. A composition comprising the antibody of claim 1 and a carrier.

4. The composition of claim 3, wherein the carrier comprises a pharmaceutically acceptable carrier.

5. An article of manufacture comprising a container and the composition of claim 4 contained within the container.

6. The article of manufacture of claim 5, further comprising a label affixed to the container, or a package insert included with the container, referring to the use of the composition of matter for the therapeutic treatment of or the diagnostic detection of an EBV infection.

7. An expression vector comprising a nucleic acid molecule encoding the antibody of claim 1, operably linked to a promoter.

8. An isolated host cell comprising the expression vector of claim 7.

9. The isolated host cell of claim 8, which is a mammalian cell, a bacterial cell, or a yeast cell.

10. A process for producing an antibody, comprising culturing the host cell of claim 8 under conditions suitable for expression of the antibody and recovering the antibody from the cell culture.

11. A method of determining the presence of an EBV gp350 protein in a sample suspected of containing the protein, comprising exposing the sample to the antibody of claim 1 and detecting binding of the antibody to a protein in the sample, wherein binding of the antibody to a protein is indicative of the presence of EBV gp350 protein in the sample.

12. The method of claim 11, wherein the antibody is detectably labeled.

13. The method of claim 12, wherein the label is selected from a radioisotope and a fluorescent label.

14. The method of claim 11, wherein the antibody is conjugated to a solid support selected from a support formed partially or entirely of glass, a polysaccharide, a polyacrylamide, a polystyrene, a polyvinyl alcohol, a silicone, an assay plate, and a purification column.

15. The method of claim 11, wherein the sample comprises a cell suspected of containing an EBV gp350 protein, and the cell is an EBV-infected cell, an epithelial cell, a B lymphocyte, an oropharyngeal cell, a nasopharyngeal cell, or a cancer cell.

16. A method of diagnosing and treating the presence of an EBV infection in a mammal, comprising determining the level of expression of a gene encoding an EBV gp350 protein in a test sample of tissue cells obtained from the mammal and in a control sample of known normal cells of the same tissue origin, wherein a higher level of expression of the EBV gp350 protein in the test sample, as compared to the control sample, is indicative of the presence of an EBV infection in the mammal from which the test sample was obtained, and wherein the mammal determined to have the presence of the EBV infection is administered a therapeutically effective amount of the antibody of claim 1.

* * * * *

SEQUENCE LISTING

```
Sequence total quantity: 293
SEQ ID NO: 1             moltype = AA   length = 121
FEATURE                  Location/Qualifiers
source                   1..121
                         mol_type = protein
                         organism = Macaca mulatta
SEQUENCE: 1
QVQLQESGPG LVKPAETLSL TCTVSGGSFS SYWWGWIRQS PGKGLEWIGH ISSGGNNYLN   60
PSLKSRVTLS LDTSKNQFSL KLNSVTAADS AVYYCARAPR IVVRGRYFDQ WGQGVLVTVS  120
S                                                                 121

SEQ ID NO: 2             moltype = DNA   length = 363
FEATURE                  Location/Qualifiers
source                   1..363
                         mol_type = genomic DNA
                         organism = Macaca mulatta
SEQUENCE: 2
caggtgcagc tgcaggagtc gggcccagga ctggtgaagc ctgcggagac cctgtccctc   60
acctgcactg tctctggtgg ctctttcagc agttactggg ggggctggat ccgtcagtcc  120
ccagggaagg gactggagtg gattgggcat atcagtagtg gtgaaaacaa ctaccttaat  180
ccgtccctca agagtcgagt caccctgtca ctagacacgt ccaagaacca gttctccctg  240
aagctgaact ctgtgaccgc cgcggactcg gccgtgtatt actgtgccag agccccccgt  300
attgttgtta gaggccgata ctttgaccaa tggggccagg gagtcctggt caccgtctcc  360
tca                                                                363

SEQ ID NO: 3             moltype = AA   length = 8
```

```
FEATURE                 Location/Qualifiers
source                  1..8
                        mol_type = protein
                        organism = Macaca mulatta
SEQUENCE: 3
GGSFSSYW                                                                    8

SEQ ID NO: 4            moltype = AA  length = 7
FEATURE                 Location/Qualifiers
source                  1..7
                        mol_type = protein
                        organism = Macaca mulatta
SEQUENCE: 4
ISSGGNN                                                                     7

SEQ ID NO: 5            moltype = AA  length = 16
FEATURE                 Location/Qualifiers
source                  1..16
                        mol_type = protein
                        organism = Macaca mulatta
SEQUENCE: 5
APAPRIVVRG RYFDQW                                                          16

SEQ ID NO: 6            moltype = AA  length = 107
FEATURE                 Location/Qualifiers
source                  1..107
                        mol_type = protein
                        organism = Macaca mulatta
SEQUENCE: 6
DIQMTQSPSS LSASVGDTVT ITCRASQGIN IYLNWFQQRP GKAPKLLIYA ATTLQSGVPS           60
RFSGSGSGTD FTLTISSLQP EDFATYYCLQ CESYPLTFGG GTKVEIK                        107

SEQ ID NO: 7            moltype = DNA  length = 321
FEATURE                 Location/Qualifiers
source                  1..321
                        mol_type = genomic DNA
                        organism = Macaca mulatta
SEQUENCE: 7
gacatccaga tgacccagtc tccatcctcc ctgtctgcat ctgtaggaga cactgtcacc           60
atcacttgcc gggcaagtca gggtatcaat atctacctga attggtttca gcagagacca         120
gggaaagccc ctaaactcct gatctatgct gcgaccactt tacaaagtgg ggtcccatca         180
agattcagcg gcagtggatc tgggacagat ttcactctca ccatcagcag cctgcagcct         240
gaagatttcg caacttatta ctgtctacag tgtgaaagtt atccgctcac tttcggcgga         300
gggaccaagg tggagatcaa a                                                   321

SEQ ID NO: 8            moltype = AA  length = 6
FEATURE                 Location/Qualifiers
source                  1..6
                        mol_type = protein
                        organism = Macaca mulatta
SEQUENCE: 8
QGINIY                                                                      6

SEQ ID NO: 9            moltype =   length =
SEQUENCE: 9
000

SEQ ID NO: 10           moltype = AA  length = 9
FEATURE                 Location/Qualifiers
source                  1..9
                        mol_type = protein
                        organism = Macaca mulatta
SEQUENCE: 10
LQCESYPLT                                                                   9

SEQ ID NO: 11           moltype = AA  length = 123
FEATURE                 Location/Qualifiers
source                  1..123
                        mol_type = protein
                        organism = Macaca mulatta
SEQUENCE: 11
QVQLQESGPG LVKPSETLSL TCTVSGGSIS GAYYYWSWIR QPPGKGLDWI GYIYGSFGSA           60
YYNPSLKSRA TISKDTPKNQ FSLKLSSVTA ADTAVYYCAR GRRLGYSNWF DVWGPGVLVT         120
VSS                                                                       123

SEQ ID NO: 12           moltype = DNA  length = 369
FEATURE                 Location/Qualifiers
source                  1..369
                        mol_type = genomic DNA
```

```
                        organism = Macaca mulatta
SEQUENCE: 12
cagGTGCAAC TGCAGGAGTC GGGCCCAGGA CTGGTGAAGC CTTCGGAGAC CCTGTCCCTC   60
acctgcactg tctctggtgg ctccatcagc ggtgcttact actactggag ctggattcga  120
cagccccCGG GGAAGGGACT GGACTGGATT GGATATATCT ATGGAAGTTT TGGGAGTGCC  180
tactacaacc cctccctcaa gagtcgagcc accatttcaa agacacgcc caagaaccag   240
ttctccctga aactgagctc tgtgaccgcc gcggacacgg ccgtgtatta ctgtgcgaga  300
ggaaggcgac taggctattc gaactggttc gatgtctggg gccgggagt cctggtcacc   360
gtctcctca                                                         369

SEQ ID NO: 13           moltype = AA   length = 10
FEATURE                 Location/Qualifiers
source                  1..10
                        mol_type = protein
                        organism = Macaca mulatta
SEQUENCE: 13
GGSISGAYYY                                                         10

SEQ ID NO: 14           moltype = AA   length = 8
FEATURE                 Location/Qualifiers
source                  1..8
                        mol_type = protein
                        organism = Macaca mulatta
SEQUENCE: 14
IYGSFGSA                                                           8

SEQ ID NO: 15           moltype = AA   length = 15
FEATURE                 Location/Qualifiers
source                  1..15
                        mol_type = protein
                        organism = Macaca mulatta
SEQUENCE: 15
ARGRRLGYSN WFDVW                                                   15

SEQ ID NO: 16           moltype = AA   length = 107
FEATURE                 Location/Qualifiers
source                  1..107
                        mol_type = protein
                        organism = Macaca mulatta
SEQUENCE: 16
DIQMTQSPSS LSASVGDKVT ITCRTSQDVS SYLAWYQQKP GKAPQLLIYA ASSLQSGVPS   60
RFTGSGSGAE FTLTISSLQP EDFASYYCQQ YKNLPLTFGG GTKVEIK               107

SEQ ID NO: 17           moltype = DNA   length = 321
FEATURE                 Location/Qualifiers
source                  1..321
                        mol_type = genomic DNA
                        organism = Macaca mulatta
SEQUENCE: 17
gacatccaga tgacccagtc tccatcttcc ctgtctgcat ctgtaggaga caaagtcacc   60
atcacttgtc ggacaagtca ggacgttagc agttatttag cctggtatca gcagaaacca  120
gggaaagccc ctcagctcct gatctatgct gcatccagtt tgcaaagtgg ggtcccatca  180
aggttcaccg gcagtggatc tgggacagaa ttcactctca ccatcagcag ccttcagcct  240
gaagattttg catcatatta ctgtcaacag tataaaaatc tcccgctcac tttcggcgga  300
gggaccaaag tggagatcaa a                                            321

SEQ ID NO: 18           moltype = AA   length = 6
FEATURE                 Location/Qualifiers
source                  1..6
                        mol_type = protein
                        organism = Macaca mulatta
SEQUENCE: 18
QDVSSY                                                             6

SEQ ID NO: 19           moltype =      length =
SEQUENCE: 19
000

SEQ ID NO: 20           moltype = AA   length = 9
FEATURE                 Location/Qualifiers
source                  1..9
                        mol_type = protein
                        organism = Macaca mulatta
SEQUENCE: 20
QQYKNLPLT                                                          9

SEQ ID NO: 21           moltype = AA   length = 129
FEATURE                 Location/Qualifiers
source                  1..129
```

```
                            mol_type = protein
                            organism = Macaca mulatta
SEQUENCE: 21
QVQLQESGPG LVKPSETLSL TCDVSGGSFS GDFYWSWIRQ PPGKGLDWIG NIHGSSAGTK      60
YKPSLKSRVT ISKDTSKNQF SLKLSSVTAA DTAVYYCTRG PLSRIVAGFG RGINWFDVWG     120
PGVLVTVSS                                                             129

SEQ ID NO: 22               moltype = DNA   length = 387
FEATURE                     Location/Qualifiers
source                      1..387
                            mol_type = genomic DNA
                            organism = Macaca mulatta
SEQUENCE: 22
caggtgcagc tgcaggagtc gggcccagga ctggtgaagc cttcggagac cctgtccctc      60
acctgcgatg tctctggtgg ctccttcagc ggtgatttct actggagctg gatccgccag     120
cccccaggga agggactgga ctggattggg aatatccatg gcagcagtgc gggcaccaaa     180
tacaagcccc ccctcaagag tcgagtcacc atttcaaaag acacgtccaa gaaccagttt     240
tccctgaaac tgagctctgt gaccgccgcg gacacggccg tctattactg tacgagaggc     300
ccccttagta ggatagtagc tggttttggg agggggatta actggttcga tgtctgggc      360
ccgggagtcc tggtcaccgt ctcctca                                         387

SEQ ID NO: 23               moltype = AA   length = 9
FEATURE                     Location/Qualifiers
source                      1..9
                            mol_type = protein
                            organism = Macaca mulatta
SEQUENCE: 23
GGSFSGDFY                                                               9

SEQ ID NO: 24               moltype = AA   length = 8
FEATURE                     Location/Qualifiers
source                      1..8
                            mol_type = protein
                            organism = Macaca mulatta
SEQUENCE: 24
IHGSSAGT                                                                8

SEQ ID NO: 25               moltype = AA   length = 22
FEATURE                     Location/Qualifiers
source                      1..22
                            mol_type = protein
                            organism = Macaca mulatta
SEQUENCE: 25
TRGPLSRIVA GFGRGINWFD VW                                               22

SEQ ID NO: 26               moltype = AA   length = 116
FEATURE                     Location/Qualifiers
source                      1..116
                            mol_type = protein
                            organism = Macaca mulatta
SEQUENCE: 26
QPVLTQPTSL SASPGASVRL SCTLSSGINV GSYSIFWYQQ KPGSPPRYLL FYFSDSSKHQ      60
GSGVPSRFSG SKDTSANAGL LLISGLQSED EADYYCAIWH SSASVLFGGG TRLTVL         116

SEQ ID NO: 27               moltype = DNA   length = 348
FEATURE                     Location/Qualifiers
source                      1..348
                            mol_type = genomic DNA
                            organism = Macaca mulatta
SEQUENCE: 27
cagcctgtgc tgacccagcc aacctccctc tcagcatctc cgggagcatc agtcagactc      60
agctgcacct tgagcagtgg catcaatgtt ggtagttaca gcatattctg gtaccagcag     120
aagccaggga gtcctccccg gtaccttctg ttctatttct cagactcaag taagcaccag     180
ggctctggag tcccccagccg ttttctctgga tccaaggata cttcagccaa tgcagggctt    240
ttactgatct ctgggctcca gtctgaagat gaggctgact attactgtgc catatggcac     300
agcagcgctt ctgtgttatt cggaggaggg accggctga cagtacta                    348

SEQ ID NO: 28               moltype = AA   length = 14
FEATURE                     Location/Qualifiers
source                      1..14
                            mol_type = protein
                            organism = Macaca mulatta
SEQUENCE: 28
TLSSGINVGS YSIF                                                        14

SEQ ID NO: 29               moltype = AA   length = 7
FEATURE                     Location/Qualifiers
source                      1..7
                            mol_type = protein
```

```
                        organism = Macaca mulatta
SEQUENCE: 29
YFSDSSK                                                                        7

SEQ ID NO: 30           moltype = AA   length = 10
FEATURE                 Location/Qualifiers
source                  1..10
                        mol_type = protein
                        organism = Macaca mulatta
SEQUENCE: 30
AIWHSSASVL                                                                    10

SEQ ID NO: 31           moltype = AA   length = 120
FEATURE                 Location/Qualifiers
source                  1..120
                        mol_type = protein
                        organism = Macaca mulatta
SEQUENCE: 31
QLQLQESGPG LVKPSETLSL TCAVSGGSIS GYYWSWIRQP PGKGPEWIGF IDGNTVGTNY             60
NPSLKSRVTL SKDTSKNQFS LKVSSVTAAD TAVYYCARKP LRRYFWFDVW GPGVLVTVSS            120

SEQ ID NO: 32           moltype = DNA   length = 360
FEATURE                 Location/Qualifiers
source                  1..360
                        mol_type = genomic DNA
                        organism = Macaca mulatta
SEQUENCE: 32
cagctgcagc tgcaggagtc gggcccagga ctggtgaagc cttcggagac cctgtccctc             60
acctgcgctg tctctggtgg ctccatcagc ggttactact ggagttggat cgccagccc            120
ccagggaagg gaccggagtg gattgggttt attgtgatgg atactgtggg caccaactac           180
aaccctccc tcaagagtcg agtcaccctt tcaaaagaca cgtccaagaa tcagttctcc            240
ctgaaggtga gttctgtgac cgccgcggac acggccgtgt attactgtgc gaggaagccg           300
ctacgccgtt atttctggtt cgatgtctgg ggcccgggag tcctggtcac cgtctcctca           360

SEQ ID NO: 33           moltype = AA   length = 8
FEATURE                 Location/Qualifiers
source                  1..8
                        mol_type = protein
                        organism = Macaca mulatta
SEQUENCE: 33
GGSISGYY                                                                       8

SEQ ID NO: 34           moltype = AA   length = 8
FEATURE                 Location/Qualifiers
source                  1..8
                        mol_type = protein
                        organism = Macaca mulatta
SEQUENCE: 34
IDGNTVGT                                                                       8

SEQ ID NO: 35           moltype = AA   length = 14
FEATURE                 Location/Qualifiers
source                  1..14
                        mol_type = protein
                        organism = Macaca mulatta
SEQUENCE: 35
ARKPLRRYFW FDVW                                                               14

SEQ ID NO: 36           moltype = AA   length = 111
FEATURE                 Location/Qualifiers
source                  1..111
                        mol_type = protein
                        organism = Macaca mulatta
SEQUENCE: 36
QSVLTQPPSV SGDPGQRVTI SCTGSSSNIG AGYYVYWYQQ FPGTAPKLLI YQDNKRPSGV             60
SDRFSGSKSG TSASLTITGL QPGDEADYYC SAWDSSLSAV MFGRGTRLTV L                    111

SEQ ID NO: 37           moltype = DNA   length = 333
FEATURE                 Location/Qualifiers
source                  1..333
                        mol_type = genomic DNA
                        organism = Macaca mulatta
SEQUENCE: 37
cagtctgtgc tgacgcagcc gccctcagtg tctggggacc ccgggcagag ggtcaccatc             60
tcgtgcactg ggagcagctc caacatcggg gcgggttatt atgtatactg gtaccagcag           120
ttcccaggaa cggcccccaa actcctcatc tatcaagata taagcgaccc tcaggggtt            180
tctgaccgat tctctggctc caagtctggt acctcagcct ccctgaccat cactgggctc           240
cagcctgggg atgaggctga ttattactgc tcagcatggg atagcagcct gagtgctgtt           300
atgttcggaa gaggcaccag gctgacagta cta                                         333
```

```
SEQ ID NO: 38            moltype = AA  length = 9
FEATURE                  Location/Qualifiers
source                   1..9
                         mol_type = protein
                         organism = Macaca mulatta
SEQUENCE: 38
SSNIGAGYY                                                              9

SEQ ID NO: 39            moltype =     length =
SEQUENCE: 39
000

SEQ ID NO: 40            moltype = AA  length = 11
FEATURE                  Location/Qualifiers
source                   1..11
                         mol_type = protein
                         organism = Macaca mulatta
SEQUENCE: 40
SAWDSSLSAV M                                                           11

SEQ ID NO: 41            moltype = AA  length = 120
FEATURE                  Location/Qualifiers
source                   1..120
                         mol_type = protein
                         organism = Macaca mulatta
SEQUENCE: 41
QLQLQESGPG VVKPSETLSL TCTISGGSFS TYYWTWIRQP PGKGLEWVGY IGNGGRSLNY       60
NPSLKSRITL SVDASKNQFS LKVTSVTAAD TAVYYCGRAR GLRGNWFDVW GPGVLVTVSS      120

SEQ ID NO: 42            moltype = DNA  length = 360
FEATURE                  Location/Qualifiers
source                   1..360
                         mol_type = genomic DNA
                         organism = Macaca mulatta
SEQUENCE: 42
caactgcagt tgcaggagtc gggcccagga gtggtgaagc cttcggagac cctgtccctc       60
acctgcacta tctctggtgg ctccttcagt acttactact ggacctggat tcgccagccc      120
ccagggaagg gactggagtg ggttgggtat atcggtaatg gtggtcgtag cctcaactac      180
aaccccctccc tcaagagtcg catcaccctg tcagtagacg cgtccaagaa ccagttctct     240
ctgaaggtga cctctgtgac cgccgcggac acggccgtct attactgtgg agagccagga      300
ggactccgcg gaaactggtt cgatgtctgg ggcccgggga tcctggtcac cgtctcctca      360

SEQ ID NO: 43            moltype = AA  length = 8
FEATURE                  Location/Qualifiers
source                   1..8
                         mol_type = protein
                         organism = Macaca mulatta
SEQUENCE: 43
GGSFSTYY                                                               8

SEQ ID NO: 44            moltype = AA  length = 8
FEATURE                  Location/Qualifiers
source                   1..8
                         mol_type = protein
                         organism = Macaca mulatta
SEQUENCE: 44
IGNGGRSL                                                               8

SEQ ID NO: 45            moltype = AA  length = 14
FEATURE                  Location/Qualifiers
source                   1..14
                         mol_type = protein
                         organism = Macaca mulatta
SEQUENCE: 45
GRARGLRGNW FDVW                                                        14

SEQ ID NO: 46            moltype = AA  length = 110
FEATURE                  Location/Qualifiers
source                   1..110
                         mol_type = protein
                         organism = Macaca mulatta
SEQUENCE: 46
QAALTQPPSV SGSPGQSVTI SCTGTSSDIG GYNYVSWYQQ HPGKAPKVMI YEVSKRPSGV       60
SDRFSGSKSG NIASLTISGL QAEDEADYYC SSYAGSNTFL FGGGTRLTVL                 110

SEQ ID NO: 47            moltype = DNA  length = 330
FEATURE                  Location/Qualifiers
source                   1..330
```

```
                        mol_type = genomic DNA
                        organism = Macaca mulatta
SEQUENCE: 47
caggctgccc tgactcagcc tccctctgtg tctgggtctc ctggacagtc ggtcaccatc    60
tcctgcactg gaaccagcag tgacatcggt ggttataact atgtctcctg gtaccaacaa   120
cacccaggca aagcccccaa agtcatgatt tatgaggtca gtaagcggcc ctcagggctc   180
tctgatcgct tctctggttc caaatctggc aacatagcct ccctgaccat ctctgggctc   240
caggctgagg acgaggctga ttattactgc agctcatatg caggcagcaa cactttctta   300
ttcggaggag ggacccggct gacagtacta                                    330

SEQ ID NO: 48           moltype = AA  length = 9
FEATURE                 Location/Qualifiers
source                  1..9
                        mol_type = protein
                        organism = Macaca mulatta
SEQUENCE: 48
SSDIGGYNY                                                             9

SEQ ID NO: 49           moltype =     length =
SEQUENCE: 49
000

SEQ ID NO: 50           moltype = AA  length = 10
FEATURE                 Location/Qualifiers
source                  1..10
                        mol_type = protein
                        organism = Macaca mulatta
SEQUENCE: 50
SSYAGSNTFL                                                           10

SEQ ID NO: 51           moltype = AA  length = 123
FEATURE                 Location/Qualifiers
source                  1..123
                        mol_type = protein
                        organism = Macaca mulatta
SEQUENCE: 51
QVQLQESGPG LVKPSETLSL TCAVSGGSIS SNYWSWIRQP PGKGLEWIGR IYGSGGSTDY     60
NPSLKSRVTI STDTSKNQFS LKVSSVTAAD TAVYYCARVR IQWVQLRGWF DVWGPGVLVT    120
VSS                                                                  123

SEQ ID NO: 52           moltype = DNA  length = 369
FEATURE                 Location/Qualifiers
source                  1..369
                        mol_type = genomic DNA
                        organism = Macaca mulatta
SEQUENCE: 52
caggtgcagc tgcaggagtc gggcccagga ctggtgaagc cttcggagac cctgtccctc     60
acctgcgctg tctctggtgg ctccatcagc agtaactact ggagctggat ccgccagccc    120
ccagggaagg gactggagtg gattggacgt atctatggta gtggtgggag caccgactac    180
aacccctccc tcaagagtcg agtcaccatt tcaacagaca cgtccaagaa ccagttctcc    240
ctgaaggtga gctctgtgac cgccgcggac acggccgtgt attactgtgc gagagtgcgg    300
atacagtggg tacagttgcg aggctggttc gatgtctggg gccggggagt cctggtcacc    360
gtctcctca                                                            369

SEQ ID NO: 53           moltype = AA  length = 10
FEATURE                 Location/Qualifiers
source                  1..10
                        mol_type = protein
                        organism = Macaca mulatta
SEQUENCE: 53
GGSISSNYWS                                                           10

SEQ ID NO: 54           moltype = AA  length = 8
FEATURE                 Location/Qualifiers
source                  1..8
                        mol_type = protein
                        organism = Macaca mulatta
SEQUENCE: 54
IYGSGGST                                                              8

SEQ ID NO: 55           moltype = AA  length = 17
FEATURE                 Location/Qualifiers
source                  1..17
                        mol_type = protein
                        organism = Macaca mulatta
SEQUENCE: 55
ARVRIQWVQL RGWFDVW                                                   17

SEQ ID NO: 56           moltype = AA  length = 107
```

| FEATURE | Location/Qualifiers |
|---|---|
| source | 1..107<br>mol_type = protein<br>organism = Macaca mulatta |

SEQUENCE: 56
```
YIQMTQSPSS LSASVGDTVT FTGPASQSFS SSLAWYQQKP GKAPNLLIYS ASSLQCGVRS   60
RFSGSKSGTD FTLTISSLQP EDIASYYCQQ YYSYPFTFGP GTKLDIK                107
```

| SEQ ID NO: 57 | moltype = DNA  length = 321 |
|---|---|
| FEATURE | Location/Qualifiers |
| source | 1..321<br>mol_type = genomic DNA<br>organism = Macaca mulatta |

SEQUENCE: 57
```
tacatacaga tgacgcagtc tccatcctcc ctgtctgcat ctgtaggaga cacagtcacc   60
ttcactggcc ccgcaagtca gagctttagt agtagtttag cctggtatca gcagaaacca  120
gggaaagccc ctaacctcct gatctatagt gcatccagtt tgcaatgtgg ggttcgttcg  180
aggttcagtg gcagtaagtc tgggacagat ttcactctca ccatcagcag cctgcagcct  240
gaagatattg ctagttatta ctgtcaacag tattacagtt atccattcac tttcggcccc  300
gggaccaaac tggatatcaa a                                            321
```

| SEQ ID NO: 58 | moltype = AA  length = 6 |
|---|---|
| FEATURE | Location/Qualifiers |
| source | 1..6<br>mol_type = protein<br>organism = Macaca mulatta |

SEQUENCE: 58
```
QSFSSS                                                              6
```

| SEQ ID NO: 59 | moltype =    length = |
|---|---|

SEQUENCE: 59
000

| SEQ ID NO: 60 | moltype = AA  length = 9 |
|---|---|
| FEATURE | Location/Qualifiers |
| source | 1..9<br>mol_type = protein<br>organism = Macaca mulatta |

SEQUENCE: 60
```
QQYYSYPFT                                                           9
```

| SEQ ID NO: 61 | moltype = AA  length = 119 |
|---|---|
| FEATURE | Location/Qualifiers |
| source | 1..119<br>mol_type = protein<br>organism = Macaca mulatta |

SEQUENCE: 61
```
QVQLQESGPG LVRPSETLSL TCAVSGGSIS SNYWSWIRQP PGKGLEWIGY ISGSTGSTYQ   60
NPSLKSRVTV SKDTSKNQFS LKLNSVTAAD TAVYYCARSG RRGSSLDLWG RGVLVTVSS   119
```

| SEQ ID NO: 62 | moltype = DNA  length = 357 |
|---|---|
| FEATURE | Location/Qualifiers |
| source | 1..357<br>mol_type = genomic DNA<br>organism = Macaca mulatta |

SEQUENCE: 62
```
caggtgcagc tgcaggagtc gggcccagga ctggtgaggc cttcggagac cctatccctc   60
acctgcgctg tctctggtgg ctccatcagc agtaactact ggagctggat cgccagccc  120
ccagggaagg ggctggagtg gattgggtat atctctggta gtactgggag cacctaccag  180
aaccccctcc tcaagagtcg agtcaccgtt tcaaaagaca cgtctaagaa ccagttctcc  240
ctgaagctga attctgtgac cgccgcggac acggccgtgt attactgtgc gagaagtggg  300
agaagaggca gctcattgga tttgtggggc cggggagttc tggtcaccgt ctcctca     357
```

| SEQ ID NO: 63 | moltype = AA  length = 8 |
|---|---|
| FEATURE | Location/Qualifiers |
| source | 1..8<br>mol_type = protein<br>organism = Macaca mulatta |

SEQUENCE: 63
```
GGSISSNY                                                            8
```

| SEQ ID NO: 64 | moltype = AA  length = 8 |
|---|---|
| FEATURE | Location/Qualifiers |
| source | 1..8<br>mol_type = protein<br>organism = Macaca mulatta |

SEQUENCE: 64
```
ISGSTGST                                                            8
```

```
SEQ ID NO: 65           moltype = AA   length = 13
FEATURE                 Location/Qualifiers
source                  1..13
                        mol_type = protein
                        organism = Macaca mulatta
SEQUENCE: 65
ARSGRRGSSL DLW                                                        13

SEQ ID NO: 66           moltype = AA   length = 111
FEATURE                 Location/Qualifiers
source                  1..111
                        mol_type = protein
                        organism = Macaca mulatta
SEQUENCE: 66
QSVLTQPPSV SGDPGQRVTI SCTGSSSNIG AGYYVYWYQQ FPGTAPKLLI YQDNKRPSGV      60
SDRFSGSKSG TSASLTITGL QPGDEADYYC SAWDSSLSAV FFGGGTRLTV L              111

SEQ ID NO: 67           moltype = DNA  length = 333
FEATURE                 Location/Qualifiers
source                  1..333
                        mol_type = genomic DNA
                        organism = Macaca mulatta
SEQUENCE: 67
cagtctgtgc tgacgcagcc gccctcagtg tctggggacc ccgggcagag ggtcaccatc      60
tcgtgcactg ggagcagctc caacatcggg gcgggttatt atgtatactg gtaccagcag    120
ttcccaggaa cggcccccaa actcctcatc tatcaagata taagcgacc ctcaggggtt     180
tctgaccgat tctctggctc caagtctggt acctcagcct ccctgaccat cactgggctc    240
cagcctgggg atgaggctga ttattactgc tcagcatggg atagcagcct gagtgctgtg    300
ttcttcggag agggacccg gctgacagta cta                                   333

SEQ ID NO: 68           moltype = AA   length = 9
FEATURE                 Location/Qualifiers
source                  1..9
                        mol_type = protein
                        organism = Macaca mulatta
SEQUENCE: 68
SSNIGAGYY                                                              9

SEQ ID NO: 69           moltype =      length =
SEQUENCE: 69
000

SEQ ID NO: 70           moltype = AA   length = 11
FEATURE                 Location/Qualifiers
source                  1..11
                        mol_type = protein
                        organism = Macaca mulatta
SEQUENCE: 70
SAWDSSLSAV F                                                           11

SEQ ID NO: 71           moltype = AA   length = 121
FEATURE                 Location/Qualifiers
source                  1..121
                        mol_type = protein
                        organism = Macaca mulatta
SEQUENCE: 71
QLQESGPGLV KPSETLSLTC TVSGGSISDT YRWSWIRQSP GKGLEWIAYI YGTTTSTNYN      60
PSLKSRLTIS KDTSKNQFSL NLRSVTAADT AVYYCARGDS GGRSAHVFHF WGQGLRVTVS    120
S                                                                    121

SEQ ID NO: 72           moltype = DNA  length = 363
FEATURE                 Location/Qualifiers
source                  1..363
                        mol_type = genomic DNA
                        organism = Macaca mulatta
SEQUENCE: 72
cagctgcagg agtcgggccc aggactggtg aagccttcgg agaccctgtc cctcacctgc      60
actgtctctg gtggctccat cagcgatact taccggtgga gctggattcg ccagtccagg    120
gggaagggac tggagtggat tgcctacatc tatggtacta ctacgagcac caactacaac    180
ccctccctca agagtcgact caccatttca aaagacacgt ccaagaacca gttctccttg    240
aacctgaggt ctgtgaccgc cgcggacacg gccgtgtatt actgtgcgag aggggatagc    300
ggtggccggg cagcgcatgt ttttcatttc tggggccaag ggctcagggt caccgtctct    360
tca                                                                  363

SEQ ID NO: 73           moltype = AA   length = 9
FEATURE                 Location/Qualifiers
source                  1..9
                        mol_type = protein
                        organism = Macaca mulatta
```

```
SEQUENCE: 73
GGSISDTYR                                                                    9

SEQ ID NO: 74            moltype = AA  length = 8
FEATURE                  Location/Qualifiers
source                   1..8
                         mol_type = protein
                         organism = Macaca mulatta
SEQUENCE: 74
IYGTTTST                                                                     8

SEQ ID NO: 75            moltype = AA  length = 16
FEATURE                  Location/Qualifiers
source                   1..16
                         mol_type = protein
                         organism = Macaca mulatta
SEQUENCE: 75
ARGDSGGRSA HVFHFW                                                           16

SEQ ID NO: 76            moltype = AA  length = 111
FEATURE                  Location/Qualifiers
source                   1..111
                         mol_type = protein
                         organism = Macaca mulatta
SEQUENCE: 76
QSVLTQPPSV FGDPGQRITI SCTGSSSNIG AGYYVYWYQQ FPGTAPKLLI YQDNKRPSGV            60
SDRFSGSKSG SSASLTITGL QPGDEADYYC SAWDSSLSVR VFGGGTRLTV L                    111

SEQ ID NO: 77            moltype = DNA  length = 333
FEATURE                  Location/Qualifiers
source                   1..333
                         mol_type = genomic DNA
                         organism = Macaca mulatta
SEQUENCE: 77
cagagtgttc tgacgcagcc gccctcagtg tttggggacc ccgggcagag gatcaccatc            60
tcgtgcactg ggagcagctc caacatcggg gcgggttatt atgtatactg gtaccagcag          120
ttcccaggaa cggcccccaa actcctcatc tatcaagata taagcgaccc tcagggggtt          180
tctgaccgat tttctggctc caagtctggt tcctcagcct ccctgaccat cactgggctc          240
cagcctgggg atgaggctga ttattactgc tcagcatggg atagcagcct gagtgtacgg          300
gttttcggag gagggacccg gctgacagta cta                                       333

SEQ ID NO: 78            moltype = AA  length = 9
FEATURE                  Location/Qualifiers
source                   1..9
                         mol_type = protein
                         organism = Macaca mulatta
SEQUENCE: 78
SSNIGAGYY                                                                    9

SEQ ID NO: 79            moltype =     length =
SEQUENCE: 79
000

SEQ ID NO: 80            moltype = AA  length = 11
FEATURE                  Location/Qualifiers
source                   1..11
                         mol_type = protein
                         organism = Macaca mulatta
SEQUENCE: 80
SAWDSSLSVR V                                                                11

SEQ ID NO: 81            moltype = AA  length = 122
FEATURE                  Location/Qualifiers
source                   1..122
                         mol_type = protein
                         organism = Macaca mulatta
SEQUENCE: 81
EVQLVESGGG LVQPGGSLRL SCAASGFTFS SYGMNWVRQA PGKGLEWVSF ITNTGKTTYY            60
ADSVRGRFTI SRDNAKKSVS LQMSSLRAED TAVYYCTRGR GRHGWSSGVF DFWGQGLRVT          120
VS                                                                         122

SEQ ID NO: 82            moltype = DNA  length = 368
FEATURE                  Location/Qualifiers
source                   1..368
                         mol_type = genomic DNA
                         organism = Macaca mulatta
SEQUENCE: 82
gaggtgcaac tggtggagtc tgaggaggc ttggtccagc ctggagggtc cctgagactc             60
tcctgtgcag cctctggatt cacccttcag tagttacggc tgaactgggt ccgccaggct          120
```

```
ccgggaaagg ggctggagtg ggtctcattc attactaaca ctggtaaaac cacatactac    180
gctgactctg tgaggggccg attcaccatc tccagagaca acgccaagaa gtcggtgtct    240
ctacaaatga gtagcctgag agccgaggac acggccgtct attactgtac taggggaaga    300
ggtagacacg gctggtccag tggtgttttt gatttctggg gccaaggtct cagggtcacc    360
gtctcttc                                                             368

SEQ ID NO: 83          moltype = AA   length = 8
FEATURE                Location/Qualifiers
source                 1..8
                       mol_type = protein
                       organism = Macaca mulatta
SEQUENCE: 83
GFTFSSYG                                                               8

SEQ ID NO: 84          moltype = AA   length = 8
FEATURE                Location/Qualifiers
source                 1..8
                       mol_type = protein
                       organism = Macaca mulatta
SEQUENCE: 84
ITNTGKTT                                                               8

SEQ ID NO: 85          moltype = AA   length = 16
FEATURE                Location/Qualifiers
source                 1..16
                       mol_type = protein
                       organism = Macaca mulatta
SEQUENCE: 85
TGRGRHGWSS GVFDFW                                                     16

SEQ ID NO: 86          moltype = AA   length = 111
FEATURE                Location/Qualifiers
source                 1..111
                       mol_type = protein
                       organism = Macaca mulatta
SEQUENCE: 86
QSVLTQPPSV FGDPGQRITI SCTGSSSNIG AGYYVYWYQQ FPGTAPKLLI YQDNKRPSGV     60
SDRFSGSKFG SSASLTITGV QRGDEGDYYC SAWDSSLSVR VLGGGTRLTV L              111

SEQ ID NO: 87          moltype = DNA  length = 333
FEATURE                Location/Qualifiers
source                 1..333
                       mol_type = genomic DNA
                       organism = Macaca mulatta
SEQUENCE: 87
cagtctgttt tgacgcagcc gccctcagtg ttcggggacc ccgggcagag gatcaccatt     60
tcgtgcactg ggagcagctc caacatcggg gcggttatt atgtatactg gtaccagcag    120
ttcccaggaa cggcccccaa actcctcatc tatcaagata taagcgacc ctcaggggtt    180
tctgaccgat tctctggctc caagtttggt tcctcagcct ccctgaccat cactgggtc    240
cagcgtgggg atgagggtga ttattactgc tcagcatggg atagcagcct gagtgtacgg    300
gttttgggag gagggacccg gctgacagta cta                                  333

SEQ ID NO: 88          moltype = AA   length = 9
FEATURE                Location/Qualifiers
source                 1..9
                       mol_type = protein
                       organism = Macaca mulatta
SEQUENCE: 88
SSNIGAGYY                                                              9

SEQ ID NO: 89          moltype =      length =
SEQUENCE: 89
000

SEQ ID NO: 90          moltype = AA   length = 11
FEATURE                Location/Qualifiers
source                 1..11
                       mol_type = protein
                       organism = Macaca mulatta
SEQUENCE: 90
SAWDSSLSVR V                                                          11

SEQ ID NO: 91          moltype = AA   length = 121
FEATURE                Location/Qualifiers
source                 1..121
                       mol_type = protein
                       organism = Macaca mulatta
SEQUENCE: 91
EVQLVESGGG LVQPGGSLRL SCVASGFTFS DRYIDWVRQA PGKGLEWVST ISTGSGDTAL     60
```

| | | |
|---|---|---|
| YSDSVKGRFT ISRDNAKNTL YLQMNSLRAE DTAVYYCARH SGTFYTHFDY WGQGVLVTVS | 120 | |
| S | 121 | |

| SEQ ID NO: 92 | moltype = DNA   length = 363 |
|---|---|
| FEATURE | Location/Qualifiers |
| source | 1..363 |
| | mol_type = genomic DNA |
| | organism = Macaca mulatta |

SEQUENCE: 92

| | |
|---|---|
| gaagtgcagt tggtggagtc tgggggaggc ttggtacagc cggggggtc cctgagactc | 60 |
| tcctgtgtag cctctggatt caccttcagt gaccgctaca tagactgggt ccgccaggct | 120 |
| ccagggaagg gcctggagtg ggtctcaact attagcactg gtagtggtga taccgcattc | 180 |
| tactcagact ctgtcaaggg ccgattcacc atctccagag acaacgccaa gaacacactg | 240 |
| tatctgcaaa tgaacagcct gagagccgaa gacacggctg tctattactg tgcgagacat | 300 |
| agtggtactt tttacaccca ctttgactac tggggccagg gagtcctggt caccgtctcc | 360 |
| tca | 363 |

| SEQ ID NO: 93 | moltype = AA   length = 8 |
|---|---|
| FEATURE | Location/Qualifiers |
| source | 1..8 |
| | mol_type = protein |
| | organism = Macaca mulatta |

SEQUENCE: 93

| | |
|---|---|
| GFTFSDRY | 8 |

| SEQ ID NO: 94 | moltype = AA   length = 9 |
|---|---|
| FEATURE | Location/Qualifiers |
| source | 1..9 |
| | mol_type = protein |
| | organism = Macaca mulatta |

SEQUENCE: 94

| | |
|---|---|
| ISTGSGDTA | 9 |

| SEQ ID NO: 95 | moltype = AA   length = 14 |
|---|---|
| FEATURE | Location/Qualifiers |
| source | 1..14 |
| | mol_type = protein |
| | organism = Macaca mulatta |

SEQUENCE: 95

| | |
|---|---|
| ARHSGTFYTH FDYW | 14 |

| SEQ ID NO: 96 | moltype = AA   length = 107 |
|---|---|
| FEATURE | Location/Qualifiers |
| source | 1..107 |
| | mol_type = protein |
| | organism = Macaca mulatta |

SEQUENCE: 96

| | |
|---|---|
| DIQMTQSPSS LSASVGDTVT FTCRASRSIS SWLAWYQQKP GRAPKVLIYK ASSLQSGVPS | 60 |
| RFSGSGSGTD FTLTISSLQS EDFATYYCQQ YSSRPPTFGQ GTKVEIR | 107 |

| SEQ ID NO: 97 | moltype = DNA   length = 321 |
|---|---|
| FEATURE | Location/Qualifiers |
| source | 1..321 |
| | mol_type = genomic DNA |
| | organism = Macaca mulatta |

SEQUENCE: 97

| | |
|---|---|
| gacatccaga tgacccagtc tccatcctcc ctgtctgcat ctgtaggaga cacagtcacc | 60 |
| ttcacctgcc gggcgagtcg gagtattagc agctggttag cctggtatca gcagaaacca | 120 |
| gggagagccc ctaaagtcct gatctataag gcgtccagtt tgcaaagtgg ggttccttca | 180 |
| aggttcagcg gcagtggatc tgggacagac ttcactctca ccatcagcag cctacagtct | 240 |
| gaagattttg caacatatta ttgtcaacag tatagtagtc gccctccgac gttcggccaa | 300 |
| gggaccaagg tggaaatcag a | 321 |

| SEQ ID NO: 98 | moltype = AA   length = 6 |
|---|---|
| FEATURE | Location/Qualifiers |
| source | 1..6 |
| | mol_type = protein |
| | organism = Macaca mulatta |

SEQUENCE: 98

| | |
|---|---|
| RSISSW | 6 |

| SEQ ID NO: 99 | moltype =    length = |
|---|---|

SEQUENCE: 99
000

| SEQ ID NO: 100 | moltype = AA   length = 9 |
|---|---|
| FEATURE | Location/Qualifiers |
| source | 1..9 |
| | mol_type = protein |

```
                        organism = Macaca mulatta
SEQUENCE: 100
QQYSSRPPT                                                           9

SEQ ID NO: 101          moltype = AA   length = 119
FEATURE                 Location/Qualifiers
source                  1..119
                        mol_type = protein
                        organism = Macaca mulatta
SEQUENCE: 101
QVQLQESGPG LLKPSETLSL TCAVSGGSFS SFWWSWLRQP PEKGLEWIGE INGDSGSTNY    60
NPSLKSRVTI SKDASKNQFS LKLTSVTAAD TAVFYCARVR RILRSLDVWG RGVLVTVSS    119

SEQ ID NO: 102          moltype = DNA  length = 357
FEATURE                 Location/Qualifiers
source                  1..357
                        mol_type = genomic DNA
                        organism = Macaca mulatta
SEQUENCE: 102
caggtgcagc tgcaggagtc gggcccagga ctgctgaagc cttcggagac cctgtccctc    60
acctgcgctg tctctggtgg ctccttcagt agtttctggt ggagctggct ccgccagccc   120
ccagaaaagg gactggagtg gattgggag atcaatgget atagtgggag caccaactac   180
aacccctccc tcaagagtcg agtcaccatt tcaaaagacg cgtccaagaa ccagttctcc   240
ctgaaactga cctctgtgac cgccgcggac acggccgttt tttactgtgc gagagttcgg   300
cgaattctga ggtcattgga tgtctggggc cggggagttc tggtcaccgt ctcctca      357

SEQ ID NO: 103          moltype = AA   length = 8
FEATURE                 Location/Qualifiers
source                  1..8
                        mol_type = protein
                        organism = Macaca mulatta
SEQUENCE: 103
GGSFSSFW                                                            8

SEQ ID NO: 104          moltype = AA   length = 8
FEATURE                 Location/Qualifiers
source                  1..8
                        mol_type = protein
                        organism = Macaca mulatta
SEQUENCE: 104
INGDSGST                                                            8

SEQ ID NO: 105          moltype = AA   length = 13
FEATURE                 Location/Qualifiers
source                  1..13
                        mol_type = protein
                        organism = Macaca mulatta
SEQUENCE: 105
ARVRRILRSL DVW                                                      13

SEQ ID NO: 106          moltype = AA   length = 107
FEATURE                 Location/Qualifiers
source                  1..107
                        mol_type = protein
                        organism = Macaca mulatta
SEQUENCE: 106
DIQMTQSPFS LFAFVGDRVT ITCQASQGIS HLLAWYQQKP GKAPKLLIYS ASTLQSGVPS    60
RFSGSGFGTE FTLTISSLQP EDFATYYCQQ HNSYPRTFGQ GTKVEIK                107

SEQ ID NO: 107          moltype = DNA  length = 321
FEATURE                 Location/Qualifiers
source                  1..321
                        mol_type = genomic DNA
                        organism = Macaca mulatta
SEQUENCE: 107
gacatccaga tgacccagtc tccttttttcc ttgtttgcat tgtaggagaa cagagtcacc   60
atcacttgcc aagccagtca gggtattagc cacttgttag cttggtatca gcagaaacca   120
gggaaagccc ctaagctcct tatttattct gcatccactt tgcaaagtgg ggtcccatca   180
aggttcagcg gcagtggatt tgggacggaa ttcactctca ccatcagcag cctgcagcct   240
gaagattttg caacttatta ctgtcaacag cataatagtt accctcggac gttcggccaa   300
gggaccaagg tggaaatcaa a                                            321

SEQ ID NO: 108          moltype = AA   length = 6
FEATURE                 Location/Qualifiers
source                  1..6
                        mol_type = protein
                        organism = Macaca mulatta
SEQUENCE: 108
QGISHL                                                              6
```

| SEQ ID NO: 109 | moltype = length = |
| --- | --- |
| SEQUENCE: 109 | |
| 000 | |

| SEQ ID NO: 110 | moltype = AA length = 9 |
| --- | --- |
| FEATURE | Location/Qualifiers |
| source | 1..9 |
| | mol_type = protein |
| | organism = Macaca mulatta |

SEQUENCE: 110

QQHNSYPRT                                                                 9

| SEQ ID NO: 111 | moltype = DNA length = 5845 |
| --- | --- |
| FEATURE | Location/Qualifiers |
| source | 1..5845 |
| | mol_type = genomic DNA |
| | organism = Macaca mulatta |

SEQUENCE: 111

```
tcgcgcgttt cggtgatgac ggtgaaaacc tctgacacat gcagctcccg gagacggtca   60
cagcttgtct gtaagcggat gccgggagca gacaagcccg tcagggcgcg tcagcggggtg  120
ttggcgggtg tcggggctgg cttaactatg cggcatcaga cggagattgta ctgagagtgc  180
accatatgcg gtgtgaaata ccgcacagat gcgtaaggag aaaataccgc atcagattgc  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgaccccg cccattgacg tcaataatga cgtatgttcc  480
catagtaacg ccaataggga cttccattg acgtcaatgg gtggagtatt tacggtaaac  540
tgcccacttg gcagtacatc aagtgtatca tatgccaagt acgccccta ttgacgtcaa  600
tgacggtaaa tggcccgcct ggcattatgc ccagtacatg accttatgga ctttcctac   660
ttggcagtac atctacgtat tagtcatcgc tattaccatg gtgatgcggt tttggcagta  720
catcaatggg cgtggatagc ggttgact acggggattt ccaagtctcc acccattga    780
cgtcaatggg agtttgtttt ggcaccaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat cccacgctgt ttgacctcca  960
tagaagacac cgggaccgat ccagcctcca tcggctcgca tctctccttc acgcgccgc  1020
cgccctacct gaggccgcca tccacgccgg ttgagtcgcg ttctgccgcc tcccgcctgt  1080
ggtgcctcct gaactgcgtc cgccgtcag gtaagtttaa agctcaggtc gagaccggc   1140
ctttgtccgg cgctccctty gagcctacct agactcaga ggctctccac gcttgcctg   1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagac  1380
caccatggga tggtcatgta tcatccttttt tctagtagca actgcaaccg gtgtacattc  1440
ccaggtgcag ctggtgcagc tgcacgagtc gggcccagga ctggtgaagc cttcggagac  1500
cctgtccctc acctgcgctg tctctggtgg ctctatcagc agtagctact ggagctggat  1560
ccgccaggcc cagggaagg gactgagtg gattgggtat gtctatggta gtggtcgtga  1620
caccaacgac aaccctccc tcaagagtcg agtcacccg tcagtagaca cgtccaagaa  1680
ccagctctcc ctgaagctga gatcgtgac cgccgcggac acggccgtgt attactgtgc  1740
gagcagcggc tggcctcctg ggttggacta ctggggccag ggagtcacgg tcaccgtctc  1800
ctcagctagc caagggcc ctagtgtgtt cctctggcc cctagcagca gaagcacatc    1860
tgaatctaca gccgccctgg gctgcctggt gaaagattac ttccccgac cgtgaccctg  1920
gtcttggaat agcggctctc tgaccagcgg cgtgcacaca tttccagctg tgctgcagag  1980
cagcggcctg tattctctga gcagcgtggt gacagtgcca agcagctctc tgggcaccca  2040
gacctacgtg tgcaacgtga accacaagcc cagcaacacc aaggtggaca gcggggtgga  2100
aatcaagaac tgtggcggcg aagcaagcc tcctacctgt cctccttgtc cagccctga   2160
actgctgggc ggacctagcg tgttcctgtt cccccaaag cccaaggaca ccctgatgat  2220
cagcagaacc cccgaagtga cctgcgtggt ggtggatgtg tccaggaag atcccgacgt  2280
gaagttcaat tggtacgtga acggcgccga ggtgcaccat gcccagacaa agcccagaga  2340
gacacagtac aacagcacct accgggtggt gtctgtgctg accgtgacac accaggactg  2400
gctgaacggc aaagagtaca tgcaaggt gtccaacaag gccctgcctg cccccatcca   2460
gaaaaccatc agcaaggaca agggccagcc cagagaacct caggtgtaca cactgccccc  2520
cagcagagag gaactgacca agaatcaggt gtccctgacc tgtctggtga aaggcttcta  2580
ccccagcgac atcgtggtgg aatgggagtc tagcggacag cccgagaaca cctacaagac  2640
cacccctcca gtgctggata gcgacggcag ctacttcctg tacagcaagc tgaccgtgga  2700
caagagcaga tggcagcagg gcaacgtgtt cagctgctct gtgatgcacg aggccctgca  2760
caaccactac acccagaagt ctctgagcct gagcccgga aagtgatgat gaacacgtgg  2820
gatccagatc tgctgtgcct tctagttgcc agccatctgt tgtttgcccc tccccgtgc   2880
cttccttgac cctggaaggt gccactccca ctgtccttt ctaataaaat gaggaaattg   2940
catcgcattg tctgagtagg tgtcattcta ttctgggggg caggacagca 3000
agggggagga ttgggaagac aatagcaggc atgctgggga tgcggtgggc tctatggta   3060
cccaggtgct gaagaattga cccgttcct cctgggccag aaagaagcag gcacatcccc  3120
ttctctgtga cacaccctgt ccacgcccct ggttcttagt tccagcccca ctcataggac  3180
actcatagct caggagggct ccgccttcaa tcccaccgc taaagtactt ggagcggtct  3240
ctccctcct catcagccca aaaaccaaa cctagctccc aagatggga agaaattaaa   3300
gcaagatagg ctattaagtg cagagggaga gaaaatgcct ccaacatgtg aggaagtaat  3360
gagagaaatc ataagatttt aaggccatga tttaaggcca tcatgccctt aatcttccgc  3420
ttcctcgctc actgactcgc tgcgctcggt cgttcggctg cggcgagcgg tatcagctca  3480
ctcaaaggcg gtaatacggt tatccacaga atcagggat aacgcaggaa agaacatgtg   3540
agcaaaaggc cagcaaaagg ccaggaaccg taaaaaaggcc gcgttgctgg cgttttccca  3600
```

```
taggctccgc cccctgacg agcatcacaa aaatcgacgc tcaagtcaga ggtggcgaaa    3660
cccgacagga ctataaagat accaggcgtt tccccctgga agctccctcg tgcgctctcc    3720
tgttccgacc ctgccgctta ccggatacct gtccgccttt ctcccttcgg aagcgtggc    3780
gctttctcat agctcacgct gtaggtatct cagttcggtg taggtcgttc gctccaagct    3840
gggctgtgtg cacgaacccc ccgttcagcc cgaccgctgc gccttatccg gtaactatcg    3900
tcttgagtcc aacccggtaa gacacgactt atcgccactg gcagcagcca ctggtaacga    3960
gattagcaga gcgaggtatg taggcggtgc tacagagttc ttgaagtggt ggcctaacta    4020
cggctacact agaagaacag tatttggtat ctgcgctctg ctgaagccag ttaccttcgg    4080
aaaaagagtt ggtagctctt gatccggcaa acaaaccacc gctggtagcg gtggtttttt    4140
tgtttgcaag cagcagatta cgcgcagaaa aaaaggatct caagaagatc ctttgatctt    4200
ttctacgggg tctgacgctc agtggaacga aaactcacgt taagggattt tggtcatgag    4260
attatcaaaa aggatcttca cctagatcct tttaaattaa aaatgaagtt ttaaatcaat    4320
ctaaagtata tatgagtaaa cttggtctga cagttaccaa tgcttaatca gtgaggcacc    4380
tatctcagcg atctgtctat ttcgttcatc catagttgcc tgactcgggg ggggggggcg    4440
ctgaggtctg cctcgtgaag aaggtgttgc tgactcatac caggcctgaa tcgccccatc    4500
atccagccag aaagtgaggg agccacggtt gatgagagct ttgttgtagg tggaccagtt    4560
ggtgattttg aacttttgct ttgccacgga acggtctgcg ttgtcgggaa gatgcgtgat    4620
ctgatccttc aactcagcaa aagttcgatt tattcaacaa agccgccgtc ccgtcaagtc    4680
agcgtaatgc tctgccagtg ttacaaccaa ttaaccaatt ctgattagaa aaactcatcg    4740
agcatcaaat gaaactgcaa tttattcata tcaggattat caataccata tttttgaaaa    4800
agccgttcct gtaatgaagg agaaaactca ccgaggcagt tccataggat ggcaagatcc    4860
tggtatcggt ctgcgattcc gactcgtcca acatcaataa aacctattaa tttcccctcg    4920
tcaaaaataa ggttatcaag tgagaaatca ccatgagtga cgactgaatc cggtgagaat    4980
ggcaaaagct tatgcatttc tttccagact tgttcaacag gccagccatt acgctcgtca    5040
tcaaaatcac tcgcatcaac caaaccgtta ttcattcgtg attgcgcctg agcgagacga    5100
aatacgcgat cgctgttaaa aggacaatta caaacaggaa tcgaatgcaa ccggcgcagg    5160
aacactgcca gcgcatcaac aatattttca cctgaatcag gatattcttc taatacctgg    5220
aatgctgttt tcccggggat cgcagtggtg agtaaccatg catcatcagg agtacggata    5280
aaatgcttga tggtcggaag aggcataaat tccgtcagcc agtttagtct gaccatctca    5340
tctgtaacat cattggcaac gctaccttg ccatgtttca gaaacaactc tggcgcatcg    5400
ggcttcccat acaatcgata gattgtcgca cctgattgcc cgacattatc gcgagcccat    5460
ttatacccat ataaatcagc atccatgttg gaatttaatc gcggcctcga gcaagacgtt    5520
tcccgttgaa tatggctcat aacaccctt gtattactgt ttatgtaagc agacagtttt    5580
attgttcatg atgatatatt tttatcttgt gcaatgtaac atcagagatt ttgagacaca    5640
acgtggcttt cccccccccc ccattattga agcatttatc aggtttattg tctcatgagc    5700
ggatacatat ttgaatgtat ttagaaaaat aaacaaatag gggttccgcg cacatttccc    5760
cgaaaagtgc cacctgacgt ctaagaaacc attattatca tgacattaac ctataaaaat    5820
aggcgtatca cgaggccctt tcgtc                                         5845

SEQ ID NO: 112         moltype = AA  length = 473
FEATURE                Location/Qualifiers
source                 1..473
                       mol_type = protein
                       organism = Macaca mulatta
SEQUENCE: 112
MGWSCIILFL VATATGVHSQ VQLVQLHESG PGLVKPSETL SLTCAVSGGS ISSSYWSWIR    60
QAPGKGLEWI GYVYGSGRDT NDNPSLKSRV TLSVDTSKNQ LSLKLRSVTA ADTAVYYCAS   120
SGWPPGLDYW GQGVTVTVSS ASTKGPSVFP LAPSSRSTSE STAALGCLVK DYFPEPVTVS   180
WNSGSLTSGV HTFPAVLQSS GLYSLSSVVT VPSSSLGTQT YVCNVNHKPS NTKVDKRVEI   240
KTCGGGSKPP TCPPCTSPEL LGGPSVFLFP PKPKDTLMIS RTPEVTCVVV DVSQEDPDVK   300
FNWYVNGAEV HHAQTKPRET QYNSTYRVVS VLTVTHQDWL NGKEYTCKVS NKALPAPIQK   360
TISKDKGQPR EPQVYTLPPS REELTKNQVS LTCLVKGFYP SDIVVEWESS GQPENTYKTT   420
PPVLDSDGSY FLYSKLTVDK SRWQQGNVFS CSVMHEALHN HYTQKSLSLS PGK          473

SEQ ID NO: 113         moltype = DNA  length = 5100
FEATURE                Location/Qualifiers
source                 1..5100
                       mol_type = genomic DNA
                       organism = Macaca mulatta
SEQUENCE: 113
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaataggga ctttccattg acgtcaatgg gtggagtatt tacggtaaac   540
tgcccacttg gcagtacatc aagtgtatca tatgccaagt acgcccccta ttgacgtcaa   600
tgacggtaaa tggcccgcct ggcattatgc ccagtacatg accttatggg acttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcgcgccgt   1080
ggtgcctcct gaactgcgtc cgccgtctag gtaagtttaa agctcaggtc gagaccgggc   1140
```

```
ctttgtccgg cgctcccttg gagcctacct agactcagcc ggctctccac gctttgcctg   1200
accctgcttg ctcaactcta gttaacggtg gagggcagtg tagtctgagc agtacacgtt   1260
gctgccgcgc gcgccaccag acataatagc tgacagacta acagactgtt cctttccatg   1320
ggtctttttct gcagtcaccg tcgtcgacac gtgtgatcag atatcgcggc cgctctagac   1380
caccatggga tggtcatgta tcatcctttt tctagtagca actgcaaccg tgtgtacattc   1440
agaaattgtg ttgacacagt ctccaggcac cctgtctttg tctccagggg aaacagccat   1500
catctcttgt cggaccagtc agtatggttc cttagcctgg tatcaacaga ggcccggcca   1560
ggcccccagg ctcgtcatct attcgggctc tactcgggcc gctggcatcc agacaggttt   1620
cagcggcagt cggtggggggc cagactacaa tctcaccatc agcaacctgg agtcgggaga   1680
ttttggtgtt tattattgcc agcagtatga attttttggc caggggacca aggtccaggt   1740
cgacattaaa cgtacggtgg ctgcaccatc tgtcttcatc ttcccgccat ctgaggatca   1800
ggtgaaatct ggaactgtct ctgttgtgtg cctgctgaat aacttctatc ccagagaggc   1860
cagcgtaaag tggaaggtgg atggtgccct caaaacgggg aactcccagg agagtgtcac   1920
agagcaggac agcaaggaca cacctacag cctgagcagc acctgacgc tgagcagcac   1980
agagtaccag agtcacaaag tctatgcctg cgaagtcacc catcagggcc tgagctcgcc   2040
cgtcaccaag agcttcaaca gaggagagtg ttagggatcc agatctgctg tgccttctag   2100
ttgccagcca tctgttgttt gcccctcccc cgtgccttcc ttgaccctgg aaggtgccac   2160
tcccactgtc ctttcctaat aaaatgagga aattgcatcg cattgtctga gtaggtgtca   2220
ttctattctg gggggtgggg tggggcagga cagcaagggg gaggattggg aagacaatag   2280
caggcatgct ggggatgcgg tgggctctat gggtacccag gtgctgaaga attgacccgg   2340
ttcctcctgg gccagaaaga agcaggcaca tccccttctc tgtgacacac cctgtccacg   2400
cccctggttc ttagttccag ccccactcat aggacactca tagctcagga gggctccgcc   2460
ttcaatccca cccgctaaag tacatggagc ggtctctccc tccctcatca gcccaccaaa   2520
ccaaacctag cctccaagag tgggaagaaa ttaaagcaag ataggctatt aagtgcagag   2580
ggagagaaaa tgcctccaac atgtgaggaa gtaatgagag aaatcataga attttaaggc   2640
catgatttaa ggccatcatg gccttaatct tccgcttcct cgctcactga ctcgctgcgc   2700
tcggtcgttc ggctgcgcgg agcggtatca gctcactcaa aggcggtaat acggttatcc   2760
acagaatcag gggataacgc aggaaagaac atgtgagcaa aaggccagca aaaggccagg   2820
aaccgtaaaa aggccgcgtt gctggcgttt ttccatag gc tccgcccccc tgacgagcat   2880
cacaaaaatc gacgctcaag tcagaggtgg cgaaacccga caggactata aagataccag   2940
gcgtttcccc ctggaagctc cctcgtgcgc tctcctgttc cgaccctgcc gcttaccgga   3000
tacctgtccg cctttctccc ttcgggaagc gtggcgcttt ctcatagctc acgctgtagg   3060
tatctcagtt cggtgtaggt cgttcgctcc aagctgggct gtgtcacga accccccgtt   3120
cagcccgacc gctgcgcctt atccgtcttg agtccaaccc ggtaagacac   3180
gacttatcgc cactggcagc agccactggt aacaggatta gcagagcgag gtatgtaggc   3240
ggtgctacag agttcttgaa gtggtggcct aactacggct acactagaag aacagtattt   3300
ggtatctgcg ctctgctgaa gccagttacc ttcggaaaaa gagttggtag ctcttgatcc   3360
ggcaaacaaa ccaccgctgg tagcggtggt ttttttgttt gcaagcagca gattacgcgc   3420
agaaaaaaag gatctcaaga agatcctttg atcttttcta cggggtctga cgctcagtgg   3480
aacgaaaact cacgttaagg gattttggtc atgagattat caaaaaggat cttcacctag   3540
atccttttaa attaaaaatg aagttttaaa tcaatctaaa gtatatatga gtaaacttgg   3600
tctgacagtt accaatgctt aatcagtgag gcacctatct cagcgatctg tctatttcgt   3660
tcatccatag ttgcctgact cggggggggg gggcgctgag gtctgcctcg tgaagaaggt   3720
gttgctgact cataccaggc ctgaatcgcc ccatcatcca gccagaaagt gagggagcca   3780
cggttgatga gctttgtt gtaggtggac cagttggtga ttttgaactt ttgctttgcc   3840
acggaacggt ctgcgttgtc gggaagatgc gtgatctgat ccttcaactc agcaaaagtt   3900
cgatttattc aacaaagccg ccgtcccgtc aagtcagcgt aatgctctgc cagtgttaca   3960
accaattaac caattctgat tagaaaaact catcgagcat caaatgaaac tgcaatttat   4020
tcatatcagg attatcaata ccatattttt gaaaagccg tttctgtaat gaaggagaaa   4080
actcaccgag gcagttccat aggatggcaa gatcctggta tcggtctgcg attccgactc   4140
gtccaaatca aatacaacct attaatttcc cctcgtcaaa aataaggtta tcaagtgaga   4200
aatcaccatg agtgacgact gaatccggtg agaatggcaa aagcttatgc atttctttcc   4260
agacttgttc aacaggccag ccattacgct cgtcatcaaa atcactcgca tcaaccaaac   4320
cgttattcat tcgtgattgc gcctgagcga cgaaatac gcgatcgctg ttaaaaggac   4380
aattacaaac aggaatcgaa tgcaaccggc gcaggaacac tgccagcgca tcaacaatat   4440
tttcacctga atcaggatat tcttctaata cctggaatgc tgttttcccg gggatcgcag   4500
tggtgagtaa ccatgcatca tcaggagtac ggataaaatg cttgatggtc ggaagaggca   4560
taaattccgt cagccagttt agtctgacca tctcatctgt aacatcattg gcaacgctac   4620
ctttgccatg tttcagaaac aactctggcg catcgggctt cccatacaat cgatagattg   4680
tcgcacctga ttgcccgaca ttatcgcgag cccatttata cccatataaa tcagcatcca   4740
tgttggaatt taatcgcggc ctcgagcaag acgtttcccg ttgaatatgg ctcataacac   4800
cccttgtatt actgtttatg taagcagaca gttttattgt tcatgatgat atatttttat   4860
cttgtgcaat gtaacatcag agattttgag acacaacgtg gctttcccc cccccccatt   4920
attgaagcat ttatcaggt tattgtctca tgagcgaata catatttgaa tgtatttaga   4980
aaaataaaca aataggggtt ccgcgcacat ttccccgaaa agtgccacct gacgtctaag   5040
aaaccattat tatcatgaca ttaacctata aaaataggcg tatcacgagg ccctttcgtc   5100
```

SEQ ID NO: 114          moltype = AA  length = 229
FEATURE                Location/Qualifiers
source                 1..229
                        mol_type = protein
                        organism = Macaca mulatta
SEQUENCE: 114
MGWSCIILFL VATATGVHSE IVLTQSPGTL SLSPGETAII SCRTSQYGSL AWYQQRPGQA  60
PRLVIYSGST RAAGIPDRFS GSRWGPDYNL TISNLESGDF GVYYCQQYEF FGQGTKVQVD  120
IKRTVAAPSV FIFPPSEDQV KSGTVSVVCL LNNFYPREAS VKWKVDGALK TGNSQESVTE  180
QDSKDNTYSL SSTLTLSSTE YQSHKVYACE VTHQGLSSPV TKSFNRGEC  229

SEQ ID NO: 115          moltype = AA  length = 235

```
FEATURE              Location/Qualifiers
source               1..235
                     mol_type = protein
                     organism = Macaca mulatta
SEQUENCE: 115
MGWSCIILFL VATATGVHSQ SALTQPPSVS GSPGQSVTIS CTGTSSDVDG YNYVSWYQQH   60
PGKAPKLMIY GVSNRPSGVS DRFSGSKSGN TASLTISGLQ AEDEADYYCC SSTTSYTYIF  120
GTGTKVTVLG QPKAAPSVTL FPPSSEELQA NKATLVCLIS DFYPGAVEVA WKADGSAVNA  180
GVETTKPSKQ SNNKYAASSY LSLTSDQWKS HKSYSCQVTH EGSTVEKTVA PAECS       235

SEQ ID NO: 116       moltype = DNA   length = 5842
FEATURE              Location/Qualifiers
source               1..5842
                     mol_type = genomic DNA
                     organism = Macaca mulatta
SEQUENCE: 116
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgaccccg  cccattgacg tcaataatga cgtatgttcc   480
catagtaacg ccaatagga  cttttccattg acgtcaatgg gtggagtatt tacggtaaac   540
tgcccacttg gcagtacatc aagtgtatca tatgccaagt acgccccta  ttgacgtcaa   600
tgacggtaaa tggcccgcct ggcattatgc ccagtacatg accttatggg acttttctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcagtagt agtttgtttt ggcaccaaaa tcaacggac  tttccaaaat gtcgtaacaa   840
ctccgccccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctaggtc  gagacgggtgc  1140
cttttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgctctagac  1380
caccatggga tggtcatgta tcatcctttt tctagtagca actgcaaccg gtgtacattc  1440
ccaactgcag ttgcaggagt cgggcccagg agtggtgaag ccttcggaga ccctgtccct  1500
cacctgcact atctctggtg gctccttcag tacttactac tggacctgga ttcgccagcc  1560
cccagggaag ggactggagt ggtttgggta tatcggtaat ggtggtcgta gcctcaacta  1620
caaccctcc  ctcaagagtc gcatcaccct gtcagtagac gcgtccaaga accagttctc  1680
cctgaaggtg acctctgtga ccgccgcgga cacggccgtc tattactgtg ggagagccag  1740
gggactccgc ggaaactggt tcgatgtctg gggcccggga gtcctggtca ccgtctcctc  1800
agctagcacc aagggcccta gtgtgttccc tctggccct  agcagcagaa gcacatctga  1860
atctacagcc gccctgggct gcctggtgaa agattacttc cccgagcccg tgaccgtgtc  1920
ttggaatagc ggctctctga ccagcggcgt gcacacattt ccagctgtgc tgcagagcag  1980
cggcctgtat tctctgagca gcgtggtgac agtgccaagc agctctctgg gcacccagac  2040
ctacgtctgc aacgtgaacc acaagcccag caacaccgag gtggacaagc gggtggaaat  2100
caagacctgt ggcggcggaa gcaagcctcc tacctgtcct ccttgtacca gccctgaact  2160
gctgggcgga cctagcgtgt tcctgttccc cccaaagccc aaggacaccc tgatgatcag  2220
cagaaccccc gaagtgacct gcgtggtggt ggatgtgtcc caggaagatc ccgacgtgaa  2280
gttcaattgg tacgtgaacg gcgccgaggt gcaccatgcc cagacaaagc ccagagagac  2340
acagtacaac agcacctacc gggtggtgtc tgtgctgacc gtgacacacc aggactggct  2400
gaacggcaaa gagtacacat gcaaggtgtc caacaaggcc ctgcctgccc catccagaa   2460
aaccatcagc aaggacaagg ccagcccag  agaacctcag gtgtacacac tgccccccag  2520
cagagaggaa ctgaccaaga atcaggtgtc cctgacctgt ctggtgaaag gcttctaccc  2580
cagcgacatc gtggtggaat gggagtctag cggacagccc gagaacaacc tcaagaccac  2640
ccctccagtg ctggatagcg acggcagcta cttcctgtac agcaagctga ccgtggacaa  2700
gagcagatgg cagcagggca acgtgttcag ctgctctgtg atgcacgagg ccctgcacaa  2760
ccactacacc cagaagtctc tgagcctgag ccccggaaaa tgatgatgaa cacgtgggat  2820
ccagatctgc tgtgccttct agttgccagc catctgttgt ttgcccctcc cccgtgcctt  2880
ccttgaccct ggaaggtgcc actcccactg tcctttccta ataaaatgag gaaattgcat  2940
cgcattgtct gagtaggtgt cattctattc tggggggtgg ggtggggcag gacagcaagg  3000
gggaggattg gaagacaat  agcaggcatg ctgggatgc  ggtgggctct atgggtaccc  3060
aggtgctgaa gaattgaccc ggttcctcct gggccagaaa gaagcaggca catcccctc   3120
tctgtgacac accctgtcca cgcccctggt tcttagttcc agccccactc ataggacact  3180
catagctcag gagggctccg ccttcaatcc caccgctaa  agtacttgga gcggtctctc  3240
cctccctcat cagcccacca aaccaaacct agcctccaag agtgggaaga aattaaagca  3300
agataggcta ttaagtgcag agggagagaa aatgcctcca acatgtgagg aagtaatgag  3360
agaaatcata gaattttaag gccatgattt aaggccatca tggccttaat cttccgcttc  3420
ctcgctcact gactcgctgc gctcggtcgt tcggctgcgg cgagcggtat cagctcactc  3480
aaaggcggta atacggttat ccacagaatc aggggataac gcaggaaaga acatgtgagc  3540
aaaaggccag caaaaggcca ggaaccgtaa aaaggccgcg ttgctggcgt ttttccatag  3600
gctccgcccc cctgacgagc atcacaaaaa tcgacgctca agtcagaggt ggcgaaaccc  3660
gacaggacta taaagatacc aggcgtttcc cctggaagct ccctcgtgcg ctctcctgt   3720
tccgaccctg ccgcttaccg gatacctgtc cgcctttctc ccttcgggaa gcgtggcgct  3780
```

```
ttctcatagc tcacgctgta ggtatctcag ttcggtgtag gtcgttcgct ccaagctggg  3840
ctgtgtgcac gaaccccccg ttcagcccga ccgctgcgcc ttatccggta actatcgtct  3900
tgagtccaac ccggtaagac acgacttatc gccactggca gcagccactg gtaacaggat  3960
tagcagagcg aggtatgtag gcggtgctac agagttcttg aagtggtggc ctaactacgg  4020
ctacactaga agaacagtat ttggtatctg cgctctgcta aagccagtta ccttcggaaa  4080
aagagttggt agctcttgat ccggcaaaca aaccaccgct ggtagcggtg gttttttttgt  4140
ttgcaagcag cagattacgc gcagaaaaaa aggatctcaa gaagatcctt tgatcttttc  4200
tacgggtct gacgctcagt ggaacgaaaa ctcacgttaa gggattttgg tcatgagatt  4260
atcaaaaagg atcttcacct agatccttt aaattaaaaa tgaagtttta aatcaatcta  4320
aagtatatat gagtaaactt ggtctgacag ttaccaatgc ttaatcagtg aggcacctat  4380
ctcagcgatc tgtctatttc gttcatccat agttgcctga ctcgggggg gggggcgctg  4440
aggtctgcct cgtgaagaag gtgttgctga ctcataccag gcctgaatcg ccccatcatc  4500
cagccagaaa gtgagggagc cacggttgat gagagctttg ttgtaggtgg accagttggt  4560
gatttgtgaac ttttgctttg ccacggaacg gtctgcgttg tcgggaagat gcgtgatctg  4620
atccttcaac tcagcaaaag ttcgatttat tcaacaaagc cgccgtcccg tcaagtcagc  4680
gtaatgctct gccagtgtta caaccaatta accaattctg attagaaaaa ctcatcgagc  4740
atcaaatgaa actgcaattt attcatatca ggattatcaa taccatattt ttgaaaaagc  4800
cgtttctgta atgaaggaga aaactcaccg aggcagttcc ataggatggc aagatcctgg  4860
tatcggtctg cgattccgac tcgtccaaca tcaatacaac ctattaattt cccctcgtca  4920
aaaataaggt tatcaagtga aaatcacca tgagtgacga ctgaatccgg tgagaatggc  4980
aaaagcttat gcatttcttt ccagacttgt tcaacaggcc agccattacg ctcgtcatca  5040
aaatcactcg catcaaccaa accgttattc attcgtgatc ggcctgagc gagacgaaat  5100
acgcgatcgc tgttaaaagg acaattacaa acaggaatcg aatgcaaccg gcgcaggaac  5160
actgccagcg catcaacaat atttttcacct gaatcaggat attcttctaa tacctggaat  5220
gctgttttcc cggggatcgc agtggtgagt aaccatgcat catcaggagt acggataaaa  5280
tgcttgatgg tcggaagagg cataaaattcc gtcagccagt ttagtctgac catctcatct  5340
gtaacatcat tggcaacgct acctttgcca tgtttcagaa acaactctgg cgcatcgggc  5400
ttcccataca atcgatagat tgtcgcacct gattgcccga cattatcgcg agcccattta  5460
tacccatata aatcagcatc catgttgaa tttaatcgcg gcctcgagca agacgtttcc  5520
cgttgaatat ggctcataac acccccttgta ttactgtta tgtaagcaga cagttttatt  5580
gttcatgatg atatattttt atcttgtgca atgtaacatc agagattttg agacacaacg  5640
tggctttccc cccccccca ttattgaagc atttatcagg gttattgtct catgagcgga  5700
tacatatttg aatgtattta gaaaatataaa caaatagggg ttccgcgcac atttcccga  5760
aaagtgccac ctgacgtcta agaaaccatt attatcatga cattaaccta taaaaatagg  5820
cgtatcacga ggccctttcg tc                                           5842

SEQ ID NO: 117          moltype = AA  length = 472
FEATURE                 Location/Qualifiers
source                  1..472
                        mol_type = protein
                        organism = Macaca mulatta
SEQUENCE: 117
MGWSCIILFL VATATGVHSQ LQLQESGPGV VKPSETLSLT CTISGGSFST YYWTWIRQPP   60
GKGLEWVGYI GNGGRSLNYN PSLKSRITLS VDASKNQFSL KVTSVTAADT AVYYCGRARG  120
LRGNWFDVWG PGVLVTVSSA STKGPSVFPL APSSRSTSES TAALGCLVKD YFPEPVTVSW  180
NSGSLTSGVH TFPAVLQSSG LYSLSSVVTV PSSSLGTQTY VCNVNHKPSN TKVDKRVEIK  240
TCGGGSKPPT CPPCTSPELL GGPSVFLFPP KPKDTLMISR TPEVTCVVVD VSQEDPDVKF  300
NWYVNGAEVH HAQTKPRETQ YNSTYRVVSV LTVTHQDWLN GKEYTCKVSN KALPAPIQKT  360
ISKDKGQPRE PQVYTLPPSR EELTKNQVSL TCLVKGFYPS DIVVEWESSG QPENTYKTTP  420
PVLDSDGSYF LYSKLTVDKS RWQQGNVFSC SVMHEALHNH YTQKSLSLSP GK          472

SEQ ID NO: 118          moltype = DNA  length = 5118
FEATURE                 Location/Qualifiers
source                  1..5118
                        mol_type = genomic DNA
                        organism = Macaca mulatta
SEQUENCE: 118
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaatagggg actttccatt gacgtcaatg ggtggagtat tacggtaaac  540
tgcccacttg gcagtacatc aagtgtatca tatgccaagt acgccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca cggctctgca tctctccttc acgcgtccca 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctccctttg gagcctacct agactcagcc ggctctccac gctttgcctg 1200
accctgcttg ctcaactcta gttaacggtg gagggcagtg tagtctgagc agtacacgtt 1260
gctgccgcgc gcgccaccag acataatagc tgacagacta acagactgtt cctttccatg 1320
```

```
ggtcttttct gcagtcaccg tcgtcgacac gtgtgatcag atatcgcggc cgctctagac  1380
caccatggga tggtcatgta tcatcctttt tctagtagca actgcaaccg gtgtacattc  1440
ccaggctgcc ctgactcagc ctccctctgt gtctgggtct cctggacagt cggtcaccat  1500
ctcctgcact ggaaccagca gtgacatcgg tggttataac tatgtctcct ggtaccaaca  1560
acacccaggc aaagccccca aagtcatgat ttatgaggtc agtaagcggc cctcagggat  1620
ctctgatcgc ttctctggtt ccaaatctgg caacatagcc tccctgacca tctctgggct  1680
ccaggctgag gacgaggctg attattactg cagctcatat gcaggcagca cactttctt  1740
attcggagga gggacccggc tgacagtact aggtcagccc aaggctgccc cctcggtcac  1800
tctcttcccg ccctcctctg aggagcttca agccaacaag gccacactag tgtgtctgat  1860
cagtgacttc tacccgggag ccgtggaagt ggcctggaag gcagatggca gcgctgtcaa  1920
cgcgggagtg gagaccacca aaccctccaa acagagcaac aacaagtacg cggccagcag  1980
ctacctgagc ctgacgtccg accagtggaa gtcccacaag agctacagct gccaggtcac  2040
gcacgaaggg agcaccgtgg agaagacagt ggcccctgca gaatgttcat agggatccag  2100
atctgtctgtg ccttctagtt gccagccatc tgttgtttgc ccctcccccg tgccttcctt  2160
gaccctggaa ggtgccactc ccactgtcct ttcctaataa aatgaggaaa ttgcatcgca  2220
ttgtctgagt aggtgtcatt ctattctggg ggtgggggtg gggcaggaca gcaagggga  2280
ggattgggaa gacaatagca ggcatgctgg gatgcggtg gctctatgg gtacccaggt  2340
gctgaagaat tgacccggtt cctcctgggc cagaaagaag caggcacatc cccttctctg  2400
tgacacaccc tgtccacgcc cctggttctt agttccagcc ccactcatag gacactcata  2460
gctcaggagg gctccgcctt caatcccacc cgctaaagta catggagcgg tctctcctc  2520
cctcatcagc ccaccaaacc aaacctagcc tccaagagtg ggaagaaatt aaagcaagat  2580
aggctattaa gtgcagaggg agagaaaatg cctccaacat ggtaggaagt aatgagagaa  2640
atcatagaat tttaaggcca tgatttaagg ccatcatggc cttaatcttc cgcttcctcg  2700
ctcactgact cgctgcgctc ggtcgttcgg ctgcggcgag cggtatcagc tcactcaaag  2760
gcggtaatac ggttatccac agaatcaggg gataacgcag gaaagaacat gtgagcaaaa  2820
ggccagcaaa aggccaggaa ccgtaaaaag gccgcgttgc tggcgttttt ccataggctc  2880
cgcccccctg acgagcatca caaaaatcga cgctcaagtc agaggtggcg aaacccgaca  2940
ggactataaa gataccaggc gtttccccct ggaagctccc tcgtgcgctc tcctgttccg  3000
accctgccgc ttaccggata cctgtccgcc tttctccctt cgggaagcgt ggcgctttct  3060
catagctcac gctgtaggta tctcagttcg gtgtaggtcg ttcgctccaa gctgggctg  3120
gtgcacgaac ccccgttca gcccgaccgc tgcgccttat ccggtaacta tcgtcttgag  3180
tccaacccgg taagacacga cttatcgcca ctggcagcag ccactggtaa caggattagc  3240
agagcgaggt atgtaggcgg tgctacagag ttcttgaagt ggtggcctaa ctacggctac  3300
actagaagaa cagtatttgg tatctgcgct ctgctgaagc cagttacctt cggaaaaaga  3360
gttggtagct cttgatccgg caaacaaacc accgctggta gcggtggttt ttttgtttgc  3420
aagcagcaga ttacgcgcag aaaaaaagga tctcaagaag atcctttgat cttttctacg  3480
gggtctgacg ctcagtggaa cgaaaactca cgttaaggga ttttggtcat gagattatca  3540
aaaaggatct tcacctagat ccttttaaat taaaaatgaa gttttaaatc aatctaaagt  3600
atatatgagt aaacttggtc tgacagttac caatgcttaa tcagtgaggc acctatctca  3660
gcgatctgtc tatttcgttc atccatagtt gcctgactcg gggggggggg gcgctgaggt  3720
ctgcctcgtg aagaaggtgt tgctgactca taccaggcct gaatcgcccc atcatccagc  3780
cagaaagtga gggagccacg gttgatgaga gctttgttgt aggtggacca gttggtgatt  3840
ttgaacttttt gctttgccac ggaacgctc gcgttgtcgg gaagatgcgt gatctgatcc  3900
ttcaactcag caaaagttcg atttattcaa caaagccgcc gtcccgtcaa gtcagctaa  3960
tgctctgcca gtgttacaac caattaacca attctgatta gaaaaactca tcgagcatca  4020
aatgaaactg caattattc atatcaggat tatcaataac atattttga aaaagccgtt  4080
tctgtaatga aggagaaac tcaccgaggc agttccatag gatggcaaga tcctggtatc  4140
ggtctgcgat tccgactcgt ccaacatcaa tacaacctat taatttcccc tcgtcaaaaa  4200
taaggttatc aagtgagaaa tcaccatgag tgacgactga atccggtgag aatggcaaaa  4260
gcttatgcat ttctttccag acttgttcaa caggccagcc attacgctcg tcatcaaaat  4320
cactcgcatc aaccaaaccg ttattcattc gtgattgcgc ctgagcgaga cgaaatacgc  4380
gatcgctgtt aaaaggacaa ttacaaacag gaatcgaatg caaccggcgc aggaacactg  4440
ccagcgcatc aacaatattt tcacctgaat caggatattc ttctaatacc tggaatgctg  4500
ttttcccggg gatcgcagtg gtgagtaacc atgcatcatc aggagtacgg ataaaatgct  4560
tgatgtcgg aagaggcata aattccgtca gccagtttag tctgaccatc tcatctgtaa  4620
catcattggc aacgctacct ttgccatgtt tcagaaacaa ctctggcgca tcgggcttcc  4680
catacaatcg atagattgtc gcacctgatt gcccgacatt atcgcgagcc catttatacc  4740
catataaatc agcatccatg ttggaattta atcgcggcct cgagcaagac gtttcccgtt  4800
gaatatggct cataacaccc cttgtattac tgtttatgta agcagacagt tttattgttc  4860
atgatgatat ttttatct tgtgcaatgt aacatcagag attttgagac acaacgtgc  4920
tttccccccc cccccattat tgaagcattt atcagggtta ttgtctcatg agcggataca  4980
tatttgaatg tatttagaaa aataaacaaa taggggttcc gcgcacattt ccccgaaaag  5040
tgccacctga cgtctaagaa accattatta tcatgacatt aacctataaa aataggcgta  5100
tcacgaggcc ctttcgtc                                                 5118
```

SEQ ID NO: 119         moltype = AA  length = 235
FEATURE                 Location/Qualifiers
source                  1..235
                         mol_type = protein
                         organism = Macaca mulatta
SEQUENCE: 119
MGWSCIILFL VATATGVHSQ AALTQPPSVS GSPGQSVTIS CTGTSSDIGG YNYVSWYQQH  60
PGKAPKVMIY EVSKRPSGVS DRFSGSKSGN IASLTISGLQ AEDEADYYCS SYAGSNTFLF  120
GGGTRLTVLG QPKAAPSVTL FPPSSEELQA NKATLVCLIS DFYPGAVEVA WKADGSAVNA  180
GVETTKPSKQ SNNKYAASSY LSLTSDQWKS HKSYSCQVTH EGSTVEKTVA PAECS  235

SEQ ID NO: 120         moltype = DNA  length = 5823
FEATURE                 Location/Qualifiers
source                  1..5823 mol_type = other DNA
organism = Synthetic construct

SEQUENCE: 120

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcgggctgg  cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgacccccg cccattgacg tcaataatga cgtatgttcc  480
catagtaacg ccaatagga  ctttccattg acgtcaatgg gtggagtatt tacggtaaac  540
tgcccacttg gcagtacatc aagtgtatca tatgccaagt acgcccccta ttgacgtcaa  600
tgacggtaaa tggcccgcct ggcattatgc ccagtacatg accttatgga actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactgtt cctttccatg 1320
ggtcttttct gcagtcaccg tcgtcgacac gtgtgatcga atatgccggc cgctctagac 1380
caccatggga tggtcatgta tcatcctttt tctagtagca actgcaaccg gtgtacattc 1440
ccaactgcag ttgcaggagt cgggcccagg agtggtgaag ccttcggaga ccctgtccct 1500
cacctgcact atctctggtg gctccttcag tacttactac tggacctgga ttcgccagcc 1560
cccagggaag ggactggagt gggttgggta tatcgggtat ggtggtcgta gcctcaacta 1620
caacccctcc ctcaagagtc gcatcaccct gtcagtagac gcgtccaaga accagttctc 1680
cctgaaggtg acctctgtga ccgccgcgga cacggccgtc tattactgtg ggagagccag 1740
gggactccgc ggaaactggt tcgatgtctg ggggcccggga gtcctggtca ccgtctcctc 1800
agctagcacc aagggcccat cggtcttccc cctggcaccc tcctccaaga gcacctctgg 1860
gggcacagcg gccctgggct gcctggtcaa ggactacttc cccgaaccgg tgacggtgtc 1920
gtggaactca ggcgccctga ccagcggcgt gcacaccttc ccggctgtcc tacagtcctc 1980
aggactctac tccctcagca gcgtggtgac cgtgccctcc agcagcttgg gcacccagac 2040
ctacatctgc aacgtgaatc acaagcccag caacaccaag gtggacaaga agttgagcc  2100
caaatctgt  gacaaaactc acacatgccc accgtgccca gcacctgaac tcctgggggg 2160
accgtcagtc ttcctcttcc ccccaaaacc caaggacacc ctcatgatct cccggacccc 2220
tgaggtcaca tgcgtggtgg tggacgtgag ccacgaagac cctgaggtca agttcaactg 2280
gtacgtggac ggcgtggagg tgcataatgc caagacaaaa ccgcgggagg agcagtacaa 2340
cagcacgtac cgtgtggtca gcgtcctcac cgtcctgcac caggactggc tgaatggcaa 2400
ggagtacaag tgcaaggtct ccaacaaagc cctcccagcc cccatcgaga aaaccatctc 2460
caaagccaaa gggcagcccc gagaaccaca ggtgtacacc ctgcccccat cccgggatga 2520
gctgaccaag aaccaggtca gcctgacctg cctggtcaaa ggcttctatc ccagcgacat 2580
cgccgtggag tgggagagca atgggcagcc ggagaacaac tacaagacca cgcctcccgt 2640
gctggactcc gacggctcct tcttcctcta cagcaagctc accgtggaca gagcaggtg  2700
gcagcagggg aacgtcttct catgctccgt gatgcatgag gctctgcaca accactacac 2760
gcagaagagc ctctccctgt ctccgggtaa atgatgagga tccagatctg ctgtgccttc 2820
tagttgccag ccatctgttg tttgcccctc cccgtgcct  tccttgaccc tggaaggtga 2880
cactcccact gtcctttcct aataaaatga ggaaattgca tcgcattgtc tgagtaggtg 2940
tcattctatt ctgggggtg  gggtggggca ggacagcaag gggaggatt  gggaagacaa 3000
tagcaggcat gctgggatg  cggtgggctc tatgggtacc caggtgctga agaattgacc 3060
cggttcctcc tgggccagaa agaagcaggc acatcccctct ctctgtgaca cccctgtcc  3120
acgcccctgg ttcttagttc cagccccact cataggacac tcatagctca ggagggctcc 3180
gccttcaatc ccaccgcta  agtacttgg  agcggtctct ccctccctca tcagcccacc 3240
aaaccaaacc tagcctccaa gagtgggaag aaattaaagc aagataggct attaagtgca 3300
gagggagaga aaatgcctcc aacatgtgag gaagtaatga gagaaatcat agaattttaa 3360
ggccatgatt taaggccatc atggccttaa tcttccgctt cctcgctcac tgactcgctg 3420
cgctcggtcg ttcggctgcg gcgagcggta tcagctcact caaaggcggt aatacggtta 3480
tccacagaat caggggataa cgcaggaaag aacatgtgag caaaaggcca gcaaaaggcc 3540
aggaaccgta aaaaggccgc gttgctggcg ttttccata  ggctccgccc cctgacgag  3600
catcacaaaa atcgacgctc aagtcagagg tggcgaaacc cgacaggact ataagatac  3660
caggcgtttc cccctggaag ctccctcgtg cgctctcctg ttccgaccct gccgcttacc 3720
ggatacctgt ccgcctttct cccttcggga agcgtggcgc tttctcatag ctcacgctgt 3780
aggtatctca gttcggtgta ggtcgttcgc tccaagctgg gctgtgtgca cgaacccccc 3840
gttcagcccg accgctgcgc cttatccggt aactatcgtc ttgagtccaa cccggtaaga 3900
cacgacttat cgccactggc agcagccact ggtaacagga ttagcagagc gaggtatgta 3960
ggcggtgcta cagagttctt gaagtggtgg cctaactacg gctacactag aagaacagta 4020
tttggtatct gcgctctgct gaagccagtt accttcggaa aaagagttgg tagctcttga 4080
tccggcaaac aaaccaccgc tggtagcggt ggtttttttg tttgcaagca gcagattacg 4140
cgcagaaaaa aaggatctca agaagatcct ttgatctttt ctacggggtc tgacgctcag 4200
tggaacgaaa actcacgtta agggattttg gtcatgagat tatcaaaaag gatcttcacc 4260
tagatccttt taaattaaaa atgaagtttt aaatcaatct aaagtatata tgagtaaact 4320
tggtctgaca gttaccaatg cttaatcagt gaggcaccta tctcagcgat ctgtctattt 4380
cgttcatcca tagttgcctg actcgggggg gggggcgct  gaggtctgcc tcgtgaagaa 4440
ggtgttgctg actcatacca ggcctgaatc gccccatcat ccagcagaa  agtgagggag 4500
ccacggttga tgagagcttt gttgtaggtg gaccagttgg tgattttgaa cttttgcttt 4560
```

```
gccacggaac ggtctgcgtt gtcgggaaga tgcgtgatct gatccttcaa ctcagcaaaa   4620
gttcgattta ttcaacaaag ccgccgtccc gtcaagtcag cgtaatgctc tgccagtgtt   4680
acaaccaatt aaccaattct gattagaaaa actcatcgag catcaaatga aactgcaatt   4740
tattcatatc aggattatca ataccatatt tttgaaaaag ccgtttctgt aatgaaggag   4800
aaaactcacc gaggcagttc catagggatgg caagatccgtc gtatcggtct gcgattccga   4860
ctcgtccaac atcaatacaa cctattaatt tcccctcgtc aaaaataagg ttatcaagtg   4920
agaaatcacc atgagtgacg actgaatccg gtgagaatgg caaaagctta tgcatttctt   4980
tccagacttg ttcaacaggc cagccattac gctcgtcatc aaaatcactc gcatcaacca   5040
aaccgttatt cattcgtgat tgcgcctgag cgagacgaaa tacgcgatcg ctgttaaaag   5100
gacaattaca aacaggaatc gaatgcaacc ggcgcaggaa cactgccagc gcatcaacaa   5160
tattttcacc tgaatcagga tattcttcta atacctggaa tgctgttttc ccggggatcg   5220
cagtggtgag taaccatgca tcatcaggag tacggataaa atgcttgatg gtcggaagag   5280
gcataaattc cgtcagccag tttagtctga ccatctcatc tgtaacatca ttggcaacgc   5340
taccttttgcc atgtttcaga aacaactctg gcgcatcggg cttcccatac aatcgataga   5400
ttgtcgcacc tgattgcccg acattatcgc gagcccattt ataccatat aaatcagcat   5460
ccatgttgga atttaatcgc ggcctcgagc aagacgtttc ccgttgaata tggctcataa   5520
cacccttgt attactgttt atgtaagcag acagttttat tgttcatgat gatatatttt   5580
tatcttgtgc aatgtaacat cagagatttt gagacacaaa gttggctttcc ccccccccc   5640
attattgaag catttatcag ggttattgtc tcatgagcgg atacatattt gaatgtatt   5700
agaaaaataa acaaataggg gttccgcgca catttcccg aaaagtgcca cctgacgtct   5760
aagaaaccat tattatcatg acattaacct ataaaaatag gcgtatcacg aggcccttc   5820
gtc                                                                  5823

SEQ ID NO: 121        moltype = AA    length = 469
FEATURE               Location/Qualifiers
source                1..469
                      mol_type = protein
                      organism = Synthetic construct
SEQUENCE: 121
MGWSCIILFL VATATGVHSQ LQLQESGPGV VKPSETLSLT CTISGGSFST YYWTWIRQPP    60
GKGLEWVGYI GNGGRSLNYN PSLKSRITLS VDASKNQFSL KVTSVTAADT AVYYCGRARG   120
LRGNWFDVWG PGVLVTVSSA STKGPSVFPL APSSKSTSGG TAALGCLVKD YFPEPVTVSW   180
NSGALTSGVH TFPAVLQSSG LYSLSSVVTV PSSSLGTQTY ICNVNHKPSN TKVDKKVEPK   240
SCDKTHTCPP CPAPELLGGP SVFLFPPKPK DTLMISRTPE VTCVVVDVSH EDPEVKFNWY   300
VDGVEVHNAK TKPREEQYNS TYRVVSVLTV LHQDWLNGKE YKCKVSNKAL PAPIEKTISK   360
AKGQPREPQV YTLPPSRDEL TKNQVSLTCL VKGFYPSDIA VEWESNGQPE NNYKTTPPVL   420
DSDGSFFLYS KLTVDKSRWQ QGNVFSCSVM HEALHNHYTQ KSLSLSPGK              469

SEQ ID NO: 122        moltype = DNA   length = 5118
FEATURE               Location/Qualifiers
source                1..5118
                      mol_type = other DNA
                      organism = Synthetic construct
SEQUENCE: 122
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcggggtg tcggggctgg cttaactatg cggcatcaga cagattgta ctgagagtgc   180
accatatgcg gtgtgaaata ccgcacagat gcgtaaggag aaaataccgc atcagattgc   240
ctattggcca ttgcatacgt tgtatccata tcataaatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggaa ctttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctccccttg gagcctacct agactcggtc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtctttttct gcagtcaccg tcgtcgacac gtgtgatcag atatcgcggc cgctctagac  1380
caccatggga tggtcatgta tcatccttttt tctagtagca actgcaaccg gtgtacattc  1440
ccaggctgcc ctgactcagc ctccctctgt gtctgggtct cctggacagt cggtcaccat  1500
ctcctgcact ggaaccagca gtgacatcgg tggtttaac tatgtctcct ggtaccaaca  1560
acacccaggc aaagccccca aagtcatgat ttatgaggtc agtaagcgg cctcaggggt  1620
ctctgatcgc ttctctggtt ccaaatctgg caacatagcc tccctgacca tctctgggct  1680
ccaggctgag gacgaggctg attattactg cagctcatat gcaggcagca cactttcttt  1740
attcggaggga gggaccaagc tgacagtcct aggtcagccc aaggctgccc cctcggtcac  1800
tctgttcccg ccctcctctg aggagcttca agccaacaag gccacactgg tgtgtctcat  1860
aagtgacttc tacccgggag ccgtgacagt ggcctgaag gcagatagca gccccgtcaa  1920
ggcgggagtg gagaccacca cccctccaa acaaagcaac aacaagtacg cggccagcag  1980
ctatctgagc ctgacgcctg agcagtggaa gtcccacaga agctacagct gccaggtcac  2040
gcatgaaggg agcaccgtgg agaagacagt ggccccctaca gaatgttcat gaggatccag  2100
```

-continued

```
atctgctgtg ccttctagtt gccagccatc tgttgtttgc ccctcccccg tgccttcctt    2160
gaccctggaa ggtgccactc ccactgtcct ttcctaataa aatgaggaaa ttgcatcgca    2220
ttgtctgagt aggtgtcatt ctattctggg gggtggggtg gggcaggaca gcaaggggga    2280
ggattgggaa gacaatagca ggcatgctgg ggatgcggtg ggctctatgg gtacccaggt    2340
gctgaagaat tgacccggtt cctcctgggc cagaaagaag caggcacatc cccttctctg    2400
tgacacaccc tgtccacgcc cctggttctt agttccagcc ccactcatag gacactcata    2460
gctcaggagg gctccgcctt caatcccacc cgctaaagta cttggagcgg tctctccctc    2520
cctcatcagc ccaccaaacc aaacctagcc tccaagagtg ggaagaaatt aaagcaagat    2580
aggctattaa gtgcagaggg agagaaaatg cctccaacat gtgaggaagt aatgagagaa    2640
atcatagaat tttaaggcca tgatttaagg ccatcatggc cttaatcttc cgcttcctcg    2700
ctcactgact cgctgcgctc ggtcgttcgg ctgcggcgag cggtatcagc tcactcaaag    2760
gcggtaatac ggttatccac agaatcaggg gataacgcag gaaagaacat gtgagcaaaa    2820
ggccagcaaa aggccaggaa ccgtaaaaag gccgcgttgc tggcgttttt ccataggctc    2880
cgccccctg acgagcatca caaaatcga cgctcaagtc agaggtggcg aaacccgaca     2940
ggactataaa gataccaggc gtttccccct ggaagctccc tcgtgcgctc tcctgttccg    3000
accctgccgc ttaccggata cctgtccgcc tttctccctt cgggaagcgt ggcgctttct    3060
catagctcac gctgtaggta tctcagttcg gtgtaggtcg ttcgctccaa gctgggctgt    3120
gtgcacgaac cccccgttca gcccgaccgc tgcgccttat ccggtaacta tcgtcttgag    3180
tccaacccgg taagacacga cttatcgcca ctggcagcag ccactggtaa caggattagc    3240
agagcgaggt atgtaggcgg tgctacagag ttcttgaagt ggtggcctaa ctacggctac    3300
actagaagaa cagtatttgg tatctgcgct ctgctgaagc cagttacctt cggaaaaaga    3360
gttggtagct cttgatccgg caaacaaacc accgctggta gcggtggttt ttttgtttgc    3420
aagcagcaga ttacgcgcag aaaaaaagga tctcaagaag atcctttgat cttttctacg    3480
gggtctgacg ctcagtggaa cgaaaactca cgttaaggga ttttggtcat gagattatca    3540
aaaaggatct tcacctagat ccttttaaat taaaatgaa gttttaaatc aatctaaagt     3600
atatatgagt aaacttggtc tgacagttac caatgcttaa tcagtgaggc acctatctca    3660
gcgatctgtc tatttcgttc atccatagtt gcctgactcg gggggggggg gcgctgaggt    3720
ctgcctcgtg aagaaggtgt tgctgactca taccaggcct gaatcgcccc atcatccagc    3780
cagaaagtga gggagccacg gttgatgaga gctttgttgt aggtggacca gttggtgatt    3840
ttgaacttt gcttttgccac ggaacggtct gcgttgtcgg gaagatgcgt gatctgatcc    3900
ttcaactcag caaagttcg atttattcaa caaagccgcc gtcccgtcaa gtcagcgtaa    3960
tgctctgcca gtgttacaac caattaacca attctgatta gaaaactca tcgagcatca     4020
aatgaaactg caatttattc atatcaggat tatcaatacc atattttga aaagccgtt      4080
tctgtaatga aggagaaaac tcaccgaggc agttccatag gatgcgaaa tcctggtatc     4140
ggtctgcgat tccgactcgt ccaacatcaa tacaacctat taatttcccc tcgtcaaaaa    4200
taaggttatc aagtgagaaa tcaccatgag tgacgactga atccggtgag aatggcaaaa    4260
gcttatgcat ttctttccag acttgttcaa caggccagcc attacgctcg tcatcaaaat    4320
cactcgcatc aaccaaaccg ttattcattc gtgattgcgc ctgagcgaga cgaaatacgc    4380
gatcgctgtt aaaaggacaa ttacaaacag gaatcggtcg caaccggcgc aggaacactg    4440
ccagcgcatc aacaatattt tcacctgaat caggatattc ttctaatacc tggaatgctg    4500
ttttcccggg gatcgcagtg gtgagtaacc atgcatcatc aggagtacgg ataaaatgct    4560
tgatggtcgg aagaggcata aattccgtca gccagtttag tctgaccatc tcatctgtaa    4620
catcattggc aacgctacct ttgccatgtt tcagaaacaa ctctgcgcga tcgggcttcc    4680
catacaatcg atagattgtc gcacctgatt gcccgacatt atcgcgagcc catttatacc    4740
catataaatc agcatccatg ttggaattta atcgcggcct cgagcaagac gtttcccgtt    4800
gaatatggct cataacaccc cttgtattac tgtttatgta agcagacagt tttattgttc    4860
atgatgatat attttatct tgtgcaatgt aacatcagag attttgagac acaacgtggc    4920
tttcccccc cccccattat tgaagcattt atcagggtta ttgtctcatg agcggataca    4980
tatttgaatg tatttagaaa aataaacaaa taggggttcc gcgcacattt ccccgaaaag    5040
tgccacctga cgtctaagaa accattatta tcatgacatt aacctataaa aataggcgta    5100
tcacgaggcc ctttcgtc                                                  5118
```

```
SEQ ID NO: 123          moltype = AA  length = 235
FEATURE                 Location/Qualifiers
source                  1..235
                        mol_type = protein
                        organism = Synthetic construct
SEQUENCE: 123
MGWSCIILFL VATATGVHSQ AALTQPPSVS GSPGQSVTIS CTGTSSDIGG YNYVSWYQQH     60
PGKAPKVMIY EVSKRPSGVS DRFSGSKSGN IASLTISGLQ AEDEADYYCS SYAGSNTFLF    120
GGGTRLTVLG QPKAAPSVTL FPPSSEELQA NKATLVCLIS DFYPGAVTVA WKADSSPVKA    180
GVETTTPSKQ SNNKYAASSY LSLTPEQWKS HRSYSCQVTH EGSTVEKTVA PTECS         235

SEQ ID NO: 124          moltype = AA  length = 907
FEATURE                 Location/Qualifiers
source                  1..907
                        mol_type = protein
                        organism = Human gammaherpesvirus 4
SEQUENCE: 124
MEAALLVCQY TIQSLIHLTG EDPGFFNVEI PEFPFYPTCN VCTADVNVTI NFDVGGKKHQ     60
LDLDFGQLTP HTKAVYQPRG AFGGSENATN LFLLELLGAG ELALTMRSKK LPINVTTGEE    120
QQVSLESVDV YFQDVFGTMW CHHAEMQNPV YLIPETVPYI KWDNCSTNI TAVVRAQGLD    180
VTLPLSLPTS AQDSNFSVKT EMLGNEIDIE CIMEDGEISQ VLPGDNKFNI TCSGYESHVP    240
SGGILTSTSP VATPIPGTGY AYSLRLTPRP VSRFLGNNSI LYVFYSGNGP KASGGDYCIQ    300
SNIVFSDEIP ASQDMPTNTT DITYVGDNAT YSVPMVTSED ANSPNVTVTA FWAWPNNTET    360
DPKCKWTLTS GTPSGCENIS GAFASNRTFD ITVSGLGTAP KTLIITRTAT NATTTHKVI     420
FSKAPESTTT SPTSNTTGFA APNTTTGLPS STHVPTNLTA PASTGPTVST ADVTSPTPAG    480
TTSGASPVTP SPSPRDNGTE SKAPDMTSPT SAVTTPTPNA TSPTSAVTTP TPNATSPTPA    540
VTTPTPNATS PTLGKTSPTS AVTTPTPNAT SPTLGKTSPT SAVTTPTPNA TSPTLGKTSP    600
```

```
TSAVTTPTPN ATSPTVGETS PQANTTNHTL GGTSSTPVVT SPPKNATSAV TTGQHNITSS    660
STSSMSLRPS SISETLSPST SDNSTSHMPL LTSAHPTGGE NITQVTPAST STHHVSTSSP    720
APRPGTTSQA SGPGNSSTST KPGEVNVTKG TPPKNATSPQ APSGQKTAVP TVTSTGGKAN    780
STTGGKHTTG HGARTSTEPT TDYGGDSTTP RTRYNATTYL PPSTSSELRP RWTFTSPPVT    840
TAQATVPVPP TSQPRFSNLS MLVLQWASLA VLTLLLLLVM ADCAFRRNLS TSHTYTTPPY    900
DDAETYV                                                              907

SEQ ID NO: 125          moltype = AA  length = 426
FEATURE                 Location/Qualifiers
source                  1..426
                        mol_type = protein
                        organism = Synthetic construct
SEQUENCE: 125
EAALLVCQYT IQSLIHLTGE DPGFFNVEIP EFPFYPTCNV CTADVNVTIN FDVGGKKHQL     60
DLDFGQLTPH TKAVYQPRGA FGGSENATNL FLLELLGAGE LALTMRSKKL PINVTTGEEQ    120
QVSLESVDVY FQDVFGTMWC HHAEMQNPVY LIPETVPYIK WDNCSTNIT AVVRAQGLDV     180
TLPLSLPTSA QDSNFSVKTE MLGNEIDIEC IMEDGEISQV LPGDNKFNIT CSGYESHVPS    240
GGILTSTSPV ATPIPGTGYA YSLRLTPRPV SRFLGNNSIL YVFYSGNGPK ASGGDYCIQS    300
NIVFSDEIPA SQDMPTNTTD ITYVGDNATY SVPMVTSEDA NSPNVTVTAF WAWPNNTETD    360
FKCKWTLTSG TPSGCENISG AFASNRTFDI TVSGLGTAPK TLIITRTATN ATTTTHKVIF    420
SKAPGS                                                               426

SEQ ID NO: 126          moltype = DNA  length = 1281
FEATURE                 Location/Qualifiers
source                  1..1281
                        mol_type = other DNA
                        organism = Synthetic construct
SEQUENCE: 126
gaagctgccc tgctcgtgtg ccagtacacc atccagagcc tgatccacct gaccggcgag     60
gaccccggct tcttcaacgt ggaaatcccc gagttcccct tctaccctac ctgcaacgtg    120
tgcaccgccg acgtgaacgt gaccatcaac ttcgacgtgg gcggcaagaa gcaccagctg    180
gacctggatt tcggccagct gacccctcac accaaggccg tgtatcagcc cagaggcgcc    240
tttggcggca gcgagaacgc caccaatctg tttctgctgg aactcctagg cgccggcgag    300
ctggccctga ccatgagaag caagaaactg cccatcaatg tgaccacagg cgaggaacag    360
caggtgtccc tggaaagcgt ggacgtgtac tttcaagacg tgttcggcac catgtggtgc    420
caccacgccg agatgcagaa ccccgtgtac ctgatccccg agacagtgcc ctacatcaag    480
tgggacaact gcaacagcac caacatcacc gccgtcgtgc gggcccaggg actggatgtg    540
acactgcctc tgagcctgcc taccagcgcc caggacagca acttcagcgt gaaaaccgag    600
atgctgggca acgagatcga catcgagtgc atcatgaagg atggcgagat cagccaggtg    660
ctgcccggcg acaacaagtt caacatcaca tgcagcggct acgagagcca cgtgccatct    720
ggcggcatcc tgaccagcac aagcccagtg gccacaccca tccctggcac aggctacgcc    780
tacagcctga gactgacccc cagacccgtg tccagattcc tgggcaacaa cagcatcctg    840
tacgtgttct acagcggcaa cggcccaaag gcctctgtgg gcgattactg tatccagagc    900
aacatcgtgt tcagcgacga gatccccgcc agccaggaca tgcccaccaa taccaccgac    960
atcacgtacg tgggcgacaa tgccacctac agcgtgccaa tggtcacctc cgaggacgcc   1020
aacagcccca acgtgaccgt gacagccttt tgggcctggc ctaacaacac cgagacagac   1080
ttcaagtgca gtggaccct gacctccggc accccctggc gtgcgagaa tatcagcgga   1140
gccttcgcca gcaaccggac cttcgatatc accgtgtctg gcctgggcac cgccccaag   1200
accctgatca tcaccagaac cgccacaat gccaccacca caacccacaa agtgatcttc   1260
agcaaggccc ccggctctgg c                                             1281

SEQ ID NO: 127          moltype = AA  length = 426
FEATURE                 Location/Qualifiers
source                  1..426
                        mol_type = protein
                        organism = Synthetic construct
SEQUENCE: 127
EAALLVCQYT IQSLIHLTGE DPGFFNVEIP EFPFYPTCNV CTADVNVTIN FDVGGKKHQL     60
DLDFGQLTPH TKAVYQPRGA FGGSENATNL FLLELLGAGE LALTMRSKKL PINVTTGEEQ    120
NVSLESVDVY FQDVFGTMWC HHAEMQNPVY LIPETVPYIK WDNCSTNIT AVVRAQGLDV     180
TLPLSLPTSA QDSNFSVKTE MLGNEIDIEC IMEDGEISQV LPGDNKFNIT CSGYESHVPS    240
GGILTSTSPV ATPIPGTGYA YSLRLTPRPV SRFLGNNSIL YVFYSGNGPK ASGGDYCIQS    300
NIVFSDEIPA SQDMPTNTTD ITYVGDNATY SVPMVTSEDA NSPNVTVTAF WAWPNNTETD    360
FKCKWTLTSG TPSGCENISG AFASNRTFDI TVSGLGTAPK TLIITRTATN ATTTTHKVIF    420
SKAPGS                                                               426

SEQ ID NO: 128          moltype = DNA  length = 1278
FEATURE                 Location/Qualifiers
source                  1..1278
                        mol_type = other DNA
                        organism = Synthetic construct
SEQUENCE: 128
gaagctgccc tgctcgtgtg ccagtacacc atccagagcc tgatccacct gaccggcgag     60
gaccccggct tcttcaacgt ggaaatcccc gagttcccct tctaccctac ctgcaacgtg    120
tgcaccgccg acgtgaacgt gaccatcaac ttcgacgtgg gcggcaagaa gcaccagctg    180
gacctggatt tcggccagct gacccctcac accaaggccg tgtatcagcc cagaggcgcc    240
tttggcggca gcgagaacgc caccaatctg tttctgctgg aactcctagg cgccggcgag    300
ctggccctga ccatgagaag caagaaactg cccatcaatg tgaccacagg cgaggaacag    360
aacgtgtccc tggaaagcgt ggacgtgtac tttcaagacg tgttcggcac catgtggtgc    420
```

```
caccacgccg agatgcagaa ccccgtgtac ctgatcccg agacagtgcc ctacatcaag    480
tgggacaact gcaacagcac caacatcacc gccgtcgtgc gggcccaggg actggatgtg    540
acactgcctc tgagcctgcc taccagcgcc caggacagca acttcagcgt gaaaaccgag    600
atgctgggca acgagatcga catcgagtgc atcatggaag atggcgagat cagccaggtg    660
ctgcccggcg acaacaagtt caacatcaca tgcagcggct acgagagcca cgtgccatct    720
ggcggcatcc tgaccagcac aagcccagtg ccacaccca tccctggcac aggctacgcc    780
tacagcctga gactgacccc cagaccgtg tccagattcc tgggcaacaa cagcatcctg    840
tacgtgttct acagcggcaa cggccccaag gcctctggcg cgattactg tatccagagc    900
aacatcgtgt tcagcgacga gatccccgcc agccaggaca tgcccaccaa taccaccgac    960
atcacgtacg tgggcgacaa tgccacctac agcgtgccaa tggtcacctc cgaggacgcc   1020
aacagcccca acgtgaccgt gacagccttt tgggcctggc ctaacaacac cgagacagac   1080
ttcaagtgca gtggaccct gacctccggc acccctagcg gctgcgagaa tatcagcgga   1140
gccttcgcca gcaaccggac cttcgatatc accgtgtctg gcctgggcac cgcccccaag   1200
accctgatca tcaccagaca cgccacaaat gccaccacca aacccacaa agtgatcttc   1260
agcaaggccc ccggctct                                                 1278

SEQ ID NO: 129          moltype = AA   length = 427
FEATURE                 Location/Qualifiers
source                  1..427
                        mol_type = protein
                        organism = Synthetic construct
SEQUENCE: 129
EAALLVCQYT IQSLIHLTGE DPGFFNVEIP EFPFYPTCNV CTADVNVTIN FDVGGKKHQL     60
DLDFGQLTPH TKAVYQPRGA FGGSENATNL FLLELLGAGE LALTMRSKKL PINVTTGEEQ    120
QVSLESVDVY FQDVFGTMWC HHAEMQNPVY LIPETVPYIK WNNSCNSTNI TAVVRAQGLD    180
VTLPLSLPTS AQDSNFSVKT EMLGNEIDIE CIMEDGEISQ VLPGDNKFNI TCSGYESHVP    240
SGGILTSTSP VATPIPGTGY AYSLRLTPRP VSRFLGNNSI LYVFYSGNGP KASGGDYCIQ    300
SNIVFSDEIP ASQDMPTNTT DITYVGDNAT YSVPMVTSED ANSPNVTVTA FWAWPNNTET    360
DFKCKWTLTS GTPSGCENIS GAFASNRTFD ITVSGLGTAP KTLIITRTAT NATTTHKVI    420
FSKAPGS                                                              427

SEQ ID NO: 130          moltype = DNA   length = 1281
FEATURE                 Location/Qualifiers
source                  1..1281
                        mol_type = other DNA
                        organism = Synthetic construct
SEQUENCE: 130
gaagctgccc tgctcgtgtg ccagtacacc atccagagcc tgatccacct gaccggcgag     60
gaccccggct tcttcaacgt ggaaatcccc gagttcccct tctaccctac ctgcaacgtg    120
tgcaccgccg acgtgaacgt gaccatcaac ttcgacgtgg gcggcaagaa gcaccagctg    180
gacctggatt tcggccagct gaccctcac accaaggccg tgtatcagcc cagaggcgcc    240
tttggcggca gcgagaacgc caccaatctg tttctgctgg aactcctagg cgccggcgag    300
ctggccctga ccatgagaag caagaaactg cccatcaatg tgaccacagg cgaggaacag    360
caggtgtccc tggaaagcgt ggacgtgtac tttcaagacg tgttcggcac catgtggtgc    420
caccacgccg agatgcagaa ccccgtgtac ctgatcccg agacagtgcc ctacatcaag    480
tggaacaaca gctgcaacag caccaacatc accgccgtcg tgcgggccca gggactggat    540
gtgacactgc ctctgagcct gcctaccagc gcccaggaca gcaacttcag cgtgaaaacc    600
gagatgctgg gcaacgagat cgacatcgag tgcatcatgg aagatggcga gatcagccag    660
gtgctgcccg gcgacaacaa gttcaacatc acatgcagcg gctacgagag ccacgtgcca    720
tctggcggca tcctgaccag cacaagccca gtggccacac ccatccctgg cacaggctac    780
gcctacagcc tgagactgac ccccagaccg tgtccagat tcctgggcaa caacagcatc    840
ctgtacgtgt tctacagcgg caacggcccc aaggcctctg gcggcgatta ctgtatccag    900
agcaacatcg tgttcagcga cgagatcccc gccagccagg acatgcccac caataccacc    960
gacatcacgt acgtgggcga caatgccacc tacagcgtgc caatggtcac ctccgaggac   1020
gccaacagcc ccaacgtgac cgtgacagcc ttttgggcct ggcctaacaa caccgagaca   1080
gacttcaagt gcaagtggac cctgacctcc ggcaccccta gcggctgcga gaatatcagc   1140
ggagccttcg ccagcaaccg gaccttcgat atcaccgtgt ctggcctggg caccgccccc   1200
aagaccctga tcatcaccag aaccgccaca atgccacca ccacaaccca aagtgatc   1260
ttcagcaagg cccccggctc t                                             1281

SEQ ID NO: 131          moltype = AA   length = 426
FEATURE                 Location/Qualifiers
source                  1..426
                        mol_type = protein
                        organism = Synthetic construct
SEQUENCE: 131
EAALLVCQYT IQSLIHLTGE DPGFFNVEIP EFPFYPTCNV CTADVNVTIN FDVGGKKHQL     60
DLDFGQLTPH TKAVYQPRGA FGGSENATNL FLLELLGAGE LALTMRSKKL PINVTTGEEQ    120
QVSLESVDVY FQDVFGTMWC HHAEMQNPVY LIPETVPYIK WDNCSTNIT AVVRAQGLDV    180
TLPLSLPTSA QDSNFSVKTE MLGNEIDIEC IMEDGEISQV LPGDNKFNIT CSGYESHVPS    240
GGILTSTSPV ATPIPGTGYA YSLRLTPRPV SRFLGNNSIL YVFYSGNGPK ASGGRYCIQS    300
NIVFSDEIPA SQDMPTNTTD ITYVGDNATY SVPMVTSEDA NSPNVTVTAF WAWPNNTETD    360
FKCKWTLTSG TPSGCENISG AFASNRTFDI TVSGLGTAPK TLIITRTATN ATTTHKVIF    420
SKAPGS                                                               426

SEQ ID NO: 132          moltype = DNA   length = 1278
FEATURE                 Location/Qualifiers
source                  1..1278
                        mol_type = other DNA
```

-continued

```
                        organism = Synthetic construct
SEQUENCE: 132
gaagctgccc tgctcgtgtg ccagtacacc atccagagcc tgatccacct gaccggcgag    60
gaccccggct tcttcaacgt ggaaatcccc gagttcccct tctacccta c ctgcaacgtg   120
tgcaccgccg acgtgaacgt gaccatcaac ttcgacgtgg cggcaagaa gcaccagctg    180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatcccg agacagtgcc ctacatcaag   480
tgggacaact gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg gccacaccca tccctggcac aggctacgcc   780
tacagcctga gactgacccc cagaccctg tccagattcc tgggcaacaa cagcatcctg   840
tacgtgttct acagcggcaa cggccccaag gcctctggcg gccggtactg tatccagagc   900
aacatcgtgt tcagcgacga gatccccgcc agccaggaca tgcccaccaa taccaccgac   960
atcacgtacg tgggcgacaa tgccacctac agcgtgccaa tggtcacctc cgaggacgcc  1020
aacagcccca acgtgaccgt gacagccttt tgggcctggc ctaacaacac cgagacagac  1080
ttcaagtgca agtggaccct gacctccggc acccctagcg gctgcgagaa tatcagcgga  1140
gccttcgcca gcaaccggac cttcgatatc accgtgtctg gcctgggcac cgcccccaag  1200
accctgatca tcaccagaac cgccacaaat gccaccacca aacccacaa agtgatcttc  1260
agcaaggccc ccggctct                                                 1278

SEQ ID NO: 133         moltype = AA   length = 426
FEATURE                Location/Qualifiers
source                 1..426
                       mol_type = protein
                       organism = Synthetic construct
SEQUENCE: 133
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVPYIK AAACNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGDYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGS                                                               426

SEQ ID NO: 134         moltype = DNA   length = 1278
FEATURE                Location/Qualifiers
source                 1..1278
                       mol_type = other DNA
                       organism = Synthetic construct
SEQUENCE: 134
gaagctgccc tgctcgtgtg ccagtacacc atccagagcc tgatccacct gaccggcgag    60
gaccccggct tcttcaacgt ggaaatcccc gagttcccct tctacccta c ctgcaacgtg   120
tgcaccgccg acgtgaacgt gaccatcaac ttcgacgtgg cggcaagaa gcaccagctg    180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatcccg agacagtgcc ctacatcaag   480
gccgcgcct gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg gccacaccca tccctggcac aggctacgcc   780
tacagcctga gactgacccc cagaccctg tccagattcc tgggcaacaa cagcatcctg   840
tacgtgttct acagcggcaa cggccccaag gcctctggcg gcgattactg tatccagagc   900
aacatcgtgt tcagcgacga gatccccgcc agccaggaca tgcccaccaa taccaccgac   960
atcacgtacg tgggcgacaa tgccacctac agcgtgccaa tggtcacctc cgaggacgcc  1020
aacagcccca acgtgaccgt gacagccttt tgggcctggc ctaacaacac cgagacagac  1080
ttcaagtgca agtggaccct gacctccggc acccctagcg gctgcgagaa tatcagcgga  1140
gccttcgcca gcaaccggac cttcgatatc accgtgtctg gcctgggcac cgcccccaag  1200
accctgatca tcaccagaac cgccacaaat gccaccacca aacccacaa agtgatcttc  1260
agcaaggccc ccggctct                                                 1278

SEQ ID NO: 135         moltype = AA   length = 426
FEATURE                Location/Qualifiers
source                 1..426
                       mol_type = protein
                       organism = Synthetic construct
SEQUENCE: 135
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVPYRK WDNCNSTNIT AVVRAQGLDV   180
TLPLSLPTSA QDSNFSVKTE MLGNEIDIEC IMEDGEISQV LPGDNKFNIT CSGYESHVPS   240
```

```
GGILTSTSPV ATPIPGTGYA YSLRLTPRPV SRFLGNNSIL YVFYSGNGPK ASGGRYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGS                                                             426

SEQ ID NO: 136          moltype = DNA  length = 1278
FEATURE                 Location/Qualifiers
source                  1..1278
                        mol_type = other DNA
                        organism = Synthetic construct
SEQUENCE: 136
gaagctgccc tgctcgtgtg ccagtacacc atccagagcc tgatccacct gaccggcgag    60
gaccccggct tcttcaacgt ggaaatcccc gagttcccct tctaccctac ctgcaacgtg   120
tgcaccgccg acgtgaacgt gaccatcaac ttcgacgtgg cggcaagaa gcaccagctg   180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatcccg agacagtgcc ctaccggaag   480
tgggacaact gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg gccacaccca tccctggcac aggctacgcc   780
tacagcctga gactgaccc cagacccgtg tccagattcc tgggcaacaa cagcatcctg   840
tacgtgttct acagcggcaa cggccccaag gcctctggcg gccggtactg tatccagagc   900
aacatcgtgt tcagcgacga gatccccgcc agccaggaca tgcccaccaa taccaccgac   960
atcacgtacg tgggcgacaa tgccacctac agcgtgccaa tggtcacctc cgaggacgcc  1020
aacagcccca acgtgaccgt gacagccttt gggcctggc ctaacaacac cgagacagac  1080
ttcaagtgca agtggaccct gacctccggc cccctagcg gctgcgagaa tatcagcgga  1140
gccttcgcca gcaaccggac cttcgatatc accgtgtctg gcctgggcac cgccccaag  1200
accctgatca tcaccagaac cgccacaaat gccaccacca caacccacaa agtgatcttc  1260
agcaaggccc ccggctct                                                1278

SEQ ID NO: 137          moltype = AA  length = 426
FEATURE                 Location/Qualifiers
source                  1..426
                        mol_type = protein
                        organism = Synthetic construct
SEQUENCE: 137
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVRYIK WDNCNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGRYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGS                                                             426

SEQ ID NO: 138          moltype = DNA  length = 1278
FEATURE                 Location/Qualifiers
source                  1..1278
                        mol_type = other DNA
                        organism = Synthetic construct
SEQUENCE: 138
gaagctgccc tgctcgtgtg ccagtacacc atccagagcc tgatccacct gaccggcgag    60
gaccccggct tcttcaacgt ggaaatcccc gagttcccct tctaccctac ctgcaacgtg   120
tgcaccgccg acgtgaacgt gaccatcaac ttcgacgtgg cggcaagaa gcaccagctg   180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatcccg agacagtgcg gtacatcaag   480
tgggacaact gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg gccacaccca tccctggcac aggctacgcc   780
tacagcctga gactgaccc cagacccgtg tccagattcc tgggcaacaa cagcatcctg   840
tacgtgttct acagcggcaa cggccccaag gcctctggcg gccggtactg tatccagagc   900
aacatcgtgt tcagcgacga gatccccgcc agccaggaca tgcccaccaa taccaccgac   960
atcacgtacg tgggcgacaa tgccacctac agcgtgccaa tggtcacctc cgaggacgcc  1020
aacagcccca acgtgaccgt gacagccttt gggcctggc ctaacaacac cgagacagac  1080
ttcaagtgca agtggaccct gacctccggc cccctagcg gctgcgagaa tatcagcgga  1140
gccttcgcca gcaaccggac cttcgatatc accgtgtctg gcctgggcac cgccccaag  1200
accctgatca tcaccagaac cgccacaaat gccaccacca caacccacaa agtgatcttc  1260
agcaaggccc ccggctct                                                1278

SEQ ID NO: 139          moltype = AA  length = 426
```

```
FEATURE                 Location/Qualifiers
source                  1..426
                        mol_type = protein
                        organism = Synthetic construct
SEQUENCE: 139
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVNYTK WDNCNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGRYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGS                                                               426

SEQ ID NO: 140          moltype = DNA   length = 1278
FEATURE                 Location/Qualifiers
source                  1..1278
                        mol_type = other DNA
                        organism = Synthetic construct
SEQUENCE: 140
gaagctgccc tgctcgtgtg ccagtacacc atccagagcc tgatccacct gaccggcgag    60
gaccccggct tcttcaacgt ggaaatcccc gagttcccct ctacccctac ctgcaacgtg   120
tgcaccgccg acgtgaacgt gaccatcaac ttcgacgtgg gcggcaagaa gcaccagctg   180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatccccg agacagtgaa ctacaccaag   480
tgggacaact gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg ccacacccca tccctggcac aggctacgcc   780
tacagcctga gactgacccc cagacccgtg tccagattcc tgggcaacaa cagcatcctg   840
tacgtgttct acagcggcaa cggccccaag gcctctggcg gccggtactg tatccagagc   900
aacatcgtgt tcagcgacga gatccccgcc agccaggaca tgcccaccaa taccaccgac   960
atcacgtacg tgggcgacaa tgccacctac agcgtgccaa tggtcacctc cgaggacgcc  1020
aacagcccca acgtgaccgt gacagccttt tgggcctggc ctaacaacac cgagacagac  1080
ttcaagtgca agtggaccct gacctccggc cccctagcg gctgcgagaa tatcagcgga  1140
gccttcgcca gcaaccggac cttcgatatc accgtgtctg gcctgggcac cgcccccaag  1200
accctgatca tcaccagaac cgccacaaat gccaccacca aacccacaa agtgatcttc  1260
agcaaggccc ccggctct                                                1278

SEQ ID NO: 141          moltype = AA    length = 426
FEATURE                 Location/Qualifiers
source                  1..426
                        mol_type = protein
                        organism = Synthetic construct
SEQUENCE: 141
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVRYRK WDNCNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGRYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGS                                                               426

SEQ ID NO: 142          moltype = DNA   length = 1278
FEATURE                 Location/Qualifiers
source                  1..1278
                        mol_type = other DNA
                        organism = Synthetic construct
SEQUENCE: 142
gaagctgccc tgctcgtgtg ccagtacacc atccagagcc tgatccacct gaccggcgag    60
gaccccggct tcttcaacgt ggaaatcccc gagttcccct ctacccctac ctgcaacgtg   120
tgcaccgccg acgtgaacgt gaccatcaac ttcgacgtgg gcggcaagaa gcaccagctg   180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctggccctga ccatgagaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatccccg agacagtgcg gtaccggaag   480
tgggacaact gcaacagcac caacatcacc gccgtcgtgc gggcccaggg actggatgtg   540
acactgcctc tgagcctgcc taccagcgcc caggacagca acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg ccacacccca tccctggcac aggctacgcc   780
tacagcctga gactgacccc cagacccgtg tccagattcc tgggcaacaa cagcatcctg   840
tacgtgttct acagcggcaa cggccccaag gcctctggcg gccggtactg tatccagagc   900
```

```
aacatcgtgt tcagcgacga gatcccgcc agccaggaca tgcccaccaa taccaccgac    960
atcacgtacg tgggcgacaa tgccacctac agcgtgccaa tggtcacctc cgaggacgcc   1020
aacagcccca acgtgaccgt gacagccttt tgggcctggc ctaacaacac cgagacagac   1080
ttcaagtgca agtggaccct gacctccggc accctagcg gctgcgagaa tatcagcgga    1140
gccttcgcca gcaaccggac cttcgatatc accgtgtctg gctgggcac cgcccccaag    1200
accctgatca tcaccagaac cgccacaaat gccaccacca caacccacaa agtgatcttc   1260
agcaaggccc ccggctct                                                1278

SEQ ID NO: 143          moltype = AA   length = 447
FEATURE                 Location/Qualifiers
source                  1..447
                        mol_type = protein
                        organism = Synthetic construct
SEQUENCE: 143
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVPYIK WDNCNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGDYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGSGLND IFEAQKIEWH EHHHHHH                                      447

SEQ ID NO: 144          moltype = DNA   length = 1341
FEATURE                 Location/Qualifiers
source                  1..1341
                        mol_type = other DNA
                        organism = Synthetic construct
SEQUENCE: 144
gaagctgccc tgctcgtgtg ccagtacacc atccagagcc tgatccacct gaccggcgag    60
gaccccggct tcttcaacgt ggaaatcccc gagttcccct tctacccta ctgcaacgtg    120
tgcaccgccg acgtgaacgt gaccatcaac ttcgacgtgg cggcaagaa gcaccagctg    180
gacctggatt tcggccagct gacccctcac accaaggccg tgtatcagcc cagaggcgcc   240
tttggcggca gcgagaacgc caccaatctg tttctgctgg aactcctagg cgccggcgag   300
ctgcccctga ccatgcgaag caagaaactg cccatcaatg tgaccacagg cgaggaacag   360
caggtgtccc tggaaagcgt ggacgtgtac tttcaagacg tgttcggcac catgtggtgc   420
caccacgccg agatgcagaa ccccgtgtac ctgatccccg agacagtgcc ctacatcaag   480
tgggacaact gcaacagcac caacatcacc gccgtcgtgc gggcccaggg actggatgtg   540
acactgcctc tgagcctgcc taccagcgcc caggacacga acttcagcgt gaaaaccgag   600
atgctgggca acgagatcga catcgagtgc atcatggaag atggcgagat cagccaggtg   660
ctgcccggcg acaacaagtt caacatcaca tgcagcggct acgagagcca cgtgccatct   720
ggcggcatcc tgaccagcac aagcccagtg gccacaccca tccctggcac aggctacgcc   780
tacagcctga gactgacccc cagacccgtg tccagattcc tgggcaacaa cagcatccta   840
tacgtgttct acagcggcaa cggccccaag gcctctggcg gcgattactg tatccagagc   900
aacatcgtgt tcagcgacga gatcccgcc agccaggaca tgcccaccaa taccaccgac    960
atcacgtacg tgggcgacaa tgccacctac agcgtgccaa tggtcacctc cgaggacgcc   1020
aacagcccca acgtgaccgt gacagccttt tgggcctggc ctaacaacac cgagacagac   1080
ttcaagtgca agtggaccct gacctccggc accctagcg gctgcgagaa tatcagcgga    1140
gccttcgcca gcaaccggac cttcgatatc accgtgtctg gctgggcac cgcccccaag    1200
accctgatca tcaccagaac cgccacaaat gccaccacca caacccacaa agtgatcttc   1260
agcaaggccc ccggctctgg cctgaacgac atttttgagg cccagaagat tgagtggcat   1320
gaacatcacc accaccacca t                                            1341

SEQ ID NO: 145          moltype = AA   length = 447
FEATURE                 Location/Qualifiers
source                  1..447
                        mol_type = protein
                        organism = Synthetic construct
SEQUENCE: 145
EAALLVCQYT IQSLIHLTGE DPGFFNVEIP EFPFYPTCNV CTADVNVTIN FDVGGKKHQL    60
DLDFGQLTPH TKAVYQPRGA FGGSENATNL FLLELLGAGE LALTMRSKKL PINVTTGEEQ   120
NVSLESVDVY FQDVFGTMWC HHAEMQNPVY LIPETVPYIK WDNCNSTNIT AVVRAQGLDV   180
TLPLSLPTSA QDSNFSVKTE MLGNEIDIEC IMEDGEISQV LPGDNKFNIT CSGYESHVPS   240
GGILTSTSPV ATPIPGTGYA YSLRLTPRPV SRFLGNNSIL YVFYSGNGPK ASGGDYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGSGLND IFEAQKIEWH EHHHHHH                                      447

SEQ ID NO: 146          moltype = DNA   length = 1341
FEATURE                 Location/Qualifiers
source                  1..1341
                        mol_type = other DNA
                        organism = Synthetic construct
SEQUENCE: 146
gaagctgccc tgctcgtgtg ccagtacacc atccagagcc tgatccacct gaccggcgag    60
gaccccggct tcttcaacgt ggaaatcccc gagttcccct tctacccta ctgcaacgtg    120
tgcaccgccg acgtgaacgt gaccatcaac ttcgacgtgg cggcaagaa gcaccagctg    180
gacctggatt tcggccagct gacccctcac accaaggccg tgtatcagcc cagaggcgcc   240
tttggcggca gcgagaacgc caccaatctg tttctgctgg aactcctagg cgccggcgag   300
```

```
ctggccctga ccatgagaag caagaaactg cccatcaatg tgaccacagg cgaggaacag    360
aacgtgtccc tggaaagcgt ggacgtgtac tttcaagacg tgttcggcac catgtggtgc    420
caccacgccg agatgcagaa ccccgtgtac ctgatcccg agacagtgcc ctacatcaag     480
tgggacaact gcaacagcac caacatcacc gccgtcgtgc gggcccaggg actggatgtg    540
acactgcctc tgagcctgcc taccagcgcc caggacagca cttcagcgt gaaaaccgag     600
atgctgggca acgagatcga catcgagtgc atcatggaag atggcgagat cagccaggtg    660
ctgcccggcg acaacaagtt caacatcaca tgcagcggct acgagagcca cgtgccatct    720
ggcggcatcc tgaccagcac aagcccagtg ccacacccca tccctggcac aggctacgcc    780
tacagcctga gactgacccc cagacccgtg tccagattcc tgggcaacaa cagcatcctg    840
tacgtgttct acagcggcaa cggccccaag gcctctggcg gcgattactg tatccagagc    900
aacatcgtgt tcagcgacga gatccccgcc agccaggaca tgcccaccaa taccaccgac    960
atcacgtacg tgggcgacaa tgccacctac agcgtgccaa tggtcacctc cgaggacgcc   1020
aacagcccca acgtgaccgt gacagccttt gggcctggc ctaacaacac cgagacagac    1080
ttcaagtgca gtggaccct gacctccggc accctagcg gctgcagaa tatcagcgga     1140
gccttcgcca gcaaccggac cttcgatatc accgtgtctg gcctgggcac cgccccaag    1200
accctgatca tcaccagaac cgccacaaat gccaccacca aacccacaa agtgatcttc    1260
agcaaggccc ccggctctgg cctgaacgac attttttgagg cccagaagat tgagtggcat   1320
gaacatcacc accaccaca t                                               1341

SEQ ID NO: 147           moltype = AA  length = 448
FEATURE                  Location/Qualifiers
source                   1..448
                         mol_type = protein
                         organism = Synthetic construct
SEQUENCE: 147
EAALLVCQYT IQSLIHLTGE DPGFFNVEIP EPFPYPTCNV CTADVNVTIN FDVGGKKHQL     60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVPYIK WNNSCNSTNI TAVVRAQGLD   180
VTLPLSLPTS AQDSNFSVKT EMLGNEIDIE CIMEDGEISQ VLPGDNKFNI TCSGYESHVP   240
SGGILTSTSP VATPIPGTGY AYSLRLTPRP VSRFLGNNSI LYVFYSGNGP KASGGDYCIQ   300
SNIVFSDEIP ASQDMPTNTT DITYVGDNAT YSVPMVTSED ANSPNVTVTA FWAWPNNTET   360
DPKCKWTLTS GTPSGCENIS GAFASNRTFD ITVSGLGTAP KTLIITRTAT NATTTHKVI    420
FSKAPGSGLN DIFEAQKIEW HEHHHHHH                                     448

SEQ ID NO: 148           moltype = DNA  length = 1344
FEATURE                  Location/Qualifiers
source                   1..1344
                         mol_type = other DNA
                         organism = Synthetic construct
SEQUENCE: 148
gaagctgccc tgctcgtgtg ccagtacacc atccagagcc tgatccacct gaccggcgag     60
gaccccggct tcttcaacgt ggaaatcccc gagttcccct ctacccctac ctgcaacgtg    120
tgcaccgccg acgtgaacgt gaccatcaac ttcgacgtg gcggcaagaa gcaccagctg     180
gacctggatt tcggccagct gaccctcac accaaggccg tgtatcagcc cagaggcgcc    240
tttggcggca gcgagaacgc caccaatctg tttctgctgg aactcctagg cgccggcgag    300
ctggccctga ccatgagaag caagaaactg cccatcaatg tgaccacagg cgaggaacag    360
caggtgtccc tggaaagcgt ggacgtgtac tttcaagacg tgttcggcac catgtggtgc    420
caccacgccg agatgcagaa ccccgtgtac ctgatcccg agacagtgcc ctacatcaag     480
tggaacaaca gctgcaacag caccaacatc accgccgtcg tgcgggccca gggactggat    540
gtgacactgc ctctgagcct gcctaccagc gcccaggaca gcaacttcag cgtgaaaacc    600
gagatgctgg gcaacgagat cgacatcgag tgcatcatgg aagatggcga gatcagccag    660
gtgctgcccg gcgacaacaa gttcaacatc acatgcagcg gctacgagag ccacgtgcca    720
tctggcggca tcctgaccag cacaagccca gtgccacacc catccctgg cacaggctac    780
gcctacagcc tgagactgac ccccagaccc gtgtccagat cctgggcaa caacagcatc    840
ctgtacgtgt tctacagcgg caacggcccc aaggcctctg gcggcgatta ctgtatccag    900
agcaacatcg tgttcagcga cgagatcccc gccagccagg acatgcccac caataccacc    960
gacatcacgt acgtgggcga caatgccacc tacagcgtgc caatggtcac ctccgaggac   1020
gccaacagcc ccaacgtgac cgtgacagcc ttgggcct ggcctaacaa caccgagaca    1080
gacttcaagt gcaagtggac cctgacctcc ggcaccccta gcggctgcga gaatatcagc    1140
ggagccttcg ccagcaaccg gaccttcgat atcaccgtgt ctggcctggg caccgcccc    1200
aagaccctga tcatcaccag aaccgccaca aatgccacca ccacaaccca caaagtgatc    1260
ttcagcaagg cccccggctc tggcctgaac gacattttttg aggcccagaa gattgagtgg   1320
catgaacatc accaccacca ccat                                           1344

SEQ ID NO: 149           moltype = AA  length = 447
FEATURE                  Location/Qualifiers
source                   1..447
                         mol_type = protein
                         organism = Synthetic construct
SEQUENCE: 149
EAALLVCQYT IQSLIHLTGE DPGFFNVEIP EPFPYPTCNV CTADVNVTIN FDVGGKKHQL     60
DLDFGQLTPH TKAVYQPRGA FGGSENATNL FLLELLGAGE LALTMRSKKL PINVTTGEEQ   120
QVSLESVDVY FQDVFGTMWC HHAEMQNPVY LIPETVPYIK WDNCSTNIT AVVRAQGLD     180
TLPLSLPTSA QDSNFSVKTE MLGNEIDIE IMEDGEISQV LPGDNKFNIT CSGYESHVPS    240
GGILTSTSPV ATPIPGTGYA YSLRLTPRPV SRFLGNNSIL YVFYSGNGPK ASGGRYCIQS   300
NIVFSDEIPA SQDMPTNTTD ITYVGDNATY SVPMVTSEDA NSPNVTVTAF WAWPNNTETD   360
FKCKWTLTSG TPSGCENISG AFASNRTFDI TVSGLGTAPK TLIITRTATN ATTTTHKVIF   420
SKAPGSGLND IFEAQKIEWH EHHHHHH                                       447
```

| SEQ ID NO: 150 | moltype = DNA  length = 1341 |
|---|---|
| FEATURE | Location/Qualifiers |
| source | 1..1341 |
| | mol_type = other DNA |
| | organism = Synthetic construct |

SEQUENCE: 150

```
gaagctgccc tgctcgtgtg ccagtacacc atccagagcc tgatccacct gaccggcgag   60
gaccccggct tcttcaacgt ggaaatcccc gagttcccct tctacccctac ctgcaacgtg  120
tgcaccgccg acgtgaacgt gaccatcaac ttcgacgtgg cggcaagaa gcaccagctg   180
gacctggatt tcggccagct gaccccctcac accaaggccg tgtatcagcc cagaggcgcc  240
tttggcggca gcgagaacgc caccaatctg tttctgctgg aactcctagg cgccggcgag  300
ctggccctga ccatgagaag caagaaactg cccatcaatg tgaccacagg cgaggaacag  360
caggtgtccc tggaaagcgt ggacgtgtac tttcaagacg tgttcggcac catgtggtgc  420
caccacgccg agatgcagaa cccgtgtac ctgatccccg agacagtgcc ctacatcaag  480
tgggacaact gcaacagcac caacatcacc gccgtcgtgc gggcccaggg actggatgtg  540
acactgcctc tgagcctgcc taccagcgcc caggacagca acttcagcgt gaaaaccgag  600
atgctgggca acgagatcga catcgagtgc atcatggaag atggcgagat cagccaggtg  660
ctgcccggcg acaacaagtt caacatcaca tgcagcggct acgagagcca cgtgccatct  720
ggcggcatcc tgaccagcac aagcccagtg gccacaccca tccctggcac aggctacgcc  780
tacagcctga gactgacccc cagacccgtg tccagattcc tgggcaacaa cagcatcctg  840
tacgtgttct acagcggcaa cggccccaag gcctctggcg gccggtactg tatccagagc  900
aacatcgtgt tcagcgacga gatccccgcc agccaggaca tgcccaccaa taccaccgac  960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaaccggac cttcgatatc accgtgtctg gcctgggcac cgccccaag  1200
accctgatca tcaccagaac cgccacaaat gccaccacca aacccacaa agtgatcttc 1260
agcaaggccc ccggctctgg cctgaacgac attttgagg cccagaagat tgagtggcat 1320
gaacatcacc accaccacca t                                            1341
```

| SEQ ID NO: 151 | moltype = AA  length = 447 |
|---|---|
| FEATURE | Location/Qualifiers |
| source | 1..447 |
| | mol_type = protein |
| | organism = Synthetic construct |

SEQUENCE: 151

```
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVPYIK AAACNSTNIT AVVRAQGLDV  180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGDYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                      447
```

| SEQ ID NO: 152 | moltype = DNA  length = 1341 |
|---|---|
| FEATURE | Location/Qualifiers |
| source | 1..1341 |
| | mol_type = other DNA |
| | organism = Synthetic construct |

SEQUENCE: 152

```
gaagctgccc tgctcgtgtg ccagtacacc atccagagcc tgatccacct gaccggcgag   60
gaccccggct tcttcaacgt ggaaatcccc gagttcccct tctacccctac ctgcaacgtg  120
tgcaccgccg acgtgaacgt gaccatcaac ttcgacgtgg cggcaagaa gcaccagctg   180
gacctggatt tcggccagct gaccccctcac accaaggccg tgtatcagcc cagaggcgcc  240
tttggcggca gcgagaacgc caccaatctg tttctgctgg aactcctagg cgccggcgag  300
ctggccctga ccatgagaag caagaaactg cccatcaatg tgaccacagg cgaggaacag  360
caggtgtccc tggaaagcgt ggacgtgtac tttcaagacg tgttcggcac catgtggtgc  420
caccacgccg agatgcagaa cccgtgtac ctgatccccg agacagtgcc ctacatcaag  480
gccgccgcct gcaacagcac caacatcacc gccgtcgtgc gggcccaggg actggatgtg  540
acactgcctc tgagcctgcc taccagcgcc caggacagca acttcagcgt gaaaaccgag  600
atgctgggca acgagatcga catcgagtgc atcatggaag atggcgagat cagccaggtg  660
ctgcccggcg acaacaagtt caacatcaca tgcagcggct acgagagcca cgtgccatct  720
ggcggcatcc tgaccagcac aagcccagtg gccacaccca tccctggcac aggctacgcc  780
tacagcctga gactgacccc cagacccgtg tccagattcc tgggcaacaa cagcatcctg  840
tacgtgttct acagcggcaa cggccccaag gcctctggcg gcgattactg tatccagagc  900
aacatcgtgt tcagcgacga gatccccgcc agccaggaca tgcccaccaa taccaccgac  960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaaccggac cttcgatatc accgtgtctg gcctgggcac cgccccaag  1200
accctgatca tcaccagaac cgccacaaat gccaccacca aacccacaa agtgatcttc 1260
agcaaggccc ccggctctgg cctgaacgac attttgagg cccagaagat tgagtggcat 1320
gaacatcacc accaccacca t                                            1341
```

| SEQ ID NO: 153 | moltype = AA  length = 447 |
|---|---|
| FEATURE | Location/Qualifiers |
| source | 1..447 |
| | mol_type = protein |

```
                        organism = Synthetic construct
SEQUENCE: 153
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVPYRK WDNCNSTNIT AVVRAQGLDV  180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGRYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                     447

SEQ ID NO: 154          moltype = DNA   length = 1341
FEATURE                 Location/Qualifiers
source                  1..1341
                        mol_type = other DNA
                        organism = Synthetic construct
SEQUENCE: 154
gaagctgccc tgctcgtgtg ccagtacacc atccagagcc tgatccacct gaccggcgag   60
gaccccggct tcttcaacgt ggaaatcccc gagttcccct tctaccctac ctgcaacgtg  120
tgcaccgccg acgtgaacgt gaccatcaac ttcgacgtgg gcggcaagaa gcaccagctg  180
gacctggatt tcggccagct gacccctcac accaaggccg tgtatcagcc cagaggcgcc  240
tttggcggca gcgagaacgc caccaatctg tttctgctga actcctaggc gccggcgag   300
ctggccctga ccatgagaag caagaaactg cccatcaatg tgaccacagg cgaggaacag  360
caggtgtccc tggaaagcgt ggacgtgtac tttcaagacg tgttcggcac catgtggtgc  420
caccacgccg agatgcagaa ccccgtgtac ctgatcccg agacagtgcc ctaccggaag  480
tggacaaact gcaacagcac caacatcacc gccgtcgtgc gggcccaggg actggatgtg  540
acactgcctc tgagcctgcc taccagcgcc caggacagca acttcagcgt gaaaaccgag  600
atgctgggca acgagatcga catcgagtgc atcatggaag atggcgagat cagccaggtg  660
ctgcccggcg acaacaagtt caacatcaca tgcagcggct acgagagcca cgtgccatct  720
ggcggcatcc tgaccagcac aagcccagtg gccacaccca tccctggcac aggctacgcc  780
tacagcctga gactgacccc cagaccegtg tccagattcc tgggcaacaa cagcatcctg  840
tacgtgttct acagcggcaa cggccccaag gcctctggcg gccggtactg tatccagagc  900
aacatcgtgt tcagcgacga gatccccgcc agccaggaca tgcccaccaa taccaccgac  960
atcacgtacg tgggcgacaa tgccacctac agcgtgccaa tggtcacctc cgaggacgcc 1020
aacagccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaaccggac cttcgatatc accgtgtctg gcctgggcac cgcccccaag 1200
accctgatca tcaccagaac cgccacaaat gccaccacca aacccacaa agtgatcttc 1260
agcaaggccc ccggctctgg cctgaacgac attttttgagg cccagaagat tgagtggcat 1320
gaacatcacc accaccacca t                                          1341

SEQ ID NO: 155          moltype = AA   length = 447
FEATURE                 Location/Qualifiers
source                  1..447
                        mol_type = protein
                        organism = Synthetic construct
SEQUENCE: 155
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVRYIK WDNCNSTNIT AVVRAQGLDV  180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGRYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                     447

SEQ ID NO: 156          moltype = DNA   length = 1341
FEATURE                 Location/Qualifiers
source                  1..1341
                        mol_type = other DNA
                        organism = Synthetic construct
SEQUENCE: 156
gaagctgccc tgctcgtgtg ccagtacacc atccagagcc tgatccacct gaccggcgag   60
gaccccggct tcttcaacgt ggaaatcccc gagttcccct tctaccctac ctgcaacgtg  120
tgcaccgccg acgtgaacgt gaccatcaac ttcgacgtgg gcggcaagaa gcaccagctg  180
gacctggatt tcggccagct gacccctcac accaaggccg tgtatcagcc cagaggcgcc  240
tttggcggca gcgagaacgc caccaatctg tttctgctgg aactcctagg cgccggcgag  300
ctggccctga ccatgagaag caagaaactg cccatcaatg tgaccacagg cgaggaacag  360
caggtgtccc tggaaagcgt ggacgtgtac tttcaagacg tgttcggcac catgtggtgc  420
caccacgccg agatgcagaa ccccgtgtac ctgatcccg agacagtgcg gtacatcaag  480
tgggacaact gcaacagcac caacatcacc gccgtcgtgc gggcccaggg actggatgtg  540
acactgcctc tgagcctgcc taccagcgcc caggacagca acttcagcgt gaaaaccgag  600
atgctgggca acgagatcga catcgagtgc atcatggaag atggcgagat cagccaggtg  660
ctgcccggcg acaacaagtt caacatcaca tgcagcggct acgagagcca cgtgccatct  720
ggcggcatcc tgaccagcac aagcccagtg gccacaccca tccctggcac aggctacgcc  780
tacagcctga gactgacccc cagaccegtg tccagattcc tgggcaacaa cagcatcctg  840
tacgtgttct acagcggcaa cggccccaag gcctctggcg gccggtactg tatccagagc  900
aacatcgtgt tcagcgacga gatccccgcc agccaggaca tgcccaccaa taccaccgac  960
atcacgtacg tgggcgacaa tgccacctac agcgtgccaa tggtcacctc cgaggacgcc 1020
```

```
aacagcccca acgtgaccgt gacagccttt tgggcctggc ctaacaacac cgagacagac  1080
ttcaagtgca agtggaccct gacctccggc acccctagcg gctgcgagaa tatcagcgga  1140
gccttcgcca gcaacggac cttcgatatc accgtgtctg gcctgggcac cgcccccaag  1200
accctgatca tcaccagaac cgccacaaat gccaccacca caacccacaa agtgatcttc  1260
agcaaggccc ccggctctgg cctgaacgac attttgagg cccagaagat tgagtggcat  1320
gaacatcacc accaccacca t                                            1341

SEQ ID NO: 157          moltype = AA  length = 447
FEATURE                 Location/Qualifiers
source                  1..447
                        mol_type = protein
                        organism = Synthetic construct
SEQUENCE: 157
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVNYTK WDNCSTNIT AVVRAQGLDV   180
TLPLSLPTSA QDSNFSVKTE MLGNEIDIEC IMEDGEISOP LPGDNKFNIT CSGYESHVPS  240
GGILTSTSPV ATPIPGTGYA YSLRLTPRPV SRFLGNNSIL YVFYSGNGPK ASGGRYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                      447

SEQ ID NO: 158          moltype = DNA  length = 1341
FEATURE                 Location/Qualifiers
source                  1..1341
                        mol_type = other DNA
                        organism = Synthetic construct
SEQUENCE: 158
gaagctgccc tgctcgtgtg ccagtacacc atccagagcc tgatccacct gaccggcgag   60
gaccccggct tcttcaacgt ggaaatcccc gagttcccct tctaccctac ctgcaacgtg  120
tgcaccgccg acgtgaacgt gaccatcaac ttcgacgtgg gcggcaagaa gcaccagctg  180
gacctggatt tcggccagct gaccccctca accaaggccg tgtatcagcc cagaggcgcc  240
tttggcggca gcgagaacgc caccaatctg tttctgctgg aactcctagg cgccggcgag  300
ctggcctga ccatgagaag caagaaactg cccatcaatg tgaccacagg cgaggaacag  360
caggtgtccc tggaaagcgt ggacgtgtac tttcaagacg tgttcggcac catgtggtgc  420
caccacgccg agatgcagaa ccccgtgtac ctgatccccg agacagtgaa ctacaccaag  480
tgggacaact gcaacagcac caacatcacc gccgtcgtgc gggcccaggg actggatgtg  540
acactgcctc tgagcctgcc taccagcgcc caggacagca acttcagcgt gaaaaccgag  600
atgctgggca acgagatcga catcgagtgc atcatgaag atggcgagat cagccagtg  660
ctgcccggcg acaacaagtt caacatcaca tgcagcggct acgagagcca cgtgccatct  720
ggcggcatcc tgaccagcac aagcccagtg gccacaccca tccctggcac aggctacgcc  780
tacagcctga gactgacccc cagacccgtg tccagattcc tgggcaacaa cagcatcctg  840
tacgtgttct acagcggcaa cggcccaag gcctctggca gtactg tatccagagc       900
aacatcgtgt tcagcgacga gatccccgcc agccaggaca tgcccaccaa taccaccgac  960
atcacgtacg tgggcgacaa tgccacctac agcgtgccaa tggtcacctc cgaggacgcc 1020
aacagcccca acgtgaccgt gacagccttt tgggcctggc ctaacaacac cgagacagac 1080
ttcaagtgca agtggaccct gacctccggc acccctagcg gctgcgagaa tatcagcgga 1140
gccttcgcca gcaacggac cttcgatatc accgtgtctg gcctgggcac cgcccccaag 1200
accctgatca tcaccagaac cgccacaaat gccaccacca caacccacaa agtgatcttc 1260
agcaaggccc ccggctctgg cctgaacgac attttgagg cccagaagat tgagtggcat 1320
gaacatcacc accaccacca t                                           1341

SEQ ID NO: 159          moltype = AA  length = 447
FEATURE                 Location/Qualifiers
source                  1..447
                        mol_type = protein
                        organism = Synthetic construct
SEQUENCE: 159
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVRYRK WDNCSTNIT AVVRAQGLDV   180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGRYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                      447

SEQ ID NO: 160          moltype = DNA  length = 1341
FEATURE                 Location/Qualifiers
source                  1..1341
                        mol_type = other DNA
                        organism = Synthetic construct
SEQUENCE: 160
gaagctgccc tgctcgtgtg ccagtacacc atccagagcc tgatccacct gaccggcgag   60
gaccccggct tcttcaacgt ggaaatcccc gagttcccct tctaccctac ctgcaacgtg  120
tgcaccgccg acgtgaacgt gaccatcaac ttcgacgtgg gcggcaagaa gcaccagctg  180
gacctggatt tcggccagct gaccccctca accaaggccg tgtatcagcc cagaggcgcc  240
tttggcggca gcgagaacgc caccaatctg tttctgctgg aactcctagg cgccggcgag  300
ctggcctga ccatgagaag caagaaactg cccatcaatg tgaccacagg cgaggaacag  360
```

```
caggtgtccc tggaaagcgt ggacgtgtac tttcaagacg tgttcggcac catgtggtgc   420
caccacgccg agatgcagaa ccccgtgtac ctgatcccg agacagtgcg gtaccggaag    480
tgggacaact gcaacagcac caacatcacc gccgtcgtgc gggcccaggg actggatgtg   540
acactgcctc tgagcctgcc taccagcgcc aggacagca acttcagcgt gaaaaccgag    600
atgctgggca acgagatcga catcgagtgc atcatgaac atggcgagat cagccaggtg    660
ctgcccggcg acaacaagtt caacatcaca tgcagcggct acgagagcca cgtgccatct   720
ggcggcatcc tgaccagcac aagcccagtg ccacacccca tccctggcac aggctacgcc   780
tacagcctga gactgacccc cagacccgtg tccagattcc tgggcaacaa cagcatcctg   840
tacgtgttct acagcggcaa cggccccaag gcctctggcg gccggtactg tatccagagc   900
aacatcgtgt tcagcgacga gatcccgcc agccaggaca tgccaccaa taccaccgac    960
atcacgtacg tgggcgacaa tgccacctac agcgtgccaa tggtcacctc cgaggacgcc  1020
aacagcccca acgtgaccgt gacagccttt tgggcctggc ctaacaacac cgagacagac  1080
ttcaagtgca agtggaccct gacctccggc accctagcg gctgcgagaa tatcagcgga  1140
gccttcgcca gcaaccggac cttcgatatc accgtgtctg gcctggccac cgcccccaag  1200
accctgatca tcaccagaac cgccacaaat gccaccacca caaccacaa agtgatcttc   1260
agcaaggccc ccggctctgg cctgaacgac atttttgagg cccagaagat tgagtggcat   1320
gaacatcacc accaccacca t                                            1341

SEQ ID NO: 161          moltype = AA   length = 119
FEATURE                 Location/Qualifiers
source                  1..119
                        mol_type = protein
                        organism = Macaca mulatta
SEQUENCE: 161
QVQLVQSGAD VRKPGASVKV SCKASTYIFT GYYIHWVRQA PGRGLEWLGW IHPNSGGTTY   60
SQMFQGRVTM TRDRSITTSY MELSRLQSDD TAIYYCATLR FVEYSFDSWG QGTLVTVSS   119

SEQ ID NO: 162          moltype = DNA   length = 357
FEATURE                 Location/Qualifiers
source                  1..357
                        mol_type = genomic DNA
                        organism = Macaca mulatta
SEQUENCE: 162
caggtgcagc tggtgcagtc tggcgcagac gtgaggaagc caggagcctc cgtgaaggtg    60
tcttgtaagg ccagcaccta catcttcaca ggctactata tcccactggg gaggcaggca   120
ccaggaaggg gcctgagtg gctgggctgg attcaccta actctggcgg caccacatac    180
agccagatgt ttcagggcag agtgaccatg acacgggaca gatccatcac cacatcttat   240
atggagctga gccggctgca gtccgacgat accgccatct actattgcgc cacactgaga   300
ttcgtggagt attctttga tagctggggc cagggcaccc tggtgacagt gagctcc      357

SEQ ID NO: 163          moltype = AA   length = 7
FEATURE                 Location/Qualifiers
source                  1..7
                        mol_type = protein
                        organism = Macaca mulatta
SEQUENCE: 163
TYIFTGY                                                              7

SEQ ID NO: 164          moltype = AA   length = 6
FEATURE                 Location/Qualifiers
source                  1..6
                        mol_type = protein
                        organism = Macaca mulatta
SEQUENCE: 164
HPNSGG                                                               6

SEQ ID NO: 165          moltype = AA   length = 10
FEATURE                 Location/Qualifiers
source                  1..10
                        mol_type = protein
                        organism = Macaca mulatta
SEQUENCE: 165
LRFVEYSFDS                                                          10

SEQ ID NO: 166          moltype = AA   length = 108
FEATURE                 Location/Qualifiers
source                  1..108
                        mol_type = protein
                        organism = Macaca mulatta
SEQUENCE: 166
EIVLTQSPGT LSLSPGERAT LSCRASQSIS STYLAWYQQI PGQAPRLLIY GASSRAAGIP   60
DRFSGGGSGT DFTLTISRLE PEDFAVYYCQ QYGSSPRSFG QGTKLEIK               108

SEQ ID NO: 167          moltype = DNA   length = 324
FEATURE                 Location/Qualifiers
source                  1..324
                        mol_type = genomic DNA
                        organism = Macaca mulatta
SEQUENCE: 167
```

```
gagatcgtgc tgacccagag cccaggcaca ctgagcctgt ccccaggaga gagggccacc    60
ctgtcctgta gagcctctca gagcatcagc tccacatacc tggcctggta tcagcagatc   120
ccaggacagg cacctaggct gctgatctac ggagcctcta gcagggcagc aggcatcccc   180
gaccgcttct ccggcggagg ctctggcacc gacttcaccc tgacaatctc tcggctggag   240
cctgaggact cgccgtgta ctattgccag cagtatggct cctctccaag gtcctttggc   300
cagggcacaa agctggagat caag                                         324

SEQ ID NO: 168         moltype = AA  length = 12
FEATURE                Location/Qualifiers
source                 1..12
                       mol_type = protein
                       organism = Macaca mulatta
SEQUENCE: 168
RASQSISSTY LA                                                       12

SEQ ID NO: 169         moltype = AA  length = 7
FEATURE                Location/Qualifiers
source                 1..7
                       mol_type = protein
                       organism = Macaca mulatta
SEQUENCE: 169
GASSRAA                                                              7

SEQ ID NO: 170         moltype = AA  length = 9
FEATURE                Location/Qualifiers
source                 1..9
                       mol_type = protein
                       organism = Macaca mulatta
SEQUENCE: 170
QQYGSSPRS                                                            9

SEQ ID NO: 171         moltype = AA  length = 119
FEATURE                Location/Qualifiers
source                 1..119
                       mol_type = protein
                       organism = Macaca mulatta
SEQUENCE: 171
EVQLLESGGA LVQPGGSLRL SCAASGFTFK TYAMSWVRQV PGKGLEWVSA ISGSGTASYY    60
ADSVKGRFTL SRDNSKNTLY LQLSSLRDED TGVYYCARRF LDWFGMDVWG LGTTVTVSS    119

SEQ ID NO: 172         moltype = DNA  length = 357
FEATURE                Location/Qualifiers
source                 1..357
                       mol_type = genomic DNA
                       organism = Macaca mulatta
SEQUENCE: 172
gaggtgcagc tgctggagag cggcggcgcc ctggtgcagc caggaggcag cctgcggctg    60
tcctgtgccg cctctggctt cacctttaag acatacgcca tgtcctgggt gaggcaggtg   120
cctggcaagg gctggagtg ggtgtctgcc atctccggct ctggcaccgc ctcttactat   180
gccgacagcg tgaagggcag gttcaccctg agccgcgata ctccaagaa tacactgtat   240
ctgcagctga gctccctgcg ggacgaggat accggcgtgt actattgcgc ccggagattc   300
ctggactggt ttggcatgga cgtgtggggc ctgggcacca gtgacagt gtctagc       357

SEQ ID NO: 173         moltype = AA  length = 7
FEATURE                Location/Qualifiers
source                 1..7
                       mol_type = protein
                       organism = Macaca mulatta
SEQUENCE: 173
GFTFKTY                                                              7

SEQ ID NO: 174         moltype = AA  length = 6
FEATURE                Location/Qualifiers
source                 1..6
                       mol_type = protein
                       organism = Macaca mulatta
SEQUENCE: 174
SGSGTA                                                               6

SEQ ID NO: 175         moltype = AA  length = 10
FEATURE                Location/Qualifiers
source                 1..10
                       mol_type = protein
                       organism = Macaca mulatta
SEQUENCE: 175
RFLDWFGMDV                                                          10

SEQ ID NO: 176         moltype = AA  length = 111
FEATURE                Location/Qualifiers
```

```
source                   1..111
                         mol_type = protein
                         organism = Macaca mulatta
SEQUENCE: 176
DIVMTQSPLS LPVTPGEPAS ISCLSSQSLL QSNGYNYVDW YLQKPGQSPQ LLIYLGSNRA    60
SGVPDRFSGS GSGTDFTLKI SRVEAEDVGV YYCMVTLHPP TFGQGAKVEI K           111

SEQ ID NO: 177           moltype = DNA   length = 333
FEATURE                  Location/Qualifiers
source                   1..333
                         mol_type = genomic DNA
                         organism = Macaca mulatta
SEQUENCE: 177
gacatcgtga tgacccagtc ccctctgtct ctgccagtga cacccggcga gcctgcctct    60
atcagctgtc tgagctccca gagcctgctg cagtccaacg gctacaatta tgtggattgg   120
tacctgcaga agccaggcca gtccccccag ctgctgatct atctgggctc taacagggcc   180
agcggcgtgc ccgacagatt ctccggctct ggcagcggca ccgacttcac cctgaagatc   240
tctcgggtgg aggcagagga cgtgggcgtg tactattgca tggtgaccct gcacccacct   300
acattcggcc agggagccaa ggtggagatc aag                                333

SEQ ID NO: 178           moltype = AA    length = 16
FEATURE                  Location/Qualifiers
source                   1..16
                         mol_type = protein
                         organism = Macaca mulatta
SEQUENCE: 178
LSSQSLLQSN GYNYVD                                                    16

SEQ ID NO: 179           moltype = AA    length = 7
FEATURE                  Location/Qualifiers
source                   1..7
                         mol_type = protein
                         organism = Macaca mulatta
SEQUENCE: 179
LGSNRAS                                                               7

SEQ ID NO: 180           moltype = AA    length = 8
FEATURE                  Location/Qualifiers
source                   1..8
                         mol_type = protein
                         organism = Macaca mulatta
SEQUENCE: 180
MVTLHPPT                                                              8

SEQ ID NO: 181           moltype = AA    length = 120
FEATURE                  Location/Qualifiers
source                   1..120
                         mol_type = protein
                         organism = Macaca mulatta
SEQUENCE: 181
EGQLVQSGGG LVQPGGSLTL SCEVSGFTFK NYEMNWVRQA PGKGLEWVSY ISSGGIAIFH    60
ADSVKGRFTV SRDNAKNLLY LQMNSLRVED TAVYYCARDE NNVRRPFDHW GQGTLVTVSS   120

SEQ ID NO: 182           moltype = DNA   length = 360
FEATURE                  Location/Qualifiers
source                   1..360
                         mol_type = genomic DNA
                         organism = Macaca mulatta
SEQUENCE: 182
gagggacagc tggtgcagtc cggcggaggc ctggtgcagc caggaggctc cctgaccctg    60
tcttgtgagg tgagcggctt caccttcaag aactacgaga tgaattgggt gcggcaggca   120
cctggcaagg gcctggagtg ggtgtcttat atcagctccg gcggaatcgc aatcttccac   180
gcagattccg tgaagggcag gtttaccgtg tctcgcgaca cgccaagaa tctgctgtac   240
ctgcagatga cagcctgcg ggtggaggac acagccgtgt actattgcgc cagggatgag   300
aacaacgtgc ggcggccctt cgaccactgg ggacagggca cctggtgac agtgtctagc   360

SEQ ID NO: 183           moltype = AA    length = 7
FEATURE                  Location/Qualifiers
source                   1..7
                         mol_type = protein
                         organism = Macaca mulatta
SEQUENCE: 183
GFTFKNY                                                               7

SEQ ID NO: 184           moltype = AA    length = 6
FEATURE                  Location/Qualifiers
source                   1..6
                         mol_type = protein
                         organism = Macaca mulatta
```

```
SEQUENCE: 184
SSGGIA                                                                         6

SEQ ID NO: 185          moltype = AA   length = 11
FEATURE                 Location/Qualifiers
source                  1..11
                        mol_type = protein
                        organism = Macaca mulatta
SEQUENCE: 185
DENNVRRPFD H                                                                  11

SEQ ID NO: 186          moltype = AA   length = 109
FEATURE                 Location/Qualifiers
source                  1..109
                        mol_type = protein
                        organism = Macaca mulatta
SEQUENCE: 186
QSVLTQPPSA SGSPGQSVTI SCTGSSSDVG AYDFVSWFQQ YPGQAPKLII YEVNKRPSGV             60
PARFSGSKSG NTASLTVSGL QAEDEADYFC FSYGGTTNLR VFGGGTKLT                        109

SEQ ID NO: 187          moltype = DNA   length = 327
FEATURE                 Location/Qualifiers
source                  1..327
                        mol_type = genomic DNA
                        organism = Macaca mulatta
SEQUENCE: 187
cagtctgtgc tgacccagcc acctagcgcc tccggctctc ccggccagag cgtgaccatc             60
tcctgtacag gcagctcctc tgacgtgggc gcctacgatt tcgtgagctg gtttcagcag           120
tatccaggcc aggcccccaa gctgatcatc tacgaggtga acaagcggcc ttccggcgtg           180
ccagccagat tcagcggctc caagtctggc aataccgcct ctctgacagt gagcggcctg           240
caggcagagg acgaggcaga ttacttctgc ttttcttatg gcggcaccac aaacctgcgg           300
gtgtttggcg gcggcaccaa gctgaca                                               327

SEQ ID NO: 188          moltype = AA   length = 14
FEATURE                 Location/Qualifiers
source                  1..14
                        mol_type = protein
                        organism = Macaca mulatta
SEQUENCE: 188
TGSSSDVGAY DFVS                                                               14

SEQ ID NO: 189          moltype = AA   length = 7
FEATURE                 Location/Qualifiers
source                  1..7
                        mol_type = protein
                        organism = Macaca mulatta
SEQUENCE: 189
EVNKRPS                                                                        7

SEQ ID NO: 190          moltype = AA   length = 11
FEATURE                 Location/Qualifiers
source                  1..11
                        mol_type = protein
                        organism = Macaca mulatta
SEQUENCE: 190
FSYGGTTNLR V                                                                  11

SEQ ID NO: 191          moltype = AA   length = 122
FEATURE                 Location/Qualifiers
source                  1..122
                        mol_type = protein
                        organism = Macaca mulatta
SEQUENCE: 191
EVQLVESGGN LVQPGASLRL SCTASRFNFN KYAMHWVRQT PGKGLEWVSA ISWDSTYIDY             60
GNSVKGRFTI SRDNTRNSLY LQMNSLTAED TALYYCAKCE DYLRLCSAYD IWGHGTMVTV            120
SS                                                                           122

SEQ ID NO: 192          moltype = DNA   length = 366
FEATURE                 Location/Qualifiers
source                  1..366
                        mol_type = genomic DNA
                        organism = Macaca mulatta
SEQUENCE: 192
gaggtgcagc tggtggagag cggcggaaac ctggtgcagc caggagcctc tctgaggctg             60
agctgtaccg cctcccgctt caactttaat aagtacgcaa tgcactgggt gcggcagacc           120
cctggcaagg gcctggagtg ggtgtctgca atcagctggg actccacata catcgattat           180
ggcaactccg tgaagggcag gttcaccatc tctcgggaca cacaagaaa tagcctgtat            240
ctgcagatga attcccctgac cgccgaggat acagcccgt actattgcgc caagtgtgag           300
gactacctgc ggctgtgctc tgcctatgat atctggggcc acggcaccat ggtgacagtg           360
```

```
                                              -continued
agctcc                                                                    366

SEQ ID NO: 193          moltype = AA  length = 7
FEATURE                 Location/Qualifiers
source                  1..7
                        mol_type = protein
                        organism = Macaca mulatta
SEQUENCE: 193
RFNFNKY                                                                     7

SEQ ID NO: 194          moltype = AA  length = 6
FEATURE                 Location/Qualifiers
source                  1..6
                        mol_type = protein
                        organism = Macaca mulatta
SEQUENCE: 194
SWDSTY                                                                      6

SEQ ID NO: 195          moltype = AA  length = 13
FEATURE                 Location/Qualifiers
source                  1..13
                        mol_type = protein
                        organism = Macaca mulatta
SEQUENCE: 195
CEDYLRLCSA YDI                                                             13

SEQ ID NO: 196          moltype = AA  length = 112
FEATURE                 Location/Qualifiers
source                  1..112
                        mol_type = protein
                        organism = Macaca mulatta
SEQUENCE: 196
DIVMTQSPLS LPVTPGESAS ISCRSSQSLL HSNGKNYLSW YLQKPGQSPQ LLIDLGSNRA           60
SGVSDRFSGS GSGTDFTLKI SRVEADDVGV YYCMQAVQTP ITFGQGTRLA IK                  112

SEQ ID NO: 197          moltype = DNA  length = 336
FEATURE                 Location/Qualifiers
source                  1..336
                        mol_type = genomic DNA
                        organism = Macaca mulatta
SEQUENCE: 197
gacatcgtga tgacccagtc tcctctgagc ctgcccgtga cacctggcga gtctgccagc           60
atctcctgtc ggagctccca gagcctgctg cactccaacg gcaagaatta cctgtcttgg         120
tatctgcaga agccaggcca gagccccag ctgctgatcg atctgggctc aacagggcc           180
tccggcgtgt ctgacagatt ctctggcagc ggctccggca ccgacttcac cctgaagatc         240
agcagggtgg aggccgacga tgtgggcgtg tactattgca tgcaggccgt gcagacccca         300
atcacattcg gccagggaac ccgcctggcc atcaag                                   336

SEQ ID NO: 198          moltype = AA  length = 16
FEATURE                 Location/Qualifiers
source                  1..16
                        mol_type = protein
                        organism = Macaca mulatta
SEQUENCE: 198
RSSQSLLHSN GKNYLS                                                          16

SEQ ID NO: 199          moltype = AA  length = 7
FEATURE                 Location/Qualifiers
source                  1..7
                        mol_type = protein
                        organism = Macaca mulatta
SEQUENCE: 199
LGSNRAS                                                                     7

SEQ ID NO: 200          moltype = AA  length = 9
FEATURE                 Location/Qualifiers
source                  1..9
                        mol_type = protein
                        organism = Macaca mulatta
SEQUENCE: 200
MQAVQTPIT                                                                   9

SEQ ID NO: 201          moltype = AA  length = 123
FEATURE                 Location/Qualifiers
source                  1..123
                        mol_type = protein
                        organism = Macaca mulatta
SEQUENCE: 201
QVQLVQSGAE LKTPGASVKV SCKASGYTFT GYYIHWVRQA PGEGLEWTGW INPNSGATRY           60
```

```
GQKFQGRVTL TSDTSSSTVY MEVSNLTSDD SAVYYCAREL SYSIRGTGPL GYWGLGTLVT    120
VSS                                                                 123

SEQ ID NO: 202          moltype = DNA  length = 369
FEATURE                 Location/Qualifiers
source                  1..369
                        mol_type = genomic DNA
                        organism = Macaca mulatta
SEQUENCE: 202
caggtgcagc tggtgcagtc cggcgcagag ctgaagaccc caggagccag cgtgaaggtg    60
tcctgtaagg cctctggcta caccttcaca ggctactata tccactgggt gcggcaggca    120
ccaggagagg gcctggagtg gaccggctgg atcaaccct a atagcggcgc cacaagatac   180
ggccagaagt tcagggccg cgtgaccctg acaagcgaca ccagctcctc tacagtgtat    240
atggaggtgt ccaacctgac ctccgacgat tctgccgtgt actattgcgc ccgggagctg   300
tcttacagca tcagaggaac aggaccactg ggatattggg gcctgggcac cctggtgaca   360
gtgagctcc                                                          369

SEQ ID NO: 203          moltype = AA  length = 7
FEATURE                 Location/Qualifiers
source                  1..7
                        mol_type = protein
                        organism = Macaca mulatta
SEQUENCE: 203
GYTFTGY                                                             7

SEQ ID NO: 204          moltype = AA  length = 6
FEATURE                 Location/Qualifiers
source                  1..6
                        mol_type = protein
                        organism = Macaca mulatta
SEQUENCE: 204
NPNSGA                                                              6

SEQ ID NO: 205          moltype = AA  length = 14
FEATURE                 Location/Qualifiers
source                  1..14
                        mol_type = protein
                        organism = Macaca mulatta
SEQUENCE: 205
ELSYSIRGTG PLGY                                                     14

SEQ ID NO: 206          moltype = AA  length = 108
FEATURE                 Location/Qualifiers
source                  1..108
                        mol_type = protein
                        organism = Macaca mulatta
SEQUENCE: 206
EIVLTQSPGT LSLSPGERAT LSCRASQSVA SKYLAWYQQK PGQAPRLLIY GASSRATGIP    60
DRFSGSGSGT DFTLTISRLE PEDFAVYYCQ YYGSSPLTFG QGTKVEIK                 108

SEQ ID NO: 207          moltype = DNA  length = 324
FEATURE                 Location/Qualifiers
source                  1..324
                        mol_type = genomic DNA
                        organism = Macaca mulatta
SEQUENCE: 207
gagatcgtgc tgacccagtc tccaggcaca ctgtccctgt ctccaggaga gagggccacc    60
ctgtcttgta gagccagcca gtccgtggcc agcaagtacc tggcctggta tcagcagaag   120
ccaggacagg cacctaggct gctgatctac ggagccagct ccagggcaac cggcatcccc   180
gaccgcttct ctggcagcgg ctccggcaca gacttcaccc tgacaatctc caggctggag   240
cctgaggact tcgccgtgta ctattgccag tactatggct ctagccccct gaccttggc    300
cagggcacaa aggtggagat caag                                         324

SEQ ID NO: 208          moltype = AA  length = 12
FEATURE                 Location/Qualifiers
source                  1..12
                        mol_type = protein
                        organism = Macaca mulatta
SEQUENCE: 208
RASQSVASKY LA                                                       12

SEQ ID NO: 209          moltype = AA  length = 7
FEATURE                 Location/Qualifiers
source                  1..7
                        mol_type = protein
                        organism = Macaca mulatta
SEQUENCE: 209
GASSRAT                                                             7
```

```
SEQ ID NO: 210          moltype = AA   length = 9
FEATURE                 Location/Qualifiers
source                  1..9
                        mol_type = protein
                        organism = Macaca mulatta
SEQUENCE: 210
QYYGSSPLT                                                                9

SEQ ID NO: 211          moltype = AA   length = 123
FEATURE                 Location/Qualifiers
source                  1..123
                        mol_type = protein
                        organism = Macaca mulatta
SEQUENCE: 211
EVQLAESGGG VVHPGGSLRL SCTASGFTFS RHSMHWVRQA PGKGLEWVAV ISHDGSHKFY         60
VDSVKGRFSI SRDNAKNTLY LQMSSLSGAD TAVYYCVKDI SSRSYGYLAG DSWGQGSLVT        120
VSS                                                                    123

SEQ ID NO: 212          moltype = DNA   length = 369
FEATURE                 Location/Qualifiers
source                  1..369
                        mol_type = genomic DNA
                        organism = Macaca mulatta
SEQUENCE: 212
gaggtgcagc tggccgagtc tggcggagga gtggtgcacc caggaggctc cctgaggctg         60
tcttgtaccg ccagcggctt cacatttttct aggcacagca tgcactgggt gcgccaggca      120
cctggcaagg gcctgagtg ggtgccgtg atctcccacg acggctctca caagttctac         180
gtggattccg tgaagggccg gtttagcatc tccagagaca cgccaagaa taccctgtat        240
ctgcagatga gctccctgtc tggcgccgac acagccgtgt actattgcgt gaaggatatc       300
tctagcagga gctacggcta tctggcaggc gatagctggg gacagggctc cctggtgacc      360
gtgtcctct                                                              369

SEQ ID NO: 213          moltype = AA   length = 7
FEATURE                 Location/Qualifiers
source                  1..7
                        mol_type = protein
                        organism = Macaca mulatta
SEQUENCE: 213
GFTFSRH                                                                  7

SEQ ID NO: 214          moltype = AA   length = 6
FEATURE                 Location/Qualifiers
source                  1..6
                        mol_type = protein
                        organism = Macaca mulatta
SEQUENCE: 214
SHDGSH                                                                   6

SEQ ID NO: 215          moltype = AA   length = 14
FEATURE                 Location/Qualifiers
source                  1..14
                        mol_type = protein
                        organism = Macaca mulatta
SEQUENCE: 215
DISSRSYGYL AGDS                                                         14

SEQ ID NO: 216          moltype = AA   length = 108
FEATURE                 Location/Qualifiers
source                  1..108
                        mol_type = protein
                        organism = Macaca mulatta
SEQUENCE: 216
DIQMTQSPSS LSASVGDIIT ITCRASQSVV TYLNWYQQKP GGAPRLLIYT TSKLQSGVPS         60
RFSGSGSGTL FTLTINGLRP EDFATYYCQQ SYGTPPFTFG PGTRVEIN                   108

SEQ ID NO: 217          moltype = DNA   length = 324
FEATURE                 Location/Qualifiers
source                  1..324
                        mol_type = genomic DNA
                        organism = Macaca mulatta
SEQUENCE: 217
gatattcaga tgactcagtc cccaagcagc ctgagcgcct ccgtgggcga catcatcacc         60
atcacatgca gggcctctca gagcgtggtg acctacctga actggtatca gcagaagcca      120
ggaggagcac ctaggctgct gatctacacc acatccaagc tgcagtctgg cgtgccatcc       180
agattctccg gctctggcag cggcaccctg tttaccctga caatcaatgg cctgcgcccc      240
gaggatttcg ccacatacta ttgtcagcag agctatggaa ccccccccttt tacttttgga    300
ccaggcacaa gagtggagat taac                                              324

SEQ ID NO: 218          moltype = AA   length = 11
```

```
FEATURE                 Location/Qualifiers
source                  1..11
                        mol_type = protein
                        organism = Macaca mulatta
SEQUENCE: 218
RASQSVVTYL N                                                            11

SEQ ID NO: 219          moltype = AA  length = 7
FEATURE                 Location/Qualifiers
source                  1..7
                        mol_type = protein
                        organism = Macaca mulatta
SEQUENCE: 219
TTSKLQS                                                                 7

SEQ ID NO: 220          moltype = AA  length = 10
FEATURE                 Location/Qualifiers
source                  1..10
                        mol_type = protein
                        organism = Macaca mulatta
SEQUENCE: 220
QQSYGTPPFT                                                              10

SEQ ID NO: 221          moltype = AA  length = 124
FEATURE                 Location/Qualifiers
source                  1..124
                        mol_type = protein
                        organism = Macaca mulatta
SEQUENCE: 221
QVHLQQWGAG LVKPSETLSL TCAVQGGPFS GYYWSWIRQP PGKGLEWIGE INHSGNTHYN        60
PSLKSRVTIS VDTSGNYFSL KLTSVTAADA AVYFCARGQQ LLRNYYYYSG MDVWGQGTTV       120
TVSS                                                                   124

SEQ ID NO: 222          moltype = DNA  length = 372
FEATURE                 Location/Qualifiers
source                  1..372
                        mol_type = genomic DNA
                        organism = Macaca mulatta
SEQUENCE: 222
caggtgcacc tgcagcagtg gggagcaggc ctggtgaagc catccgagac actgtctctg        60
acatgtgcag tgcagggagg acccttctct ggctactatt ggagctggat caggcagcca      120
cctggcaagg gcctggagtg gatcggcgag atcaaccaca cggcaatac ccactacaac       180
ccctctctga agagccgggt gaccatcagc gtggacacat cttctccctg                 240
aagctgacct ctgtgacagc cgccgatgcc gccgtgtatt tttgcgcccg gggccagcag      300
ctgctgagaa actactatta ctattccggc atggacgtgt ggggacaggg aaccacagtg      360
acagtgagct cc                                                          372

SEQ ID NO: 223          moltype = AA  length = 7
FEATURE                 Location/Qualifiers
source                  1..7
                        mol_type = protein
                        organism = Macaca mulatta
SEQUENCE: 223
GGPFSGY                                                                 7

SEQ ID NO: 224          moltype = AA  length = 5
FEATURE                 Location/Qualifiers
source                  1..5
                        mol_type = protein
                        organism = Macaca mulatta
SEQUENCE: 224
NHSGN                                                                   5

SEQ ID NO: 225          moltype = AA  length = 16
FEATURE                 Location/Qualifiers
source                  1..16
                        mol_type = protein
                        organism = Macaca mulatta
SEQUENCE: 225
GQQLLRNYYY YSGMDV                                                       16

SEQ ID NO: 226          moltype = AA  length = 107
FEATURE                 Location/Qualifiers
source                  1..107
                        mol_type = protein
                        organism = Macaca mulatta
SEQUENCE: 226
EIVLTQSPGT LSLSPGERAT LSCRASQSVT STYLAWYQQK LGQPPRLLIF GASNRATGIP        60
DRFSGSGSGT DFTLTITRLE PEDFAVYYCQ RYGGSITFGQ GTRLEIK                    107
```

```
SEQ ID NO: 227            moltype = DNA   length = 321
FEATURE                   Location/Qualifiers
source                    1..321
                          mol_type = genomic DNA
                          organism = Macaca mulatta
SEQUENCE: 227
gagatcgtgc tgacacagtc cccaggcacc ctgagcctgt ccccaggaga gcgggccaca    60
ctgtcctgta gagcctctca gagcgtgacc tctacatacc tggcctggta tcagcagaag   120
ctggggccag ccccctaggct gctgatcttc ggcgcctcta acagggccac aggcatccct  180
gaccgcttct ccggctctgg cagcggcacc gacttcaccc tgacaatcac cagactggag  240
cccgaggact cgccgtgta ctattgccag cggtacggcg gcagcatcac atttggccag   300
ggcaccgac tggagatcaa g                                              321

SEQ ID NO: 228            moltype = AA    length = 12
FEATURE                   Location/Qualifiers
source                    1..12
                          mol_type = protein
                          organism = Macaca mulatta
SEQUENCE: 228
RASQSVTSTY LA                                                        12

SEQ ID NO: 229            moltype = AA    length = 7
FEATURE                   Location/Qualifiers
source                    1..7
                          mol_type = protein
                          organism = Macaca mulatta
SEQUENCE: 229
GASNRAT                                                               7

SEQ ID NO: 230            moltype = AA    length = 8
FEATURE                   Location/Qualifiers
source                    1..8
                          mol_type = protein
                          organism = Macaca mulatta
SEQUENCE: 230
QRYGGSIT                                                              8

SEQ ID NO: 231            moltype = AA    length = 126
FEATURE                   Location/Qualifiers
source                    1..126
                          mol_type = protein
                          organism = Macaca mulatta
SEQUENCE: 231
EVQLVQSGGG VVQPRRSLRL SCAASGFTFS NYGMHWVRQV PGKGLQWVAI IWYDGSNKHY    60
AASVQGRFRI SRDNSKNTVY LQMDGLRAED TGMYYCVRDA TTATTEGTSQ YYFDLWGQGA   120
LVTVSS                                                              126

SEQ ID NO: 232            moltype = DNA   length = 378
FEATURE                   Location/Qualifiers
source                    1..378
                          mol_type = genomic DNA
                          organism = Macaca mulatta
SEQUENCE: 232
gaggtgcagc tggtgcagtc cggcggagga gtggtgcagc cacggagatc tctgaggctg    60
agctgtgccg cctccggctt cacctttct aactacggaa tgcactgggt gcgccaggtg   120
cctggcaagg gcctgcagtg ggtggccatc atctggtacg acggctccaa taagcactat  180
gccgcctctg tgcagggcag gttccgcatc tctcgggata cagcaagaa taccgtgtat   240
ctgcagatgg acggcctgcg ggccgaggat acaggcatgt actattgcgt gagagacgcc  300
accacagcca ccacagaggg caccagccag tactattttg atctgtgggg acagggcgcc  360
ctggtgacag tgagctcc                                                378

SEQ ID NO: 233            moltype = AA    length = 7
FEATURE                   Location/Qualifiers
source                    1..7
                          mol_type = protein
                          organism = Macaca mulatta
SEQUENCE: 233
GFTFSNY                                                               7

SEQ ID NO: 234            moltype = AA    length = 6
FEATURE                   Location/Qualifiers
source                    1..6
                          mol_type = protein
                          organism = Macaca mulatta
SEQUENCE: 234
WYDGSN                                                                6

SEQ ID NO: 235            moltype = AA    length = 17
```

```
FEATURE                 Location/Qualifiers
source                  1..17
                        mol_type = protein
                        organism = Macaca mulatta
SEQUENCE: 235
DATTATTEGT SQYYFDL                                                      17

SEQ ID NO: 236          moltype = AA  length = 113
FEATURE                 Location/Qualifiers
source                  1..113
                        mol_type = protein
                        organism = Macaca mulatta
SEQUENCE: 236
DIVMTQSPDS LAVSLGERAT INCKSSQTLL YTSNSKNYLA WYQQKVGQPP RLLIYWASTR        60
ESGVPDRFSG SGSGTDFTLT ISSLLAEDVA VYYCQQYYTT PLTFGGGTKV EVK              113

SEQ ID NO: 237          moltype = DNA  length = 339
FEATURE                 Location/Qualifiers
source                  1..339
                        mol_type = genomic DNA
                        organism = Macaca mulatta
SEQUENCE: 237
gacatcgtga tgacccagag ccccgattcc ctggccgtgt ctctgggaga gagggcaaca        60
atcaactgta agagctccca gaccctgctg tacacatcca actctaagaa ttacctggcc      120
tggtatcagc agaaagtggg acagccacct aggctgctga tctattgggc ctctaccagg      180
gagagcggcg tgccagacag attcagcggc tccggctctg gcacagactt caccctgaca      240
atctctagcc tgctggccga ggacgtggcc gtgtactatt gccagcagta ctataccaca      300
cccctgacct tcggcggcgg cacaaaggtg gaggtgaag                             339

SEQ ID NO: 238          moltype = AA  length = 17
FEATURE                 Location/Qualifiers
source                  1..17
                        mol_type = protein
                        organism = Macaca mulatta
SEQUENCE: 238
KSSQTLLYTS NSKNYLA                                                      17

SEQ ID NO: 239          moltype = AA  length = 7
FEATURE                 Location/Qualifiers
source                  1..7
                        mol_type = protein
                        organism = Macaca mulatta
SEQUENCE: 239
WASTRES                                                                  7

SEQ ID NO: 240          moltype = AA  length = 9
FEATURE                 Location/Qualifiers
source                  1..9
                        mol_type = protein
                        organism = Macaca mulatta
SEQUENCE: 240
QQYYTTPLT                                                                9

SEQ ID NO: 241          moltype = AA  length = 130
FEATURE                 Location/Qualifiers
source                  1..130
                        mol_type = protein
                        organism = Macaca mulatta
SEQUENCE: 241
EVQLVESGGG VVHPGKSLTL SCEASGFTFN DHGIHWVRRA PGKGLEWLAL ISKDGSKEYS        60
TDSVKGRFTV SRDNSRNTVF LQMKSLTTED TAIYYCAKDM GQCSSPSCST MDSYFAMDVW      120
GQGTTVIVSS                                                             130

SEQ ID NO: 242          moltype = DNA  length = 390
FEATURE                 Location/Qualifiers
source                  1..390
                        mol_type = genomic DNA
                        organism = Macaca mulatta
SEQUENCE: 242
gaggtgcagc tggtggagtc cggcggagga gtggtgcacc ctggcaagtc tctgaccctg        60
agctgtgagg ccagcggctt caccttcaac gaccacggca tccactgggt gcggagagca      120
cctggcaagg gctggagtg gctggccctg atctctaagg acggcagcaa ggagtacagc       180
accgattccg tgaagggccg gttcacagtg tccaggata ctctcgcaa taccgtgttt        240
ctgcagatga gtctctgac cacagaggac acagccatct actattgcgc caaggatatg      300
ggccagtgca gctccccctc ctgttctacc atggacagct atttcgcaat ggacgtgtgg      360
ggacagggaa ccacagtgat cgtgtctagc                                       390

SEQ ID NO: 243          moltype = AA  length = 7
FEATURE                 Location/Qualifiers
```

```
source                        1..7
                              mol_type = protein
                              organism = Macaca mulatta
SEQUENCE: 243
GFTFNDH                                                                  7

SEQ ID NO: 244                moltype = AA  length = 6
FEATURE                       Location/Qualifiers
source                        1..6
                              mol_type = protein
                              organism = Macaca mulatta
SEQUENCE: 244
SKDGSK                                                                   6

SEQ ID NO: 245                moltype = AA  length = 21
FEATURE                       Location/Qualifiers
source                        1..21
                              mol_type = protein
                              organism = Macaca mulatta
SEQUENCE: 245
DMGQCSSPSC STMDSYFAMD V                                                 21

SEQ ID NO: 246                moltype = AA  length = 113
FEATURE                       Location/Qualifiers
source                        1..113
                              mol_type = protein
                              organism = Macaca mulatta
SEQUENCE: 246
DIVMTQSPLS LPVTPGEPAS ISCRSSQNLR HNNGYNYLNW YLQKPGQSPQ LLIYLGSIRA        60
SGVPDRFSGS GSGTDFTLKI SRVEAEDVGV YYCMQALQTP PWTFGQGTKV DFK              113

SEQ ID NO: 247                moltype = DNA  length = 339
FEATURE                       Location/Qualifiers
source                        1..339
                              mol_type = genomic DNA
                              organism = Macaca mulatta
SEQUENCE: 247
gacatcgtga tgacccagtc ccctctgtct ctgccagtga cacccggcga gcctgcctct        60
atcagctgtc ggagctccca gaacctgaga cacaacaatg gctacaacta tctgaattgg      120
tacctgcaga agccaggcca gtctcccag ctgctgatct atctgggcag catcagggcc       180
tccggcgtgc cgaccgcttt ctccggctct ggcagcggca ccgacttcac cctgaagatc      240
agccgggtgg aggcagagga cgtgggcgtg tactattgca tgcaggccct gcagaccccc      300
ccttggacat tcggccaggg caccaaggtg gacttcaag                             339

SEQ ID NO: 248                moltype = AA  length = 16
FEATURE                       Location/Qualifiers
source                        1..16
                              mol_type = protein
                              organism = Macaca mulatta
SEQUENCE: 248
RSSQNLRHNN GYNYLN                                                       16

SEQ ID NO: 249                moltype = AA  length = 7
FEATURE                       Location/Qualifiers
source                        1..7
                              mol_type = protein
                              organism = Macaca mulatta
SEQUENCE: 249
LGSIRAS                                                                  7

SEQ ID NO: 250                moltype = AA  length = 10
FEATURE                       Location/Qualifiers
source                        1..10
                              mol_type = protein
                              organism = Macaca mulatta
SEQUENCE: 250
MQALQTPPWT                                                              10

SEQ ID NO: 251                moltype = AA  length = 118
FEATURE                       Location/Qualifiers
source                        1..118
                              mol_type = protein
                              organism = Macaca mulatta
SEQUENCE: 251
QVQLVQSGAE VKKPGASVKV SCKASGYTFT SHYMHWVRQA PGQGLEWMGI ISPTGDFTNY        60
AQKFQGRVTL TRDTSTSTDY MEVTSLRSED TAVYYCARDC SAWAPDYWGQ GTLVTVSS        118

SEQ ID NO: 252                moltype = DNA  length = 354
FEATURE                       Location/Qualifiers
```

```
source                  1..354
                        mol_type = genomic DNA
                        organism = Macaca mulatta
SEQUENCE: 252
caggtgcagc tggtgcagtc cggcgcagag gtgaagaagc caggagccag cgtgaaggtg    60
tcctgtaagg cctctggcta caccttcaca tctcactata tgcactgggt gcggcaggca   120
ccaggacagg gcctggagtg gatgggcatc atcagcccta caggcgactt caccaactac   180
gcccagaagt tcagggccg ggtgaccctg acaagagaca cctctacaag caccgattat    240
atggaggtga catccctgag gtctgaggat accgccgtgt actattgcgc aagggactgt   300
tccgcctggg ccccgatta ctggggacag ggcacactgg tgaccgtgag ctcc           354

SEQ ID NO: 253          moltype = AA  length = 7
FEATURE                 Location/Qualifiers
source                  1..7
                        mol_type = protein
                        organism = Macaca mulatta
SEQUENCE: 253
GYTFTSH                                                                7

SEQ ID NO: 254          moltype = AA  length = 6
FEATURE                 Location/Qualifiers
source                  1..6
                        mol_type = protein
                        organism = Macaca mulatta
SEQUENCE: 254
SPTGDF                                                                 6

SEQ ID NO: 255          moltype = AA  length = 9
FEATURE                 Location/Qualifiers
source                  1..9
                        mol_type = protein
                        organism = Macaca mulatta
SEQUENCE: 255
DCSAWAPDY                                                              9

SEQ ID NO: 256          moltype = AA  length = 108
FEATURE                 Location/Qualifiers
source                  1..108
                        mol_type = protein
                        organism = Macaca mulatta
SEQUENCE: 256
QSALTRPPSV SRCPGQSITI SCSGTSSDVG HDNHVSWYQQ HPGRAPKLMV YEVRNRPSGV     60
SDRFSGSKSG NTASLTISGL QAEDEATYYC CSYTTTHRYI FGGGTKLT                 108

SEQ ID NO: 257          moltype = DNA  length = 324
FEATURE                 Location/Qualifiers
source                  1..324
                        mol_type = genomic DNA
                        organism = Macaca mulatta
SEQUENCE: 257
cagtctgccc tgacaaggcc cccttctgtg agccgctgcc ctggacagag catcacaatc    60
tcctgttctg gcaccagctc cgacgtgggc cacgataacc acgtgtcctg gtaccagcag   120
cacccaggaa gggcacccaa gctgatggtg tatgaggtgc ggaacagacc aagcggcgtg   180
tccgacaggt tcagcggctc caagtctggc aatacagcct ctctgaccat cagcggcctg   240
caggcagagg atgaggcaac ctactattgc tgttcttaca ccacaaccca ccggtatatc   300
tttggcggcg gcacaaagct gacc                                          324

SEQ ID NO: 258          moltype = AA  length = 14
FEATURE                 Location/Qualifiers
source                  1..14
                        mol_type = protein
                        organism = Macaca mulatta
SEQUENCE: 258
SGTSSDVGHD NHVS                                                       14

SEQ ID NO: 259          moltype = AA  length = 7
FEATURE                 Location/Qualifiers
source                  1..7
                        mol_type = protein
                        organism = Macaca mulatta
SEQUENCE: 259
EVRNRPS                                                                7

SEQ ID NO: 260          moltype = AA  length = 10
FEATURE                 Location/Qualifiers
source                  1..10
                        mol_type = protein
                        organism = Macaca mulatta
SEQUENCE: 260
```

```
CSYTTTHRYI                                                          10

SEQ ID NO: 261           moltype = AA  length = 123
FEATURE                  Location/Qualifiers
source                   1..123
                         mol_type = protein
                         organism = Macaca mulatta
SEQUENCE: 261
QVQLLGSGPG LVKPSETLSL TCTVSGASIS SPGYYWGFIR QSPGKGLEWI GSMVSGGTTY    60
YNPSLKSRVT ISMDMSNNQF SLRLNSVTAA DTALYYCARG SRQLVRRATI DYWGQGALFT   120
VSP                                                                 123

SEQ ID NO: 262           moltype = DNA  length = 369
FEATURE                  Location/Qualifiers
source                   1..369
                         mol_type = genomic DNA
                         organism = Macaca mulatta
SEQUENCE: 262
caggtgcagc tgctgggcag cggcccaggc ctggtgaagc cttctgagac actgagcctg    60
acctgtacag tgtctggcgc cagcatcagc tccccaggct actattgggg cttcatcagg   120
cagagcccca gcaagggcct ggagtggatc ggctccatgg tgtctggcgg cacccacatac 180
tataacccta gcctgaagtc ccgggtgaca atctccatgg acatgtctaa caatcagttc   240
agcctgaggc tgaattccgt gaccgccgcc gatacagccc tgtactattg cgcaaggggc   300
tcccgccagc tggtgcggag agcaaccatc gactactggg gacagggcgc cctgtttaca   360
gtgtctccc                                                           369

SEQ ID NO: 263           moltype = AA  length = 9
FEATURE                  Location/Qualifiers
source                   1..9
                         mol_type = protein
                         organism = Macaca mulatta
SEQUENCE: 263
GASISSPGY                                                           9

SEQ ID NO: 264           moltype = AA  length = 5
FEATURE                  Location/Qualifiers
source                   1..5
                         mol_type = protein
                         organism = Macaca mulatta
SEQUENCE: 264
VSGGT                                                               5

SEQ ID NO: 265           moltype = AA  length = 13
FEATURE                  Location/Qualifiers
source                   1..13
                         mol_type = protein
                         organism = Macaca mulatta
SEQUENCE: 265
GSRQLVRRAT IDY                                                      13

SEQ ID NO: 266           moltype = AA  length = 108
FEATURE                  Location/Qualifiers
source                   1..108
                         mol_type = protein
                         organism = Macaca mulatta
SEQUENCE: 266
QSVLTGPPSV SAGPGQQVFI SCSGNSSNIG NNYVSWYQQL PGTAPKLLIY DSNKRPSGIP    60
DRFSGSKSGT SATLGITGLQ TGDEADYYCG TWDSSLSAGV FGGGTKLT                108

SEQ ID NO: 267           moltype = DNA  length = 324
FEATURE                  Location/Qualifiers
source                   1..324
                         mol_type = genomic DNA
                         organism = Macaca mulatta
SEQUENCE: 267
cagtctgtgc tgaccggacc accttccgtg tctgccggac aggacagca ggtgttcatc     60
agctgttccg gcaacagctc caatatcggc aacaattacg tgtcttggta tcagcagctg   120
ccaggcacag ccccccaagct gctgatctac gactctaaca gcggcctag cggcatccca   180
gatagattct ctggcagcaa gtccggcacc agcgccacac tgggcatcac cggcctgcag   240
acaggcgacg aggcagatta ctattgcgga acctgggact ctagcctgtc cgccggcgtg   300
tttggaggag gaaccaagct gaca                                          324

SEQ ID NO: 268           moltype = AA  length = 13
FEATURE                  Location/Qualifiers
source                   1..13
                         mol_type = protein
                         organism = Macaca mulatta
SEQUENCE: 268
SGNSSNIGNN YVS                                                      13
```

```
SEQ ID NO: 269          moltype = AA   length = 7
FEATURE                 Location/Qualifiers
source                  1..7
                        mol_type = protein
                        organism = Macaca mulatta
SEQUENCE: 269
DSNKRPS                                                                   7

SEQ ID NO: 270          moltype = AA   length = 11
FEATURE                 Location/Qualifiers
source                  1..11
                        mol_type = protein
                        organism = Macaca mulatta
SEQUENCE: 270
GTWDSSLSAG V                                                             11

SEQ ID NO: 271          moltype = AA   length = 124
FEATURE                 Location/Qualifiers
source                  1..124
                        mol_type = protein
                        organism = Macaca mulatta
SEQUENCE: 271
EVQLVESGGG LVKPGESLRL SCAASGFTFS SYSMSWVRQA PGKGLEWVSC ITSSGHTYYA         60
DSVKGRFAIS RDNGKNSLYL QMNNLRAEDT AVYFCAKELG AHSGLFYNGV FDYWGQGNPV        120
TVSS                                                                    124

SEQ ID NO: 272          moltype = DNA   length = 372
FEATURE                 Location/Qualifiers
source                  1..372
                        mol_type = genomic DNA
                        organism = Macaca mulatta
SEQUENCE: 272
gaggtgcagc tggtggagtc cggcggaggc ctggtgaagc caggcgagtc tctgaggctg         60
agctgtgccg cctccggctt caccttagc tcctacagca tgtcctgggt gcgccaggca        120
cctggcaagg gcctggagtg ggtgtcctgc atcacctcta gcggccacac atactatgcc        180
gactctgtga agggccggtt cgccatcagc cgggataacg gcaagaatag cctgtacctg        240
cagatgaaca atctgcgggc cgaggacacc gccgtgtatt tttgtgcaaa ggagctggga        300
gcacactctg gcctgttcta caacggcgtg tttgattatt ggggccaggg caatcccgtg        360
acagtgtcct ct                                                           372

SEQ ID NO: 273          moltype = AA   length = 7
FEATURE                 Location/Qualifiers
source                  1..7
                        mol_type = protein
                        organism = Macaca mulatta
SEQUENCE: 273
GFTFSSY                                                                   7

SEQ ID NO: 274          moltype = AA   length = 5
FEATURE                 Location/Qualifiers
source                  1..5
                        mol_type = protein
                        organism = Macaca mulatta
SEQUENCE: 274
TSSGH                                                                     5

SEQ ID NO: 275          moltype = AA   length = 16
FEATURE                 Location/Qualifiers
source                  1..16
                        mol_type = protein
                        organism = Macaca mulatta
SEQUENCE: 275
ELGAHSGLFY NGVFDY                                                        16

SEQ ID NO: 276          moltype = AA   length = 108
FEATURE                 Location/Qualifiers
source                  1..108
                        mol_type = protein
                        organism = Macaca mulatta
SEQUENCE: 276
QSALTQPASV SGSPGQSITI SCTGTSSDVG GYNYVSWYQQ HPGKAPKLMI YEVSNRPSGV         60
SNRFSGSKGN TASLTISGLR GEDEADYYCS SYTSSSTLVV FGGGTKLT                    108

SEQ ID NO: 277          moltype = DNA   length = 324
FEATURE                 Location/Qualifiers
source                  1..324
                        mol_type = genomic DNA
                        organism = Macaca mulatta
```

-continued

```
SEQUENCE: 277
cagtccgccc tgacccagcc agcctccgtg tctggcagcc ccggccagtc tatcacaatc    60
agctgtaccg gcacaagctc cgacgtgggc ggctacaact acgtgagctg gtaccagcag   120
cacccaggca aggcacctaa gctgatgatc tatgaggtgt ccaacaggcc aagcggcgtg   180
tccaatagat tctccggctc taagggcaat accgcctccc tgacaatctc tggcctgagg   240
ggagaggacg aggcagatta ctattgctct agctacacct cctctagcac actggtggtg   300
tttggcggcg gcaccaagct gaca                                          324

SEQ ID NO: 278            moltype = AA   length = 14
FEATURE                   Location/Qualifiers
source                    1..14
                          mol_type = protein
                          organism = Macaca mulatta
SEQUENCE: 278
TGTSSDVGGY NYVS                                                      14

SEQ ID NO: 279            moltype = AA   length = 7
FEATURE                   Location/Qualifiers
source                    1..7
                          mol_type = protein
                          organism = Macaca mulatta
SEQUENCE: 279
EVSNRPS                                                               7

SEQ ID NO: 280            moltype = AA   length = 11
FEATURE                   Location/Qualifiers
source                    1..11
                          mol_type = protein
                          organism = Macaca mulatta
SEQUENCE: 280
SSYTSSSTLV V                                                         11

SEQ ID NO: 281            moltype = AA   length = 124
FEATURE                   Location/Qualifiers
source                    1..124
                          mol_type = protein
                          organism = Macaca mulatta
SEQUENCE: 281
QVHLQQWGAG LVKPSETLSL TCAVQGGPFS GYYWSWIRQP PGKGLEWIGE INHSGNTHYN    60
PSLKSRVTIS VDTSGNYFSL KLTSVTAADA AVYFCARGQQ LLRNYYYYSG MDVWGQGTTV   120
TVSS                                                                124

SEQ ID NO: 282            moltype = DNA   length = 372
FEATURE                   Location/Qualifiers
source                    1..372
                          mol_type = genomic DNA
                          organism = Macaca mulatta
SEQUENCE: 282
caggtgcacc tgcagcagtg gggagcaggc ctggtgaagc catccgagac actgtctctg    60
acatgtgcag tgcaggagg accctctctct ggctactatt ggagctggat caggcagcca   120
cctggccaagg gcctggagtg gatcggcgag atcaaccaca gcggcaatac ccactacaac   180
ccctctctga agagccgggt gaccatcagc gtggacacat ccggcaatta cttctcccctg   240
aagctgacct ctgtgacagc cgccgatgcc gccgtgtatt tttgcgcccg gggccagcag   300
ctgctgagaa actactatta ctattccggc atggacgtgt ggggacaggg aaccacagtg   360
acagtgagct cc                                                       372

SEQ ID NO: 283            moltype = AA   length = 7
FEATURE                   Location/Qualifiers
source                    1..7
                          mol_type = protein
                          organism = Macaca mulatta
SEQUENCE: 283
GGPFSGY                                                               7

SEQ ID NO: 284            moltype = AA   length = 5
FEATURE                   Location/Qualifiers
source                    1..5
                          mol_type = protein
                          organism = Macaca mulatta
SEQUENCE: 284
NHSGN                                                                 5

SEQ ID NO: 285            moltype = AA   length = 16
FEATURE                   Location/Qualifiers
source                    1..16
                          mol_type = protein
                          organism = Macaca mulatta
SEQUENCE: 285
GQQLLRNYYY YSGMDV                                                    16
```

```
SEQ ID NO: 286           moltype = AA  length = 108
FEATURE                  Location/Qualifiers
source                   1..108
                         mol_type = protein
                         organism = Macaca mulatta
SEQUENCE: 286
QSALTQPASV SGSPGQSITI SCTETSRDVG DYNYVSWYQQ HPGPAPKLIM YEVHKRPSGI   60
SNRFSGSKSG TTASLTISGL QADDEGDYYC SSYTDKNTYV FGSGTQVT               108

SEQ ID NO: 287           moltype = DNA  length = 324
FEATURE                  Location/Qualifiers
source                   1..324
                         mol_type = genomic DNA
                         organism = Macaca mulatta
SEQUENCE: 287
cagtctgccc tgacccagcc agcctctgtg agcggctccc ctggccagtc catcacaatc    60
tcttgtaccg agacatctcg ggacgtgggc gattacaact atgtgagctg gtaccagcag  120
cacccaggac ctgcaccaaa gctgatcatg tatgaggtgc acaagcgccc tctggcatc   180
agcaatagat tctctggcag caagtccggc accacagcca gcctgaccat ctccggcctg  240
caggcagacg atgagggcga ctactattgc agctcctaca ccgataagaa cacatacgtg  300
ttcggcagcg gcacccaggt gaca                                         324

SEQ ID NO: 288           moltype = AA  length = 14
FEATURE                  Location/Qualifiers
source                   1..14
                         mol_type = protein
                         organism = Macaca mulatta
SEQUENCE: 288
TETSRDVGDY NYVS                                                     14

SEQ ID NO: 289           moltype = AA  length = 7
FEATURE                  Location/Qualifiers
source                   1..7
                         mol_type = protein
                         organism = Macaca mulatta
SEQUENCE: 289
EVHKRPS                                                              7

SEQ ID NO: 290           moltype = AA  length = 10
FEATURE                  Location/Qualifiers
source                   1..10
                         mol_type = protein
                         organism = Macaca mulatta
SEQUENCE: 290
SSYTDKNTYV                                                          10

SEQ ID NO: 291           moltype = AA  length = 447
FEATURE                  Location/Qualifiers
source                   1..447
                         mol_type = protein
                         organism = Synthetic construct
SEQUENCE: 291
EAALLVCQYT IQSLIHLTGE DPGFFNVEIP EFPFYPTCNV CTADVNVTIN FDVGGKKHQL   60
DLDFGQLTPH TKAVYQPRGA FGGSENATNL FLLELLGAGE LALTMRSKKL PINVTTGEEQ  120
QVSLESVDVY FQDVFGTMWC HHAEMQNPVY LIPETVPYID WDNCSTNIT AVVRAQGLDV   180
TLPLSLPTSA QDSNFSVKTE MLGNEIDIEC IMEDGEISQV LPGDNKFNIT CSGYESHVPS  240
GGILTSTSPV ATPIPGTGYA YSLRLTPRPV SRFLGNNSIL YVFYSGNGPK ASGGRYCIQS  300
NIVFSDEIPA SQDMPTNTTD ITYVGDNATY SVPMVTSEDA NSPNVTVTAF WAWPNNTETD  360
FKCKWTLTSG TPSGCENISG AFASNRTFDI TVSGLGTAPK TLIITRTATN ATTTTHKVIF  420
SKAPGSGLND IFEAQKIEWH EHHHHHH                                     447

SEQ ID NO: 292           moltype = DNA  length = 1341
FEATURE                  Location/Qualifiers
source                   1..1341
                         mol_type = other DNA
                         organism = Synthetic construct
SEQUENCE: 292
gaagctgccc tgctcgtgtg ccagtacacc atccagagcc tgatccacct gaccggcgag   60
gaccccggct tcttcaacgt ggaaatcccc gagttcccct tctaccctac ctgcaacgtg  120
tgcaccgccg acgtgaacgt gaccatcaac ttcgacgtgg gcggcaagaa gcaccagctg  180
gacctggatt tcggccagct gacccctcac accaaggccg tgtatcagcc cagaggcgcc  240
tttggcggca gcgagaacgc caccaatctg tttctgctgg aactcctagg cgccggcgag  300
ctgccctga ccatgagaag caagaaactg cccatcaatg tgaccacagg cgaggaacag   360
caggtgtccc tggaaagcgt ggacgtgtac tttcaagacg tgttcggcac catgtggtgc  420
caccacgccg agatgcagaa ccccgtgtac ctgatccccg agacagtgcc ctacatcgat  480
tgggacaact gcaacagcac caacatcacc gccgtcgtgc gggcccaggg actggatgtg  540
acactgcctc tgagcctgcc taccagcgcc aggacagca acttcagcgt gaaaaccgag  600
atgctgggca acgagatcga catcgagtgc atcatggaag atggcgagat cagccaggtg  660
```

```
ctgcccggcg acaacaagtt caacatcaca tgcagcggct acgagagcca cgtgccatct    720
ggcggcatcc tgaccagcac aagcccagtg ccacaccca tccctggcac aggctacgcc    780
tacagcctga gactgacccc cagaccgtg tccagattcc tgggcaacaa cagcatcctg    840
tacgtgttct acagcggcaa cggccccaag gcctctggcg gccggtactg tatccagagc    900
aacatcgtgt tcagcgacga gatccccgcc agccaggaca tgcccaccaa taccaccgac    960
atcacgtacg tgggcgacaa tgccacctac agcgtgccaa tggtcacctc cgaggacgcc    1020
aacagcccca acgtgaccgt gacagccttt tgggcctggc ctaacaacac cgagacagac    1080
ttcaagtgca agtggaccct gacctccggc acccctagcg gctgcgagaa tatcagcgga    1140
gccttcgcca gcaaccggac cttcgatatc accgtgtctg gctgggcac cgcccccaag    1200
accctgatca tcaccagaac cgccacaaat gccaccacca caacccacaa agtgatcttc    1260
agcaaggccc ccggctctgg cctgaacgac atttttgagg cccagaagat tgagtggcat    1320
gaacatcacc accaccacca t                                              1341

SEQ ID NO: 293            moltype = DNA   length = 5118
FEATURE                   Location/Qualifiers
source                    1..5118
                          mol_type = genomic DNA
                          organism = Macaca mulatta
SEQUENCE: 293
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
tggcgggtg tcggggctgg cttaactatg cggcatcaga gcagattgta ctgagagtgc    180
accatatgcg gtgtgaaata ccgcacagat gcgtaaggag aaaataccgc atcagattgc    240
ctattggcca ttgcatacgt tgtatccata tcataaatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga cttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag cgtgtacgg tgggaggtct atataagcag    900
agctcgttta gtgaaccgtc agatcgcctg gagacgccat ccacgctgtt tgacctcca    960
tagaagacac cgggaccgat ccagcctcca tcggctcgca tctctccttc acgcgcccgc    1020
cgccctacct gaggccgcca tccacgccgg ttgagtcgcg ttctgccgcc tcccgccgtgt    1080
ggtgcctcct gaactgcgtc cgccgtctag gtaagtttaa agctcaggtc gagaccgggc    1140
ctttgtccgg cgctccccttg gagcctacct agactcagca ggctctccac gcttttgccctg    1200
accctgcttg ctcaactcta gttaacggtg gagggcagtg tagtctgagc agtacacgtt    1260
gctgccgcgc gcgccaccag acataatagc tgacagacta acagactgtt cctttccatg    1320
ggtctttttct gcagtcaccg tcgtcgacac gtgtgatcag atatcgcggc cgctctagac    1380
caccatggga tggtcatgta tcatccttt tctagtagca atgcaaccg tgtacattc    1440
ccagtctgcc ctgactcagc ctccctctgt gtctgggtct cctggacagt cggtcaccat    1500
ctcctgcact ggaaccagca gtgacgttga tggttataac tatgtctcct ggtaccaaca    1560
acatccaggc aaagccccca aactcatgat ttatggtgtc agcaatcggc cctcaggggt    1620
ctctgatcgc ttctctggct ccaagtctgg caacacggcc tccctgacca tctctgggct    1680
ccaggctgag gacgaggctg attattactg ttgttcatct acaaccagtt acacttacat    1740
cttcggaact gggaccaagg tcacagtact aggtcagccc aaggctgccc cctcggtcac    1800
tctcttcccg ccctcctctg aggagcttca agccaacaag gccacactag tgtgtctgat    1860
cagtgacttc tacccgggag ccgtggaagt ggctgagga cagatgccga gcgctgtaca    1920
cgcgggagtg gagaccacca aaccctccaa acagagcaac aacaagtacg cggccagcag    1980
ctacctgagc ctgacgtccg accagtggaa gtcccacaag agctacagct gccaggtcac    2040
gcacgaaggg agcaccgtgg agaagacagt ggcccctgca gaatgttcat agggatccag    2100
atctgctgtg ccttctagtt gccagccatc tgttgtttgc ccctcccccg tgccttcctt    2160
gaccctggaa ggtgccactc ccactgtcct ttcctaataa aatgaggaaa ttgcatcgca    2220
ttgtctgagt aggtgtcatt ctattctggg ggtggggtg gggcaggaca gcaaggggga    2280
ggattgggaa gacaatagca ggcatgctgg ggatgcggtg ggctctatgg gtacccaggt    2340
gctgaagaat tgacccggtt cctcctgggc cagaaagaag caggcacatc cccttctctg    2400
tgacacacc tgtccacgcc cctggttctt agttccagcc ccactcatag gacactcata    2460
gctcaggagg gctccgcctt caatcccacc cgctaaagta catggagcgg tctctcccctc    2520
cctcatcagc ccaccaaacc aaacctagcc tccaagagtg ggaagaaatt aaagcaagat    2580
aggctattaa gtgcagaggg agagaaaatg cctccaacat gtgaggaagt aatgagagaa    2640
atcataqaat tttaaqqcca tqatttaaqq ccatcatqtq cttaatctto cqcttcctcq    2700
ctcactgact cgctgcgctc ggtcgttcgg ctgcggcgag cggtatcagc tcactcaaag    2760
gcggtaatac ggttatccac agaatcaggg ataacgcag aaagaacat gtgagcaaaa    2820
ggccagcaaa aggccaggaa ccgtaaaaag gccgcgttgc tggcgttttt ccataggctc    2880
cgccccctg acgagcatca caaaaatcga cgctcaagtc agaggtggcg aaacccgaca    2940
ggactataaa gataccaggc gtttccccct ggaagctccc tcgtgcgctc tcctgttccg    3000
accctgccgc ttaccggata cctgtccgcc tttctccctt cgggaagcgt ggcgctttct    3060
catagctcac gctgtaggta tctcagttcg gtgtaggtcg ttcgctccaa gctgggctgt    3120
gtgcacgaac cccccgttca gcccgaccgc tgcgccttat ccggtaacta tcgtcttgag    3180
tccaacccgg taagacacga cttatcgcca ctggcagcag ccactggtaa caggattagc    3240
agagcgaggt atgtaggcgg tgctacagag ttcttgaagt ggtggcctaa ctacggctac    3300
actagaagaa cagtatttgg tatctgcgct ctgctgaagc cagttacctt cggaaaaaga    3360
gttggtagct cttgatccgg caaacaaacc accgctggta gcggtggttt ttttgtttgc    3420
aagcagcaga ttacgcgcag aaaaaaagga tctcaagaag atcctttgat cttttctacg    3480
gggtctgacg ctcagtggaa cgaaaactca cgttaaggga ttttggtcat gagattatca    3540
aaaaggatct tcacctagat ccttttaaat taaaaatgaa gttttaaatc aatctaaagt    3600
```

```
atatatgagt aaacttggtc tgacagttac caatgcttaa tcagtgaggc acctatctca 3660
gcgatctgtc tatttcgttc atccatagtt gcctgactcg ggggggggggg gcgctgaggt 3720
ctgcctcgtg aagaaggtgt tgctgactca taccaggcct gaatcgcccc atcatccagc 3780
cagaaagtga gggagccacg gttgatgaga gctttgttgt aggtggacca gttggtgatt 3840
ttgaacttt gctttgccac ggaacggtct gcgttgtcgg gaagatgcgt gatctgatcc 3900
ttcaactcag caaagttcg atttattcaa caaagccgcc gtcccgtcaa gtcagcgtaa 3960
tgctctgcca gtgttacaac caattaacca attctgatta gaaaaactca tcgagcatca 4020
aatgaaactg caatttattc atatcaggat tatcaatacc atattttga aaaagccgtt 4080
tctgtaatga aggagaaaac tcaccgaggc agttccatag gatggcaaga tcctggtatc 4140
ggtctgcgat tccgactcgt ccaacatcaa tacaacctat taatttcccc tcgtcaaaaa 4200
taaggttatc aagtgagaaa tcaccatgag tgacgactga atccggtgag aatggcaaaa 4260
gcttatgcat ttctttccag acttgttcaa caggccagcc attacgctcg tcatcaaaat 4320
cactcgcatc aaccaaaccg ttattcattc gtgattgcgc ctgagcgaga cgaaatacgc 4380
gatcgctgtt aaaaggacaa ttacaaacag gaatcgaatg caaccggcgc aggaacactg 4440
ccagcgcatc aacaatattt tcacctgaat caggatattc ttctaatacc tggaatgctg 4500
ttttcccggg gatcgcagtg gtgagtaacc atgcatcatc aggagtacgg ataaaatgct 4560
tgatggtcgg aagaggcata aattccgtca gccagtttag tctgaccatc tcatctgtaa 4620
catcattggc aacgctacct ttgccatgtt tcagaaacaa ctctggcgca tcgggcttcc 4680
catacaatcg atagattgtc gcacctgatt gcccgacatt atcgcgagcc catttatacc 4740
catataaatc agcatccatg ttggaattta atcgcggcct cgagcaagac gtttcccgtt 4800
gaatatggct cataacaccc cttgtattac tgtttatgta agcagacagt tttattgttc 4860
atgatgatat atttttatct tgtgcaatgt aacatcagca attttgagac acaacgtggc 4920
tttccccccc cccccattat tgaagcattt atcagggtta ttgtctcatg agcggataca 4980
tatttgaatg tatttagaaa aataaacaaa taggggttcc gcgcacattt ccccgaaaag 5040
tgccacctga cgtctaagaa accattatta tcatgacatt aacctataaa aataggcgta 5100
tcacgaggcc ctttcgtc                                                5118
```